US010533040B2

(12) United States Patent
Wang

(10) Patent No.: US 10,533,040 B2
(45) Date of Patent: Jan. 14, 2020

(54) COLON AND PANCREAS CANCER PEPTIDOMIMETICS

(71) Applicant: PRECISION BIOLOGICS, INC., Rockville, MD (US)

(72) Inventor: Xue-Ping Wang, Port Washington, NY (US)

(73) Assignee: PRECISION BIOLOGICS, INC., Rockville, MD (US)

( * ) Notice: Subject to any disclaimer, the term of this patent is extended or adjusted under 35 U.S.C. 154(b) by 19 days.

(21) Appl. No.: 15/633,184

(22) Filed: Jun. 26, 2017

(65) Prior Publication Data

US 2017/0362288 A1 Dec. 21, 2017

Related U.S. Application Data

(60) Division of application No. 14/725,477, filed on May 29, 2015, now Pat. No. 9,718,866, which is a division of application No. 13/825,717, filed as application No. PCT/US2011/053064 on Sep. 23, 2011, now Pat. No. 9,068,014, and a continuation-in-part of application No. PCT/US2011/041502, filed on Jun. 22, 2011.

(60) Provisional application No. 61/385,587, filed on Sep. 23, 2010, provisional application No. 61/407,112, filed on Oct. 27, 2010, provisional application No. 61/435,176, filed on Jan. 21, 2011, provisional application No. 61/435,163, filed on Jan. 21, 2011, provisional application No. 61/467,896, filed on Mar. 25, 2011.

(51) Int. Cl.

| | |
|---|---|
| ***C07K 14/47*** | (2006.01) |
| ***A61K 39/00*** | (2006.01) |
| ***A61K 45/06*** | (2006.01) |
| ***C07K 16/30*** | (2006.01) |
| ***G01N 33/574*** | (2006.01) |
| ***A61K 47/64*** | (2017.01) |
| *A61K 38/00* | (2006.01) |

(52) U.S. Cl.

CPC ...... *C07K 14/4727* (2013.01); *A61K 39/0011* (2013.01); *A61K 45/06* (2013.01); *A61K 47/64* (2017.08); *A61K 47/643* (2017.08); *A61K 47/645* (2017.08); *A61K 47/646* (2017.08); *C07K 14/4748* (2013.01); *C07K 16/3092* (2013.01); *G01N 33/57419* (2013.01); *G01N 33/57438* (2013.01); *A61K 38/00* (2013.01); *A61K 2039/505* (2013.01); *C07K 2317/34* (2013.01); *C07K 2317/732* (2013.01); *C07K 2319/00* (2013.01); *G01N 2333/4725* (2013.01)

(58) Field of Classification Search

CPC ............................ C07K 14/47; C07K 14/4748

See application file for complete search history.

(56) References Cited

U.S. PATENT DOCUMENTS

| | | | |
|---|---|---|---|
| 9,068,014 | B2 | 6/2015 | Wang |
| 9,718,866 | B2 | 8/2017 | Wang |
| 2008/0227965 | A1 | 9/2008 | Arlen et al. |

FOREIGN PATENT DOCUMENTS

| | | |
|---|---|---|
| WO | WO 97/08320 | 3/1997 |
| WO | 00/50447 | 8/2000 |
| WO | WO 02/083872 | 10/2002 |
| WO | WO 2006/113546 | 10/2006 |
| WO | WO 2012/040617 | 3/2012 |

OTHER PUBLICATIONS

Chen, Q. et al. "EMP1 [Plasmodium falciparum] GenBank: ACN65084.1", Mar. 16, 2009. https://www.ncbi.nlm.nih.gov/protein/ACN65084.1?report=gpwithparts&log$=seqview.

Worden, A.Z. et al., "glycosyltransferase family 25 protein [Micromonas pusilla CCMP1545]GenBank: EEH50869.1", Apr. 9, 2009. https://www.ncbi.nlm.nih.gov/protein/EEH50869.1?report=gpwithparts&log$=seqview.

Arlen, P.M. et al., "Abstract B124: Preclinical development of a novel therapeutic antibody to treat pancreas and colorectal cancers", Molecular Cancer Therapeutics; 8(12 Suppl):B124, Dec. 2009.

Baldwin, A.J. and Lewis, E.K., "NMR spectroscopy brings invisible protein states into focus", Chemical Biology, Nature America, Inc., 5(11): 808-814, Nov. 2009.

Corfield et al., "Muciris and mucosal protection in the gastrointestinal tract: new prospects for mucins in the pathology of gastrointestinal disease", Gut; 47:589-594, 2000.

Einhauer, A. and Jungbauer, A., "The FLAG(TM) peptide, a versatile fusion tag for the purification of recombinant proteins", J. Biochem. Biophys. Methods 49:455-465, 2001.

Hoshi, H. et al., "Tumor-associated MUC5AC stimulates in vivo tumorigenicity of human pancreatic cancer", International Journal of Oncology, 38:619-627, 2011.

Semenuk, M. et al., "Diagnostic/Prognostic Utility of a New Serum Biomarker (NPC-1 Antigen) ELISA for Colorectal and Pancreatic Cancers", Presentation at the ASCO-NCI-EORTC Annual Meeting on Molecular Markers in Cancer—From Discovery to Clinical Practice; Hollywood, FL; Oct. 19, 2010.

(Continued)

*Primary Examiner* — Karen Cochrane Carlson

(74) *Attorney, Agent, or Firm* — Robin L. Teskin; Baker, Donelson, Bearman, Caldwell & Berkowitz PC

(57) ABSTRACT

The invention relates to a peptidomimetic of an NPC-1 epitope on the MUC5AC protein which is differentially expressed in pancreatic and colorectal cancer, and diagnostic and therapeutic usages. Further, antibodies that selectively bind the NPC-1 epitope peptidomimetics and may be used in diagnostic and therapeutic methods.

9 Claims, 14 Drawing Sheets

Specification includes a Sequence Listing.

(56) References Cited

OTHER PUBLICATIONS

Visvanathan, S. et al., "Identificiation and Characterization of a Peptide Mimetic That May Detect a Species of Disease-Associated Anticardiolipin Antibodies in Patients With the Antiphospholipid Syndrome", Arthritis & Rheumatism, 48(3):737-745, Mar. 2003.

Database Geneseq [Online] "Human mucin (MUC5AC) prtoein, SEQ ID 38.", Retrieved from EBI accession No. GSP: AZU46659; retrieved from the Internet Feb. 10, 2012.

Database GenBank [Online] "AJ298318, *Homo sapiens* partiai MUC5AC gene for mucin 5, clone A", Retrieved from the Internet Feb. 10, 2012.

Rudikoff S, et al. "Single amino acid substitution altering antigen-binding specificity," Proc Natl Acad Sci U S A. Mar. 1982;79(6):1979-83.

Guglielmo, et al. "How a single amino acid change may alter the immunological information of a peptide," Frontiers in Bioscience, Jan. 2012; 4:1843-1852.

```
4-1-4-C5    ---FPEDYFRYTNQK-----------------  (SEQ ID NO: 4)
4-1-4-C9    ---FPEDYFRYTNQK-----------------  (SEQ ID NO: 4)
4-1-3-C10   ---FPEDYFRYTNQK-----------------  (SEQ ID NO: 4)
4-1-3-C9    ---FPEDYFRYTNQK-----------------  (SEQ ID NO: 4)
4-1-3-C7    ---FPEDYFRYTNQK-----------------  (SEQ ID NO: 4)
4-1-3-C3    ---FPEDYFRYTNQK-----------------  (SEQ ID NO: 4)
4-1-3-C2    ---FPEDYFRYTNQK-----------------  (SEQ ID NO: 4)
4-1-3-C1    ---FPEDYFRYTNQK-----------------  (SEQ ID NO: 4)
4-1-2-C6    ---FPEDYFRYTNQK-----------------  (SEQ ID NO: 4)
4-1-4-C2    --SLPDDWFRYINY------------------  (SEQ ID NO: 5)
4-1-4-C3    --SLPDDWFRYINY------------------  (SEQ ID NO: 5)
4-1-4-C4    --SLPDDWFRYINY------------------  (SEQ ID NO: 5)
4-1-4-C6    --SLPDDWFRYINY------------------  (SEQ ID NO: 5)
4-1-4-C7    --SLPDDWFRYINY------------------  (SEQ ID NO: 5)
4-1-4-C12   --SLPDDWFRYINY------------------  (SEQ ID NO: 5)
4-1-4-C11   --SFPVNCCRYKK?------------------  (SEQ ID NO: 6, 7)
4-1-3-C12   ---FLEVYIRKVIRRVEVQRNFDRCLAESHTR  (SEQ ID NO: 8)
4-1-2-C11   AETVESCLAKSHTENSFTNV------------  (SEQ ID NO: 9)
4-1-3-C4    AETVESCLAKSHTENS----------------  (SEQ ID NO: 10)
4-1-2-C5    WHTLP---EKSLDEN-----------------  (SEQ ID NO: 11)
4-1-2-C8    WHTLP---EKSLDEN-----------------  (SEQ ID NO: 11)
4-1-2-C10   WHTLP---EKSLDEN-----------------  (SEQ ID NO: 11)
4-1-2-C7    WHTLP---ESGEVTS-----------------  (SEQ ID NO: 12)
4-1-2-C9    WHTLP---ESGEVTS-----------------  (SEQ ID NO: 12)
4-1-3-C5    WHTLP---ESGEVTS-----------------  (SEQ ID NO: 12)
4-1-3-C6    WHTLP---ESGEVTS-----------------  (SEQ ID NO: 12)
4-1-3-C8    WHTLP---ESGEVTS-----------------  (SEQ ID NO: 12)
4-1-2-C2    ----EYGLQQGTPNSK----------------  (SEQ ID NO: 13)
4-1-2-C4    ---FPAIMSRTPAAT-----------------  (SEQ ID NO: 14)
4-1-3-C11   ---VHAIEDNWSPRG-----------------  (SEQ ID NO: 15)
4-1-2-C1    ----EASKSSHTLWTD----------------  (SEQ ID NO: 16)
4-1-2-C12   --SQKPTHIQKALS------------------  (SEQ ID NO: 17)
4-1-2-C3    ---FNDGGALSSLRR-----------------  (SEQ ID NO: 18)
```

FIGURE 6

```
Short        1    tthsqpvtrd chlrctWtkw fdvdfpspgp Hggdketynn iirsgekicr
4-1-3-C9     1    ---------- ---------- ---------- ---------- ----------
4-1-4-C12    1    ---------- ---------- ---------- ---------- ----------

Short       51    rpeeitrlqc raeSHPEVSI EhlGQvvqcs reeglvcrnq dqqgpFKmcL
4-1-3-C9     1    ---------- ----FPE--- DY-------- ---------- -----FRY-T
4-1-4-C12    1    ---------- ---SLPD--- DW-------- ---------- -----FRY-I

Short      101    NYEvrvlcce tpkgcpVTSt pvtapstp (SEQ ID NO: 41)
4-1-3-C9    10    NQK------- ---------- -------- (SEQ ID NO: 4)
4-1-4-C12   11    NY-------- ---------- -------- (SEQ ID NO: 5)
```

FIGURE 13

COLON AND PANCREAS CANCER PEPTIDOMIMETICS

RELATED PATENT APPLICATIONS

This application is a Divisional of U.S. application Ser. No. 14/725,477, filed May 29, 2015, which is now U.S. Pat. No. 9,718,866, which is a Divisional of Ser. No. 13/825,717 filed Mar. 22, 2013, which is now U.S. Pat. No. 9,068,014, which is a national stage application of International Patent Application No. PCT/US2011/053064, filed Sep. 23, 2011, which claims priority to U.S. Provisional Application No. 61/467,896, filed Mar. 25, 2011, and to U.S. Provisional Application No. 61/435,163, filed Jan. 21, 2011, and to U.S. Provisional Application No. 61/435,176, filed Jan. 21, 2011, and to U.S. Provisional Application No. 61/407,112, filed Oct. 27, 2010, and to U.S. Provisional Application No. 61/385,587, filed Sep. 23, 2010, each of which is hereby incorporated by reference in its entirety.

SEQUENCE LISTING DISCLOSURE

This application includes as part of its disclosure a biological sequence listing which is being concurrently submitted through EFS-Web. Said biological sequence listing is contained in a file named "43282o1604.txt" which was created on Jun. 26, 2017, and has a size of 120,347, bytes, and is hereby incorporated by reference in its entirety.

BACKGROUND OF THE INVENTION

Molecular Biology of Cancer

Cancer is caused by a malfunction in the growth control systems of a cell. Cells control their growth via combination of proliferation inhibition by tumor suppressor genes (e.g., Retinoblastoma protein (pRb), p53) and proliferation activation by oncogenes (proto-oncogenes) (e.g., RAS, WNT, MYC, EKR, and TRK). A mutation in either a tumor suppressor gene and/or a protooncogene in a cell results in unusually high rates of cell proliferation (e.g., a tumor cell). See Knudson (1971) *Proc. Natl. Acad. Sci. USA* 68(4): 820-823. The cell may exhibit early signs of aberrant growth such as aberrant morphology or unusually large size (hyperplasia). The tumor cells also may proliferate at a higher than usual but not lethal rate, forming a growth, known as benign tumor (dysplasia). In later stages of cancer, the tumor cells proliferate at an unusually high rate resulting in uncontrolled growth that threatens the health of the patient known as malignant tumors (or in situ cancer). Many tumors can "metastasize" or spread throughout the body forming tumors. Metastasis is generally a sign of late stage, terminal cancer. Weinberg (September 1996) "How Cancer Arises" *Scientific American* 62-70.

Prostate cancer, lung cancer, and colorectal cancer are the three most common cancers among men. Lung cancer, prostate cancer, liver cancer, and colorectal cancer are the leading causes of cancer deaths among men. Breast cancer, lung cancer, and colorectal cancer are the three most common cancers among women. Lung cancer, breast cancer, and colorectal cancer are the leading causes of cancer death among women. CDC Features—United States Cancer Statistics (USCS) (2011). At present, there is an urgent need for diagnoses and therapies for colorectal, pancreatic, prostate, lung, liver, and breast cancer. For example, each year in the United States alone, more than 43,000 people are diagnosed with pancreas cancer. National Cancer Institute (2010) "What You Need to Know about Cancer of the Pancreas."

Although advancements in cancer detection and therapy have been made over the last two decades, the current options for early detection and treatment of cancer are limited and there exists a great need for new methods and materials that provide for the detection and treatment of cancer, especially colorectal and pancreatic cancer.

MUC5AC

Mucins are high molecular weight glycoproteins with O-linked oligosaccharides attached to serine or threonine residues of the apomucin protein backbone expressed in a cell and tissue-specific pattern in normal tissues. The mucin family includes proteins that contain tandem repeat structures with a high proportion of prolines, threonines, and serines (which constitute the PTS domain). Mucins are further defined by extensive glycosylation of the PTS domain through GalNAc O-linkages at the threonine and serine residues. Each mucin has a central region with a variable number of tandem repeat with about eight amino acid residues, but there is a little similarity. There are two structurally and functionally distinct classes of mucins: secreted gel-forming mucins and transmembrane mucins. Secreted gel-forming mucins include the products of the MUC2, MUC5AC, MUC5B and MUC6 genes. See Kocer, et al. (2006) *BMC Gastroenterology* 6: 4; See also Hollingsworth & Swanson (2004) *Nature Reviews* 4: 45-60.

The human mucin (MUC) family consists of members designated MUC1 to MUC21—subclassified into secreted and transmembrane forms. The secreted mucins (e.g., MUC2, MUC5AC, MUC5B and MUC6) form a physical barrier, which acts as a mucous gel that provides protection for epithelial cells that line the respiratory and gastrointestinal tracts and form the ductal surfaces of organs such as the liver, breast, pancreas, and kidney. The transmembrane mucins (e.g., MUC1, MUC4, MUC13 and MUC16) have a single membrane-spanning region and contribute to the protective mucous gel through their ectodomains of O-glycosylated tandem repeats that form rod-like structures. Kufe (2009) *Nature Reviews* 9: 874-885. MUC5AC expression is found on apical epithelial cells of the mucus glands of gastric antrum and body, tracheobronchial epithelium, superficial epithelium of the gallbladder and endocervix epithelium.

MUC5AC is highly expressed in adenoma. See Kocer, et al. (2006) *BMC Gastroenterology* 6: 4. Additionally, MUC5AC is expressed in tumors of gastrointestinal, pancreatiobiloary, and endocervical origin (e.g., colon, esophagus, liver, lung, pancreas, stomach, and uterus). See Lau, et al. (2004) *Am. J. Clin Pathol.* 122: 61-69. MUC5AC is also highly expressed in breast and gastric cancers. Zhang, et al. (1998) *Clinical Cancer Research* 4: 2669-2676. Further, MUC5AC glycan variants have been associated with pancreatic neoplasms. Haab, et al. (May 2010) *Annals of Surgery* 251(5): 937-945. MUC5AC is aberrantly expressed by colorectal polyps and colorectal carcinoma. Kocer, et al. (2006) *BMC Gastroenterology* 6(4): 1-9. Thus, there exists a need in the art for epitope peptidomimetics thereof for use in diagnostic and therapeutic compositions and methods for treating pancreatic and colorectal cancer.

SUMMARY OF THE INVENTION

The present invention provides peptidomimetics of a NPC-1 epitope derived from MUC5AC, including compositions comprising the same as well as methods of manufacture and use.

In one embodiment, the invention provides an isolated polypeptide comprising a polypeptide at least about 80% identical to the amino acid sequence of $SX^1PX^2DX^3FRYX^4NX^5$ (SEQ ID NO: 1), wherein $X^1$ is for L; $X^2$ is E or D; $X^3$ is Y or W; $X^4$ is T or I and $X^5$ is Q or Y; $SX^1PX^2DX^3FRYX^4NX^5K$ (SEQ ID NO: 2), wherein $X^1$ is for L; $X^2$ is E or D; $X^3$ is Y or W; $X^4$ is T or I and $X^5$ is Q or Y; $SLEPEX^1DWX^2FRYX^3NY$ (SEQ ID NO: 3), wherein $X^1$ is E or D; $X^2$ is W or Y; and $X^3$ is T or I; FPEDYFRYTNQK (SEQ ID NO: 4); SLPDDWFRYINY (SEQ ID NO: 5); or any one of the amino acid sequences of SEQ ID NOs: 6-24. In another embodiment, the invention provides a polypeptide that is at least about 90% identical to the amino acid sequence of $SX^1PX^2DX^3FRYX^4NX^5$ (SEQ ID NO: 1), wherein $X^1$ is for L; $X^2$ is E or D; $X^3$ is Y or W; $X^4$ is T or I and $X^5$ is Q or Y; $SX^1PX^2DX^3FRYX^4NX^5K$ (SEQ ID NO: 2), wherein $X^1$ is for L; $X^2$ is E or D; $X^3$ is Y or W; $X^4$ is T or I and $X^5$ is Q or Y; $SLEPEX^1DWX^2FRYX^3NY$ (SEQ ID NO: 3), wherein $X^1$ is E or D; $X^2$ is W or Y; and $X^3$ is T or I; FPEDYFRYTNQK (SEQ ID NO: 4); SLPDDWFRYINY (SEQ ID NO: 5); or any one of the amino acid sequences of SEQ ID NOs: 6-24. In another embodiment, the invention provides a polypeptide comprises the amino acid sequence of $SX^1PX^2DX^3FRYX^4NX^5$ (SEQ ID NO: 1), wherein $X^1$ is for L; $X^2$ is E or D; $X^3$ is Y or W; $X^4$ is T or I and $X^5$ is Q or Y; $SX^1PX^2DX^3FRYX^4NX^5K$ (SEQ ID NO: 2), wherein $X^1$ is for L; $X^2$ is E or D; $X^3$ is Y or W; $X^4$ is T or I and $X^5$ is Q or Y; $SLEPEX^1DWX^2FRYX^3NY$ (SEQ ID NO: 3), wherein $X^1$ is E or D; $X^2$ is W or Y; and $X^3$ is T or I; FPEDYFRYTNQK (SEQ ID NO: 4); SLPDDWFRYINY (SEQ ID NO: 5); or any one of the amino acid sequences of SEQ ID NOs: 6-24. In a further embodiment, the polypeptide may comprise the amino acid sequence of FPEDYFRYTNQK (SEQ ID NO: 4). In a further embodiment, the polypeptide may comprise the amino acid sequence of SLPDDWFRYINY (SEQ ID NO: 5)

In one embodiment, the invention provides an isolated fusion protein comprising a polypeptide comprises the amino acid sequence of $SX^1PX^2DX^3FRYX^4NX^5$ (SEQ ID NO: 1), wherein $X^1$ is for L; $X^2$ is E or D; $X^3$ is Y or W; $X^4$ is T or I and $X^5$ is Q or Y; $SX^1PX^2DX^3FRYX^4NX^5K$ (SEQ ID NO: 2), wherein $X^1$ is for L; $X^2$ is E or D; $X^3$ is Y or W; $X^4$ is T or I and $X^5$ is Q or Y; $SLEPEX^1DWX^2FRYX^3NY$ (SEQ ID NO: 3), wherein $X^1$ is E or D; $X^2$ is W or Y; and $X^3$ is T or I; FPEDYFRYTNQK (SEQ ID NO: 4); SLPDDWFRYINY (SEQ ID NO: 5); or any one of the amino acid sequences of SEQ ID NOs: 6-24. In a further embodiment, the fusion protein may comprise a polypeptide comprising the amino acid sequence of FPEDYFRYTNQK (SEQ ID NO: 4). In a further embodiment, the fusion protein may comprise a polypeptide comprising the amino acid sequence of SLPDDWFRYINY (SEQ ID NO: 5). In another embodiment, the isolated fusion protein may comprise a polypeptide that is at least about 80% or 90% identical to the amino acid sequence of the amino acid sequence of SEQ ID NOs: 1-24. In another embodiment, the fusion protein may comprise a detectable label covalently or non-covalently directly or indirectly attached thereto. In another embodiment, the detectable label may be selected from the group consisting of polyHis tag, FLAG tag, MBP, GST protein, and GFP.

The invention also provides a conjugate comprising a polypeptide comprises the amino acid sequence of $SX^1PX^2DX^3FRYX^4NX^5$ (SEQ ID NO: 1), wherein $X^1$ is for L; $X^2$ is E or D; $X^3$ is Y or W; $X^4$ is T or I and $X^5$ is Q or Y; $SX^1PX^2DX^3FRYX^4NX^5K$ (SEQ ID NO: 2), wherein $X^1$ is for L; $X^2$ is E or D; $X^3$ is Y or W; $X^4$ is T or I and $X^5$ is Q or Y; $SLEPEX^1DWX^2FRYX^3NY$ (SEQ ID NO: 3), wherein $X^1$ is E or D; $X^2$ is W or Y; and $X^3$ is T or I; FPEDYFRYTNQK (SEQ ID NO: 4); SLPDDWFRYINY (SEQ ID NO: 5); or any one of the amino acid sequences of SEQ ID NOs: 6-24, directly or indirectly, conjugated to a cytotoxic agent, a therapeutic agent, label, carbohydrate, carrier, immunoglobulin or immunoglobulin fragment, or an immunomodulatory agent. In another embodiment, the conjugate may comprise a polypeptide with at least about 80% or 90% identical to the amino acid sequence of $SX^1PX^2DX^3FRYX^4NX^5$ (SEQ ID NO: 1), wherein $X^1$ is for L; $X^2$ is E or D; $X^3$ is Y or W; $X^4$ is T or I and $X^5$ is Q or Y; $SX^1PX^2DX^3FRYX^4NX^5K$ (SEQ ID NO: 2), wherein $X^1$ is for L; $X^2$ is E or D; $X^3$ is Y or W; $X^4$ is T or I and $X^5$ is Q or Y; $SLEPEX^1DWX^2FRYX^3NY$ (SEQ ID NO: 3), wherein $X^1$ is E or D; $X^2$ is W or Y; and $X^3$ is T or I; FPEDYFRYTNQK (SEQ ID NO: 4); SLPDDWFRYINY (SEQ ID NO: 5); or any one of the amino acid sequences of SEQ ID NOs: 6-24, directly or indirectly, conjugated to a cytotoxic agent, a therapeutic agent, label, carbohydrate, carrier, immunoglobulin or immunoglobulin fragment, or an immunomodulatory agent. In another embodiment, the carbohydrate may be mannose, fucose, glucose, GlcNAs, or maltose. In another embodiment, the carrier may be Keyhole Limpit Hemocyannin (KLH), diphtheria toxoid, cholera toxoid, ovalbumin, bovine serum albumin (BSA), *Pseudomonas* exoprotein A, or microbial outer membrane proteins (OMPS). In a further embodiment, the conjugate may comprise a polypeptide comprising the amino acid sequence of FPEDYFRYTNQK (SEQ ID NO: 4) conjugated to KLH. In a further embodiment, the conjugate may comprise a polypeptide comprising the amino acid sequence of SLPDDWFRYINY (SEQ ID NO: 5) conjugated to KLH. In another embodiment, the label may be a chemiluminescent label, paramagnetic label, MRI contrast agent, fluorescent label, bioluminescent label, or radioactive label. In another embodiment, the paramagnetic label may be aluminum, manganese, platinum, oxygen, lanthanum, lutetium, scandium, yttrium, or gallium. In another embodiment, the cytotoxic agent may be a moiety that inhibits DNA, RNA, or protein synthesis, a radionuclide, or ribosomal inhibiting protein. In another embodiment, the cytotoxic agent may be $^{212}Bi$, $^{131}I$, $^{188}Re$, $^{90}Y$, vindesine, methotrexate, adriamycin, cisplatin, pokeweed antiviral protein, *Pseudomonas* exotoxin A, ricin, diphtheria toxin, ricin A chain, or cytotoxic phospholipase enzyme.

In one embodiment, the invention provides a composition comprising the polypeptide of any one of the amino acid sequences of SEQ ID NO: 1-24, or combinations thereof. In another embodiment, the composition further comprises a pharmaceutically acceptable carrier, diagnostically acceptable carrier, adjuvant, or excipient. In a further embodiment, the composition may comprise the polypeptide comprising the amino acid sequence of SEQ ID NO: 4. In a further embodiment, the composition may comprise the polypeptide comprising the amino acid sequence of SEQ ID NO: 5. In one embodiment, the composition may be a pharmaceutical composition, an antigenic composition, or an immunogenic composition. In another embodiment, the invention provides a diagnostic kit comprising the polypeptide of any one of the amino acid sequences of SEQ ID NO: 1-24, or combinations thereof. In another embodiment, the polypeptide of the kit is directly or indirectly attached to a solid phase support or cell membrane. In another embodiment, the solid phase support may be a bead, plate, matrix, polymer, test tube, sheet, culture dish, or test strip. In another embodiment, the solid phase support may be an array. In another embodiment, the polypeptide may be at least about 80% or 90% identical to any one of the amino acid sequences of SEQ ID NO: 1-24, or combinations thereof.

In one embodiment, the invention provides a composition comprising a fusion protein comprising the polypeptide of any one of the amino acid sequences of SEQ ID NO: 1-24, or combinations thereof. In another embodiment, the composition further comprises a pharmaceutically acceptable carrier, diagnostically acceptable carrier, adjuvant, or excipient. In one embodiment, the composition may be a pharmaceutical composition, an antigenic composition, or an immunogenic composition. In another embodiment, the invention provides a diagnostic kit comprising a fusion protein comprising the polypeptide of any one of the amino acid sequences of SEQ ID NO: 1-24, or combinations thereof. In another embodiment, the polypeptide of the kit is directly or indirectly attached to a solid phase support or cell membrane. In another embodiment, the solid phase support may be a bead, plate, matrix, polymer, test tube, sheet, culture dish, or test strip. In another embodiment, the solid phase support may be an array. In another embodiment, the polypeptide may be at least about 80% or 90% identical to any one of the amino acid sequences of SEQ ID NO: 1-24, or combinations thereof.

In one embodiment, the invention provides a composition comprising a conjugate comprising the polypeptide of any one of the amino acid sequences of SEQ ID NO: 1-24, or combinations thereof. In another embodiment, the composition further comprises a pharmaceutically acceptable carrier, diagnostically acceptable carrier, adjuvant, or excipient. In one embodiment, the composition may be a pharmaceutical composition, an antigenic composition, or an immunogenic composition. In another embodiment, the invention provides a diagnostic kit comprising a conjugate comprising the polypeptide of any one of the amino acid sequences of SEQ ID NO: 1-24, or combinations thereof. In another embodiment, the polypeptide of the kit is directly or indirectly attached to a solid phase support or cell membrane. In another embodiment, the solid phase support may be a bead, plate, matrix, polymer, test tube, sheet, culture dish, or test strip. In another embodiment, the solid phase support may be an array. In another embodiment, the polypeptide may be at least about 80% or 90% identical to any one of the amino acid sequences of SEQ ID NO: 1-24, or combinations thereof.

In one embodiment, the invention provides an isolated polynucleotide that encodes the polypeptide of any one of the amino acid sequences of SEQ ID NO: 1-24. In another embodiment, the invention provides an isolated expression vector comprising an isolated polynucleotide that encodes the polypeptide of any one of the amino acid sequences of SEQ ID NO: 1-24. In another embodiment, an isolated host cell comprises an isolated expression vector comprising an isolated polynucleotide that encodes the polypeptide of any one of the amino acid sequences of SEQ ID NO: 1-24. In a further embodiment, a non-human transgenic animal may comprise a host cell comprises an expression vector comprising an isolated polynucleotide that encodes the polypeptide of any one of the amino acid sequences of SEQ ID NO: 1-24. The invention also provides for a composition that may comprise an isolated polynucleotide that encodes the polypeptide of any one of the amino acid sequences of SEQ ID NO: 1-24. In another embodiment, the composition may further comprise a pharmaceutically acceptable carrier, adjuvant, or excipient. In another embodiment, the polypeptide may be at least about 80% or 90% identical to any one of the amino acid sequences of SEQ ID NO: 1-24, or combinations thereof.

In one embodiment, the invention provides an isolated polynucleotide that encodes a fusion protein comprising a polypeptide comprising any one of the amino acid sequences of SEQ ID NO: 1-24. In another embodiment, the invention provides an isolated expression vector comprising an isolated polynucleotide that encodes a fusion protein comprising a polypeptide comprising any one of the amino acid sequences of SEQ ID NO: 1-24. In another embodiment, an isolated host cell comprises an isolated expression vector comprising an isolated polynucleotide that encodes a fusion protein comprising a polypeptide comprising any one of the amino acid sequences of SEQ ID NO: 1-24. In a further embodiment, a non-human transgenic animal may comprise a host cell comprises an expression vector comprising an isolated polynucleotide that encodes a fusion protein comprising a polypeptide comprising any one of the amino acid sequences of SEQ ID NO: 1-24. The invention also provides for a composition that may comprise an isolated polynucleotide that encodes a fusion protein comprising a polypeptide comprising any one of the amino acid sequences of SEQ ID NO: 1-24. In another embodiment, the composition may further comprise a pharmaceutically acceptable carrier, adjuvant, or excipient. In another embodiment, the polypeptide may be at least about 80% or 90% identical to any one of the amino acid sequences of SEQ ID NO: 1-24, or combinations thereof.

The invention also provides for an isolated antibody or an antigen-binding fragment thereof that selectively binds a polypeptide comprising any one of the amino acid sequences of SEQ ID NO: 1-24. The invention also provides for an isolated antibody or an antigen-binding fragment thereof that selectively binds a fusion protein comprising a polypeptide comprising any one of the amino acid sequences of SEQ ID NO: 1-24. The invention also provides for an isolated antibody or an antigen-binding fragment thereof that selectively binds a conjugate comprising a polypeptide comprising any one of the amino acid sequences of SEQ ID NO: 1-24. In another embodiment, the antibody or antigen-binding fragment thereof may be produced using a polypeptide comprising any one of the amino acid sequences of SEQ ID NO: 1-24, a fusion protein comprising a polypeptide comprising any one of the amino acid sequences of SEQ ID NO: 1-24, or a conjugate comprising a polypeptide comprising any one of the amino acid sequences of SEQ ID NO: 1-24 as the immunogen. In another embodiment, the polypeptide may be at least about 80% or 90% identical to any one of the amino acid sequences of SEQ ID NO: 1-24, or combinations thereof.

In another embodiment, the antibody or antigen-binding fragment thereof may be recombinant. In another embodiment, the antibody or antigen-binding fragment thereof may have anti-tumor activity. In one embodiment, the fragment may be a Fab, Fab', F(ab')2, Fv, CDR, paratope, or portion of an antibody that is capable of binding the antigen. In another embodiment, the antibody or antigen-binding fragment thereof may be chimeric, humanized, anti-idiotypic, single-chain, bifunctional, or co-specific. In one embodiment, the antibody or antigen-binding fragment thereof may be directly or indirectly conjugated to a label, cytotoxic agent, therapeutic agent, or an immunosuppressive agent. In one embodiment, the label may be a chemiluminescent label, paramagnetic label, MRI contrast agent, fluorescent label, bioluminescent label, or radioactive label. In one embodiment, the paramagnetic label may be aluminum, manganese, platinum, oxygen, lanthanum, lutetium, scandium, yttrium, or gallium. In one embodiment, the cytotoxic agent may be a moiety that inhibits DNA, RNA, or protein synthesis, a radionuclide, or ribosomal inhibiting protein, $^{212}Bi$, $^{131}I$, $^{188}Re$, $^{90}Y$, vindesine, methotrexate, adriamycin, cisplatin, pokeweed antiviral protein, *Pseudomonas* exotoxin A, ricin, diphtheria toxin, ricin A chain, or cytotoxic phospholipase enzyme. In one embodiment, the therapeutic agent may be a lymphokine or growth factor, growth factor receptor, Toll Receptor or an agonist or antagonist of any of the foregoing. In one embodiment, the immunmodulatory agent may be an immunosuppressive agent selected from a cyclosporine, leflunomide, methotrexate, azothiprine, mercaptopurine, dactinomycin, tacrolimus, or sirolimus.

The invention also provides a composition comprising an antibody or antibody fragment which selectively binds a polypeptide comprising any one of the amino acid sequences of SEQ ID NO: 1-24, a fusion protein comprising a polypeptide comprising any one of the amino acid sequences of SEQ ID NO: 1-24, or a conjugate comprising a polypeptide comprising any one of the amino acid sequences of SEQ ID NO: 1-24. In another embodiment, the composition may further comprise a pharmaceutically acceptable carrier, adjuvant, or excipient. In another embodiment, the polypeptide may be at least about 80% or 90% identical to any one of the amino acid sequences of SEQ ID NO: 1-24, or combinations thereof. A diagnostic kit comprising an antibody or antibody fragment which selectively binds a polypeptide comprising any one of the amino acid sequences of SEQ ID NO: 1-24, a fusion protein comprising a polypeptide comprising any one of the amino acid sequences of SEQ ID NO: 1-24, or a conjugate comprising a polypeptide comprising any one of the amino acid sequences of SEQ ID NO: 1-24. In another embodiment, the polypeptide of the kit is directly or indirectly attached to a solid phase support or cell membrane. In another embodiment, the solid phase support may be a head, plate, matrix, polymer, test tube, sheet, culture dish, or test strip. In another embodiment, the solid phase support may be an array.

In another embodiment, the invention provides a composition for treating cancer comprising an effective amount of the polypeptide a polypeptide comprising any one of the amino acid sequences of SEQ ID NO: 1-24. In a further embodiment, the composition for treating cancer may comprise an effective amount of a fusion protein comprising a polypeptide comprising any one of the amino acid sequences of SEQ ID NO: 1-24. In a further embodiment, the composition for treating cancer may comprise an effective amount of a conjugate comprising a polypeptide comprising any one of the amino acid sequences of SEQ ID NO: 1-24. In a further embodiment, the composition for treating cancer may comprise an effective amount of an antibody or antibody fragment which selectively binds a polypeptide comprising any one of the amino acid sequences of SEQ ID NO: 1-24, a fusion protein comprising a polypeptide comprising any one of the amino acid sequences of SEQ ID NO: 1-24, or a conjugate comprising a polypeptide comprising any one of the amino acid sequences of SEQ ID NO: 1-24. In another embodiment, the cancer may be selected from the group consisting of lung, breast, ovarian, stomach, pancreas, uterine, esophageal, colorectal, and liver cancer. In another embodiment, the cancer is pancreas or colorectal cancer.

The invention also provides for the use of a polypeptide comprising any one of the amino acid sequences of SEQ ID NO: 1-24 in the preparation of a medicament for treating cancer. In another embodiment, the use of a fusion protein comprising a polypeptide comprising any one of the amino acid sequences of SEQ ID NO: 1-24 in the preparation of a medicament for treating cancer. In a further embodiment, use of a conjugate comprising a polypeptide comprising any one of the amino acid sequences of SEQ ID NO: 1-24 in the preparation of a medicament for treating cancer. In a further embodiment, use of an antibody or antibody fragment which selectively binds a polypeptide comprising any one of the amino acid sequences of SEQ ID NO: 1-24, a fusion protein comprising a polypeptide comprising any one of the amino acid sequences of SEQ ID NO: 1-24, or a conjugate comprising a polypeptide comprising any one of the amino acid sequences of SEQ ID NO: 1-24 in the preparation of a medicament for treating cancer. In another embodiment, the cancer may be selected from the group consisting of lung, breast, ovarian, stomach, pancreas, uterine, esophageal, colorectal, and liver cancer. In another embodiment, the cancer is pancreas or colorectal cancer.

The invention also provides a method for treating cancer may comprise administering an effective amount of a polypeptide comprising any one of the amino acid sequences of SEQ ID NO: 1-24. In another embodiment, a method for slowing the growth of a tumor may comprise administering an effective amount of a polypeptide comprising any one of the amino acid sequences of SEQ ID NO: 1-24. In one embodiment, a method for promoting tumor regression in a subject may comprise administering an effective amount of a polypeptide comprising any one of the amino acid sequences of SEQ ID NO: 1-24. In one embodiment, a method for activating dendritic cells may comprise removing dendritic cells from a patient, contacting cells ex viva with an effective amount of a polypeptide comprising any one of the amino acid sequences of SEQ ID NO: 1-24, and reintroducing activated the dendritic cells into said patient. In one embodiment, a method for activating antigen-specific immunity may comprise administering an effective amount of a polypeptide comprising any one of the amino acid sequences of SEQ ID NO: 1-24.

The invention also provides a method for treating cancer may comprise administering an effective amount of a fusion protein comprising a polypeptide comprising any one of the amino acid sequences of SEQ ID NO: 1-24. In one embodiment, a method for slowing the growth of a tumor may comprise administering an effective amount of a fusion protein comprising a polypeptide comprising any one of the amino acid sequences of SEQ ID NO: 1-24. In one embodiment, a method for promoting tumor regression in a subject may comprise administering an effective amount of a fusion protein comprising a polypeptide comprising any one of the amino acid sequences of SEQ ID NO: 1-24. In one embodiment, a method for activating dendritic cells may comprise removing dendritic cells from a patient, contacting cells ex vivo with an effective amount of a fusion protein comprising a polypeptide comprising any one of the amino acid sequences of SEQ ID NO: 1-24, and reintroducing activated the dendritic cells into said patient. In one embodiment, a method for activating antigen-specific immunity may comprise administering an effective amount of a fusion protein comprising a polypeptide comprising any one of the amino acid sequences of SEQ ID NO: 1-24.

The invention also provides a method for treating cancer may comprise administering an effective amount of a conjugate comprising a polypeptide comprising any one of the amino acid sequences of SEQ ID NO: 1-24. In one embodiment, a method for slowing the growth of a tumor may comprise administering an effective amount of a conjugate comprising a polypeptide comprising any one of the amino acid sequences of SEQ ID NO: 1-24. In one embodiment, a method for promoting tumor regression in a subject may comprise administering an effective amount of a conjugate comprising a polypeptide comprising any one of the amino acid sequences of SEQ ID NO: 1-24. In one embodiment, a method for activating dendritic cells may comprise removing dendritic cells from a patient, contacting cells ex vivo with an effective amount of a conjugate comprising a polypeptide comprising any one of the amino acid sequences of SEQ ID NO: 1-24, and reintroducing activated the dendritic cells into said patient. In one embodiment, a method for activating antigen-specific immunity may comprise administering an effective amount of a fusion protein or conjugate comprising a polypeptide comprising any one of the amino acid sequences of SEQ ID NO: 1-24.

The invention further provides a method for treating cancer comprising administering an effective amount of an antibody or antibody fragment which selectively binds a polypeptide comprising any one of the amino acid sequences of SEQ ID NO; 1-24, a fusion protein comprising a polypeptide comprising any one of the amino acid sequences of SEQ ID NO: 1-24, or a conjugate comprising a polypeptide comprising any one of the amino acid sequences of SEQ ID NO: 1-24. In one embodiment, a method for slowing the growth of a tumor and/or inhibiting metastasis may comprise administering an effective amount of an antibody or antibody fragment which selectively binds a polypeptide comprising any one of the amino acid sequences of SEQ ID NO: 1-24, a fusion protein comprising a polypeptide comprising any one of the amino acid sequences of SEQ ID NO: 1-24, or a conjugate comprising a polypeptide comprising any one of the amino acid sequences of SEQ ID NO: 1-24. In one embodiment, a method for promoting tumor regression in a subject may comprise administering an effective amount of an antibody or antibody fragment which selectively binds a polypeptide comprising any one of the amino acid sequences of SEQ ID NO: 1-24, a fusion protein comprising a polypeptide comprising any one of the amino acid sequences of SEQ ID NO: 1-24, or a conjugate comprising a polypeptide comprising any one of the amino acid sequences of SEQ ID NO: 1-24. In one embodiment, a method for activating dendritic cells may comprise removing dendritic cells from a patient, contacting cells ex vivo with an effective amount of an antibody or antibody fragment which selectively binds a polypeptide comprising any one of the amino acid sequences of SEQ ID NO: 1-24, a fusion protein comprising a polypeptide comprising any one of the amino acid sequences of SEQ ID NO: 1-24, or a conjugate comprising a polypeptide comprising any one of the amino acid sequences of SEQ ID NO: 1-24, and reintroducing activated the dendritic cells into said patient. In one embodiment, a method for activating antigen-specific immunity may comprise administering an effective amount of an antibody or antibody fragment which selectively binds a polypeptide comprising any one of the amino acid sequences of SEQ ID NO: 1-24, a fusion protein comprising a polypeptide comprising any one of the amino acid sequences of SEQ ID NO: 1-24, or a conjugate comprising a polypeptide comprising any one of the amino acid sequences of SEQ ID NO: 1-24.

In one embodiment, the invention provides a method for detecting a NPC-1 epitope comprising: contacting a test sample with an antibody, or fragment thereof, that binds a polypeptide of any one amino acid sequence of SEQ ID NO: 1-26, and assaying for antibody-epitope complexes, wherein the presence of said epitope is indicative of a carcinoma. In another embodiment, the invention provides a method for detecting the presence of a NPC-1 epitope in a patient comprising administering to said patient a labeled monoclonal antibody, or antigen-binding fragment thereof, that binds a polypeptide of any one of any one amino acid sequence of SEQ ID NO: 1-26, and detecting the presence of a NPC-1 epitope, wherein the presence of said epitope is indicative of a carcinoma.

In another embodiment, the method may comprise imaging the NPC-1 epitope. In a further embodiment, the imaging may be selected from the group consisting of positron emission tomography (PET), CCD low-light monitoring system, x-ray, CT scanning, scintigraphy, photo acoustic imaging, single photon emission computed tomography (SPECT), magnetic resonance imaging (MRI), ultrasound, paramagnetic imaging, and endoscopic optical coherence tomography.

In another embodiment, the polypeptide, fusion protein, conjugate, or antibody may be administered in combination with another antibody, a lymphokine, or a hematopoietic growth factor. In another embodiment, the agent may be administered simultaneously or sequentially with the antibody. In another embodiment, the cancer may be lung, breast, ovarian, stomach, pancreas, uterine, esophageal, colorectal, or liver cancer. In a further embodiment, the cancer is pancreas or colorectal cancer. In a still further embodiment, the cancer may be pancreas cancer. In another embodiment, the cancer is colorectal cancer.

In another embodiment, the cancer may be a stage 1, 2, 3 or 4 cancer. In another embodiment, the cancer may have metastasized. In another embodiment, the patient may express detectable levels of a NPC-1 epitope. In another embodiment, the antigen may be detected in a tumor biopsy sample or in the blood, stool, urine, or lymph fluid. In another embodiment, the patient may be at risk of cancer. In another embodiment, the patient may be a patient without symptoms.

In one embodiment, the antibody or antigen-binding fragment thereof may be recombinant. In another embodiment, the antibody or antigen-binding fragment thereof may have anti-tumor activity. In a further embodiment, the antigen-binding fragment thereof may be a Fab, Fab', F(ab')2, Fv, CDR, paratope, or portion of an antibody that is capable of binding the antigen. In another embodiment, the antibody may be chimeric, humanized, anti-idiotypic, single-chain, bifunctional, or co-specific.

In one embodiment, the antibody or antigen-binding fragment may be conjugated to a label. In one embodiment, the label may be a chemiluminescent label, paramagnetic label, an MRI contrast agent, fluorescent label, bioluminescent label, or radioactive label. In one embodiment, the paramagnetic label may be aluminum, manganese, platinum, oxygen, lanthanum, lutetium, scandium, yttrium, or gallium.

In a further embodiment, the antibody may be attached to a solid support. In a further embodiment, the solid support may be a bead, test tube, sheet, culture dish, or test strip. In a further embodiment, the solid support may be an array. In a further embodiment, the sample may be a tissue biopsy, lymph, urine, cerebrospinal fluid, amniotic fluid, inflammatory exudate, blood, serum, stool, or liquid collected from the colorectal tract.

In a further embodiment, the antibody-epitope complex may be detected by an assay selected from the group consisting of Western blots, radioimmunoassays, ELISA (enzyme linked immunosorbent assay), "sandwich" immunoassays, immunoprecipitation assays, precipitation reactions, gel diffusion precipitation reactions, immunodiffusion assays, agglutination assays, complement-fixation assays, immunohistochemical assays, fluorescent immunoassays, and protein A immunoassays.

In a further embodiment, the method may detect colorectal polyps. In one embodiment, the method may further comprise additional testing for the presence of tumors. In a further embodiment, the method may detect benign tumors. In a further embodiment, the method may malignant tumors.

In a further embodiment, the method may metastatic tumors. In a further embodiment, the method may non-metastatic tumors. In another embodiment, the method may detect pre-cancerous cells that express a cell marker comprising a NPC-1 epitope. In another embodiment, the test sample may be obtained from a patient at risk of cancer. In another embodiment, the test sample may be obtained from a patient without symptoms.

In one embodiment, the invention provides a method of making antibodies comprising: immunizing an animal with a polypeptide of any one of the amino acid sequences of SEQ ID NOs: 1-24, removing said animal's spleen and prepare a single cell suspension, fusing a spleen cell with a myeloma cell, culturing post-fusion cells in hybridoma selection medium, culturing the resultant hybridomas, screening for specific antibody production, and selecting hybridomas which produce the desired antibody. In another embodiment, the invention provides a method of making antibodies comprising: immunizing an animal with a polypeptide of FPEDYFRYTNQK (SEQ ID NO: 4) or SLPDDWFRYINY (SEQ ID NO: 5), removing said animal's spleen and prepare a single cell suspension, fusing a spleen cell with a myeloma cell, culturing post-fusion cells in hybridoma selection medium, culturing the resultant hybridomas, screening for specific antibody production, and selecting hybridomas which produce the desired antibody.

In one embodiment, the invention provides a method of making antibodies comprising: immunizing an animal with a fusion protein comprising a polypeptide of any one of the amino acid sequences of SEQ ID NOs: 1-24, removing said animal's spleen and prepare a single cell suspension, fusing a spleen cell with a myeloma cell, culturing post-fusion cells in hybridoma selection medium, culturing the resultant hybridomas, screening for specific antibody production, and selecting hybridomas which produce the desired antibody. In another embodiment, the invention provides a method of making antibodies comprising: immunizing an animal with a fusion protein comprising a polypeptide of FPEDYFRYTNQK (SEQ ID NO: 4) or SLPDDWFRYINY (SEQ ID NO: 5), removing said animal's spleen and prepare a single cell suspension, fusing a spleen cell with a myeloma cell, culturing post-fusion cells in hybridoma selection medium, culturing the resultant hybridomas, screening for specific antibody production, and selecting hybridomas which produce the desired antibody.

In one embodiment, the invention provides a method of making antibodies comprising: immunizing an animal with a conjugate comprising a polypeptide of any one of the amino acid sequences of SEQ ID NOs: 1-24, removing said animal's spleen and prepare a single cell suspension, fusing a spleen cell with a myeloma cell, culturing post-fusion cells in hybridoma selection medium, culturing the resultant hybridomas, screening for specific antibody production, and selecting hybridomas which produce the desired antibody. In another embodiment, the invention provides a method of making antibodies comprising: immunizing an animal with a conjugate comprising a polypeptide of FPEDYFRYTNQK (SEQ ID NO: 4) or SLPDDWFRYINY (SEQ ID NO: 5), removing said animal's spleen and prepare a single cell suspension, fusing a spleen cell with a myeloma cell, culturing post-fusion cells in hybridoma selection medium, culturing the resultant hybridomas, screening for specific antibody production, and selecting hybridomas which produce the desired antibody.

BRIEF DESCRIPTION OF THE DRAWINGS

FIG. 2A depicts a scatter plot of NPC-1 antigen detection in cancer patients undergoing treatment at 1 month, 2 months, and 3 months compared to normal controls. Serial blood draws of cancer patients over an approximate 3 month period were tested. The NEO-101 sandwich ELISA was performed at a 7:24 serum dilution. Results are presented as a scatter plot of each experimental group, with the mean and standard error of the mean. There were 28 normal sera, 41 colon/pancreas cancer sera at 1-month, 33 colon/pancreas cancer sera at 2-month, and 25 colon/pancreas cancer sera at 3-month. FIG. 2B depicts a scatter plot showing that colorectal and pancreas cancer sera are detected similarly by NEO-101. Serum specimens were sorted according to patients diagnosed with either colorectal (n=36) or pancreas cancer (n=5). These were compared to the average of all cancer specimens and the normal serum specimens

FIG. 6 depicts the results of peptide sequencing following several rounds of phage library biopanning identified using NEO-101 antibody and 4B6 anti-idiotypic antibody.

FIG. 8A depicts NEO-101 the percent binding inhibition by phage M13 clones. M13 clones were diluted 1:30 and competed with NEO-101-biotin (250 ng/ml) on colon cancer antigen (3 μg/ml) coated plates. In FIG. 8B, Inhibition %=[OD of NEO-101-biotin (250 ng/ml)−OD of NEO-101-biotin (250 ng/ml)+1:30 diluted M13]÷OD of NEO-101-biotin (250 ng/ml).

FIG. 9B is a bar graph depicting NPC-1C beads binding inhibition (%) by cloned phage in beads assay.

FIG. 13 depicts a comparison of the amino acid sequences of the NPC-1 short antigen with the 4-1-3-C9 and 4-1-4-C12 peptides.

DETAILED DESCRIPTION OF THE INVENTION

Figure 1:
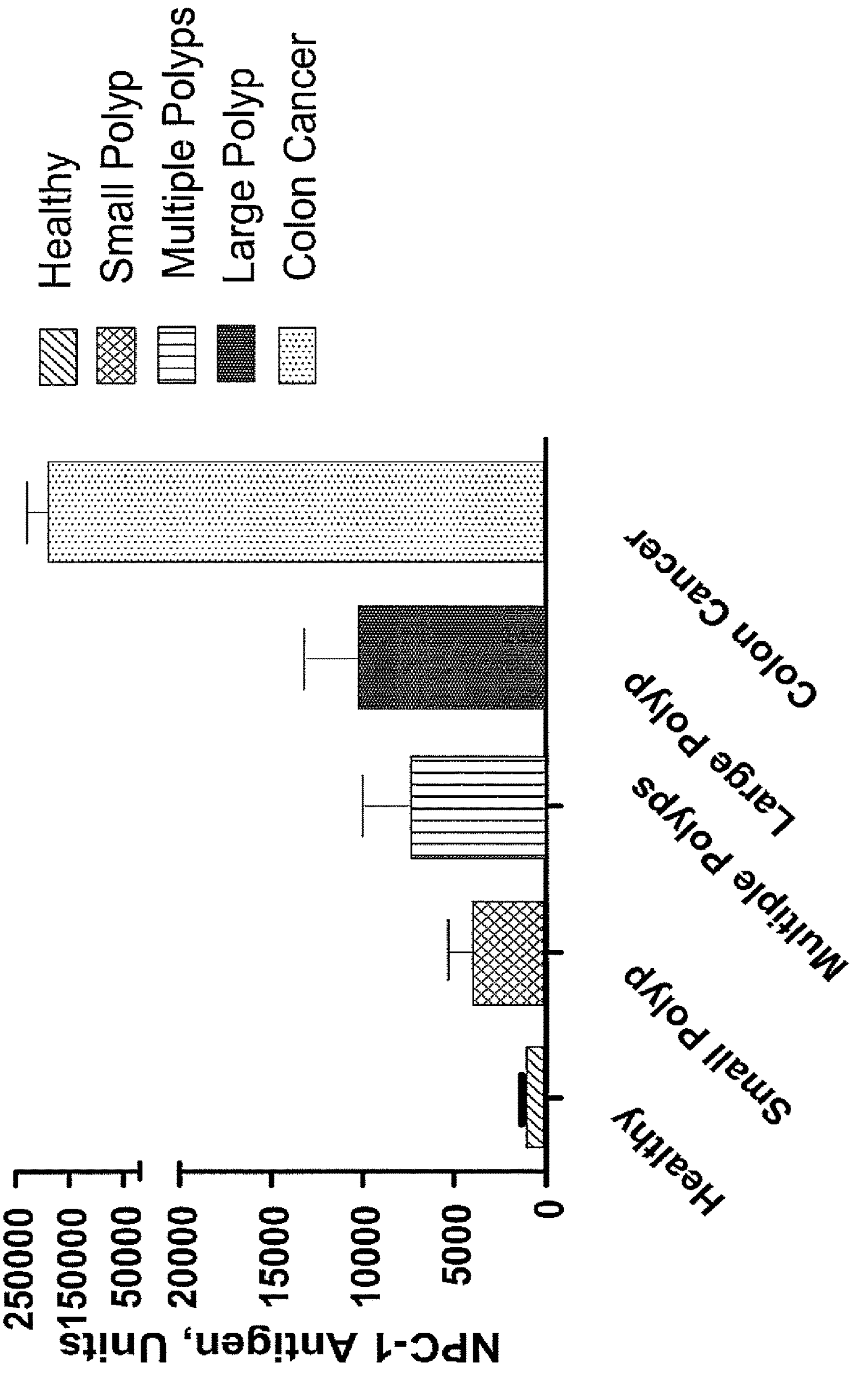
FIG. 1 depicts the results of detecting NPC-1 antigen in stool from patients with a normal colonoscopy result, small polyps (SP), multiple polyps (MP), large polyps (LP), and colon cancer (CC). The results shown in FIG. 1 suggests a correlation between the level of NPC-1 antigen detecting in a stool sample with the presence of polyps and/or colon cancer, where the higher the NPC-1 antigen amount detected is correlated the larger the polyps or the higher the number of polyps. Further, the data is suggestive of the high levels of NPC-1 antigen (e.g., over 20,000 units of NPC-1 antigen in a sample) as indicative of colon cancer.

In order that the invention herein described may be fully understood, the following detailed description is set forth. Various embodiments of the invention are described in detail and may be further illustrated by the provided examples.

Definitions

Unless defined otherwise, all technical and scientific terms used herein have the same meaning as those commonly understood by one of ordinary skill in the art to which this invention belongs. Although methods and materials similar or equivalent to those described herein may be used in the invention or testing of the present invention, suitable methods and materials are described herein. The materials, methods and examples are illustrative only, and are not intended to be limiting.

As used in the description herein and throughout the claims that follow, the meaning of "a," "an," and "the" includes plural reference unless the context clearly dictates otherwise.

"Adjuvant," as used herein, refers broadly to any substance which is incorporated into or administered simultaneously with NPC-1 epitope peptidomimetic of the invention which potentiates the immune response in the subject. Adjuvants include but are not limited to aluminum compounds, e.g., gels, aluminum hydroxide and aluminum phosphate, and Freund's complete or incomplete adjuvant (e.g., in which the PS/A antigen is incorporated in the aqueous phase of a stabilized water in paraffin oil emulsion). The paraffin oil may be replaced with different types of oils, e.g., squalene or peanut oil. Other materials with adjuvant properties. include BCG (attenuated *Mycobacterium tuberculosis*), calcium phosphate, levamisole, isoprinosine, polyanions (e.g., poly A:U), lentinan, pertussis toxin, lipid A, saponins, QS-21 and peptides, e.g. muramyl dipeptide. Rare earth salts, e.g., lanthanum and cerium, may also be used as adjuvants. The amount of adjuvants depends on the subject and the particular antigen used and can be readily determined by one skilled in the art without undue experimentation.

"Amino acid," as used herein, refers broadly to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Antibody," as used herein, refers broadly to any polypeptide chain-containing molecular structure with a specific shape that fits to and recognizes an epitope, where one or more non-covalent binding interactions stabilize the complex between the molecular structure and the epitope. The archetypal antibody molecule is the immunoglobulin, and all types of immunoglobulins, IgG, IgM, IgA, IgE, IgD, from all sources, e.g., human, rodent, rabbit, cow, sheep, pig, dog, chicken, are considered to be "antibodies." Antibodies include but are not limited to chimeric antibodies, human antibodies and other non-human mammalian antibodies, humanized antibodies, single chain antibodies (scFvs), camelbodies, nanobodies, IgNAR (single-chain antibodies derived from sharks), small-modular immunopharmaceuticals (SMIPs), and antibody fragments (e.g., Fabs, Fab', $F(ab')_2$.) Numerous antibody coding sequences have been described; and others may be raised by methods well-known in the art. See Streltsov, et al. (2005) *Protein Sci.* 14(11): 2901-9; Greenberg, et al. (1995) *Nature* 374(6518): 168-173; Nuttall, et al. (2001) *Mol Immunol.* 38(4): 313-26; Hamers-Casterman, et al. (1993) *Nature* 363(6428): 446-8; Gill, et al. (2006) *Curr Opin Biotechnol.* 17(6): 653-8.

"Antigen," as used herein, refers broadly to a molecule or a portion of a molecule capable of being bound by an antibody which is additionally capable of inducing an animal to produce an antibody capable of binding to an epitope of that antigen. An antigen may have one epitope, or have more than one epitope. The specific reaction referred to herein indicates that the antigen will react, in a highly selective manner, with its corresponding antibody and not with the multitude of other antibodies which may be evoked by other antigens. Antigens may be tumor specific (e.g., expressed by neoplastic cells of pancreatic and colon carcinoma.)

"Antigenic composition," as used herein, refers broadly to a composition that elicits an immune response.

"Cancer," as used herein, refers broadly to any neoplastic disease (whether invasive or metastatic) characterized by abnormal and uncontrolled cell division causing malignant growth or tumor.

"Chimeric antibody," as used herein, refers broadly to an antibody molecule in which the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug; or the variable region, or a portion thereof, is altered, replaced or exchanged with a variable region having a different or altered antigen specificity.

"Conservatively modified variants," as used herein, applies to both amino acid and nucleic acid sequences, and with respect to particular nucleic acid sequences, refers broadly to conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) may be modified to yield a functionally identical molecule.

"Complementarity determining region," "hypervariable region," or "CDR," as used herein, refers broadly to one or more of the hyper-variable or complementarily determining regions (CDRs) found in the variable regions of light or heavy chains of an antibody. See Kabat, et al. (1987) "*Sequences of Proteins of Immunological Interest*" National Institutes of Health, Bethesda, Md. These expressions include the hypervariable regions as defined by Kabat, et al. (1983) "*Sequences of Proteins of Immunological Interest*" U.S. Dept. of Health and Human Services or the hypervariable loops in 3-dimensional structures of antibodies. Chothia and Lesk (1987) *J Mol. Biol.* 196: 901-917. The CDRs in each chain are held in close proximity by framework regions and, with the CDRs from the other chain, contribute to the formation of the antigen binding site. Within the CDRs there are select amino acids that have been described as the selectivity determining regions (SDRs) which represent the critical contact residues used by the CDR in the antibody-antigen interaction. Kashmiri (2005) *Methods* 36: 25-34.

"Control amount," as used herein, refers broadly to a marker can be any amount or a range of amounts to be compared against a test amount of a marker. For example, a control amount of a marker may be the amount of a marker in a patient with a particular disease or condition or a person without such a disease or condition. A control amount can be either in absolute amount (e.g., microgram/ml) or a relative amount (e.g., relative intensity of signals).

"Differentially present," as used herein, refers broadly to differences in the quantity or quality of a marker present in a sample taken from patients having a disease or condition as compared to a comparable sample taken from patients who do not have one of the diseases or conditions. For example, a nucleic acid fragment may optionally be differentially present between the two samples if the amount of the nucleic acid fragment in one sample is significantly different from the amount of the nucleic acid fragment in the other sample, for example as measured by hybridization and/or NAT-based assays. A polypeptide is differentially present between the two samples if the amount of the polypeptide in one sample is significantly different from the amount of the polypeptide in the other sample. It should be noted that if the marker is detectable in one sample and not detectable in the other, then such a marker may be considered to be differentially present. Optionally, a relatively low amount of up-regulation may serve as the marker.

"Diagnostic," as used herein, refers broadly to identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

"Diagnosing," as used herein, refers broadly to classifying a disease or a symptom, determining a severity of the disease, monitoring disease progression, forecasting an outcome of a disease and/or prospects of recovery. The term "detecting" may also optionally encompass any of the foregoing. Diagnosis of a disease according to the present invention may, in some embodiments, be affected by determining a level of a polynucleotide or a polypeptide of the present invention in a biological sample obtained from the subject, wherein the level determined can be correlated with predisposition to, or presence or absence of the disease. It should be noted that a "biological sample obtained from the subject" may also optionally comprise a sample that has not been physically removed from the subject.

"Effective amount," as used herein, refers broadly to the amount of a compound, antibody, antigen, or cells that, when administered to a patient for treating a disease, is sufficient to effect such treatment for the disease. The effective amount may be an amount effective for prophylaxis, and/or an amount effective for prevention. The effective amount may be an amount effective to reduce, an amount effective to prevent the incidence of signs/symptoms, to reduce the severity of the incidence of signs/symptoms, to eliminate the incidence of signs/symptoms, to slow the development of the incidence of signs/symptoms, to prevent the development of the incidence of signs/symptoms, and/or effect prophylaxis of the incidence of signs/symptoms. The "effective amount" may vary depending on the disease and its severity and the age, weight, medical history, susceptibility, and pre-existing conditions, of the patient to be treated. The term "effective amount" is synonymous with "therapeutically effective amount" for purposes of this invention.

"Expression vector," as used herein, refers broadly to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression cassettes which contain only the minimum elements needed for transcription of the recombinant nucleic acid.

"Framework region" or "FR," as used herein, refers broadly to one or more of the framework regions within the variable regions of the light and heavy chains of an antibody. See Kabat, et al. (1987) "*Sequences of Proteins of Immunological Interest*," National Institutes of Health, Bethesda, Md. These expressions include those amino acid sequence regions interposed between the CDRs within the variable regions of the light and heavy chains of an antibody.

"Heterologous," as used herein, refers broadly to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

"High affinity," as used herein, refers broadly to an antibody having a KD of at least $10^{-8}$ M, more preferably at least $10^{-9}$ M and even more preferably at least $10^{-10}$ M for a target antigen. However, "high affinity" binding can vary for other antibody isotypes. For example, "high affinity" binding for an IgM isotype refers to an antibody having a KD of at least $10^{-7}$ M, more preferably at least $10^{-8}$ M.

"Homology," as used herein, refers broadly to a degree of similarity between a nucleic acid sequence and a reference nucleic acid sequence or between a polypeptide sequence and a reference polypeptide sequence. Homology may be partial or complete. Complete homology indicates that the nucleic acid or amino acid sequences are identical. A partially homologous nucleic acid or amino acid sequence is one that is not identical to the reference nucleic acid or amino acid sequence. The degree of homology can be determined by sequence comparison. The term "sequence identity" may be used interchangeably with "homology."

"Host cell," as used herein, refers broadly to a cell that contains an expression vector and supports the replication or expression of the expression vector. Host cells may be prokaryotic cells such as *E. coli*, or eukaryotic cells such as yeast, insect (e.g., SF9), amphibian, or mammalian cells such as CHO, HeLa, HEK-293, e.g., cultured cells, explants, and cells in vivo.

"Hybridization," as used herein, refers broadly to the physical interaction of complementary (including partially complementary) polynucleotide strands by the formation of hydrogen bonds between complementary nucleotides when the strands are arranged antiparallel to each other.

"K-assoc" or "Ka", as used herein, refers broadly to the association rate of a particular antibody-antigen interaction, whereas the term "Kdiss" or "Kd," as used herein, refers to the dissociation rate of a particular antibody-antigen interaction. The term "KD", as used herein, is intended to refer to the dissociation constant, which is obtained from the ratio of Kd to Ka (i.e., Kd/Ka) and is expressed as a molar concentration (M). KD values for antibodies can be determined using methods well established in the art.

"Immunoassay," as used herein, refers broadly to an assay that uses an antibody to specifically bind an antigen. The immunoassay may be characterized by the use of specific binding properties of a particular antibody to isolate, target, and/or quantify the antigen.

"Isolated," as used herein, refers broadly to material removed from its original environment in which it naturally occurs, and thus is altered by the hand of man from its natural environment. Isolated material may be, for example, exogenous nucleic acid included in a vector system, exogenous nucleic acid contained within a host cell, or any material which has been removed from its original environment and thus altered by the hand of man (e.g., "isolated antibody or isolated peptidomimetic").

"Label" or a "detectable moiety" as used herein, refers broadly to a composition detectable by spectroscopic, photochemical, biochemical, immunochemical, chemical, or other physical means.

"Low stringency," "medium stringency," "high stringency," or "very high stringency conditions," as used herein, refers broadly to conditions for nucleic acid hybridization and washing. Guidance for performing hybridization reactions can be found in Ausubel, et al. (2002) *Short Protocols in Molecular Biology* ($5^{th}$ Ed.) John Wiley & Sons, NY. Exemplary specific hybridization conditions include but are not limited to: (1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60° C.; (3) high stringency hybridization conditions in 6×SSC at about 45° C., followed by one or more washes in 0.2×SSC, 0.1% SDS at 65° C.; and (4) very high stringency hybridization conditions are 0.5M sodium phosphate, 7% SDS at 65° C., followed by one or more washes at 0.2×SSC, 1% SDS at 65° C.

"Mammal," as used herein, refers broadly to any and all warm-blooded vertebrate animals of the class Mammalia, including humans, characterized by a covering of hair on the skin and, in the female, milk-producing mammary glands for nourishing the young. Examples of mammals include but are not limited to alpacas, armadillos, capybaras, cats, camels, chimpanzees, chinchillas, cattle, dogs, gerbils, goats, gorillas, hamsters, horses, humans, lemurs, llamas, mice, non-human primates, pigs, rats, sheep, shrews, squirrels, and tapirs. Mammals include but are not limited to bovine, canine, equine, feline, murine, ovine, porcine, primate, and rodent species. Mammal also includes any and all those listed on the Mammal Species of the World maintained by the National Museum of Natural History, Smithsonian Institution in Washington D.C.

"Nucleic acid" or "nucleic acid sequence," as used herein, refers broadly to a deoxy-ribonucleotide or ribonucleotide oligonucleotide in either single- or double-stranded form. The term encompasses nucleic acids, i.e., oligonucleotides, containing known analogs of natural nucleotides. The term also encompasses nucleic-acid-like structures with synthetic backbones. Unless otherwise indicated, a particular nucleic acid sequence also implicitly encompasses conservatively modified variants thereof (e.g., degenerate codon substitutions) and complementary sequences, as well as the sequence explicitly indicated. The term nucleic acid is used interchangeably with gene, cDNA, mRNA, oligonucleotide, and polynucleotide.

"Operatively linked", as used herein, refers broadly to when two DNA fragments are joined such that the amino acid sequences encoded by the two DNA fragments remain in-frame.

"Paratope," as used herein, refers broadly to the part of an antibody which recognizes an antigen (e.g., the antigen-binding site of an antibody.) Paratopes may be a small region (e.g., 15-22 amino acids) of the antibody's Fv region and may contain parts of the antibody's heavy and light chains. See Goldsby, et al. *Antigens* (*Chapter* 3) Immunology ($5^{th}$ Ed.) New York: W.H. Freeman and Company, pages 57-75.

"Patient," as used herein, refers broadly to any animal who is in need of treatment either to alleviate a disease state or to prevent the occurrence or reoccurrence of a disease state. Also, "Patient" as used herein, refers broadly to any animal who has risk factors, a history of disease, susceptibility, symptoms, signs, was previously diagnosed, is at risk for, or is a member of a patient population for a disease. The patient may be a clinical patient such as a human or a veterinary patient such as a companion, domesticated, livestock, exotic, or zoo animal. The term "subject" may be used interchangeably with the term "patient".

"Peptidomimetic," as used herein refers broadly to a compound that can imitate or block the biological effect of a peptide on a molecular level. Peptidomimetics may be polymers designed to mimic a peptide, such as peptoids and β-peptides, or may be a peptide that mimics a different peptide.

"Polypeptide," "peptide" and "protein," are used interchangeably and refer broadly to a polymer of amino acid residues. The terms apply to amino acid polymers in which one or more amino acid residue is an analog or mimetic of a corresponding naturally occurring amino acid, as well as to naturally occurring amino acid polymers. The terms apply to amino acid polymers in which one or more amino acid residue is an artificial chemical mimetic of a corresponding naturally occurring amino acid, as well as to naturally occurring amino acid polymers and non-naturally occurring amino acid polymer. Polypeptides can be modified, e.g., by the addition of carbohydrate residues to form glycoproteins. The terms "polypeptide," "peptide" and "protein" include glycoproteins, as well as non-glycoproteins.

"Promoter," as used herein, refers broadly to an array of nucleic acid sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation.

"Prophylactically effective amount," as used herein, refers broadly to the amount of a compound that, when administered to a patient for prophylaxis of a disease or prevention of the reoccurrence of a disease, is sufficient to effect such prophylaxis for the disease or reoccurrence. The prophylactically effective amount may be an amount effective to prevent the incidence of signs and/or symptoms. The "prophylactically effective amount" may vary depending on the disease and its severity and the age, weight, medical history, predisposition to conditions, preexisting conditions, of the patient to be treated.

"Prophylaxis," as used herein, refers broadly to a course of therapy where signs and/or symptoms are not present in the patient, are in remission, or were previously present in a patient. Prophylaxis includes preventing disease occurring subsequent to treatment of a disease in a patient. Further, prevention includes treating patients who may potentially develop the disease, especially patients who are susceptible to the disease (e.g., members of a patent population, those with risk factors, or at risk for developing the disease).

"Recombinant" as used herein, refers broadly with reference to a product, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

"Specifically (or selectively) binds" to an antibody or "specifically (or selectively) immunoreactive with," or "specifically interacts or binds," as used herein, refers broadly to a protein or peptide (or other epitope), refers, in some embodiments, to a binding reaction that is determinative of the presence of the protein in a heterogeneous population of proteins and other biologics. For example, under designated immunoassay conditions, the specified antibodies bind to a particular protein at least two times greater than the background (non-specific signal) and do not substantially bind in a significant amount to other proteins present in the sample. Typically a specific or selective reaction will be at least twice background signal or noise and more typically more than about 10 to 100 times background.

"Specifically hybridizable" and "complementary" as used herein, refer broadly to a nucleic acid can form hydrogen bond(s) with another nucleic acid sequence by either traditional Watson-Crick or other non-traditional types. The binding free energy for a nucleic acid molecule with its complementary sequence is sufficient to allow the relevant function of the nucleic acid to proceed, e.g., RNAi activity. Determination of binding free energies for nucleic acid molecules is well known in the art. See, e.g., Turner, et al. (1987) *CSH Symp. Quant. Biol.* LII: 123-33; Frier, et al. (1986) *PNAS* 83: 9373-77; Turner, et al. (1987) *J. Am. Chem. Soc.* 109: 3783-85. A percent complementarity indicates the percentage of contiguous residues in a nucleic acid molecule that can form hydrogen bonds (e.g., Watson-Crick base pairing) with a second nucleic acid sequence (e.g., about at least 5, 6, 7, 8, 9, 10 out of 10 being about at least 50%, 60%, 70%, 80%, 90%, and 100% complementary, inclusive). "Perfectly complementary" or 100% complementarity refers broadly all of the contiguous residues of a nucleic acid sequence hydrogen bonding with the same number of contiguous residues in a second nucleic acid sequence. "Substantial complementarity" refers to polynucleotide strands exhibiting about at least 90% complementarity, excluding regions of the polynucleotide strands, such as overhangs, that are selected so as to be noncomplementary. Specific binding requires a sufficient degree of complementarity to avoid non-specific binding of the oligomeric compound to non-target sequences under conditions in which specific binding is desired, i.e., under physiological conditions in the case of in viva assays or therapeutic treatment, or in the case of in vitro assays, under conditions in which the assays are performed. The non-target sequences typically may differ by at least 5 nucleotides.

"Signs" of disease, as used herein, refers broadly to any abnormality indicative of disease, discoverable on examination of the patient; an objective indication of disease, in contrast to a symptom, which is a subjective indication of disease.

"Solid support," "support," and "substrate," as used herein, refers broadly to any material that provides a solid or semi-solid structure with which another material can be attached including but not limited to smooth supports (e.g., metal, glass, plastic, silicon, and ceramic surfaces) as well as textured and porous materials.

"Subjects" as used herein, refers broadly to anyone suitable to be treated according to the present invention include, but are not limited to, avian and mammalian subjects, and are preferably mammalian. Mammals of the present invention include, but are not limited to, canines, felines, bovines, caprines, equines, ovines, porcincs, rodents (e.g., rats and mice), lagomorphs, primates, humans. Any mammalian subject in need of being treated according to the present invention is suitable. Human subjects of both genders and at any stage of development (i.e., neonate, infant, juvenile, adolescent, adult) can be treated according to the present invention. The present invention may also be carried out on animal subjects, particularly mammalian subjects such as mice, rats, dogs, cats, cattle, goats, sheep, and horses for veterinary purposes, and for drug screening and drug development purposes. "Subjects" is used interchangeably with "patients."

"Symptoms" of disease as used herein, refers broadly to any morbid phenomenon or departure from the normal in structure, function, or sensation, experienced by the patient and indicative of disease.

"Therapy," "therapeutic," "treating," or "treatment", as used herein, refers broadly to treating a disease, arresting, or reducing the development of the disease or its clinical symptoms, and/or relieving the disease, causing regression of the disease or its clinical symptoms. Therapy encompasses prophylaxis, treatment, remedy, reduction, alleviation, and/or providing relief from a disease, signs, and/or symptoms of a disease. Therapy encompasses an alleviation of signs and/or symptoms in patients with ongoing disease signs and/or symptoms (e.g., tumor growth, metastasis). Therapy also encompasses "prophylaxis". The term "reduced", for purpose of therapy, refers broadly to the clinical significant reduction in signs and/or symptoms. Therapy includes treating relapses or recurrent signs and/or symptoms (e.g., tumor growth, metastasis). Therapy encompasses but is not limited to precluding the appearance of signs and/or symptoms anytime as well as reducing existing signs and/or symptoms and eliminating existing signs and/or symptoms. Therapy includes treating chronic disease ("maintenance") and acute disease. For example, treatment includes treating or preventing relapses or the recurrence of signs and/or symptoms (e.g., tumor growth, metastasis).

"Variable region" or "VR," as used herein, refers broadly to the domains within each pair of light and heavy chains in an antibody that are involved directly in binding the antibody to the antigen. Each heavy chain has at one end a variable domain ($V_H$) followed by a number of constant domains. Each light chain has a variable domain ($V_L$) at one end and a constant domain at its other end; the constant domain of the light chain is aligned with the first constant domain of the heavy chain, and the light chain variable domain is aligned with the variable domain of the heavy chain.

"Vector," as used herein, refers broadly to a plasmid, cosmid, phagemid, phage DNA, or other DNA molecule which is able to replicate autonomously in a host cell, and which is characterized by one or a small number of restriction endonuclease recognition sites at which such DNA sequences may be cut in a determinable fashion without loss of an essential biological function of the vector, and into which DNA may be inserted in order to bring about its replication and cloning. The vector may further contain a marker suitable for use in the identification of cells transformed with the vector.

The techniques and procedures are generally performed according to conventional methods well known in the art and as described in various general and more specific references that are cited and discussed throughout the present specification. See, e.g., Sambrook, et al. (2001) *Molec. Cloning: Lab. Manual* [$3^{rd}$ Ed] Cold Spring Harbor Laboratory Press. Standard techniques may be used for recombinant DNA, oligonucleotide synthesis, and tissue culture, and transformation (e.g., electroporation, lipofection). Enzymatic reactions and purification techniques may be performed according to manufacturer's specifications or as commonly accomplished in the art or as described herein. The nomenclatures utilized in connection with, and the laboratory procedures and techniques of, analytical chemistry, synthetic organic chemistry, and medicinal and pharmaceutical chemistry described herein are those well known and commonly used in the art. Standard techniques may be used for chemical syntheses, chemical analyses, pharmaceutical preparation, formulation, and delivery, and treatment of patients.

Tumor Specific Variants of MUC5AC Comprise a NPC-1 Epitope

The present invention describes peptidomimetics of cancer-specific epitopes on MUC5AC which are specifically bound by NEO-100 series antibodies described in International Patent Application No. PCT/US2011/41502 (e.g., NEO-101, NEO-102, NEO-103). The peptidomimetics described herein, $SX^1PX^2DX^3FRYX^4NX^5$ (SEQ ID NO: 1), wherein $X^1$ is for L; $X^2$ is E or D; $X^3$ is Y or W; $X^4$ is T or I and $X^5$ is Q or Y; $SX^1PX^2DX^3FRYX^4NX^5K$ (SEQ ID NO: 2), wherein $X^1$ is for L; $X^2$ is B or D; $X^3$ is Y or W; $X^4$ is T or I and $X^5$ is Q or Y and $SLEPEX^1DWX^2FRYX^3NY$ (SEQ ID NO: 3), wherein $X^1$ is E or D; $X^2$ is W or Y; and $X^3$ is T or I; and the peptidomimetics described in the amino acid sequences of SEQ ID NOs: 4-24, mimic epitopes expressed by tumor-specific variants of a MUC5AC antigen, including glycosylation variants. These peptidomimetics may be used in methods for treating and detecting cancer as well as the production of tumor-specific antibodies.

Tumor-Specific Variant Form of MUC5AC

A glycosylation variant of MUC5AC is expressed by tumor cells. This glycosylation variant may be due to a defect in transferases or other enzymes involved in glycosylation. MUC5AC isolated from CFPAC-1 supernate (pancreatic cancer cell line CFPAC-1) was digested with thermolysin and these fragments (e.g., SEQ ID NOs: 27-33) are bound by a NEO-101 antibody. This lead to the discovery of the NPC-1 epitope, as disclosed in International Patent Application No. PCT/US2011/41502, which is a tumor-specific glycotype within the tandem repeat region of MUC5AC. This analysis produced a 15 residue stretch TTSTTSAPTTSTTSAP (SEQ ID NO: 34) that overlaps 100% with the peptides generated from the thermolysin digestion of MUC5AC construct. This region is enriched in Proline-Threonine-Serine and may act as a scaffold for aberrant carbohydrate epitope recognized by a NEO-100 antibody (e.g., NEO-101, NEO-102, NEO-103). This was corroborated by deletion studies of MUC5AC that suggests the peptide stretch of GCPVTSTPVTAPSTP (SEQ ID NO: 35) binds to a NEO-100 antibody (e.g., NEO-101, NEO-102, NEO-103). This region is believed to act as a scaffold for aberrant glycosylation in tumor cells, forming an aberrant glycoprotein pattern that is recognized by a NEO-100 antibody. The NPC-1 epitope is also sensitive to neuramididase treatment but not to other enzymes (e.g., β-Glucosaminidase, O-Glycosidase, PNGase F, Neuraminidase (α2→3), β (1→4) galactosidase).

Using peptide phage display, synthetic epitopes that act as peptidomimetics of the NPC-1 glycotope were identified: $SX^1PX^2DX^3FRYX^4NX^5$ (SEQ ID NO: 1), wherein $X^1$ is for L; $X^2$ is E or D; $X^3$ is Y or W; $X^4$ is T or I and $X^5$ is Q or Y; $SX^1PX^2DX^3FRYX^4NX^5K$ (SEQ ID NO: 2), wherein $X^1$ is for L; $X^2$ is E or D; $X^3$ is Y or W; $X^4$ is T or I and $X^5$ is Q or Y and $SLEPEX^1DWX^2FRYX^3NY$ (SEQ ID NO: 3), wherein $X^1$ is E or D; $X^2$ is W or Y; and $X^3$ is T or I; and the peptidomimetics described in the amino acid sequences of SEQ ID NOs: 4-24. There is no significant homology between peptide sequences and MUC5AC sequence, which suggest the peptides comprises NPC-1 epitope peptidomimetics. Such a peptidomimetics are likely to be a glycomimetic of the aberrant glycosylation expressed by tumor cells but not by normal colon or pancreas tissues. This may be useful as a tag in diagnostic assays or a control peptide to measure NEO-101 antibody binding. Further, the NPC-1 epitope peptidomimetics may be used in diagnostic or therapeutic methods for colon, pancreas, stomach, ovarian, lung, breast, or esophagus cancer.

As described in International Patent Application No. PCT/US2011/41502, glycosylation variants of MUC5AC correlate with tumor cells and have characterized tumor-specific MUC5AC antigens (e.g., epitopes or antigenic determinants) that may be used in therapeutic and diagnostic methods (e.g., treatment of cancer involving tumor-specific MUC5AC antigens and the detection of tumor-specific MUC5AC variant antigens.) The immunohistochemistry studies demonstrate that NPC-1 epitope may be useful as a tissue biomarker of colon, pancreas, stomach, ovarian, lung, breast, or esophagus cancer presence and progression. For example, antibodies targeting the NPC-1 epitope may inhibit tumor progression. Also, NPC-1 epitope levels detected in sera appear to increase as cancer progresses, thus NPC-1 may be used as a non-invasive diagnostic marker for colon, pancreas, stomach, ovarian, lung, breast, or esophagus cancer. Thus the NPC-1 epitope peptidomimetic described herein may be used as both a diagnostic and therapeutic target specific for colon, pancreas, stomach, ovarian, lung, breast, or esophagus cancer.

NEO-1 Monoclonal Antibody

As described in International Patent Application No. PCT/US2011/41502, NEO-100 antibodies (e.g., NEO-101, NEO-102, NEO-103) bind to tumor cells and initiates antibody-dependent cell-mediated cytotoxicity (ADCC) in this cell and/or inhibits cell proliferation. For example, a NEO-101 antibody was produced by means of the hybridoma technique, cloned, chimerized with human constant regions, and also fully humanized. The inventors surprisingly discovered that the NPC-1 epitope is contained within the tandem repeat (TR) regions of the MUC5AC glycoprotein and that a NEO-100 antibody recognizes an apparently aberrantly glycosylated form of MUC5AC expressed by tumor cells. This is in contrast with other anti-MUC5AC antibodies (e.g., 1-13M1, SOMU1, 463M) which predominantly bind near the N-terminus or C-terminus region and not a glycotope in the tandem repeat regions. See Table 1. Further, the NPC-1 epitope is sensitive to glycolytic enzymes and thus, suggests that it is a glycotope. Additionally, none of the commercially available antibodies against MUC5AC which were tested by the inventors were found to cross-react with binding by NPC-1. Using these antibodies, the inventors isolated a peptidomimetic that binds the NEO-101 antibody but does not share any significant homology with the NPC-1 epitope.

TABLE 1

| Antibody clone | Source | Binding site | Compete with NEO-1 antibody? |
|---|---|---|---|
| 45M1 | Abcam Inc. | Uncharacterized | No |
| H00004586 | Abnova Inc. | Last 100 residues at carboxyl terminal | No |
| CLH-2 | Millipore Inc. | Tandem repeat | No |
| 2-11M1 | Abcam Inc. | Amino terminal | No |
| 9-13M1 | Abcam Inc. | Amino terminal | No |
| 1-13M1 | Abcam Inc. | TSP-1 Cys-2 region | No |
| 2-12M1 | Abcam Inc. | Carboxyl terminal region | No |
| Polyclonal rabbit (H-160) | Santa Cruz Biotechnology Inc. | residues 1214-1373 | No |

Tumor cell binding activity of NEO-101 was performed by flow cytometry using colorectal and pancreatic tumor cell lines. As shown in Table 2, the NEO-101 antibody reacted with a sampling of human colorectal and pancreatic tumor cell lines. An isotype control antibody did not react with the colorectal and pancreatic tumor cells, demonstrating the antigen-specific reactivity of NEO-101 with these colorectal and pancreatic tumor cell lines. See International Patent Application No. PCT/US2011/41502.

TABLE 2

Flow cytometry: Tumor Cell Binding by NEO-101

| | % Cells Stained (mfi) | |
|---|---|---|
| Tumor Cell Line | Isotype Control | NEO-101 |
| LS174T Colorectal | 3.85 (35) | 89.72 (103) |
| Colo-205 Colorectal | 2.33 (34) | 94.67 (175) |
| SW480 Colorectal | 3.38 (56) | 58.98 (118) |
| CFPAC-1 Pancreatic | 1.79 (25) | 52.56 (59) |

Table 3 shows that 43% of colon cancers and 48% of pancreas cancers stained positively with the NEO-101 antibody. It was observed that only one of four normal colon samples showed moderate positivity with NEO-101. Furthermore, in certain instances where normal colon tissue stained positively with NEO-101, the tissue was found to have been surgically removed from regions adjacent to colon cancer. Consequently, the positively stained "normal" tissues may have already undergone genotypic changes ("pre-cancerous") resulting in the expression of the aberrantly glycosylated MUC5AC antigen that could lead to detection of carcinoma with NEO-101.

TABLE 3

| Immunohistochemistry: Human Tissues With Biotinylated NEO-101 | | | | | | | |
|---|---|---|---|---|---|---|---|
| Human tissue sample | Tissue staining intensity | | | | | | |
| (source) | Negative | Weak | +1 | +2 | +3 | +4 | Total Positive |
| Colon cancer | 27/48 (56%) | 5/48 (10%) | 7/48 (15%) | 4/48 (8%) | | 5/48 (10%) | 21/48 (43%) |
| Normal colon | 3/4 (75%) | | | 1/4 (25%) | | | 1/4 (25%) |
| Pancreas cancer | 56/108 (52%) | | 17/108 (16%) | 7/108 (6%) | 18/108 (17%) | 10/108 (9%) | 52/108 (48%) |
| Normal pancreas | 3/3 (100%) | | | | | | 0/3 (0%) |
| Uterus cancer | 32/42 (76%) | | | 2/42 (5%) | 8/42 (19%) | | 10/42 (24%) |
| Normal uterus | 12/12 (100%) | | | | | | 0/12 (0%) |
| Prostate cancer | 30/40 (15%) | | 5/40 (12%) | 5/40 (12%) | | | 10/40 (25%) |
| Normal prostate | 4/4 (100%) | | | | | | 0/4 (0%) |

Staining with a human IgG1 isotype control antibody showed no reactivity against the same tissues. Immunohistochemical studies demonstrate NEO-101 tissue staining in pancreatic adenocarcinoma tissue, and lack of staining in normal pancreas tissue.

In summary, antibody-staining results with NEO-101 demonstrated specific immunoreactivity with cancer tissues from colon and pancreas patients, whereas only weak binding, if at all, was observed in normal pancreas or colon tissues. Furthermore, no cross-reactivity was observed in other normal human tissues stained, indicating a strong positive correlation of the NEO-101 binding to colon and pancreas cancer tissues. Thus, the NPC-1 epitope is expressed by colon and pancreatic tumor cells but not normal colon or pancreatic tumor cells. Therefore, the NPC-1 epitope may be used as a tumor-specific marker or a therapeutic target for colon and pancreatic cancer. Further, peptidomimetics of the NPC-1 epitope (e.g., the polypeptide of SEQ ID NO: 1-24) as described herein may be used in the detection and treatment of cancer (e.g., colon, pancreas, breast, lung, ovarian, stomach, esophageal).

NPC-1 Epitope Peptidomimetics

The invention provides NPC-1 epitope peptidomimetics. The inventors surprisingly discovered that MUC5AC comprises at least one NPC-1 epitope. Exemplary polypeptides comprising at least one NPC-1 epitope are provided in GCPVTSTPVTAPSTP (SEQ ID NO: 35). The peptidomimetics of the NPC-1 epitope may comprise the following sequences: $SX^1PX^2DX^3FRYX^4NX^5$ (SEQ ID NO: 1), wherein $X^1$ is for L; $X^2$ is E or D; $X^3$ is Y or W; $X^4$ is T or I and $X^5$ is Q or Y; $SX^1PX^2DX^3FRYX^4NX^5K$ (SEQ ID NO: 2), wherein $X^1$ is for L; $X^2$ is E or D; $X^3$ is Y or W; $X^4$ is T or I and $X^5$ is Q or Y and $SLEPEX^1DWX^2FRYX^3NY$ (SEQ ID NO: 3), wherein $X^1$ is E or D; $X^2$ is W or Y; and $X^3$ is T or I; FPEDYFRYTNQK (SEQ ID NO: 4); SLPDDWFRYINY (SEQ ID NO: 5); and the peptidomimetics described in the amino acid sequences of SEQ ID NOs: 6-24.

Nucleic acids encoding polypeptides comprising at least one NPC-1 epitope peptidomimetic may be modified using standard molecular biological techniques that result in variants polypeptides comprising at least one NPC-1 epitope including but not limited to deletions, additions and substitutions in the amino acid sequence, that retain the specific antigenicity of the NPC-1 epitope (e.g., the NPC-1 epitope is bound by the NEO-1 antibody). Additionally, variant polypeptides comprising at least one NPC-1 epitope may also retain the antigenicity of a NPC-1 epitope (e.g., raise a specific immune response against the NPC-1 epitopes, respectively, upon immunization in a subject). The NPC-1 epitope peptidomimetics may be formulated with a pharmaceutical carrier to manufacture an antigen composition useful as a "cancer vaccine" (e.g., a pharmaceutical composition that elicits a specific immune response against the NPC-1 epitope, that produces anti-tumor antibodies after immunization in a subject). For example, a cancer vaccine may comprise a composition comprising a polypeptide comprising an amino acid sequence of any one of SEQ ID NOs: 1-24, or combinations thereof. A cancer vaccine may comprise a composition comprising a polypeptide comprising an amino acid sequence of any one of SEQ ID NO: 4 or 5 and an adjuvant or pharmaceutical carrier. Also, a cancer vaccine may comprise a composition comprising a polypeptide comprising an amino acid sequence of any one of SEQ ID NO: 4 or 5 conjugate to a carrier such as KLH. The NPC-1 epitope peptidomimetic may be a small peptide. Further, the peptide structure of the peptidomimetic may have an altered chemical structure is designed to improve stability or biological activity. Such modifications include altered backbones and the incorporation of nonnatural amino acids.

Polypeptide Derivatives and Analogs

It will be appreciated that the NPC-1 epitope peptidomimetics described herein may be polypeptides, degradation products, synthetic peptides, or recombinant peptides as well as peptidomimetics, synthetic peptides, peptoids, and semipeptoids (e.g., peptide analogs, which may have, for example, modifications rendering the peptides more stable while in a body or more capable of penetrating into cells.) Modifications of the NPC-1 epitope peptidomimetics described herein include, but are not limited to N-terminus modification, C-terminus modification, peptide bond modification (e.g., $CH_2$—NH, $CH_2$—S═O, O═C—NH, $CH_2$—O, $CH_2$—$CH_2$, S═C—NH, CH═CH or CF═CH), backbone modifications, and residue modification. Methods for preparing peptidomimetic compounds are well known in the art. Martin (2010) *Quantitative Drug Design: A Critical Introduction* [$2^{nd}$ Ed.] CRC Press.

Peptide bonds (—CO—NH—) within the peptide may be substituted, for example, by N-methylated bonds (—N($CH_3$)—CO—), ester bonds (—C(R)H—C—O—O—C (R)—N—), ketomethylen bonds (—CO—CH2-), α-aza bonds (—NH—N(R)—CO—), wherein R is any alkyl, e.g., methyl, carba bonds (—$CH_2$—NH—), hydroxyethylene bonds (—CH(OH)—$CH_2$—), thioamide bonds (—CS—NH—), olefinic double bonds (—CH═CH—), retro amide bonds (—NH—CO—), peptide derivatives (—N(R)—$CH_2$—CO—), wherein R is the "normal" side chain, naturally presented on the carbon atom. These modifications can occur at any of the bonds along the peptide chain and even at several (2-3) at the same time.

Natural aromatic amino acids, Trp, Tyr and Phe, may be substituted by synthetic non-natural acid such as phenylglycine, TIC, naphthylelanine (Nol), ring-methylated derivatives of phenylalanine, halogenated derivatives of phenylalanine or o-methyl-tyrosine. In addition to the above, the polypeptides of the present invention may also include one or more modified amino acids or one or more non-amino acid monomers (e.g. fatty acids, complex carbohydrates), for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Since the polypeptides of the present invention are preferably utilized in therapeutics which requires the peptides to be in soluble form, the polypeptides of the present invention may comprise one or more non-natural or natural polar amino acids, including but not limited to serine and threonine which are capable of increasing peptide solubility due to their hydroxyl-containing side chain.

The NPC-1 epitope peptidomimetics of the present invention may be in a linear form, although it will be appreciated that circular forms may also be utilized.

The NPC-1 epitope peptidomimetics described herein may be purified from cells that have been altered to express it (e.g., recombinant). DNA sequences encoding the NPC-1 epitope peptidomimetics may be inserted into an expression vector and then transformed (or transfected) in an appropriate host cell and/or expressed in a transgenic animal. The NPC-1 epitope peptidomimetics so expressed may then be isolated by methods known in the art. See, e.g., Maniatis, et al. (2001) *Molecular Cloning: A Laboratory Manual* [$3^{rd}$ Ed.] Cold Spring Harbor Laboratory Press.

The NPC-1 epitope peptidomimetics of the present invention may be biochemically synthesized such as by using standard solid phase techniques. These methods include exclusive solid phase synthesis, partial solid phase synthesis methods, fragment condensation, classical solution synthesis. Solid phase peptide synthesis procedures are well known in the art and further described by Stewart (1984) *Solid Phase Peptide Syntheses* [$2^{nd}$ Ed.] Pierce Chemical Company and Benoiton (2005) *Chemistry of Peptide Synthesis* CRC Press. Synthetic peptides may be purified by preparative high performance liquid chromatography and the composition of which may be confirmed via amino acid sequencing. See Creighton (1992) [$2^{nd}$ Ed.] *Proteins, Structures and Molecular Principles* W.H. Freeman and Company; Aguilar (2004) [Ed.] *HPLC of Peptides and Proteins: Methods and Protocols* Humana Press; Simpson (2002) *Protein Sequencing Protocols* [$2^{nd}$ Ed.] Humana Press.

In cases where large amounts of the NPC-1 epitope peptidomimetics of the present invention are desired, the NPC-1 epitope peptidomimetics of the present invention may be generated using recombinant techniques such as described by Invitrogen (2002) "*Guide to Baculovirus Expression Vector Systems* (*BEVs*) *and Insect Culture Techniques" Instruction Manual*; Hatti-Kaul and Mattiasson (2003) [Eds] *Isolation and Purification of Proteins*; Ahmed (2004) *Principles and Reactions of Protein Extraction, Purification and Characterization* CRC Press. Further recombinant techniques such as described by, for example, Bitter, et al. (1987) *Methods in Enzymol.* 153; 516-544, Studier, et al. (1990) *Methods in Enzymol.* 185: 60-89, Brisson, et al. (1984) *Nature* 310: 511-514, Takamatsu, et al. (1987) *EMBO J.* 6: 307-311, Coruzzi, et al. (1984) *EMBO J.* 3: 1671-1680 and Brogli, et al. (1984) *Science* 224: 838-843, Gurley, et al. (1986) *Mol. Cell. Biol.* 6: 559-565 and Weissbach & Weissbach (1988) *Methods for Plant Molecular Biology*, Academic Press, NY, Section VIII, pages 421-463.

Polypeptide Sequence Variants

For any NPC-1 epitope peptidomimetic sequence described herein, further characterization or optimization may be achieved by systematically either adding or removing amino acid residues to generate longer or shorter peptides, and testing those and sequences generated by walking a window of the longer or shorter size up or down the antigen from that point. Coupling this approach to generating new candidate targets with testing for effectiveness of antigenic molecules based on those sequences in an immunogenicity assay, as known in the art or as described herein, may lead to further manipulation of the antigen. Further still, such optimized sequences may be adjusted by, e.g., the addition, deletions, or other mutations as known in the art and/or discussed herein to further optimize the NPC-1 epitope peptidomimetic (e.g., increasing serum stability or circulating half-life, increasing thermal stability, enhancing delivery, enhance immunogenicity, increasing solubility, targeting to a particular in viva location or cell type).

The NPC-1 epitope peptidomimetics described herein may comprise conservative substitution mutations, (i.e., the substitution of one or more amino acids by similar amino acids). For example, conservative substitution refers to the substitution of an amino acid with another within the same general class, e.g., one acidic amino acid with another acidic amino acid, one basic amino acid with another basic amino acid, or one neutral amino acid by another neutral amino acid.

NPC-1 epitope peptidomimetic sequences may have at least about 60, 65, 70, 75, 80, 81, 82, 83, 84, 85, 86, 87, 88, 89, 90, 91, 92, 93, 94, 95, 96, 97, 98, 99, or 100% sequence homology to any at least one of the polypeptide sequences of SEQ ID NOs: 1-24. Further, the variant NPC-1 epitope peptidomimetics described herein may retain the antigenitcity of the sequence from which they were derived. More preferably, the invention contemplates polypeptide sequences having at least about 95% sequence homology, even more preferably at least about 98% sequence homology, and still more preferably at least about 99% sequence homology to any one or more of the polypeptide sequences of NPC-1 epitope peptidomimetic sequences set forth in SEQ ID NOs: 1-24. Methods for determining homology between amino acid sequences, as well as nucleic acid sequences, are well known to those of ordinary skill in the art. See, e.g., Nedelkov & Nelson (2006) *New and Emerging Proteomic Techniques* Humana Press.

Thus, a NPC-1 epitope peptidomimetic may have at least about 80%, 81%, 82%, 83%, 84%, 85%, 86%, 87%, 88%, 89%, 90%, 91%, 92%, 93%, 94%, 95%, 96%, 97%, 98%, 99%, or 100% sequence homology with a polypeptide sequence of SEQ ID NOs: 1-24. For example, a NPC-1 epitope peptidomimetic may have at least about 80%, 81%, 82%, 83%, 84%, 85%, 86%, 87%, 88%, 89%, 90%, 91%, 92%, 93%, 94%, 95%, 96%, 97%, 98%, 99%, or 100% sequence homology with SEQ ID NOs: 1-24. The variant NPC-1 epitope peptidomimetics described herein may retain the antigeniticity of the sequence from which they were derived (e.g., a variant NPC-1 epitope peptidomimetic with at least about 80% homology to the amino acid sequence of SEQ ID NO: 5 may have the same antigenicity as a polypeptide with the amino acid sequence of SEQ ID NO: 5).

The term homology, or identity, is understood as meaning the number of agreeing amino acids (identity) with other proteins, expressed in percent. The identity is preferably determined by comparing a given sequence with other proteins with the aid of computer programs. If sequences which are compared with each other are different in length, the identity is to be determined in such a way that the number of amino acids which the short sequence shares with the longer sequence determines the percentage identity. The identity can be determined routinely by means of known computer programs which are publicly available such as, for example, ClustalW. Thompson, et al. (1994) *Nucleic Acids Research* 22: 4673-4680. ClustalW is publicly available from the European Molecular Biology Laboratory and may be downloaded from various internet pages, inter alia the IGBMC (Institut de Génétique et de Biologie Moléculaire et Cellulaire) and the EBI and all mirrored EBI internet pages (European Bioinformatics Institute). If the ClustalW computer program Version 1.8 is used to determine the identity between, for example, the reference protein of the present application and other proteins, the following parameters are to be set: KTUPLE=1, TOPDIAG=5, WINDOW=5, PAIRGAP=3, GAPOPEN=10, GAPEXTEND=0.05, GAPDIST=8, MAXDIV=40, MATRIX=GONNET, ENDGAPS (OFF), NOPGAP, NOHGAP. See also European Bioinformatics Institute (EBI) toolbox available on-line and Smith (2002) *Protein Sequencing Protocols* [$2^{nd}$ Ed.] Humana Press.

One possibility of finding similar sequences is to carry out sequence database researches. Here, one or more sequences may be entered as what is known as a query. This query sequence is then compared with sequences present in the selected databases using statistical computer programs. Such database queries (blast searches) are known to the skilled worker and may be carried out at different suppliers. If, for example, such a database query is carried out at the NCBI (National Center for Biotechnology Information), the standard settings for the respective comparison query should be used. For protein sequence comparisons (blastp), these settings are: Limit entrez=not activated; Filter=low complexity activated; Expect value=10; word size=3; Matrix=BLOSUM62; Gap costs: Existence=11, Extension=1. The result of such a query is, among other parameters, the degree of identity between the query sequence and the similar sequences found in the databases.

NPC-1 epitope peptidomimetics include functional fragments of said peptidomimetics. A “functional fragment” of said polypeptide includes a fragment of the gene or cDNA encoding said NPC-1 epitope, which fragment is capable of eliciting an immune response (e.g., humoral or cellular immune response.) Thus, for example, fragments of the NPC-1 epitope according to the invention which correspond to amino acid residues that contribute to the immunogenicity of the antigen and which fragments may serve to function as antigens to elicit an immune response (e.g., humoral or cellular immune response.) This aspect of the invention also includes differentially spliced isoforms and transcriptional starts of the polypeptides according to the invention. The polypeptides according to the invention also may comprise fragments, derivatives and allelic variants of the NPC-1 epitope peptidomimetics. Methods and materials for making fragments of NPC-1 epitope peptidomimetics are well known in the art. See, e.g., Maniatis, et al. (2001) *Molecular Cloning: A Laboratory Manual* [$3^{rd}$ Ed.] Cold Spring Harbor Laboratory Press.

Variant NPC-1 epitope peptidomimetics may retain their antigenic specificity to bind their respective antibodies (e.g., a variant NPC-1 epitope peptidomimetic binds NEO-101 antibody.) Fully antigenic variants may contain only conservative variations or variations in non-critical residues or in non-critical regions. Antigenic variants may also contain substitution of similar amino acids that result in no change or an insignificant change in antigenicity. Alternatively, such substitutions may positively or negatively affect antigenicity to some degree. Non-antigenic variants typically contain one or more non-conservative amino acid substitutions, deletions, insertions, inversions, or truncation or a substitution, insertion, inversion, or deletion in a critical residue or critical region of an epitope. Molecular biology and biochemistry techniques for modifying NPC-1 epitope peptidomimetics while preserving specific antigenicity of the polypeptides for their respective antibodies are well known in the art. See, e.g., Ho, et al. (1989) *Gene* 77(1): 51-59; Landt, et al. (1990) *Gene* 96(1): 125-128; Hopp & Woods (1991) *Proc. Natl. Acad. Sci. USA* 78(6): 3824-3828; Kolaskar & Tongaonkar (1990) *FEBS Letters* 276(1-2): 172-174; and Welling, et al. (1985) *FEBS Letters* 188(2): 215-218

Amino acids that are essential for function may be identified by methods known in the art, such as site-directed mutagenesis or alanine-scanning mutagenesis. Cunningham, et al. (1989) *Sci.* 244: 1081-85. The latter procedure introduces single alanine mutations at every residue in the molecule. The resulting mutant molecules are then tested for biological activity such as epitope binding or in vitro ADCC activity. Sites that are critical for ligand-receptor binding may also be determined by structural analysis such as crystallography, nuclear magnetic resonance, or photoaffinity labeling. Smith, et al. (1992) *J. Mol. Biol.* 224: 899-904; de Vos, et al. (1992) *Sci.* 255: 306-12.

For example, one class of substitutions is conserved amino acid substitutions. Such substitutions are those that substitute a given amino acid in a NPC-1 epitope peptidomimetic with another amino acid of like characteristics. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg, replacements among the aromatic residues Phe, Tyr. Guidance concerning which amino acid changes are likely to be phenotypically silent is found in, for example, Bowie, et al. (1990) *Sci.* 247: 1306-10. Hence, one of ordinary skill in the art appreciates that the inventors possess peptide variants without delineation of all the specific variants. As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a “conservatively modified variant” where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. See, e.g., Creighton (1992) *Proteins: Structures and Molecular Properties* [2nd Ed.] W.H. Freeman.

Moreover, the NPC-1 epitope peptidomimetics may contain amino acids other than the twenty "naturally occurring" amino acids. Further, many amino acids, including the terminal amino acids, may be modified by natural processes, such as processing and other post-translational modifications, or by chemical modification techniques well known in the art. Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, g-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See Creighton (1992) *Proteins: Structure and Molecular Properties* [2nd Ed.] and Lundblad (1995) *Techniques in Protein Modification* [1st Ed.] Many detailed reviews are available on this subject. See, e.g., Wold (1983) *Posttranslational Covalent Modification of Proteins* Acad. Press, NY; Seifter, et al. (1990) *Meth. Enzymol.* 182: 626-46; and Rattan, et al. (1992) *Ann. NY Acad. Sci.* 663: 48-62.

Fusion Proteins

Fusions comprising the NPC-1 epi lope peptidomimetics are also within the scope of the present invention. For example, the fusion proteins may comprise a NPC-1 epitope peptidomimetic sequence fused to the C-terminus of the GST sequences. Such fusion proteins may facilitate the purification of the recombinant NPC-1 epitope peptidomimetics. Alternatively, NPC-1 epitope peptidomimetics may be fused with a protein that binds B-cell follicles, thus initiating both a humoral immune response and activation of T cells. Berney, et al. (1999) *J. Exp. Med.* 190: 851-60. Alternatively, for example, the NPC-1 epitope peptidomimetics may be genetically coupled with and anti-dendritic cell antibody to deliver the antigen to the immune system and stimulate a cellular immune response. He, et al. (2004) *Clin. Cancer Res.* 10: 1920-27. A chimeric or fusion protein of the invention may be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. The fusion gene may be synthesized by conventional techniques including automated DNA synthesizers.

Fusion proteins may include C-terminal or N-terminal translocation sequences. Further, fusion proteins comprising NPC-1 epitope peptidomimetics may comprise additional elements, e.g., for protein detection, purification, or other applications. Detection and purification facilitating domains including but not limited to metal chelating peptides such as polyhistidine tracts, histidine-tryptophan modules, or other domains that allow purification on immobilized metals; maltose binding protein; protein A domains that allow purification on immobilized immunoglobulin; or the domain utilized in the FLAG extension/affinity purification system (Immunex Corp, Seattle Wash.)

A fusion protein comprising a NPC-1 epitope peptidomimetic may be prepared from a protein of the invention by fusion with a portion of an immunoglobulin comprising a constant region of an immunoglobulin. More preferably, the portion of the immunoglobulin comprises a heavy chain constant region which is optionally and more preferably a human heavy chain constant region. The heavy chain constant region is most preferably an IgG heavy chain constant region, and optionally and most preferably is an Fc chain, most preferably an IgG Fc fragment that comprises CH2 and CH3 domains. Although any IgG subtype may optionally be used, the IgG1 subtype is preferred. The Fc chain may optionally be a known or "wild type" Fc chain, or alternatively may be mutated. See, e.g., U.S. Patent Application Publication No. 2006/0034852. The term "Fc chain" also optionally comprises any type of Fc fragment. Several of the specific amino acid residues that are involved in antibody constant region-mediated activity in the IgG subclass have been identified. Inclusion, substitution or exclusion of these specific amino acids therefore allows for inclusion or exclusion of specific immunoglobulin constant region-mediated activity. Furthermore, specific changes may result in aglycosylation for example and/or other desired changes to the Fc chain. At least some changes may optionally be made to block a function of Fc which is considered to be undesirable, such as an undesirable immune system effect. See McCafferty, et al. (2002) *Antibody Engineering: A Practical Approach* (Eds.) Oxford University Press.

The inclusion of a cleavable linker sequences such as Factor Xa (see, e.g., Ottavi, (1998) *Biochimie* 80: 289-93), subtilisin protease recognition motif (see, e.g., Polyak (1997) *Protein Eng.* 10: 615-19); enterokinase (Invitrogen, San Diego, Calif.), between the translocation domain (for efficient plasma membrane expression) and the rest of the newly translated polypeptide may be useful to facilitate purification. For example, one construct can include a polypeptide encoding a nucleic acid sequence linked to six histidine residues followed by a thioredoxin, an enterokinase cleavage site (see, e.g., Williams (1995) *Biochemistry* 34: 1787-97), and an C-terminal translocation domain. The histidine residues facilitate detection and purification while the enterokinase cleavage site provides a means for purifying the desired protein(s) from the remainder of the fusion protein. Technology pertaining to vectors encoding fusion proteins and application of fusion proteins are well described in the scientific and patent literature. See, e.g., Kroll (1993) *DNA Cell. Biol.* 12: 441-53.

Conjugates

The NPC-1 epitope peptidomimetics may be conjugated to other moieties. Such conjugates are often used in the preparation of vaccines. The NPC-1 epitope peptidomimetic may be conjugated to a carbohydrate carrier (e.g., mannose, fucose, glucose, GlcNAs, maltose), which is recognized by the mannose receptor present on dendritic cells and macrophages. The ensuing binding, aggregation, and receptor-mediated endocytosis and phagocytosis functions provide enhanced innate and adaptive immunity. See Mahnke, et al. (2000) *J. Cell Biol.* 151: 673-84; Dong, et al. (1999) *J. Immonol.* 163: 5427-34. Other moieties suitable for conjugation include carriers which elicit an immune response includes but not limited to Keyhole Limpit Hemocyannin (KLH), ovalbumin, bovine serum albumin (BSA), diphtheria toxoid, cholera toxoid, *Pseudomonas* exoprotein A, and microbial outer membrane proteins (OMPS). Further, NPC-1 epitope peptidomimetic conjugates may be used to raise antibodies including but not limited to monoclonal antibodies that bind the NPC-1 epitope peptidomimetic and thus, selectively bind MUC5AC in tumor cells but not normal cells.

Polypeptide Isolation

The present invention also provides methods for isolation of the NPC-1 epitope peptidomimetics. For example, relevant cell lines or tumor samples may be obtained from a cancer patient. After homogenization and solubilization in a detergent, the antigen is chromatographically purified. Size-exclusion or affinity chromatography may be used for this, and may be used in conjunction with NEO-101 antibody binding. See International Patent Application No. PCT/US2011/041502 for a description of the NEO-100 antibodies including the NEO-101 antibody. For example, NEO-101 antibody may be immobilized on a solid support (e.g., coupled to resins, magnetic beads) for simple antigen adsorption, washing, and elution from the solid support. The eluted protein is then studied further for antigen presence, characterization, and identification. See Walker (2002) *Protein Protocols Handbook* [2$^{nd}$ Ed.] Humana Press and Cultur (2003) [Ed.] *Protein Purification Protocols* Humana Press.

The antigen isolated in this way may be used for preparing a pharmaceutical using the conventional pharmaceutical excipient and carrier substance. For example, in-vivo administration of the purified antigen in a physiological NaCl solution.

Additionally, the NPC-1 epitope peptidomimetics according to the invention may serve as an antigen in the identification of activities as part of a high-throughput screening. High-throughput screening methods are known to persons skilled in the art. Wells (2002) *High Throughout Bioanalytical Sample Preparation* Elsevier Health Sciences.

Antibodies which Bind NPC-1 Epitope Peptidomimetic

The present invention also provides antibodies that bind the NPC-1 epitope peptidomimetic including but not limited monoclonal and humanized monoclonal antibodies (e.g., NEO-101 antibody as described in International Patent Application No. PCT/US2011/041502). Such antibodies also selectively bind aberrant MUC5AC in tumor cells but not normal cells (e.g., healthy cells). The NPC-1 epitope peptidomimetics binding antibodies may be admixed in compositions with pharmaceutical carriers and antibodies (e.g., NEO-201 and/or NEO-301 monoclonal antibodies). Exemplary NPC-1 binding antibodies (e.g., NEO-100 antibodies) are provided in Table 4.

TABLE 4

NEO-100 Series Antibodies which selectively bind a NPC-1 epitope.

| Antibody | Aliases | Antigen | Exemplary SEQ ID NOs | Description |
|---|---|---|---|---|
| NPC-1 | | NPC-1 | | Murine hybridoma that expresses NPC-1 IgG1 (ATCC) |
| NEO-101 | NPC-1C, ensituximab | NPC-1 | Light Chain (SEQ ID NOs: 57, 58)<br>LC CDRs (SEQ ID NOs: 59-61)<br>Heavy Chain (SEQ ID NOs: 62, 63)<br>HC CDRs (SEQ ID NOs: 64-66) | Chimeric NEO-101 antibody, engineered in CHO-DG44 production cell clone 4B7; targets a variant of MUC5AC |
| NEO-102 | | NPC-1 | Light Chain (SEQ ID NOs: 67, 68)<br>LC CDRs (SEQ ID NOs: 69-71)<br>Heavy Chain (SEQ ID NOs: 72, 73)<br>HC CDRs (SEQ ID NOs: 74-76) | Chimeric NEO-101 antibody, engineered in CHO-M production cells, contains 2 amino acid changes in HC constant domain* |
| NEO-103 | | NPC-1 | Light Chain (SEQ ID NOs: 77, 78)<br>Heavy Chain (SEQ ID NOs: 79, 80) | Humanized NEO-101 antibody |

Antibodies may comprise of two identical light polypeptide chains of molecular weight approximately 23,000 daltons ("light chain"), and two identical heavy chains of molecular weight 53,000-70,000 ("heavy chain"). See Edelman (1971) *Ann. NY. Acad. Sci.* 190: 5. The four chains are joined by disulfide bonds in a "Y" configuration wherein the light chains bracket the heavy chains starting at the mouth of the "Y" configuration. The "branch" portion of the "Y" configuration is designated the $F_{ab}$ region; the stem portion of the "Y" configuration is designated the $F_c$ region. The amino acid sequence orientation runs from the N-terminal end at the top of the "Y" configuration to the C-terminal end at the bottom of each chain. The N-terminal end possesses the variable region having specificity for the antigen that elicited it, and is about 100 amino acids in length, there being slight variations between light and heavy chain and from antibody to antibody.

The variable region is linked in each chain to a constant region that extends the remaining length of the chain and that within a particular class of antibody does not vary with the specificity of the antibody (i.e., the antigen eliciting it). There are five known major classes of constant regions that determine the class of the immunoglobulin molecule (e.g., IgG, IgM, IgA, IgD, and IgE corresponding to γ, μ, α, δ, and ε heavy chain constant regions). The constant region or class determines subsequent effector function of the antibody, including activation of complement (Kabat (1976) *Structural Concepts in Immunology and Immunochemistry* [2$^{nd}$ Ed.] pages 413-4-36; Holt, Rinehart, Winston) and other cellular responses (Andrews, et al. (1980) *Clinical Immunobiology* 1-18; Kohl, et al. (1983) *Immunology* 48: 187) while the variable region determines the antigen with which it will react. Light chains are classified as either κ (kappa) or λ (lambda). Each heavy chain class may be prepared with either kappa or lambda light chain. The light and heavy chains are covalently bonded to each other, and the "tail" portions of the two heavy chains are bonded to each other by covalent disulfide linkages when the immunoglobulins are generated either by hybridomas or by B cells.

Specific binding to an antibody under such conditions may require an antibody that is selected for its specificity for a particular protein. For example, polyclonal antibodies raised to seminal basic protein from specific species such as rat, mouse, or human can be selected to obtain only those polyclonal antibodies that are specifically immunoreactive with seminal basic protein and not with other proteins, except for polymorphic variants and alleles of seminal basic protein. This selection may be achieved by subtracting out antibodies that cross-react with seminal basic protein molecules from other species. A variety of immunoassay formats may be used to select antibodies specifically immunoreactive with a particular protein. For example, solid-phase ELISA immunoassays are routinely used to select antibodies specifically immunoreactive with a protein. See, e.g., Harlow & Lane (1998) *USING ANTIBODIES: A LABORATORY MANUAL* Cold Spring Harbor Laboratory, for a description of immunoassay formats and conditions that can be used to determine specific immunoreactivity. Typically a specific or selective reaction will be at least twice background signal or noise and more typically more than about 10 to 100 times background.

Polyclonal Antibody

Polyclonal antibodies are heterogeneous populations of antibody molecules derived from the sera of animals immunized with an antigen. Polyclonal antibodies which selectively bind the NPC-1 epitope peptidomimetic may be made by methods well-known in the art. See, e.g., Howard & Kaser (2007) *Making and Using Antibodies: A Practical Handbook* CRC Press.

Monoclonal Antibody

A monoclonal antibody contains a substantially homogeneous population of antibodies specific to antigens, which population contains substantially similar epitope binding sites. Monoclonal antibodies may be obtained by methods known to those skilled in the art. See, e.g. Kohler and Milstein (1975) *Nature* 256: 495-497; U.S. Pat. No. 4,376,110; Ausubel, et al. [Eds.] (2011) *CURRENT PROTOCOLS IN MOLECULAR BIOLOGY*, Greene Publishing Assoc. and Wiley Interscience, NY.; and Harlow & Lane (1998) *USING ANTIBODIES: A LABORATORY MANUAL* Cold Spring Harbor Laboratory; Colligan, et al. (2005) [Eds.] *Current Protocols in Immunology* Greene Publishing Assoc. and Wiley Interscience, NY. Such antibodies may be of any immunoglobulin class including IgG, IgM, IgE, IgA, GILD and any subclass thereof. A hybridoma producing an antibody of the present invention may be cultivated in vitro, in situ, or in vivo. Examples of monoclonal antibodies that bind a NPC-1 epitope peptidomimetic include but are not limited to an NEO-101 antibody which selectively binds the NPC-1 epitope (e.g., exemplary light chain are depicted in SEQ ID NO: 57, 58 with CDRs depicted in SEQ ID NO: 59-61 and heavy chain are depicted in SEQ ID NO: 62, 63 with CDRs depicted in SEQ ID NO: 64-66, exemplary light chain are depicted in SEQ ID NO: 67, 68 with CDRs depicted in SEQ ID NO: 69-71 and heavy chain are depicted in SEQ ID NO: 72, 73 with CDRs depicted in SEQ ID NO: 74-76, and exemplary light chain are depicted in SEQ ID NO: 77, 78 and heavy chain are depicted in SEQ ID NO: 79, 80).

Chimeric Antibody

Chimeric antibodies are molecules different portions of which are derived from different animal species, such as those having variable region derived from a murine antibody and a human immunoglobulin constant region, which are primarily used to reduce immunogenicity in application and to increase yields in production, for example, where murine monoclonal antibodies have higher yields from hybridomas but higher immunogenicity in humans, such that human murine chimeric monoclonal antibodies are used. Chimeric antibodies and methods for their production are known in the art. See Cabilly, et al. (1984) *Proc. Natl. Acad. Sci. USA* 81: 3273-3277; Morrison, et al. (1994) *Proc. Natl. Acad. Sci. USA* 81: 6851-6855, Boulianne, et al. (1984) *Nature* 312: 643-646; Neuberger, et al. (1985) *Nature* 314: 268-270; European Patent Application 173494 (1986); WO 86/01533 (1986); European Patent Application 184187 (1986); Sahagan, et al. (1986) *J. Immunol.* 137: 1066-1074; Liu, et al. (1987) *Proc. Natl. Acad. Sci. USA* 84: 3439-3443; Sun, et al. (1987) *Proc. Natl. Acad. Sci. USA* 84: 214-218; Better, et al. (1988) *Science* 240: 1041-1043; and Harlow & Lane (1998) *USING ANTIBODIES: A LABORATORY MANUAL* Cold Spring Harbor Laboratory; U.S. Pat. No. 5,624,659. Exemplary chimeric antibodies include but are not limited to NEO-101 (NEO-101) which selectively binds NPC-1 epitope (e.g., exemplary light chain are depicted in SEQ ID NOs: 52, 58 with CDRS depicted in SEQ ID NOs: 59-61 and heavy chain depicted in SEQ ID NOs: 62, 63 with CDRs depicted in SEQ ID NOs: 64-66); NEO-102 which selectively binds NPC-1 epitope (e.g., exemplary light chain are depicted in SEQ ID NOs: 67, 68 with CDRS depicted in SEQ ID NOs: 69-71 and heavy chain depicted in SEQ ID NOs: 72, 73 with CDRs depicted in SEQ ID NOs: 74-76).

Humanized Antibody

Humanized antibodies are engineered to contain even more human-like immunoglobulin domains, and incorporate only the complementarity-determining regions of the animal-derived antibody. This may be accomplished by examining the sequence of the hyper-variable loops of the variable regions of the monoclonal antibody, and fitting them to the structure of the human antibody chains. See, e.g., U.S. Pat. No. 6,187,287. Likewise, other methods of producing humanized antibodies are now well known in the art. See, e.g., U.S. Pat. Nos. 5,225,539; 5,530,101; 5,585,089; 5,693,762; 6,054,297; 6,180,370; 6,407,213; 6,548,640; 6,632,927; and 6,639,055; Jones, et al. (1986) *Nature* 321: 522-525; Reichmann, et al. (1988) *Nature* 332: 323-327; Verhoeyen, et al. (1988) *Science* 239: 1534-36; and Zhiqiang An (2009) [Ed.] *Therapeutic Monoclonal Antibodies: From Bench to Clinic* John Wiley & Sons, Inc. Examples of humanized antibodies include but are not limited to NEO-103 which selectively binds the NPC-1 epitope (e.g., exemplary light chain are depicted in SEQ ID NO: 77, 78 and heavy chain are depicted in SEQ ID NO: 79, 80).

Antibody Fragments

In addition to entire immunoglobulins (or their recombinant counterparts), immunoglobulin fragments comprising the epitope binding site (e.g., Fab', $F(ab')_2$, or other fragments) may be synthesized. “Fragment,” or minimal immunoglobulins may be designed utilizing recombinant immunoglobulin techniques. For instance “Fv” immunoglobulins for use in the present invention may be produced by synthesizing a fused variable light chain region and a variable heavy chain region. Combinations of antibodies are also of interest, e.g. diabodies, which comprise two distinct Fv specificities. Antigen-binding fragments of immunoglobulins include but are not limited to SMIPs (small molecule immunopharmaceuticals), camelbodies, nanobodies, and IgNAR.

Anti-Idiotypic Antibody

An anti-idiotypic (anti-Id) antibody is an antibody which recognizes unique determinants generally associated with the antigen-binding site of an antibody. An Id antibody may be prepared by immunizing an animal of the same species and genetic type (e.g., mouse strain) as the source of the antibody with the antibody to which an anti-Id is being prepared. The immunized animal will recognize and respond to the idiotypic determinants of the immunizing antibody by producing an antibody to these idiotypic determinants (the anti-Id antibody). See e.g., U.S. Pat. No. 4,699,880. The anti-Id antibody may also be used as an “immunogen” to induce an immune response in yet another animal, producing a so-called anti-anti-Id antibody. The anti-anti-Id may be epitopically identical to the original antibody which induced the anti-Id. Thus, by using antibodies to the idiotypic determinants of an antibody it is possible to identify other clones expressing antibodies of identical specificity. An exemplary anti-idiotypic antibody is 4B6, which selectively binds the NEO-101 antibody, both of which are described in International Patent Application No. PCT/US2011/041502. This anti-idiotypic antibody specific for NEO-1 antibody. In one embodiment, the light chain of said antibody may be encoded by the nucleic acid sequence of SEQ ID NO: 81. In one embodiment, the light chain of said antibody may comprise the amino acid sequence of SEQ ID NO: 82. In one embodiment, the light chain of said antibody may comprise CDRs comprising the amino acid sequence of SEQ ID NO: 83 and 84 and the peptide sequence Trp-Ala-Ser. In one embodiment, the heavy chain of said antibody may be encoded by the nucleic acid sequence of SEQ ID NO: 85. In one embodiment, the heavy chain of said antibody may comprise the amino acid sequence of SEQ ID NO: 86. In one embodiment, the heavy chain of said antibody may comprise CDRs comprising the amino acid sequence of SEQ ID NO: 87, 88, and 89.

Engineered and Modified Antibodies

An antibody of the invention further may be prepared using an antibody having one or more of the VH and/or VL sequences derived from an antibody starting material to engineer a modified antibody, which modified antibody may have altered properties from the starting antibody. An antibody may be engineered by modifying one or more residues within one or both variable regions (i.e., VH and/or VL), for example within one or more CDR regions and/or within one or more framework regions. Additionally or alternatively, an antibody may be engineered by modifying residues within the constant region(s), for example to alter the effector function(s) of the antibody.

One type of variable region engineering that may be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties. See, e.g., Riechmann, et al. (1998) *Nature* 332: 323-327; Jones, et al. (1986) *Nature* 321: 522-525; Queen, et al. (1989) *Proc. Natl. Acad. U.S.A.* 86: 10029-10033; U.S. Pat. Nos. 5,225,539; 5,530,101; 5,585,089; 5,693,762; and 6,180,370.

Suitable framework sequences may be obtained from public DNA databases or published references that include germline antibody gene sequences. For example, germline DNA sequences for human heavy and light chain variable region genes may be found in the "VBase" human germline sequence database (available on the Internet), as well as in Kabat, E. A., et al. (1991) *Sequences of Proteins of Immunological Interest*, Fifth Edition, U.S. Department of Health and Human Services, NIH Publication No. 91-3242; Tomlinson, et al. (1992) "*The Repertoire of Human Germline VH Sequences Reveals about Fifty Groups of VH Segments with Different Hypervariable Loops*" J. Mol. Biol. 227: 776-798; and Cox, et al. (1994) *Eur. J Immunol.* 24: 827-836.

Another type of variable region modification is to mutate amino acid residues within the VH and/or VL CDR 1, CDR2 and/or CDR3 regions to thereby improve one or more binding properties (e.g., affinity) of the antibody of interest. Site-directed mutagenesis or PCR-mediated mutagenesis may be performed to introduce the mutation(s) and the effect on antibody binding, or other functional property of interest, may be evaluated in appropriate in vitro or in vivo assays. Preferably conservative modifications (as discussed herein) may be introduced. The mutations may be amino acid substitutions, additions or deletions, but are preferably substitutions. Moreover, typically no more than one, two, three, four or five residues within a CDR region are altered.

Engineered antibodies of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues may be identified by comparing the antibody framework sequences to the germline sequences from which the antibody is derived.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties may be attached to the antibody) or be modified to alter its glycosylation, again to alter one or more functional properties of the antibody. Such embodiments are described further below. The numbering of residues in the Fc region is that of the EU index of Kabat.

The hinge region of CH1 may be modified such that the number of cysteine residues in the hinge region is altered, e.g., increased or decreased. See U.S. Pat. No. 5,677,425. The number of cysteine residues in the hinge region of CH1 may be altered to, for example, facilitate assembly of the light and heavy chains or to increase or decrease the stability of the antibody.

The Fc hinge region of an antibody may be mutated to decrease the biological half life of the antibody. More specifically, one or more amino acid mutations may be introduced into the CH2-CH3 domain interface region of the Fc-hinge fragment such that the antibody has impaired Staphylococcyl protein A (SpA) binding relative to native Fc-hinge domain SpA binding. See, e.g., U.S. Pat. No. 6,165,745.

The antibody may be modified to increase its biological half life. Various approaches are possible. For example, one or more of the following mutations may be introduced: T252L, T254S, T256F. See U.S. Pat. No. 6,277,375. Alternatively, to increase the biological half life, the antibody may be altered within the CH1 or CL region to contain a salvage receptor binding epitope taken from two loops of a CH2 domain of an Fc region of an IgG. See U.S. Pat. Nos. 5,869,046 and 6,121,022.

The Fc region may be altered by replacing at least one amino acid residue with a different amino acid residue to alter the effector function(s) of the antibody. For example, one or more amino acids selected from amino acid residues 234, 235, 236, 237, 297, 318, 320 and 322 may be replaced with a different amino acid residue such that the antibody has an altered affinity for an effector ligand but retains the antigen-binding ability of the parent antibody. The effector ligand to which affinity may be altered may be, for example, an Fc receptor or the Cl component of complement. See U.S. Pat. Nos. 5,624,821 and 5,648,260.

The Fc region may be modified to increase the ability of the antibody to mediate antibody dependent cellular cytotoxicity (ADCC) and/or to increase the affinity of the antibody for an Fcy receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. See WO 00/42072. Moreover, the binding sites on human IgG1 for FcγRI, FcγRII, FcγRIII and FeRn have been mapped and variants with improved binding. See Shields, et al. (2001) *J. Biol. Chem.* 276: 6591-6604. Specific mutations at positions 256, 290, 298, 333, 334 and 339 are shown to improve binding to FcγRIII. Additionally, the following combination mutants are shown to improve FcγRIII binding: T256A/S298A, S298A/E333A, S298A/K224A and S298A/E333A/K334A.

The glycosylation of an antibody may be modified. For example, an aglycoslated antibody may be made (i.e., the antibody lacks glycosylation). Glycosylation may be altered to, for example, increase the affinity of the antibody for antigen. Such carbohydrate modifications may be accomplished by, for example, altering one or more sites of glycosylation within the antibody sequence. For example, one or more amino acid substitutions may be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, an antibody may be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications may be accomplished by, for example, expressing the antibody in a host cell with altered glycosylation machinery. Cells with altered glycosylation machinery have been described in the art and may be used as host cells in which to express recombinant antibodies of the invention to thereby produce an antibody with altered glycosylation. See U.S. Patent Application Publication No. 2004/011.0704 and Yamane-Ohnuki, et al. (2004) *Biotechnol Bioeng.* 87: 614-22; EP 1176195 (2002); WO 2003/035835; Shields, et al. (2002) *J. Biol. Chem.* 277: 26733-26740; WO 99/54342; Umana, et al. (1999) *Nat. Biotech.* 17: 176-180; and Tarentino, et al. (1975) *Biochem.* 14: 5516-23.

An antibody may be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer).

The invention also provides variants and equivalents that are substantially homologous to the antibodies, antibody fragments, diabodies, SMIPs, camelbodies, nanobodies, IgNAR, polypeptides, variable regions and CDRs set forth herein. These may contain, e.g., conservative substitution mutations, (i.e., the substitution of one or more amino acids by similar amino acids). For example, conservative substitution refers to the substitution of an amino acid with another within the same general class, e.g., one acidic amino acid with another acidic amino acid, one basic amino acid with another basic amino acid, or one neutral amino acid by another neutral amino acid.

Methods of Engineering Antibodies

Antibodies having VH and VL sequences disclosed herein may be used to create new variant antibodies by modifying the VH and/or VL sequences, or the constant region(s) attached thereto. Thus, the structural features of an variant antibody of the invention, are used to create structurally related variant antibodies that retain at least one functional property of the antibodies of the invention, such as binding to NPC-1 epitope peptidomimetic. The starting material for the engineering method may be one or more of the VH and/or VK sequences provided herein, or one or more CDR regions thereof. To create the engineered antibody, it is not necessary to actually prepare (i.e., express as a protein) an antibody having one or more of the VH and/or VK sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein. Standard molecular biology techniques may be used to prepare and express altered antibody sequence.

Mutations may be introduced randomly or selectively along all or part of an antibody coding sequence and the resulting modified antibodies may be screened for binding activity and/or other desired functional properties. See WO 2002/092780 and WO 2003/074679.

Nucleic Acids Encoding the NPC-1 Epitope Peptidomimetic

Another aspect of the invention pertains to nucleic acid molecules that encode the NPC-1 epitope peptidomimetic. The nucleic acids may be present in whole cells, in a cell lysate, or in a partially purified or substantially pure form. A nucleic acid may be isolated by purification away from other cellular components or other contaminants (e.g., other cellular nucleic acids or proteins) by standard techniques, including alkaline/SDS treatment, CsCl banding, column chromatography, agarose gel electrophoresis and others well known in the art. See Ausubel, et al. (2011) *Current Protocols in Molecular Biology* John Wiley & Sons, Inc. A nucleic acid of the invention may be, for example, DNA or RNA and may or may not contain intronic sequences. The nucleic acid may be a cDNA molecule.

Nucleic acids of the invention may be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma may be obtained by standard PCR amplification or eDNA cloning techniques. For antibodies obtained from an immunoglobulin gene library (e.g., using phage display techniques), nucleic acid encoding the antibody may be recovered from the library.

Specifically, degenerate codon substitutions may be achieved by generating, e.g., sequences in which the third position of one or more selected codons is substituted with mixed-base and/or deoxyinosine residues. Batzer, et al.

(1991) *Nucleic Acid Res.* 19: 5081; Ohtsuka, et al. (1985) *J. Biol. Chem.* 260: 2605-08; Rossolini, et al. (1994) *Mol. Cell. Probes* 8: 91-98.

Methods of Producing Recombinantly Producing NPC-1 Epitope Peptidomimetics

The present invention also provides methods for recombinantly producing the NPC-1 epitope peptidomimetic. Methods of producing peptidomimetics are well known to those of ordinary skill in the art.

NPC-1 epitope peptidomimetics of the invention may also be produced by constructing, using conventional techniques well known to those of ordinary skill in the art, an expression vector containing an operon and a DNA sequence encoding the NPC-1 epitope peptidomimetics. Furthermore, the invention relates to vectors, especially plasmids, cosmids, viruses, bacteriophages and other vectors common in genetic engineering, which contain the above-mentioned nucleic acid molecules of the invention. The nucleic acid molecules contained in the vectors may be linked to regulatory elements that ensure the transcription in prokaryotic and eukaryotic cells.

Vectors contain elements that facilitate manipulation for the expression of a foreign protein within the target host cell. Conveniently, manipulation of sequences and production of DNA for transformation is first performed in a bacterial host (e.g., *E. coli*) and usually vectors will include sequences to facilitate such manipulations, including a bacterial origin of replication and appropriate bacterial selection marker. Selection markers encode proteins necessary for the survival or growth of transformed host cells grown in a selective culture medium. Host cells not transformed with the vector containing the selection gene will not survive in the culture medium. Typical selection genes encode proteins that confer resistance to antibiotics or other toxins, complement auxotrophic deficiencies, or supply critical nutrients not available from complex media. Exemplary vectors and methods for transformation of yeast are described in the art. See, e.g., Burke, et al. (2000) *Methods in Yeast Genetics* Cold Spring Harbor Laboratory Press.

The polypeptide coding sequence of NPC-1 epitope peptidomimetics may be operably linked to transcriptional and translational regulatory sequences that provide for expression of the polypeptide in yeast cells. These vector components may include, but are not limited to, one or more of the following: an enhancer element, a promoter, and a transcription termination sequence. Sequences for the secretion of the polypeptide may also be included (e.g., a signal sequence).

Nucleic acids are "operably linked" when placed into a functional relationship with another nucleic acid sequence. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence. Generally, "operably linked" refers broadly to contiguous linked DNA sequences, and, in the case of a secretory leader, contiguous and in reading frame. However, enhancers do not have to be contiguous.

Promoters are untranslated sequences located upstream (5') to the start codon of a structural gene (generally within about 100 to 1000 bp) that control the transcription and translation of particular nucleic acid sequences to which they are operably linked. Such promoters fall into several classes: inducible, constitutive, and repressible promoters (e.g., that increase levels of transcription in response to absence of a repressor). Inducible promoters may initiate increased levels of transcription from DNA under their control in response to some change in culture conditions (e.g., the presence or absence of a nutrient or a change in temperature.)

The expression vectors are transfected into a host cell by convention techniques well known to those of ordinary skill in the art to produce a transfected host cell, said transfected host cell cultured by conventional techniques well known to those of ordinary skill in the art to produce said NPC-1 epitope peptidomimetics.

The host cells used to express the NPC-1 epitope peptidomimetics may be either a bacterial cell such as *E. coli*, yeast (e.g., *S. cerevisiae*), or a eukaryotic cell (e.g., a mammalian cell line). A mammalian cell of a well-defined type for this purpose, such as a myeloma cell, 3T3, HeLa, C6A2780, Vero, MDCK II, a Chinese hamster ovary (CHO), Sf9, Sf21, COS, NSO, or HEK293 cell line may be used.

The general methods by which the vectors may be constructed, transfection methods required to produce the host cell and culturing methods required to produce the antibodies, and fragments thereof, from said host cells all include conventional techniques. Although preferably the cell line used to produce the NPC-1 epitope peptidomimetics is a mammalian cell line, any other suitable cell line, such as a bacterial cell line such as an *E. coli*-derived bacterial strain, or a yeast cell line, may be used.

Similarly, once produced the NPC-1 epitope peptidomimetics may be purified according to standard procedures in the art, such as for example cross-flow filtration, ammonium sulphate precipitation, and affinity column chromatography.

Generation of Monoclonal Antibodies that Bind a NPC-1 Epitope Peptidomimetic Using Animals Antibodies that selectively bind NPC-1 epitope peptidomimetics may be human monoclonal antibodies. Such human monoclonal antibodies directed against a NPC-1 epitope peptidomimetic may be generated using transgenic or transchromosomic mice carrying parts of the human immune system rather than the mouse system. These transgenic and transchromosomic mice include mice referred to herein as the HuMAb Mouse® and KM Mouse® respectively, and are collectively referred to herein as "human Ig mice." The HuMAb Mouse® (Medarex. Inc.) contains human immunoglobulin gene miniloci that encode unrearranged human heavy (μ and γ) and κ light chain immunoglobulin sequences, together with targeted mutations that inactivate the endogenous μ and κ chain loci. See, e.g., Lonberg, et al. (1994) *Nature* 368(6474): 856-859. Accordingly, the mice exhibit reduced expression of mouse IgM or κ, and in response to immunization, the introduced human heavy and light chain transgenes undergo class switching and somatic mutation to generate high affinity human IgGκ monoclonal. Lonberg (1994) *Handbook of Experimental Pharmacology* 113: 49-101; Lonberg and Huszar (1995) *Intern. Rev. Immunol.* 13: 65-93, and Harding and Lonberg (1995) *Ann. NY. Acad. Sci.* 764: 536-546. The preparation and use of the HuMab Mouse®, and the genomic modifications carried by such mice, is further described in Taylor, et al. (1992) *Nucleic Acids Research* 20: 6287-6295; Chen, et al. (1993) *International Immunology* 5: 647-656; Tuaillon, et al. (1993) *Proc. Natl. Acad. Sci. USA* 90: 3720-3724; Choi, et al. (1993) *Nature Genetics* 4: 117-123; Chen, et al. (1993) *EMBO J.* 12: 821-830; Tuaillon, et al. (1994) *J. Immunol.* 152: 2912-2920; Taylor, et al. (1994) *International Immunology* 6: 579-591; and Fishwild, et al. (1996) *Nature Biotechnology* 14: 845-851. See further, U.S. Pat. Nos. 5,545,806; 5,569,825; 5,625,126; 5,633,425; 5,789,650; 5,877,397; 5,661,016; 5,814,318; 5,874,299; 5,770, 429; and 5,545,807; WO 92/03918, WO 93/12227, WO 94/25585; WO 97/13852; WO 98/24884; WO 99/45962; and WO 01/14424.

Human antibodies that selectively bind the NPC-1 epitope peptidomimetics of the invention may be raised using a mouse that carries human immunoglobulin sequences on transgenes and transchromosomes, such as a mouse that carries a human heavy chain transgene and a human light chain transchromosome. Such mice, referred to herein as "KM Mice®", are described in detail in WO 02/43478.

Still further, alternative transgenic animal systems expressing human immunoglobulin genes are available in the art and may be used to raise antibodies that selectively bind NPC-1 epitope peptidomimetics. For example, an alternative transgenic system referred to as the Xenomouse (Abgenix, Inc.) may be used; such mice are described in, for example, U.S. Pat. Nos. 5,939,598; 6,075,181; 6,114,598; 6,150,584 and 6,162,963.

Moreover, alternative transchromosomic animal systems expressing human immunoglobulin genes are available in the art and may be used to raise antibodies that selectively bind NPC-1 epitope peptidomimetics. For example, mice carrying both a human heavy chain transchromosome and a human light chain transchromosome, referred to as "TC mice" may be used. See Tomizuka, et al. (2000) *Proc. Natl. Acad Sci. USA* 97: 722-727. Furthermore, cows carrying human heavy and light chain transchromosomes have been described in the art (Kuroiwa, et al. (2002) *Nature Biotechnology* 20: 889-894) and may be used to raise antibodies that selectively bind NPC-1 epitope peptidomimetics.

Human monoclonal antibodies of the invention may also be prepared using phage display methods for screening libraries of human immunoglobulin genes. Such phage display methods for isolating human antibodies are established in the art. See, for example, U.S. Pat. Nos. 5,223,409; 5,403,484; 5,571,698; 5,427,908; 5,580,717; 5,969,108; 6,172,197; 5,885,793; 6,521,404; 6,544,731; 6,555,313; 6,582,915 and 6,593,081.

Human monoclonal antibodies of the invention may also be prepared using SCID mice into which human immune cells have been reconstituted such that a human antibody response may be generated upon immunization. See, e.g., U.S. Pat. Nos. 5,476,996 and 5,698,767.

When human Ig mice are used to raise human antibodies of the invention, such mice may be immunized with a purified or enriched preparation of NPC-1 epitope peptidomimetic, as described by Lonberg, et al. (1994) *Nature* 368(6474): 856-859; Fishwild, et al. (1996) *Nature Biotechnology* 14: 845-851; WO 98/24884 and WO 01/14424. Preferably, the mice will be 6-16 weeks of age upon the first infusion. For example, a purified or recombinant preparation (5-50 μg) of NPC-1 epitope may be used to immunize the human Ig mice intraperitoneally.

Prior experience with various antigens by others has shown that the transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response may be monitored over the course of the immunization protocol with plasma samples being obtained by retroorbital bleeds. The plasma may be screened by ELISA (as described below), and mice with sufficient titers of anti-NPC-1 human immunoglobulin may be used for fusions. Mice may be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCo12 strains are used. In addition, both HCo7 and HCo12 transgene may be bred together into a single mouse having two different human heavy chain transgenes (HCo7/HCo12). Alternatively or additionally, the KM Mouse® strain may be used.

Generation of Hybridomas Producing Human Monoclonal Antibodies of the Invention

To generate hybridomas producing human monoclonal antibodies of the invention, splenocytes and/or lymph node cells from immunized mice may be isolated and fused to an appropriate immortalized cell line, such as a mouse myeloma cell line. The resulting hybridomas may be screened for the production of antigen-specific antibodies. For example, single cell suspensions of splenic lymphocytes from immunized mice may be fused to one-sixth the number of P3X63-Ag8.653 nonsecreting mouse myeloma cells (ATCC, CRL 1580) with 50% PEG. Cells may be plated at approximately $2\times10^{-5}$ in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells may be cultured in medium in which the HAT is replaced with HT. Individual wells may then be screened by ELISA for human monoclonal IgM and IgG antibodies. Once extensive hybridoma growth occurs, medium may be observed usually after 10-14 days. The antibody secreting hybridomas may be replated, screened again, and if still positive for human IgG, the monoclonal antibodies may be subcloned at least twice by limiting dilution. The stable subclones may then be cultured in vitro to generate small amounts of antibody in tissue culture medium for characterization.

To purify human monoclonal antibodies, selected hybridomas may be grown in two-liter spinner-flasks for monoclonal antibody purification. Supernatants may be filtered and concentrated before affinity chromatography with protein A-Sepharose (Pharmacia, Piscataway, N.J.) Eluted IgG may be checked by gel electrophoresis and high performance liquid chromatography to ensure purity. The buffer solution may be exchanged into PBS, and the concentration may be determined by OD280 using 1.43 extinction coefficient. The monoclonal antibodies may be aliquoted and stored at −80° C.

Polynucleotides Encoding NPC-1 Epitope Peptidomimetics

The present invention also provides MUC5AC antigen nucleotides which encode NPC-1 epitope peptidomimetics. The present invention also provides for fragments, sequences hybridizable with, and sequences homologous to the polynucleotide sequences that encode a NPC-1 epitope peptidomimetic which are at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 98.5%, 99%, 99.5%, 99.8%, 99.9%, or 100%.

The invention also provides polynucleotides comprising at least one NPC-1 epitope peptidomimetic sequence encoding similar polypeptides with different codon usage, altered sequences characterized by mutations, such as deletion, insertion or substitution of one or more nucleotides, either naturally occurring or man induced, either randomly or in a targeted fashion. The present invention also encompasses homologous nucleic acid sequences (e.g., which form a part of a polynucleotide sequence of the present invention), which include sequence regions unique to the polynucleotides of the present invention.

The present invention also encompasses nucleic acids encoding homologues of NPC-1 epitope peptidomimetics, such homologues can be at least about 80%, 81%, 82%, 83%, 84%, 85%, 86%, 87%, 88%, 89%, 90%, 91%, 92%, 93%, 94%, 95%, 96%, 97%, 98%, 99%, 99.5%, 99.8%, 99.9%, or 100% identical homologous to the amino acid sequences set forth herein, as may be determined using BlastP software of the National Center of Biotechnology Information (NCBI) using default parameters. The present invention also encompasses fragments of the above described polynucleotides and polypeptides having mutations, such as deletions, insertions or substitutions of one or more nucleic acids, either naturally occurring or man induced, either randomly or in a targeted fashion.

Nucleic acid molecules may encode a NPC-1 epitope peptidomimetic of said nucleic acid molecule. A "functional fragment" of said nucleic acid includes a fragment of the gene or cDNA encoding said NPC-1 epitope peptidomimetic, which fragment is capable of being expressed to produce a NPC-1 epitope capable of eliciting an immune response (e.g., antibodies which selectively bind the NPC-1 epitope) Thus, for example, fragments of the NPC-1 epitope peptidomimetic according to the invention which correspond to amino acid residues that contribute to the immunogenicity of the antigen and which fragments may serve to function as antigens to elicit an immune response (e.g., Immoral or cellular immune response.) This aspect of the invention also includes differentially spliced isoforms and transcriptional starts of the nucleic acids according to the invention. The nucleic acid molecules according to the invention also comprise fragments, derivatives and allelic variants of the nucleic acid molecules described above that encodes a NPC-1 epitope peptidomimetic according to the invention. Methods and materials for making nucleic acids encoding fragments of NPC-1 epitope peptidomimetics are well known in the art. See, e.g., Maniatis, et al. (2001) *Molecular Cloning: A Laboratory Manual* [$3^{rd}$ Ed.] Cold Spring Harbor Laboratory Press.

Furthermore, identity refers broadly to the that functional and/or structural equivalence that exists between the nucleic acid molecules concerned or the proteins coded by them. The nucleic acid molecules, which are homologous to the molecules described above and constitute derivatives of these molecules, are generally variations of these molecules, which constitute modifications, which execute the same biological function. At the same time, the variations may occur naturally, for example they may be sequences from other species, or they may be mutants, wherein these mutants may have occurred in a natural manner or have been introduced by objective mutagenesis. The variations may also be synthetically manufactured sequences. The allelic variants may be both naturally occurring variants and also synthetically manufactured variants or variants produced by recombinant DNA techniques. Nucleic acid molecules, which deviate from nucleic acid molecules according to the invention due to degeneration of the genetic code, constitute a special form of derivatives.

Included also within the scope of the invention is any nucleotide sequence that encodes the amino acid sequence of NPC-1 epitope peptidomimetics thereof. Because the genetic code is degenerate, more than one codon may be used to encode a particular amino acid. Using the genetic code, one or more different nucleotides may be identified, each of which would be capable of encoding the amino acid. The probability that a particular nucleotide will, in fact, constitute the actual codon encoding sequence may be estimated by considering abnormal base pairing relationships and the frequency with which a particular codon is actually used (to encode a particular amino acid) in eukaryotic or prokaryotic cells expressing a NPC-1 epitope peptidomimetic thereof. Such "codon usage rules" are disclosed by Lathe, et al. (1985) *J. Molec. Biol.* 183: 1-12.

Modified NPC-1 Epitope Peptidomimetics

The nucleotides of the present invention may be modified polynucleotides. Unmodified nucleotide are often less optimal in some applications, e.g., prone to degradation by cellular nucleases. Chemical modifications to one or more of the subunits of oligonucleotide may confer improved properties, e.g., may render polynucleotides more stable to nucleases. Typical oligonucleotide modifications are well-known in the art and may include one or more of: (i) alteration, e.g., replacement, of one or both of the non-linking phosphate oxygens and/or of one or more of the linking phosphate oxygens in the phosphodiester intersugar linkage; (ii) alteration, e.g., replacement, of a constituent of the ribose sugar, e.g., of the modification or replacement of the 2' hydroxyl on the ribose sugar; (iii) wholesale replacement of the phosphate moiety; (iv) modification or replacement of a naturally occurring base with a non-natural base; (v) replacement or modification of the ribose-phosphate backbone, e.g. with peptide nucleic acid (PNA); (vi) modification of the 3' end or 5' end of the oligonucelotide; and (vii) modification of the sugar, e.g., six membered rings. Polynucleotides used in accordance with this invention may be synthesized by any number of means well-known in the art, or purchased from a variety of commercial vendors (LC Sciences, Houston, Tex.; Promega, Madison, Wis.; Invitrogen, Carlsbad, Calif.).

Isolation and expression of the NPC-1 epitope peptidomimetic, or fragments and variants thereof, of the invention may be effected by well-established cloning procedures using probes or primers constructed based on the NPC-1 epitope peptidomimetic nucleic acids sequences disclosed in the application. Related NPC-1 epitope peptidomimetic sequences may also be identified from human or other species genomic databases using the sequences disclosed herein and known computer-based search technologies, e.g., BLAST sequence searching. The pseudogenes disclosed herein may be used to identify functional alleles or related genes.

Expression vectors can then be used to infect or transfect host cells for the functional expression of these sequences. These genes and vectors can be made and expressed in vitro or in vivo. One of skill will recognize that desired phenotypes for altering and controlling nucleic acid expression can be obtained by modulating the expression or activity of the genes and nucleic acids (e.g., promoters, enhancers) within the vectors of the invention. Any of the known methods described for increasing or decreasing expression or activity can be used.

The polynucleotide sequences provided herein may be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the polynucleotides is well within the capabilities of one skilled in the art. See, e.g., Maniatis, et al. (2001) *Molecular*

*Cloning: A Laboratory Manual* [3rd Ed.] Cold Spring Harbor Laboratory Press; Swamy (2008) *Laboratory Manual on Biotechnology* Rastogi Publications; Herdewijn (2005) [Ed.] *Methods in Molecular Biolog: Oligonucleotide Synthesis: Methods and Applications* Volume 288 Humana Press; and Rapley (2000) [Ed.] *The Nucleic Acid Protocols Handbook* Humana Press. Double-stranded DNA fragments may then be obtained either by synthesizing the complementary strand and annealing the strands together under appropriate conditions, or by adding the complementary strand using DNA polymerase with an appropriate primer sequence.

Techniques for the manipulation of nucleic acids, such as, for example, for generating mutations in sequences, subcloning, labeling probes, sequencing, hybridization are well described in the scientific and patent literature. See, e.g., Sambrook, et al. (2001) (Eds.) *Molecular Cloning: A Laboratory Manual* (3rd Ed.) Cold Spring Harbor Laboratory; Ausubel, et al. (2011) Ed., *Current Protocols in Molecular Biology*, John Wiley & Sons, Inc., New York; Tijssen (1993) [Ed.] *Laboratory Techniques in Biochemistry and Molecular Biology: Hybridization With Nucleic Acid Probes, Part I, Theory and Nucleic Acid Preparation*, Elsevier, N.Y.

Hybridization and the strength of hybridization (e.g., the strength of the association between polynucleotides) is impacted by many factors well known in the art including the degree of complementarity between the polynucleotides, and the stringency of the conditions involved, which is affected by such conditions as the concentration of salts, the presence of other components (e.g., the presence or absence of polyethylene glycol), the molarity of the hybridizing strands and the G+C content of the polynucleotide strands, all of which results in a characteristic melting temperature ($T_m$) of the formed hybrid. Techniques of nucleic acid hybridization are disclosed by Sambrook, et al. (2001) (Eds.) *Molecular Cloning: A Laboratory Manual* [3[Td] Ed.] Cold Spring Harbor Laboratory, and by Haymes, et al. (1985) in *NUCLEIC ACID HYBRIDIZATION, A PRACTICAL APPROACH* (IRL Press, DC). Hybridization wash conditions may include wash solution of 0.2×SSC/0.1% SDS and incubation with rotation for 10 minutes at room temperature, (low stringency wash), wash solution of prewarmed (42° C.) 0.2×SSC/0.1% SDS and incubation with rotation for 15 minutes at 42° C. (medium stringency wash) and wash solution of prewarmed (68° C.) 0.1×SSC/0.1% SDS and incubation with rotation for 15 minutes at 68° C. (high stringency wash). See Ausubel, et al. (2011) [Ed.] *Current Protocols in Molecular Biology* John Wiley & Sons, Inc.

Oligonucleotide primers may be used to amplify nucleic acids encoding a NPC-1 epitope peptidomimetics. The nucleic acids described herein can also be cloned or measured quantitatively using amplification techniques. Amplification methods are also well known in the art, and include, e.g., polymerase chain reaction (PCR) (Innis (1990) [Ed.] *PCR Protocols. a Guide to Methods and Applications*, Academic Press, NY.; Innis (1995) [Ed.] *PCR Strategies*, Academic Press, inc., NY.); ligase chain reaction (LCR) (Wu (1989) *Genomics* 4: 560; Landegren (1988) *Science* 241: 1077; Barringer (1990) *Gene* 89: 117); transcription amplification (Kwoh (1989) *PNAS* 86: 1173); self-sustained sequence replication (Guatelli (1990) *PNAS* 87: 1874); Q Beta replicase amplification (Smith (1997) *J. Clin. Microbiol.* 35: 1477-91)); automated Q-beta replicase amplification assay (Burg (1996) *Mol. Cell. Probes* 10: 257-71); and other RNA polymerase mediated techniques (e.g., NASBA, Cangene, Mississauga, Ontario). See, also, Berger (1987) *Methods Enzymol.* 152: 307-16; Sambrook, et al. (2001) (Eds.) *Molecular Cloning: A Laboratory Manual* (3rd Ed.) Cold Spring Harbor Laboratory; Ausubel, et al. (2011) [Ed.] *Current Protocols in Molecular Biology*, John Wiley & Sons, Inc., New York; Maniatis, et al. (2001) *Molecular Cloning: A Laboratory Manual* [3rd Ed.] Cold Spring Harbor Laboratory Press; U.S. Pat. Nos. 4,683,195 and 4,683,202; Sooknanan (1995) *Biotechnology* 13: 563-64.

Paradigms to design degenerate primer pairs are well known in the art. For example, a Consensus Degenerate Hybrid Oligonucleotide Primer (CODEHOP) strategy computer program is readily accessible and is directly linked from the BlockMaker multiple sequence alignment site for hybrid primer prediction beginning with a set of related protein sequences, such as the NPC-1 epitope peptidomimetic sequences provided herein. See, e.g., Rose (1998) *Nucleic Acids Res.* 26: 1628-35; Singh (1998) *Biotechniques* 24: 318-19.

Polymorphic variants, alleles, and interspecies homologs that are substantially identical to NPC-1 epitopes disclosed herein may be isolated using the nucleic acid probes described above. Alternatively, expression libraries can be used to clone NPC-1 epitope peptidomimetics and polymorphic variants, alleles, and interspecies homologs thereof, by detecting expressed homologs immunologically with antisera or purified antibodies made against a NPC-1 epitope peptidomimetic, which also recognize and selectively bind to the NPC-1 epitope peptidomimetic homolog.

Nucleic acids that encode NPC-1 epitope peptidomimetics may be generated by amplification (e.g., PCR) of appropriate nucleic acid sequences using appropriate (perfect or degenerate) primer pairs. The amplified nucleic acid can be genomic DNA from any cell or tissue or mRNA or cDNA derived from NPC-1 expressing cells. Methods for expression of heterologous sequences in host cells are well known in the art. See, e.g., Maniatis, et al. (2001) *Molecular Cloning: A Laboratory Manual* [3rd Ed.] Cold Spring Harbor Laboratory Press.

Fusion Proteins Comprising a NPC-1 Epitope Peptidomimetics

Hybrid protein-coding sequences comprising nucleic acids encoding NPC-1 epitope peptidomimetics fused to a translocation sequences may be constructed. Also provided are hybrid NPC-1 epitopes comprising the motifs and antigenic regions. These nucleic acid sequences may be operably linked to transcriptional or translational control elements, e.g., transcription and translation initiation sequences, promoters and enhancers, transcription and translation terminators, polyadenylation sequences, and other sequences useful for transcribing DNA into RNA. In construction of recombinant expression cassettes, vectors, and transgenics, a promoter fragment can be employed to direct expression of the desired nucleic acid in all desired cells or tissues.

Fusion proteins may comprise C-terminal or N-terminal translocation sequences. Further, fusion proteins can comprise additional elements, e.g., for protein detection, purification, or other applications. Detection and purification facilitating domains include, e.g., metal chelating peptides such as polyhistidine tracts, histidine-tryptophan modules, or other domains that allow purification on immobilized metals; maltose binding protein; protein A domains that allow purification on immobilized immunoglobulin; or the domain utilized in the FLAGS extension/affinity purification system (Immunex Corp, Seattle Wash.)

The inclusion of a cleavable linker sequences such as Factor Xa (see, e.g., Ottavi, (1998) *Biochimie* 80: 289-93), subtilisin protease recognition motif (see, e.g., Polyak (1997) *Protein Eng.* 10: 615-19); enterokinase (Invitrogen, San Diego, Calif.), between the translocation domain (for efficient plasma membrane expression) and the rest of the newly translated polypeptide may be useful to facilitate purification. For example, one construct can include a polypeptide encoding a nucleic acid sequence linked to six histidine residues followed by a thioredoxin, an enterokinase cleavage site (see, e.g., Williams (1995) *Biochemistry* 34: 1787-97), and an C-terminal translocation domain. The histidine residues facilitate detection and purification while the enterokinase cleavage site provides a means for purifying the desired protein(s) from the remainder of the fusion protein. Technology pertaining to vectors encoding fusion proteins and application of fusion proteins are well described in the scientific and patent literature. See, e.g., Kroll (1993) *DNA Cell. Biol.* 12: 441-53.

Systems for Recombinant Expression of the NPC-1 Epitope Peptidomimetics

Expression vectors, either as individual expression vectors or as libraries of expression vectors, comprising the ligand-binding region encoding sequences may be introduced into a genome or into the cytoplasm or a nucleus of a cell and expressed by a variety of conventional techniques, well described in the scientific and patent literature. See, e.g., Sambrook, et al. (2001) [Eds.] *Molecular Cloning: A Laboratory Manual* ($3^{rd}$ Ed.) Cold Spring Harbor Laboratory; Ausubel, et al. (2011) [Ed.] *Current Protocols in Molecular Biology* John Wiley & Sons, Inc.

The nucleic acids can be expressed in expression cassettes, vectors or viruses which are stably or transiently expressed in cells (e.g., episomal expression systems). Selection markers can be incorporated into expression cassettes and vectors to confer a selectable phenotype on transformed cells and sequences. For example, selection markers can code for episomal maintenance and replication such that integration into the host genome is not required. For example, the marker may encode antibiotic resistance (e.g., chloramphenicol, kanamycin, G418, bleomycin, hygromycin) or herbicide resistance (e.g., chlorosulfurone or Basta) to permit selection of those cells transformed with the desired DNA sequences. See, e.g., Ausubel, et al. (2011) [Ed.] *Current Protocols in Molecular Biology* John Wiley & Sons, Inc.; and Walker & Papley (2009) *Molecular Biology and Biotechnology* [$5^{th}$ Ed.] Royal Society of Chemistry. Because selectable marker genes conferring resistance to substrates like neomycin or hygromycin can only be utilized in tissue culture, chemoresistance genes are also used as selectable markers in vitro and in vivo.

To enable cellular expression of the polynucleotides of the present invention, a nucleic acid construct according to the present invention may be used, which includes at least a coding region of one of the above nucleic acid sequences, and further includes at least one cis acting regulatory element. Preferably, the promoter utilized by the nucleic acid construct of the present invention is active in the specific cell population transformed. Examples of cell type-specific and/or tissue-specific promoters are well-known in the art. See Bernardi (2003) [Ed.] *Gene Transfer and Expression in Mammalian Cells* Volume 38 Elsevier Science B.V. The nucleic acid construct of the present invention can further include an enhancer, which can be adjacent or distant to the promoter sequence and can function in up regulating the transcription therefrom.

The nucleic acid construct of the present invention preferably further includes an appropriate selectable marker and/or an origin of replication. Preferably, the nucleic acid construct utilized is a shuttle vector, which can propagate both in *E. coli* (wherein the construct comprises an appropriate selectable marker and origin of replication) and be compatible for propagation in cells, or integration in a gene and a tissue of choice. The construct according to the present invention can be, for example, a plasmid, a bacmid, a phagemid, a cosmid, a phage, a virus or an artificial chromosome.

Examples of suitable constructs include, but are not limited to, pcDNA3, pcDNA3.1 (+/−), pGL3, PzeoSV2 (+/−), pDisplay, pEF/myc/cyto, pCMV/myc/cyto each of which is commercially available from Invitrogen Co. (Carlsbad, Calif.) Examples of retroviral vector and packaging systems are those sold by Clontech (San Diego, Calif.), including Retro-X vectors pLNCX and pLXSN, which permit cloning into multiple cloning sites and the transgene is transcribed from CMV promoter. Vectors derived from Mo-MuLV are also included such as pBabe, where the transgene will be transcribed from the 5' LTR promoter.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to includes promoters, enhancers and other expression control elements (e.g., polyadenylation signals). Such regulatory sequences are described, for example, in Goeddel (1990) *Gene Expression Technology: Methods in Enzymology* 185, Academic Press, San Diego, Calif. Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired. The expression vectors of the invention can be introduced into host cells to thereby produce proteins or peptides, including fusion proteins or peptides, encoded by nucleic acids as described herein.

The recombinant expression vectors of the invention may be designed for production of variant proteins in prokaryotic or eukaryotic cells. For example, proteins of the invention can be expressed in bacterial cells such as *Escherichia coli*, insect cells (e.g., using baculovirus expression vectors), yeast cells, or mammalian cells. Suitable host cells are discussed further in Goeddel (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, to the amino or C terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin, PreScission, TEV and enterokinase. Typical fusion expression vectors include pGEX (Pharmacia Biotech Inc; Smith and Johnson (1988) *Gene* 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

The recombinant mammalian expression vector is capable of directing expression of the nucleic acid may be in a particular cell type (e.g., tissue-specific regulatory elements are used to express the nucleic acid). Tissue-specific regulatory elements are known in the art. For efficient production of the protein, it is preferable to place the nucleotide sequences encoding the protein of the invention under the control of expression control sequences optimized for expression in a desired host. For example, the sequences may include optimized transcriptional and/or translational regulatory sequences (e.g., altered Kozak sequences).

One strategy to maximize recombinant protein expression in *E. coli* is to express the protein in a host bacterium with an impaired capacity to proteolytically cleave the recombinant protein. See, e.g., Gottesman (1990) *Gene Expression Technology: Methods in Enzymology* Academic Press, San Diego, Calif. 185: 119-128. Another strategy is to alter the nucleic acid sequence of the nucleic acid to be inserted into an expression vector so that the individual codons for each amino acid are those preferentially utilized in *E. coli*. See, e.g., Wada, et al. (1992) *Nucl. Acids Res.* 20: 2111-2118. Such alteration of nucleic acid sequences of the invention can be carried out by standard DNA synthesis techniques. Another strategy to solve codon bias is by using BL21-codon plus bacterial strains (Invitrogen) or Rosetta bacterial strain (Novagen), these strains contain extra copies of rare *E. coli* tRNA genes.

The expression vector encoding for the protein of the invention may be a yeast expression vector. Examples of vectors for expression in yeast *Saccharomyces cerevisiae* include pYepSec1 (Baldari, et al. (1987) *EMBO J.* 6: 229-234), pMFa (Kurjan and Herskowitz (1982) *Cell* 30: 933-943), pJRY88 (Schultz, et al. (1987) *Gene* 54: 113-123), pYES2 (Invitrogen Corporation, San Diego, Calif.), and picZ (Invitrogen Corp, San Diego, Calif.)

Alternatively, polypeptides of the present invention can be produced in insect cells using baculovirus expression vectors. Baculovirus vectors available for expression of proteins in cultured insect cells (e.g., SF9 cells) include the pAc series (Smith, et al. (1983) *Mol. Cell. Biol.* 3: 2156-2165) and the pVL series (Lucklow and Summers (1989) *Virology* 170: 31-39). In yet another embodiment, a nucleic acid of the invention is expressed in mammalian cells using a mammalian expression vector. Examples of mammalian expression vectors include pCDM8 (Seed (1987) *Nature* 329: 840) and pMT2PC (Kaufman, et al. (1987) *EMBO J.* 6: 187-195), pIRESpuro (Clontech), pUB6 (Invitrogen), pCEP4 (Invitrogen) pREP4 (Invitrogen), pcDNA3 (Invitrogen). When used in mammalian cells, the expression vector's control functions are often provided by viral regulatory elements. For example, commonly used promoters are derived from polyoma, adenovirus 2, cytomegalovirus, Rous Sarcoma Virus, and simian virus 40. For other suitable expression systems for both prokaryotic and eukaryotic cells. See, e.g., Sambrook, et al. (2001) (Eds.) *Molecular Cloning: A Laboratory Manual* ($3^{rd}$ Ed.) Cold Spring Harbor Laboratory.

A host cell can be any prokaryotic or eukaryotic cell. For example, protein of the invention can be produced in bacterial cells such as *E. coli*, insect cells, yeast, plant or mammalian cells (e.g., Chinese Hamster Ovary cells (CHO), COS, HEK293 cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (2001) [Eds.] *Molecular Cloning: A Laboratory Manual* ($3^{rd}$ Ed.) Cold Spring Harbor Laboratory and other laboratory manuals.

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell. See, e.g., Sambrook, et al. (2001) (Eds.) *Molecular Cloning: A Laboratory Manual* ($3^{rd}$ Ed.) Cold Spring Harbor Laboratory and Walker & Papley (2009) *Molecular Biology and Biotechnology* [$5^{th}$ Ed.] Royal Society of Chemistry. It is only necessary that the particular genetic engineering procedure used be capable of successfully introducing at lest one nucleic acid molecule into the host cell capable of expressing the NPC-1 epitope peptidomimetic.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin, puromycin, blasticidin, and methotrexate. Nucleic acids encoding a selectable marker can be introduced into a host cell on the same vector as that encoding protein of the invention or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) protein of the invention. Accordingly, the invention further provides methods for producing proteins of the invention using the host cells of the invention. In one embodiment, the method comprises culturing the host cell of the present invention (into which a recombinant expression vector encoding protein of the invention has been introduced) in a suitable medium such that the protein of the invention is produced. In another embodiment, the method further comprises isolating protein of the invention from the medium or the host cell.

After the expression vector is introduced into the cells, the transfected cells are cultured under conditions favoring expression of the receptor, fragment, or variant of interest, which is then recovered from the culture using standard techniques. Examples of such techniques are well known in the art. See, e.g., WO 00/06593.

Labels

The NPC-1 epitope peptidomimetics described herein may be modified post-translationally to add effector moieties such as chemical linkers, detectable moieties such as for example fluorescent dyes, enzymes, substrates, bioluminescent materials, radioactive materials, chemiluminescent moieties, a cytotoxic agent, radioactive materials, or functional moieties.

A wide variety of entities, e.g., ligands, may be coupled to the oligonucleotides as known in the art. Ligands may include naturally occurring molecules, or recombinant or synthetic molecules. Exemplary ligands include, but are not limited to, avadin, biotin, peptides, peptidomimetics, polylysine (PLL), polyethylene glycol (PEG), mPEG, cationic groups, spermine, spermidine, polyamine, thyrotropin, melanotropin, lectin, glycoprotein, surfactant protein A, mucin, glycosylated polyaminoacids, transferrin, aptamer, immunoglobulins (e.g., antibodies), insulin, transferrin, albumin, sugar, lipophilic molecules (e.g., steroids, bile acids, cholesterol, cholic acid, and fatty acids), vitamin A, vitamin E, vitamin K, vitamin B, folic acid, B12, riboflavin, biotin, pyridoxal, vitamin cofactors, lipopolysaccharide, hormones and hormone receptors, lectins, carbohydrates, multivalent carbohydrates, radiolabeled markers, fluorescent dyes, and derivatives thereof. See, e.g., U.S. Pat. Nos. 6,153,737; 6,172,208; 6,300,319; 6,335,434; 6,335,437; 6,395,437; 6,444,806; 6,486,308; 6,525,031; 6,528,631; and 6,559,279.

Additionally, moieties may be added to the NPC-1 epitope peptidomimetic to increase half-life in vivo (e.g., by lengthening the time to clearance from the blood stream. Such techniques include, for example, adding PEG moieties (also termed pegilation), and are well-known in the art. See U.S. Patent Application Publication No. 2003/0031671.

An peptidomimetic, antibody or antigen binding fragment thereof, described herein may be "attached" to a substrate when it is associated with the solid label through a non-random chemical or physical interaction. The attachment may be through a covalent bond. However, attachments need not be covalent or permanent. Materials may be attached to a label through a "spacer molecule" or "linker group." Such spacer molecules are molecules that have a first portion that attaches to the biological material and a second portion that attaches to the label. Thus, when attached to the label, the spacer molecule separates the label and the biological materials, but is attached to both. Methods of attaching biological material (e.g., label) to a label are well known in the art, and include but are not limited to chemical coupling.

Detectable Labels

The NPC-1 epitope peptidomimetic described herein may be modified post-translationally to add effector labels such as chemical linkers, detectable labels such as for example fluorescent dyes, enzymes, substrates, bioluminescent materials, radioactive materials, and chemiluminescent labels, or functional labels such as for example streptavidin, avidin, biotin, a cytotoxin, a cytotoxic agent, and radioactive materials. Further exemplary enzymes include, but are not limited to, horseradish peroxidase, acetylcholinesterase, alkaline phosphatase, β-galactosidase and luciferase. Further exemplary fluorescent materials include, but are not limited to, rhodamine, fluorescein, fluorescein isothiocyanate, umbelliferone, dichlorotriazinylamine, phycoerythrin and dansyl chloride. Further exemplary chemiluminescent labels include, but are not limited to, luminol. Further exemplary bioluminescent materials include, but are not limited to, luciferin and aequorin. Further exemplary radioactive materials include, but are not limited to, bismuth-213 ($^{213}$Bs), carbon-14 ($^{14}$C), carbon-11 ($^{11}$C), chlorine-18 (Cl$^{18}$), chromium-51 ($^{51}$Cr), cobalt-57 ($^{57}$Co), cobalt-60 ($^{60}$Co), copper-64 ($^{64}$Cu), copper-67 ($^{67}$Cu), dysprosium-165 ($^{165}$Dy), erbium-169 ($^{169}$Er), fluorine-18 ($^{18}$F), gallium-67 ($^{67}$Ga), gallium-68 ($^{68}$Ga), germanium-68 ($^{68}$Ge), holmium-166 ($^{166}$Ho), indium-111 ($^{111}$In), iodine-125 ($^{125}$I), iodine-123 ($^{124}$I), iodine-124 ($^{124}$I), iodine-131 ($^{131}$I), iridium-192 ($^{192}$Ir), iron-59 ($^{59}$Fe), krypton-81 ($^{81}$Kr), lead-212 ($^{212}$Pb), lutetium-177 ($^{177}$Lu), molybdenum-99 ($^{99}$Mo), nitrogen-13 ($^{13}$N), oxygen-15 ($^{15}$O), palladium-103 ($^{103}$Pd), phosphorus-32 ($^{32}$P), potassium-42 ($^{42}$K), rhenium-186 ($^{186}$Re), rhenium-188 ($^{188}$Re), rubidium-81 ($^{81}$Rb), rubidium-82 ($^{82}$Rb), samarium-153 ($^{153}$Sm), selenium-75 ($^{75}$Se), sodium-24 ($^{24}$Na), strontium-82 ($^{82}$Sr), strontium-89 ($^{89}$Sr), sulfur 35 ($^{35}$S), technetium-99m ($^{99}$Tc), thallium-201 ($^{201}$Tl), tritium ($^{3}$H), xenon-133 ($^{133}$Xe), ytterbium-169 ($^{169}$Yb), ytterbium-177 ($^{177}$Yb), and yttrium-90 ($^{90}$Y).

Cytotoxic Agents

The NPC-1 epitope peptidomimetic described herein may be conjugated to cytotoxic agents including, but are not limited to, methotrexate, aminopterin, 6-mercaptopurine, 6-thioguanine, cytarabine, 5-fluorouracil decarbazine; alkylating agents such as mechlorethamine, thioepa chlorambucil, melphalan, carmustine (BSNU), mitomycin C, lomustine (CCNU), 1-methylnitrosourea, cyclothosphamide, mechlorethamine, busulfan, dibromomannitol, streptozotocin, mitomycin C, cis-dichlorodiamine platinum (II) (DDP) cisplatin and carboplatin (paraplatin); anthracyclines include daunorubicin (formerly daunomycin), doxorubicin (adriamycin), detorubicin, carminomycin, idarubicin, epirubicin, mitoxantrone and bisantrene; antibiotics include dactinomycin (actinomycin D), bleomycin, calicheamicin, mithramycin, and anthramycin (AMC); and antimytotic agents such as the *vinca* alkaloids, vincristine and vinblastine. Other cytotoxic agents include paclitaxel (TAXOL®), ricin, *pseudomonas* exotoxin, gemcitabine, cytochalasin B, gramicidin D, ethidium bromide, emetine, etoposide, tenoposide, colchicin, dihydroxy anthracin dione, 1-dehydrotestosterone, glucocorticoids, procaine, tetracaine, lidocaine, propranolol, puromycin, procarbazine, hydroxyurea, asparaginase, corticosteroids, mytotane (O,P'-(DDD)), interferons, and mixtures of these cytotoxic agents.

Further cytotoxic agents include, but are not limited to, chemotherapeutic agents such as carboplatin, cisplatin, paclitaxel, gemcitabine, calicheamicin, doxorubicin, 5-fluorouracil, mitomycin C, actinomycin D, cyclophosphamide, vincristine, bleomycin, VEGF antagonists, EGFR antagonists, platins, taxols, irinotecan, 5-fluorouracil, gemcytabine, leucovorine, steroids, cyclophosphamide, melphalan, *vinca* alkaloids (e.g., vinblastine, vincristine, vindesine and vinorelbine), mustines, tyrosine kinase inhibitors, radiotherapy, sex hormone antagonists, selective androgen receptor modulators, selective estrogen receptor modulators, PDGF antagonists, TNF antagonists, IL-1 antagonists, interleukins (e.g. IL-12 or IL-2), IL-12R antagonists, Toxin conjugated monoclonal antibodies, tumor antigen specific monoclonal antibodies, Erbitux®, Avastin®, Pertuzumab, anti-CD20 antibodies, Rituxan®, ocrelizumab, ofatumumab, DXL625, Herceptin®, or any combination thereof. Toxic enzymes from plants and bacteria such as ricin, diphtheria toxin and *Pseudomonas* toxin may be conjugated to the humanized antibodies, or binding fragments thereof, to generate cell-type-specific-killing reagents. Youle, et al. (1980) *Proc. Nat'l Acad. Sci. USA* 77: 5483; Gilliland, et al. (1980) *Proc. Nat'l Acad. Sci. USA* 77: 4539; Krolick, et al. (1980) *Proc. Nat'l Acad. Sci. USA* 77: 5419. Other cytotoxic agents include cytotoxic ribonucleases. See U.S. Pat. No. 6,653,104.

The NPC-1 epitope peptidomimetics described herein may be conjugated to a radionuclide that emits alpha or beta particles (e.g., radioimmunoconjuagtes). Such radioactive isotopes include but are not limited to beta-emitters such as phosphorus-32 ($^{32}P$), scandium-47 ($^{47}Sc$), copper-67 ($^{67}Cu$), gallium-67 ($^{67}Ga$), yttrium-88 ($^{88}Y$), yttrium-90 ($^{90}Y$), iodine-125 ($^{125}I$), iodine-131 ($^{131}I$), samarium-153 ($^{153}Sm$), lutetium-177 ($^{177}Lu$), rhenium-186 ($^{186}Re$), rhenium-188 ($^{188}Re$), and alpha-emitters such as astatine-211 ($^{211}At$), lead-212 ($^{212}Pb$), bismuth-212 ($^{212}Bi$), bismuth-213 ($^{213}Bi$) or actinium-225 ($^{225}Ac$).

Methods are known in the art for conjugating a NPC-1 epitope peptidomimetics described herein to a label, such as those methods described by Hunter, et al (1962) *Nature* 144: 945; David, et al. (1974) *Biochemistry* 13: 1014; Pain, et al. (1981) *J. Immunol. Meth.* 40: 219; and Nygren (1982) *Histochem, and Cytochem,* 30: 407.

Substrates

The NPC-1 epitope peptidomimetics described herein may be attached to a substrate. A number of substrates (e.g., solid supports) known in the art are suitable for use with the NPC-1 epitope peptidomimetics described herein. The substrate may be modified to contain channels or other configurations. See Fung (2004) [Ed.] *Protein Arrays: Methods and Protocols* Humana Press and Kambhampati (2004) [Ed.] *Protein Microarray Technology* John Wiley & Sons.

Substrate materials include, but are not limited to acrylics, agarose, borosilicate glass, carbon (e.g., carbon nanofiber sheets or pellets), cellulose acetate, cellulose, ceramics, gels, glass (e.g., inorganic, controlled-pore, modified, soda-lime, or functionalized glass), latex, magnetic beads, membranes, metal, metalloids, nitrocellulose, NYLON®, optical fiber bundles, organic polymers, paper, plastics, polyacryloylmorpholide, poly(4-methylbutene), poly(ethylene terephthalate), poly(vinyl butyrate), polyacrylamide, polybutylene, polycarbonate, polyethylene, polyethyleneglycol terephthalate, polyformaldehyde, polymethacrylate, polymethylmethacrylate, polypropylene, polysaccharides, polystyrene, polyurethanes, polyvinylacetate, polyvinylchloride, polyvinylidene difluoride (PVDF), polyvinylpyrrolidinone, rayon, resins, rubbers, semiconductor materials, SEPHAROSE®, silica, silicon, styrene copolymers, TEFLON®, and variety of other polymers.

Substrates need not be flat and can include any type of shape including spherical shapes (e.g., beads) or cylindrical shapes (e.g., fibers). Materials attached to solid supports may be attached to any portion of the solid support (e.g., may be attached to an interior portion of a porous solid support material).

The substrate body may be in the form of a bead, box, column, cylinder, disc, dish (e.g., glass dish, PETRI dish), fiber, film, filter, microtiter plate (e.g., 96-well microtiter plate), multi-bladed stick, net, pellet, plate, ring, rod, roll, sheet, slide, stick, tray, tube, or vial. The substrate may be a singular discrete body (e.g., a single tube, a single bead), any number of a plurality of substrate bodies (e.g., a rack of 10 tubes, several beads), or combinations thereof (e.g., a tray comprises a plurality of microtiter plates, a column filled with beads, a microtiter plate filed with beads).

A NPC-1 epitope peptidomimetic may be "attached" to a substrate when it is associated with the solid substrate through a non-random chemical or physical interaction. The attachment may be through a covalent bond. However, attachments need not be covalent or permanent. Materials may be attached to a substrate through a "spacer molecule" or "linker group." Such spacer molecules are molecules that have a first portion that attaches to the biological material and a second portion that attaches to the substrate. Thus, when attached to the substrate, the spacer molecule separates the substrate and the biological materials, but is attached to both. Methods of attaching biological material (e.g., label) to a substrate are well known in the art, and include but are not limited to chemical coupling.

Plates, such as microtiter plates, which support and contain the solid-phase for solid-phase synthetic reactions may be used. Microtiter plates may house beads that are used as the solid-phase. By "particle" or "microparticle" or "nanoparticle" or "bead" or "microbead" or "microsphere" herein is meant microparticulate matter having any of a variety of shapes or sizes. The shape may be generally spherical but need not be spherical, being, for example, cylindrical or polyhedral. As will be appreciated by those in the art, the particles may comprise a wide variety of materials depending on their use, including, but not limited to, cross-linked starch, dextrans, cellulose, proteins, organic polymers including styrene polymers such as polystyrene and methylstyrene as well as other styrene co-polymers, plastics, glass, ceramics, acrylic polymers, magnetically responsive materials, colloids, thoriasol, carbon graphite, titanium dioxide, nylon, latex, and TEFLON®. See e.g., "Microsphere Detection Guide" from Bangs Laboratories, Fishers, Ind.

The NPC-1 epitope peptidomimetics described herein may be attached to on any of the forms of substrates described herein (e.g., bead, box, column, cylinder, disc, dish (e.g., glass dish, PETRI dish), fiber, film, filter, microtiter plate (e.g., 96-well microtiter plate), multi-bladed stick, net, pellet, plate, ring, rod, roll, sheet, slide, stick, tray, tube, or vial). In particular, particles or beads may be a component of a gelling material or may be separate components such as latex beads made of a variety of synthetic plastics (e.g., polystyrene). The label (e.g., streptavidin) may be bound to a substrate (e.g., bead).

Pharmaceutical Compositions

A "pharmaceutical composition" refers to a chemical or biological composition suitable for administration to a mammal. Such compositions may be specifically formulated for administration via one or more of a number of routes, including but not limited to buccal, epicutaneous, epidural, inhalation, intraarterial, intracardial, intracerebroventricular, intradermal, intramuscular, intranasal, intraocular, intraperitoneal, intraspinal, intrathecal, intravenous, oral, parenteral, rectally via an enema or suppository, subcutaneous, subdermal, sublingual, transdermal, and transmucosal. In addition, administration may occur by means of injection, powder, liquid, gel, drops, or other means of administration.

A "pharmaceutical excipient" or a "pharmaceutically acceptable excipient" is a carrier, usually a liquid, in which an active therapeutic agent is formulated. In one embodiment of the invention, the active therapeutic agent is a humanized antibody described herein, or one or more fragments thereof. The excipient generally does not provide any pharmacological activity to the formulation, though it may provide chemical and/or biological stability, and release characteristics. Exemplary formulations may be found, for example, in Grennaro (2005) [Ed.] *Remington: The Science and Practice of Pharmacy* [$21^{st}$ Ed.]

Pharmaceutical compositions typically must be sterile and stable under the conditions of manufacture and storage. The invention contemplates that the pharmaceutical composition is present in lyophilized form. The composition may be formulated as a solution, microemulsion, liposome, or other ordered structure suitable to high drug concentration. The carrier may be a solvent or dispersion medium containing, for example, water, ethanol, polyol (for example, glycerol, propylene glycol, and liquid polyethylene glycol), and suitable mixtures thereof. The invention further contemplates the inclusion of a stabilizer in the pharmaceutical composition.

The NPC-1 epitope peptidomimetics described herein may be formulated into pharmaceutical compositions of various dosage forms. To prepare the pharmaceutical compositions of the invention, at least one NPC-1 epitope peptidomimetic as the active ingredient may be intimately mixed with appropriate carriers and additives according to techniques well known to those skilled in the art of pharmaceutical formulations. See Grennaro (2005) [Ed.] *Remington: The Science and Practice of Pharmacy* [21$^{st}$ Ed.] For example, the NPC-1 epitope peptidomimetics described herein may be formulated in phosphate buffered saline pH 7.2 and supplied as a 5.0 mg/mL clear colorless liquid solution.

Similarly, compositions for liquid preparations include solutions, emulsions, dispersions, suspensions, syrups, and elixirs, with suitable carriers and additives including but not limited to water, alcohols, oils, glycols, preservatives, flavoring agents, coloring agents, and suspending agents. Typical preparations for parenteral administration comprise the active ingredient with a carrier such as sterile water or parenterally acceptable oil including but not limited to polyethylene glycol, polyvinyl pyrrolidone, lecithin, *arachis* oil or sesame oil, with other additives for aiding solubility or preservation may also be included. In the case of a solution, it may be lyophilized to a powder and then reconstituted immediately prior to use. For dispersions and suspensions, appropriate carriers and additives include aqueous gums, celluloses, silicates, or oils.

For each of the recited embodiments, NPC-1 epitope peptidomimetics may be administered by a variety of dosage forms. Any biologically-acceptable dosage form known to persons of ordinary skill in the art, and combinations thereof, are contemplated. Examples of such dosage forms include, without limitation, reconstitutable powders, elixirs, liquids, solutions, suspensions, emulsions, powders, granules, particles, microparticles, dispersible granules, cachets, inhalants, aerosol inhalants, patches, particle inhalants, implants, depot implants, injectables (including subcutaneous, intramuscular, intravenous, and intradermal), infusions, and combinations thereof.

In many cases, it will be preferable to include isotonic agents, e.g., sugars, polyalcohols such as mannitol, sorbitol, or sodium chloride in the composition. Prolonged absorption of the injectable compositions may be brought about by including in the composition an agent which delays absorption, e.g., monostearate salts and gelatin. Moreover, the compounds described herein may be formulated in a time release formulation, e.g. in a composition that includes a slow release polymer. The NPC-1 epitope peptidomimetics may be prepared with carriers that will protect the compound against rapid release, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

Optionally, adjuvants may also be included in a composition. Adjuvants which may be used include, but are not limited to: (1) aluminum salts (alum), such as aluminum hydroxide, aluminum phosphate, aluminum sulfate, etc.; (2) oil-in-water emulsion formulations (with or without other specific immunostimulating agents; (3) saponin adjuvants, such as QS21 may be used or particles generated therefrom such as ISCOMs (immunostimulating complexes); (4) Complete Freund's Adjuvant (CFA) and Incomplete Freund's Adjuvant (IFA); (5) cytokines, such as interleukins (IL-1, IL-2, IL-4, IL-5, IL-6, IL-7, IL-12, interferons (e.g., gamma interferon), macrophage colony stimulating factor (M-CSF), tumor necrosis factor (TNF); (6) detoxified mutants of a bacterial ADP-ribosylating toxin such as a cholera toxin (CT), a pertussis toxin (PT), or an *E. coli* heat-labile toxin (LT); (7) MPL or 3-O-deacylated MPL (3dMPL); (8) combinations of 3dMPL with, for example, QS21 and/or oil-in-water emulsions; (9) oligonucleotides comprising CpG motifs; (10) a polyoxyethylene ether or a polyoxyethylene ester; (11) a polyoxyethylene sorbitan ester surfactant in combination with an octoxynol or a polyoxyethylene alkyl ether or ester surfactant in combination with at least one additional non-ionic surfactant such as an octoxynol; (12) a saponin and an immunostimulatory oligonucleotide such as a CpG oligonucleotide; (13) an immunostimulant and a particle of metal salt; and (14) other substances that act as immunostimulating agents to enhance the effectiveness of the composition.

As described herein, an antigenic composition may elicit an "immunological response" to an antigen or composition is the development in a subject of a humoral and/or a cellular immune response to an antigen present in the composition of interest. For purposes of the present invention, a "humoral immune response" refers broadly to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of nonspecific effecter cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T lymphocytes can be generated to allow for the future protection of an immunized host.

The ability of a particular immunogen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. Methods of measuring cell-mediated immune response include measurement of intracellular cytokines or cytokine secretion by T-cell populations, or by measurement of epitope specific T-cells.

Accordingly, the term "immunogenic composition" as used herein refers broadly a composition that comprises an antigenic molecule where administration of the composition to a subject results in the development in the subject of a humoral and/or a cellular immune response to the antigenic molecule of interest. The immunogenic composition may be introduced directly into a recipient subject, such as by injection, inhalation, oral, intranasal and mucosal (e.g., intra-rectally or intra-vaginally) administration.

For example, the composition may be an antigenic composition or an immunogenic composition. The compositions described herein may comprise at least one excipient, carrier, or adjuvant. Further, the compositions described herein may be a pharmaceutical composition. In still another embodiment, the composition is comprises a pharmaceutical carrier. In a further embodiment, the composition may elicit an immune response. In another embodiment, the immune response may be a protective immune response. In one embodiment, the composition may elicit a humoral immune response, wherein said humoral immune response may be specific for the NPC-1 epitope. In one embodiment, the composition may elicit a cellular immune response, wherein said cellular immune response may be specific for the NPC-1 epitope. For example, an antigenic composition comprising an NPC-1 epitope pepitomimetic may be administered to a mammal which elicits an immune response including the production of antibodies which selectively bind the NPC-1 epitope. These antibodies which selectively bind the NPC-1 epitope may, in turn, act to bind to and trigger the immunogical clearance (e.g., lysis) of tumor cells expressing an NPC-1 epitope.

A person of skill in the art would be able to determine an effective dosage and frequency of administration through routine experimentation, for example guided by the disclosure herein and the teachings in Goodman, et al. (2011) *Goodman & Gilman's The Pharmacological Basis of Therapeutics* [$12^{th}$ Ed.]; Howland, et al. (2005) *Lippincott's Illustrated Reviews: Pharmacology* [$2^{nd}$ Ed.]; and Golan, (2008) *Principles of Pharmacology: The Pathophysiologic Basis of Drug Therapy* [$2^{nd}$ Ed.] See, also, Grennaro (2005) [Ed.] *Remington: The Science and Practice of Pharmacy* [$21^{st}$ Ed.]

Routes of Administration

The compositions described herein may be administered in any of the following routes: buccal, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. The preferred routes of administration are intravenous injection or infusion. The administration can be local, where the composition is administered directly, close to, in the locality, near, at, about, or in the vicinity of, the site(s) of disease, e.g., tumor, or systemic, wherein the composition is given to the patient and passes through the body widely, thereby reaching the site(s) of disease. Local administration (e.g., injection) may be accomplished by administration to the cell, tissue, organ, and/or organ system, which encompasses and/or is affected by the disease, and/or where the disease signs and/or symptoms are active or are likely to occur (e.g., tumor site). Administration can be topical with a local effect, composition is applied directly where its action is desired (e.g., tumor site).

For each of the recited embodiments, the compounds can be administered by a variety of dosage forms as known in the art. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, gum, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, and combinations thereof.

Other compounds which can be included by admixture are, for example, medically inert ingredients (e.g., solid and liquid diluent), such as lactose, dextrosesaccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration can be syrups, emulsions, solutions, or suspensions. The syrups can contain as a carrier, for example, saccharose or saccharose with glycerol and/or mannitol and/or sorbitol. The suspensions and the emulsions can contain a carrier, for example a natural gum, agar, sodium alginate, pectin, methylcellulose, carboxymethylcellulose, or polyvinyl alcohol.

In further embodiments, the present invention provides kits including one or more containers comprising pharmaceutical dosage units comprising an effective amount of one or more antibodies and fragments thereof of the present invention. Kits may include instructions, directions, labels, marketing information, warnings, or information pamphlets.

Dosages

The amount of NPC-1 epitope peptidomimetics in a therapeutic composition according to any embodiments of this invention may vary according to factors such as the disease state, age, gender, weight, patient history, risk factors, predisposition to disease, administration route, pre-existing treatment regime (e.g., possible interactions with other medications), and weight of the individual. Dosage regimens may be adjusted to provide the optimum therapeutic response. For example, a single bolus may be administered, several divided doses may be administered over time, or the dose may be proportionally reduced or increased as indicated by the exigencies of therapeutic situation.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of antibodies, and fragments thereof, calculated to produce the desired therapeutic effect in association with the required pharmaceutical carrier. The specification for the dosage unit forms of the invention are dictated by and directly dependent on the unique characteristics of the antibodies, and fragments thereof, and the particular therapeutic effect to be achieved, and the limitations inherent in the art of compounding such an antibodies, and fragments thereof, for the treatment of sensitivity in individuals. In therapeutic use for treatment of conditions in mammals (e.g., humans) for which the antibodies and fragments thereof of the present invention or an appropriate pharmaceutical composition thereof are effective, the antibodies and fragments thereof of the present invention may be administered in an effective amount. The dosages as suitable for this invention may be a composition, a pharmaceutical composition or any other compositions described herein.

The dosage may be administered as a single dose, a double dose, a triple dose, a quadruple dose, and/or a quintuple dose. The dosages may be administered singularly, simultaneously, and sequentially.

The dosage form may be any form of release known to persons of ordinary skill in the art. The compositions of the present invention may be formulated to provide immediate release of the active ingredient or sustained or controlled release of the active ingredient. In a sustained release or controlled release preparation, release of the active ingredient may occur at a rate such that blood levels are maintained within a therapeutic range but below toxic levels over an extended period of time (e.g., 4 to 24 hours). The preferred dosage forms include immediate release, extended release, pulse release, variable release, controlled release, timed release, sustained release, delayed release, long acting, and combinations thereof, and are known in the art.

It will be appreciated that the pharmacological activity of the compositions may be monitored using standard pharmacological models that are known in the art. Furthermore, it will be appreciated that the compositions comprising a NPC-1 epitope peptidomimetic may be incorporated or encapsulated in a suitable polymer matrix or membrane for site-specific delivery, or may be functionalized with specific targeting agents capable of effecting site specific delivery. These techniques, as well as other drug delivery techniques are well known in the art. Determination of optimal dosages for a particular situation is within the capabilities of those skilled in the art. See, e.g., Grennaro (2005) [Ed.] *Remington: The Science and Practice of Pharmacy* [$21^{st}$ Ed.]

Methods of Treatment

The NPC-1 epitope peptidomimetics described herein may be used in methods for treating cancer, promoting tumor regression, killing tumor cells, activating an immune response against NPC-1 epitope expressing tumor cells (e.g., cytotoxic immune response), activating dendritic cells, or activating antigen-specific immunity comprising administering an effective amount of a NPC-1 epitope peptidomimetic thereof to a subject in need thereof. Further, the NPC-1 epitope peptidomimetic described herein may be used to manufacture medicaments for use in treating cancer, promoting tumor regression, killing tumor cells, activating an immune response against NPC-1 epitope expressing tumor cells (e.g., cytotoxic immune response), activating dendritic cells, or activating antigen-specific immunity comprising an effective amount of a NPC-1 epitope peptidomimetic described herein. The NPC-1 epitope peptidomimetics described herein may be admixed with a pharmaceutically acceptable carrier to manufacture a composition for treating cancer, promoting tumor regression, killing tumor cells, activating an immune response against NPC-1 epitope expressing tumor cells (e.g., cytotoxic immune response), activating dendritic cells, or activating antigen-specific immunity comprising an effective amount of a NPC-1 epitope peptidomimetic described herein.

The cancer treated by the NPC-1 epitope peptidomimetics described herein may be lung, breast, pancreas, prostate, uterine, esophageal, colorectal, or liver cancer. The cancer may be a stage 1, 2, 3 or 4 cancer. The cancer may have metastasized. The patient may be a mammal, such as a human, suffering from cancer where tumor cells express NPC-1 epitopes, aberrant NPC-1 epitopes, and/or tumorigenesis of neoplastic cells expressing a NPC-1 epitope. The amount sufficient to inhibit or reduce the NPC-1 epitope is an amount sufficient to ameliorate the disorder, which may be monitored as a decrease in either cancer progression or tumor mass.

The patient may express detectable levels of NPC-1 epitope as detected in a tumor biopsy sample or in the blood, stool, urine or lymph fluid. See FIG. 1. Further, the patient may be at risk of cancer or a patient without symptoms. The methods described herein may be used on cells, e.g., human cells, in vitro or ex vivo. Alternatively, the method may be performed on cells present in a subject as part of an in vivo (e.g., therapeutic) protocol.

The NPC-1 epitope peptidomimetics may be admixed with additional chemotherapeutic agents, cytotoxic agent, antibodies (e.g., NEO-201 or NEO-301 monoclonal antibodies), lymphokine, or hematopoietic growth factor. The NPC-1 epitope peptidomimetics may also be administered in combination with another antibody, a lymphokine, cytotoxic agent (e.g., a moiety that inhibits DNA, RNA, or protein synthesis, a radionuclide, or ribosomal inhibiting protein, e.g., $^{212}Bi$, $^{131}I$, $^{188}Re$, $^{90}Y$, vindesine, methotrexate, adriamycin, cisplatin, pokeweed antiviral protein, *Pseudomonas* exotoxin A, ricin, diphtheria toxin, ricin A chain, or cytotoxic phospholipase enzyme), immunosuppressive agent (e.g., cyclosporine, leflunomide, methotrexate, azothiprine, mercaptopurine, dactinomycin, tacrolimus, or sirolimus) or a hematopoietic growth factor. The NPC-1 epitope peptidomimetics may be label with a chemiluminescent label, paramagnetic label (e.g., aluminum, manganese, platinum, oxygen, lanthanum, lutetium, scandium, yttrium, or gallium), an MRI contrast agent, fluorescent label, bioluminescent label, or radioactive label. In the methods described herein, the second agent may be administered simultaneously or sequentially with the antibody.

The NPC-1 epitope peptidomimetics described herein may be used in the manufacture of compositions for use in treating cancer and methods of treating cancer including but not limited to solid and soft tumors, such as esophageal carcinoma, renal cancer, cancer of breast, thyroid, spleen, uterus, kidney, colorectal, lung, prostate, testicles, gastric, pancreas, cervical, bone, skin, brain, head & neck, bladder, head and neck, liver, pancreas, melanoma, osteosarcoma, fibrosarcoma, rhabdomyosarcoma, teratocarcinoma, neuroblastoma, glioma, glioblastoma and hematological malignancies such as acute lymphocytic leukemia, chronic lymphocytic leukemia, acute myelogenous leukemia, chronic myelogenous leukemia, multiple myeloma, Hodgkin's lymphoma and Non-Hodgkin's lymphoma, and wherein the cancer is invasive or metastatic.

The invention provides for methods of treating a subject with pancreas or colon cancer comprising administering a NPC-1 epitope peptidomimetics to a subject who may be receiving secondary antihyperplastic therapy. Examples of secondary antihyperplastic therapy include chemotherapy, radiotherapy, immunotherapy, phototherapy, cryotherapy, toxin therapy, hormonal therapy, or surgery. Thus, the invention contemplates use of the methods and compositions in conjunction with standard anti-cancer therapies. The patient to be treated may be of any age. One of skill in the art will recognize the presence and development of other anticancer therapies which may be used in conjugation with the NPC-1 epitope peptidomimetics.

Determination of dose is within the level of ordinary skill in the art. The NPC-1 epitope peptidomimetics may be administered for acute treatment, over one week or less, often over a period of one to three days or may be used in chronic treatment, over several months or years. In general, a therapeutically effective amount of the NPC-1 epitope peptidomimetics is an amount sufficient to produce a clinically significant change in NPC-1 epitope shed, decreased cancer progression, or decreased tumor size.

Diagnostic Methods

The NPC-1 epitope peptidomimetics may be used in diagnostic methods for detecting the presence or absence of an NPC-1 epitope. The NPC-1 epitope peptidomimetics may be used in methods comprising (a) contacting a test sample with an antibody, or fragment thereof, that binds a NPC-1 epitope peptidomimetic, and (b) assaying for antibody-epitope complexes, wherein the presence of said epitope is indicative of a carcinoma. Further, the NPC-1 epitope peptidomimetics may be used in a method for detecting the presence of a NPC-1 epitope in a patient comprising (a) administering to said patient a labeled monoclonal antibody, or fragment thereof, that binds a NPC-1 epitope peptidomimetic and (b) detecting the presence of a NPC-1 epitope; wherein the presence of said epitope is indicative of a carcinoma. The antibody-epitope complex may be detected by Western blot, radioimmunoassay, ELISA (enzyme linked immunosorbent assay), "sandwich" immunoassay, immunoprecipitation assay, precipitation reaction, gel diffusion precipitation reaction, immunodiffusion assay, agglutination assay, complement-fixation assay, immunohistochemical assay, fluorescent immunoassay, and protein A immunoassay. The sample may be sample is a tissue biopsy, lymph, urine, cerebrospinal fluid, amniotic fluid, inflammatory exudate, blood, serum, stool, or liquid collected from the colorectal tract.

The NPC-1 epitope peptidomimetics may be used in diagnostic methods for detecting the presence or absence of an NPC-1 epitope, wherein the presence of the antigen is indicative of cancer including but not limited to lung, breast, pancreas, uterine, esophageal, colorectal, or liver cancer. The diagnostic methods may be used with patients at risk of cancer or patients without symptoms.

The antibodies which selectively bind a NPC-1 epitope peptidomimetic may be recombinant. The fragments of antibodies which selectively bind a NPC-1 epitope peptidomimetics may be a Fab, Fab', F(ab')2, Fv, CDR, paratope, or portion of an antibody that is capable of binding the antigen. The antibodies which selectively bind a NPC-1 epitope peptidomimetics may be chimeric, humanized, anti-idiotypic, single-chain, bifunctional, or co-specific. The antibodies which selectively bind a NPC-1 epitope peptidomimetics may be or fragment is conjugated to a label, including but not limited to a chemiluminescent label, paramagnetic label (e.g., aluminum, manganese, platinum, oxygen, lanthanum, lutetium, scandium, yttrium, or gallium), an MRI contrast agent, fluorescent label, bioluminescent label, or radioactive label.

Additionally, NPC-1 epitopes peptidomimetics may be attached to a solid support (e.g., bead, test tube, sheet, culture dish, or test strip) such as an array.

The method may detect colorectal polyps. The method may further comprise additional testing for the presence of tumors including but not limited to benign tumors, malignant tumors, metastatic tumors, and non-metastatic tumors. For example, the diagnostic method may detect pre-cancerous cells that express a cell marker comprising detecting a NPC-1 epitope.

The method may comprise imaging a NPC-1 epitope by positron emission tomography (PET), CCD low-light monitoring system, x-ray, CT scanning, scintigraphy, photo acoustic imaging, single photon emission computed tomography (SPECT), magnetic resonance imaging (MRI), ultrasound, paramagnetic imaging, and endoscopic optical coherence tomography.

The invention also provides a method for genetic diagnosis of a risk for cancer comprising taking a nucleic acid sample from a patient, analyzing said nucleic acid comprising comparing to cancer specific MUC5AC sequence, wherein if the patient's nucleic acid sample matches the cancer specific MUC5AC sequence, the patient is at risk for developing cancer.

The NPC-1 epitopes may be used as a cancer biomarker. Detection of the NPC-1 epitopes in a biological sample, such as a subject's serum, biopsied neoplastic cells or fecal sample, may be performed by means of antibodies that selectively bind a NPC-1 epitope peptidomimetic. For example, a biological sample (e.g., a tumor, serum or fecal sample) is obtained from a subject, then NPC-1 epitope is measured (e.g., by ELISA or PCR), and compared with corresponding samples from normal subjects. Measuring methods include any method of nucleic acid detection, for example in situ hybridization using antisense NPC-1 epitope DNA or cRNA oligonucleotide probes, ultra-high throughput sequencing, nanostring technology, microarrays, rolling circle amplification, proximity-mediated ligation, PCR, qRT-PCR ChIP, ChIP-qPCR, or NPC-1 epitope-binding antibodies. Comparatively high levels of NPC-1 epitopes indicate the presence and/or severity of pancreas or colon cancer, and may indicate metastasis or poor cancer prognosis.

The NPC-1 epitope peptidomimetics may be used in SQUID (Superconducting Quantum Interference Device) techniques for diagnostic methods. The SQUID technique comprises attaching nanoparticles of iron oxide to antibodies, which are then injected into the patient. If a tumor is present, the antibodies with conjugated nanoparticles recognize and bind to the NPC-1 epitope on tumor cells. See, e.g., Hao, et al. (2010) *Journal of Physics* 43: 474004. In a SQUID method, the patient is then surrounded with sensitive magnetic coils in a superconducting quantum interference device (SQUID). A magnetic field is generated and all of the metal nanoparticles align in one direction. When the magnetic field is broken, the nanoparticles emit an electromagnetic signal as they relax back into their original state. By measuring the strength of the signal, one may tell how many metal particles, and therefore how many tumor cells, may be present, and where in the patient the tumor cells are located. See, e.g., Shao, et al. (2010) *Beilstein Journal of Nanotechnology* 1: 142-154.

Samples and Procurement of Samples

The samples used in the methods described herein may be taken from a subject (patient) include but are not limited to a body fluid or secretion including but not limited to blood, serum, urine, plasma, prostatic fluid, seminal fluid, semen, the external secretions of the skin, respiratory, intestinal, and genitourinary tracts, tears, cerebrospinal fluid, sputum, saliva, milk, peritoneal fluid, pleural fluid, cyst fluid, secretions of the breast ductal system (and/or lavage thereof), broncho alveolar lavage, lavage of the reproductive system and lavage of any other part of the body or system in the body; samples of any organ including isolated cell(s) or tissue(s), wherein the cell or tissue can be obtained from an organ selected from, but not limited to lung, colon, ovarian and/or breast tissue; stool or a tissue sample, or any combination thereof. In some embodiments, the term encompasses samples of in vivo cell culture constituents. Prior to be subjected to the diagnostic assay, the sample can optionally be diluted with a suitable diluent.

Numerous well known tissue or fluid collection methods can be utilized to collect the biological sample from the subject in order to determine the level of DNA, RNA and/or polypeptide of the marker of interest in the subject. Examples of tissue or fluid collection methods include, but are not limited to, fine needle biopsy, needle biopsy, core needle biopsy and surgical biopsy (e.g., brain biopsy), and lavage. Regardless of the procedure employed, once a biopsy/sample is obtained the level of the marker may be determined and a diagnosis can thus be made.

Detection of NPC-1 Epitope

The invention provides a method for detecting the NPC-1 epitopes of this invention in a biological sample, comprising: contacting a biological sample with an antibody specifically recognizing a NPC-1 epitope peptidomimetic according to the present invention and detecting said interaction; wherein the presence of an interaction correlates with the presence of a NPC-1 epitope in the biological sample.

The NPC-1 epitopes described herein are non-limiting examples of markers for diagnosing a disease and/or an indicative condition. Each marker of the present invention may be used alone or in combination, for various uses, including but not limited to, prognosis, prediction, screening, early diagnosis, determination of progression, therapy selection and treatment monitoring of a cancer (e.g., pancreas, liver, colorectal, lung, or breast cancer).

The cancers that may be detected using the methods described herein include but are not limited to non-solid and solid tumors, cancer of the breast, prostate, lung, ovary, colon, uterus, stomach, cervix, liver, pancreas, and wherein the cancer may be invasive or metastatic.

Each NPC-1 epitopes of the present invention may be used alone or in combination, for various uses, including but not limited to, prognosis, prediction, screening, early diagnosis, determination of progression, therapy selection and treatment monitoring of cancers such as non-solid and solid tumors, cancer of the breast, prostate, lung, ovary, colon, uterus, stomach, cervix, liver, pancreas, and wherein the cancer may be invasive or metastatic. Such a combination may optionally comprise any subcombination of markers, and/or a combination featuring at least one other marker, for example a known marker. Furthermore, such a combination may optionally and preferably be used as described above with regard to determining a ratio between a quantitative or semi-quantitative measurement of any marker described herein to any other marker described herein, and/or any other known marker, and/or any other marker.

Markers of the present invention may optionally be used alone or in combination with known markers for lung cancer, including but not limited to CEA, CA15-3, β-2-microglobulin, CA19-9, TPA, and/or in combination with the known proteins for the variant marker as described herein.

Markers of the present invention might optionally be used alone or in combination with known markers for ovarian cancer, including but not limited to CEA, CA125 (Mucin 16), CA72-4TAG, CA-50, CA 54-61, CA-195 and CA 19-9 in combination with CA-125, and/or in combination with the known proteins for the variant marker as described herein.

Markers of the present invention might optionally be used alone or in combination with known markers for colon cancer, including but not limited to CEA, CA19-9, CA50, and/or in combination with the known proteins for the variant marker as described herein.

Typically the level of the marker in a biological sample obtained from the subject is different (i.e., increased or decreased) from the level of the same marker in a similar sample obtained from a healthy individual (examples of biological samples are described herein).

Determining the level of the same marker in normal tissues of the same origin may be effected along-side to detect an elevated expression and/or amplification and/or a decreased expression, of the marker as opposed to the normal tissues.

The present invention also provides methods, uses, devices and assays for the diagnosis of cancers such as non-solid and solid tumors, cancer of the breast, prostate, lung, ovary, colon, uterus, stomach, cervix, liver, pancreas, and wherein the cancer may be invasive or metastatic. Optionally a plurality of markers may be used with the present invention. The plurality of markers may optionally include a markers described herein, and/or one or more known markers. The plurality of markers is preferably then correlated with the disease or condition. For example, such correlation may optionally comprise determining the concentration of each of the plurality of markers, and individually comparing each marker concentration to a threshold level. Optionally, if the marker concentration is above or below the threshold level (depending upon the marker and/or the diagnostic test being performed), the marker concentration correlates with the disease or condition. Optionally and preferably, a plurality of marker concentrations correlates with the disease or condition.

Alternatively, such correlating may optionally comprise determining the concentration of each of the plurality of markers, calculating a single index value based on the concentration of each of the plurality of markers, and comparing the index value to a threshold level. Also, such correlating may optionally comprise determining a temporal change in at least one of the markers, and wherein the temporal change is used in the correlating step.

Such correlating may optionally comprise determining whether at least "X" number of the plurality of markers has a concentration outside of a predetermined range and/or above or below a threshold (as described above). The value of "X" may optionally be one marker, a plurality of markers or all of the markers; alternatively or additionally, rather than including any marker in the count for "X", one or more specific markers of the plurality of markers may optionally be required to correlate with the disease or condition (according to a range and/or threshold).

Correlating may optionally comprise determining whether a ratio of marker concentrations for two markers is outside a range and/or above or below a threshold. Optionally, if the ratio is above or below the threshold level and/or outside a range, the ratio correlates with the disease or condition. Optionally, a combination of two or more these correlations may be used with a single panel and/or for correlating between a plurality of panels. Optionally, the method distinguishes a disease or condition with a sensitivity of at least 70% at a specificity of at least 85% when compared to normal subjects. As used herein, sensitivity relates to the number of positive (diseased) samples detected out of the total number of positive samples present; specificity relates to the number of true negative (non-diseased) samples detected out of the total number of negative samples present. Preferably, the method distinguishes a disease or condition with a sensitivity of at least 80% at a specificity of at least 90% when compared to normal subjects. More preferably, the method distinguishes a disease or condition with a sensitivity of at least 90% at a specificity of at least 90% when compared to normal subjects. Also more preferably, the method distinguishes a disease or condition with a sensitivity of at least 70% at a specificity of at least 85% when compared to subjects exhibiting symptoms that mimic disease or condition symptoms.

A marker panel may be analyzed in a number of fashions well known to those of skill in the art. For example, each member of a panel may be compared to a "normal" value, or a value indicating a particular outcome. A particular diagnosis/prognosis may depend upon the comparison of each marker to this value; alternatively, if only a subset of markers is outside of a normal range, this subset may be indicative of a particular diagnosis/prognosis. The skilled artisan will also understand that diagnostic markers, differential diagnostic markers, prognostic markers, time of onset markers, disease or condition differentiating markers, may be combined in a single assay or device. Markers may also be commonly used for multiple purposes by, for example, applying a different threshold or a different weighting factor to the marker for the different purpose(s).

The panels may comprise markers for the following purposes: diagnosis of a disease; diagnosis of disease and indication if the disease is in an acute phase and/or if an acute attack of the disease has occurred; diagnosis of disease and indication if the disease is in a non-acute phase and/or if a non-acute attack of the disease has occurred; indication whether a combination of acute and non-acute phases or attacks has occurred; diagnosis of a disease and prognosis of a subsequent adverse outcome; diagnosis of a disease and prognosis of a subsequent acute or non-acute phase or attack; disease progression (for example for cancer, such progression may include for example occurrence or recurrence of metastasis).

The above diagnoses may also optionally include differential diagnosis of the disease to distinguish it from other diseases, including those cancers such as non-solid and solid tumors, cancer of the breast, prostate, lung, ovary, colon, uterus, stomach, cervix, liver, pancreas, and wherein the cancer may be invasive or metastatic that may feature one or more similar or identical symptoms.

One or more diagnostic or prognostic indicators are correlated to a condition or disease by merely the presence or absence of the indicator(s). In other embodiments, threshold level(s) of a diagnostic or prognostic indicator(s) can be established, and the level of the indicator(s) in a patient sample can simply be compared to the threshold level(s). The sensitivity and specificity of a diagnostic and/or prognostic test depends on more than just the analytical "quality" of the test—they also depend on the definition of what constitutes an abnormal result. In practice, Receiver Operating Characteristic curves, or "ROC" curves, are typically calculated by plotting the value of a variable versus its relative frequency in "normal" and "disease" populations, and/or by comparison of results from a subject before, during and/or after treatment.

NPC-1 epitopes may be featured as a biomarker for detecting cancers such as non-solid and solid tumors, cancer of the breast, prostate, lung, ovary, colon, uterus, stomach, cervix, liver, pancreas, and wherein the cancer may be invasive or metastatic.

The present invention optionally and preferably encompasses any amino acid sequence or fragment thereof encoded by a nucleic acid sequence corresponding to NPC-1 epitopes as described herein. Any oligopeptide or peptide relating to such an amino acid sequence or fragment thereof may optionally also (additionally or alternatively) be used as a biomarker.

The present invention provides a method for detecting a polynucleotide of this invention in a biological sample, using NAT based assays, comprising: hybridizing the isolated nucleic acid molecules or oligonucleotide fragments of at least about a minimum length to a nucleic acid material of a biological sample and detecting a hybridization complex; wherein the presence of a hybridization complex correlates with the presence of the polynucleotide in the biological sample. Non-limiting examples of methods or assays are described herein. The present invention also relates to kits based upon such diagnostic methods or assays.

Additionally, the NPC-1 epitopes may be used as specific biomarkers for pancreas and colon cancer, and can be measured in biopsied tissue as well as in subject serum and fecal samples, as described herein. Additionally, diagnostic procedures used to detect colorectal cancer including but not limited to fecal occult blood test (FOBT), colonoscopy, computed tomographic colonography (virtual colonoscopy) [detects colorectal lesions larger than 6 mm in diameter with the same sensitivity as colonoscopy], flexible sigmoidoscopy, double-contrast barium enema, and digital rectal examination. Winawer, et al. (1997) *Am J. Gastoenterology* 112: 594-642; Blum (1995) *Eur. J. Canc.* 31: 1369-72; Ransohoff & Sandler (2002) *N. Engl. J. Med.* 346: 346-44; Bruzzi (2002) *N. Engl. J. Med.* 346: 1672-74; and Laghi, et al. (2002) *Am. J. Surg.* 183: 124-31.

Immunoassays

The NPC-1 peptidomimetics may be used in immunoassays to qualitatively or quantitatively detect and analyze markers in a sample. This method comprises providing an antibody specifically binds to a NPC-1 epitope peptidomimetic; contacting a sample with the antibody; and detecting the presence of a complex of the antibody bound to the marker in the sample.

An NPC-1 epitope may be detected and/or quantified using any of a number of well recognized immunological binding assays. Useful assays include, for example, an enzyme immune assay (EIA) such as enzyme-linked immunosorbent assay (ELISA), a radioimmunoassay (RIA), a Western blot assay, or a slot blot assay. See, e.g., U.S. Pat. Nos. 4,366,241; 4,376,110; 4,517,288; and 4,837,168. Generally, a sample obtained from a subject can be contacted with the antibody specifically binds the NPC-1 epitope.

Optionally, the antibody can be fixed to a solid support to facilitate washing and subsequent isolation of the complex, prior to contacting the antibody with a sample. Examples of solid supports include but are not limited to glass or plastic in the form of, e.g., a microtiter plate, a stick, a bead, or a microbead. Antibodies may be attached to a solid support.

After incubating the sample with antibodies, the mixture is washed and the antibody-marker complex formed may be detected. This can be accomplished by incubating the washed mixture with a detection reagent. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker are incubated simultaneously with the mixture.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, marker, volume of solution, concentrations. Usually the assays will be carried out at ambient temperature, although they can be conducted over a range of temperatures (e.g., about 10° C.-40° C.).

The immunoassay can be used to determine a test amount of a marker in a sample from a subject. First, a test amount of a marker in a sample may be detected using the immunoassay methods described above. If a marker is present in the sample, it will form an antibody-marker complex with an antibody specifically binds the marker under suitable incubation conditions described above. The amount of an antibody-marker complex can optionally be determined by comparing to a standard. As noted above, the test amount of marker need not be measured in absolute units, as long as the unit of measurement can be compared to a control amount and/or signal. Several immunoassays are known in the art and the NPC-1 epitope, and antibodies specific for said antigens described herein may used in such immunoassays including but not limited to radio-immunoassay (RIA), enzyme linked immunosorbent assay (ELISA), magnetic immunoassay, immunoblot, Western blot, immunoprecipitation assays, immunohistochemical analysis, and fluorescence activated cell sorting (FACS). See Wild, (2008) [Ed.] *The Immunoassay Handbook* [3rd Ed.] Elsevier.

Radio-Imaging Methods

The NPC-1 epitope peptidomimetics and antibodies that selectively bind NPC-1 epitope peptidomimetics may be used in radio-imaging methods to diagnosis cancer including pancreatic and colorectal cancer, or monitor the progression of tumors. These methods include but are not limited to, positron emission tomography (PET) single photon emission computed tomography (SPECT). Both of these techniques are non-invasive, and can be used to detect and/or measure a wide variety of tissue events and/or functions, such as detecting cancerous cells for example. SPECT may optionally be used with two labels simultaneously. See U.S. Pat. No. 6,696,686.

Commercial Applications and Methods

The present invention further provides for the production of NPC-1 epitope, antibodies and antigen binding fragments thereof which selectively bind to NPC-1 epitope to reach commercial quantities. The NPC-1 epitope, antibodies and antigen binding fragments thereof which selectively bind to NPC-1 epitope may be produced on a large scale, stored if necessary, and supplied to hospitals, clinicians or other healthcare facilities.

Methods of production, storage, and distribution of NPC-1 epitope, antibodies and antigen binding fragments thereof which selectively bind to NPC-1 epitope may be produced by the methods disclosed herein. Following production, the NPC-1 epitope, antibodies and antigen binding fragments thereof which selectively bind to NPC-1 epitope may be harvested, purified, and optionally stored prior to a patient's treatment. For example, once a patient presents with an indication such as, for example, pancreatic, colorectal, esophageal, oral, or breast cancer, NPC-1 epitope, antibodies and antigen binding fragments thereof which selectively bind to NPC-1 epitope may be ordered and provided in a timely manner. Accordingly, the present invention relates to methods of producing NPC-1 epitope to attain antibodies on a commercial scale, pharmaceutical compositions comprising antibodies and antigen binding fragments thereof which selectively bind to NPC-1 epitope, as well as methods of providing (i.e., producing, optionally storing, and selling) antibodies and antigen binding fragments thereof which selectively bind to NPC-1 epitope to hospitals and clinicians. The production of NPC-1 epitope, antibodies and antigen binding fragments thereof which selectively bind to NPC-1 epitope may be scaled up for commercial use.

The present invention also provides for methods of conducting a pharmaceutical business comprising establishing a distribution system for distributing the preparation for sale or may include establishing a sales group for marketing the pharmaceutical preparation.

All publications (e.g., Non-Patent Literature), patents, patent application publications, and patent applications mentioned in this specification are indicative of the level of skill of those skilled in the art to which this invention pertains. All such publications (e.g., Non-Patent Literature), patents, patent application publications, and patent applications are herein incorporated by reference to the same extent as if each individual publication, patent, patent application publication, or patent application was specifically and individually indicated to be incorporated by reference.

EXAMPLES

The invention now being generally described, it will be more readily understood by reference to the following examples, which are included merely for purposes of illustration of certain aspects and embodiments of the present invention, and are not intended to limit the invention.

Example 1

Identification of the NPC-1 Epitope

A NEO-100 antibody was generated in mice immunized with the so-called "Hollinshead colon cancer vaccine". Hollinshead, et al. (1985) *Cancer* 56: 480-489. A NEO-100 antibody and the chimeric form, NEO-101, are described in U.S. Pat. Nos. 7,314,622 and 7,763,720. Several protein purifications were prepared using both mouse NPC-1 and recombinant, chimeric NEO-101 antibodies. Tumor cell lines including LS174T and HT-29 (human colorectal tumor), CFPAC-1 (human pancreatic tumor), colon cancer patient tumor specimen, and the Hollinshead colon cancer vaccines served as tumor antigen sources for protein extracts. The NPC-1 epitope is secreted into the medium of the human tumor cell lines, and the antigen was purified from tumor cell supernatant of cells grown in the absence of serum for 5 to 7 days. NEO-101 antibody was coupled to resins for the antigen purification, including magnetic beads, for simple adsorption, washing, and elution from the beads. Protein that eluted from a NEO-100 antibody-beads was studied further for antigen presence, characterization, and identification.

Western blotting of human tumor cell extracts and supernatants using NEO-101 antibody. Proteins from AsPC-1, LS174T or CFPAC-1 cell supernatants or cell pellet detergent extracts were run on SDS-PAGE, transferred to PVDF membrane, then stained with NEO-101 antibody. A high molecular mass species cross-reactive with a NEO-100 antibody estimated to be 1,000-2,000 kDa was identified by SDS-PAGE. A protein immunoblot of tumor antigen from cells using NEO-101 antibody including AsPC-1 cell pellet, AsPC-1 supernatant, LS174T cell pellet, LS174T supernatant, CFPAC-1 cell pellet, and CFPAC-1 supernatant along with molecular weight markers.

Immunopurified protein from LS174T tumor cells was subjected to proteolytic cleavage by either trypsin or protease V8, followed by Western Blot analysis of the protein fragments. A 1,000-2,000 kDa immunopurified antigen was digested into four discrete fragments ranging in mass from approximately 60 kDa to 220 kDa, each containing an NPC-1 immunoreactive peptide epitope. A protein immunoblot of proteolytic digested tumor antigen from cells using NEO-101 antibody was run with LS174T cell pellet, LS174T supernatant, trypsin-digested immunopurified antigen, protease V8-digested immunopurified antigen along with a molecular weight marker. The data suggested that there are multiple NEO-101 antibody binding regions present on each molecule of the tumor antigen.

The NPC-1 epitope was prepared for identification by mass spectrometry by running immunopurified antigen preparation from several different tumor sources on SDS-PAGE, excising the high molecular mass, NPC-1 immunoreactive band from the polyacrylamide gel, and subjecting the protein to trypsin digestion followed by LC/MS/MS on an LTQ Orbitrap XL mass spectrometer. Trypsin peptide product ion data defined by mass and charge were searched against the concatenated forward and reverse IPI human database using the Mascot search engine. The database was appended with commonly observed background proteins to prevent false assignments of peptides derived from those proteins. Mascot output files were parsed into the Scaffold program for filtering to assess false discovery rates and allow only correct protein identifications. Rat, mouse, and human derived samples are searched against the International Protein Index (IPI) database. The antigen sources for these experiments were derived from human colorectal (LS174T, HT-29) and pancreatic (CFPAC-1) tumor cell lines. The results of six mass spectrometry experiments suggested the presence of MUC5AC-derived peptides in the NPC-1 immunopurification preparation.

The amino acid sequence of MUC5AC as reported in the IPI database (IPI00103397). The sequence consists of 5,030 amino acids with a predicted mass of 526,585 Da (without post-translational modifications including glycosylation). Comparing the peptide coverage from the mass spectrometry experiments with the amino acid sequence of MUC5AC (SEQ ID NO: 36), and other peptide coverage maps, reveal that most of the peptides sequenced after trypsin digestion derive from either the N-terminal third or the C-terminal third of the molecule. In each experiment, there were very few peptides that derived from the central third of the MUC5AC molecule, which contains “tandem repeats” of 8 amino acid residues including, for example, TTSTTSAP (SEQ ID NO: 42), GSTPSPVP (SEQ ID NO: 43), and TASTTSGP (SEQ ID NO: 44). Silverman, et al., (2001) *Glycobiology* 11: 459-71. This region of MUC5AC is highly glycosylated in normal MUC5AC-expressing tissues, such as lung and colon endothelium. It is probable that the lack of peptide sequence coverage in the central region of MUC5AC, as detected by mass spectrometry, is due to a high degree of glycosylation in the region, which interferes with digestion by trypsin. These results suggest that the tandem repeat region of MUC5AC comprises at least one NPC-1 epitope.

Example 2

NPC-1 Epitope Knockdown

A small inhibitory RNA (siRNA) target sequence designed against a region of MUC5AC was used in cells known to express the NPC-1 epitope. Several siRNA oligonucleotides were designed based upon MUC5AC sequences. The sequences of the human MUC5AC siRNA oligonucleotides are shown in Table 5:

TABLE 5

Sequence of MUC5AC siRNA oligonucleotides

| Oligonucleotide | Strand | Sequence |
|---|---|---|
| siRNA ID #: s9074 | Sense | AGAUGUGCCUCAACUACGAtt (SEQ ID NO: 51) |
| | Anti-Sense | UCGUAGUUGAGGCACAUCUtg (SEQ ID NO: 52) |
| siRNA ID #: s9075 | Sense | GCUCUGGAACGUGAGCAUAtt (SEQ ID NO: 53) |
| | Anti-Sense | UAUGCUCACGUUCCAGAGCcg (SEQ ID NO: 54) |
| siRNA ID #: s9076 | Sense | GCGUGCUCGUCGACAACUAtt (SEQ ID NO: 55) |
| | Anti-Sense | UAGUUGUCGACGAGCACGCgg (SEQ ID NO: 56) |

The siRNAs were transfected into LS174 and CFPAC-1 tumor cells, as well as A549 cells. A549 is a human lung adenocarcinoma cell line that expresses MUC5AC (as shown by PCR and detection using commercially available antibodies against MUC5AC), but not NPC-1 epitope. The MUC5AC species expressed by A549 cells is not immunoreactive with NEO-101 antibody, a characteristic that demonstrates the tumor specificity of the NPC-1 epitope in contrast to the commercially available antibodies against MUC5AC. The A549 cells serve as a control to show the pancreas/colon tumor-binding specificity of the NEO-101 antibody. Following transfection of the siRNA into tumor cells, the MUC5AC expressed by the cells was measured by specific PCR to measure the levels of MUC5AC mRNA, and a sandwich ELISA using NEO-101 antibody to measure the levels of MUC5AC. The data shown in Table 6 demonstrate that a cocktail of three siRNA oligonucleotides resulted in significant decreases of both MUC5AC mRNA and NEO-101-reactive MUC5AC protein (e.g., NPC-1 epitope).

TABLE 6

| siRNA knockdown of MUC5AC in human pancreatic (CFPAC-1) and colorectal (LS174T) tumor cells | | Normalized MUC5AC mRNA* | Normalized MUC5AC protein** |
|---|---|---|---|
| Untreated CFPAC-1 | | 1 | 1 |
| CFPAC-1 Treated with | 20 pmol | 0.2737 | 0.6967 |
| SiRNA cocktail | 50 pmol | 0.3057 | 0.6901 |
| | 200 pmol | 0.1368 | 0.3566 |
| Untreated LS174T | | 1 | 1 |
| LS174T Treated with | 20 pmol | 0.6917 | 0.53 |
| SiRNA cocktail | 50 pmol | 0.3858 | 0.402 |
| | 200 pmol | 0.235 | 0.117 |

*MUC5AC mRNA level was measured by RT-PCR, normalized as a percent of mRNA levels detected in untreated cells.
**MUC5AC protein level secreted into cell supernatants was measured by sandwich ELISA [NEO-101 to capture and anti-MUC5AC antibody 1-13M (Abcam catalog #ab24070) to detect], normalized as a percent detected in untreated cells.

The amount of decreased MUC5AC expression was dependent on the dose of the siRNA cocktail transfected into the cells. Approximately 70%-90% of MUC5AC expression (mRNA and protein) was inhibited in both LS174T and CFPAC-1 cell lines at 200 pmoles of the siRNA cocktail. These results confirmed that MUC5AC is the target of the NEO-101 antibody. The A549 cells used as a control in these experiments showed decreased MUC5AC expression by mRNA analysis but there was no change in the NEO-101 sandwich ELISA because the MUC5AC expressed by these cells is not recognized by a NEO-100 antibody. Thus, the siRNA data demonstrates that reducing MUC5AC expression lead to a concurrent decrease in NEO-101 antibody binding.

Example 3

NPC-1 Epitope Mapping

The data by western blots of trypsin-digested MUC5AC indicated that there may be several NEO-101 antibody binding sites on each molecule of MUC5AC, suggesting that a binding region may be present in each of the tandem repeat units located in the central region of the molecule. An exemplary amino acid sequence of MUC5AC is presented in SEQ ID NO: 36 with an exemplary nucleic acid sequence encoding MUC5AC presented in SEQ ID NO: 37. Therefore, a recombinant expression plasmid was designed and constructed that encoded residues upstream of tandem repeat units and two tandem repeat units (“MUC5AC-long” SEQ ID NO: 38 with the corresponding nucleic acid sequence of SEQ ID NO: 39). The MUC5AC long peptide corresponds to amino acid residues 2636 to 2942 of the MUC5AC protein (SEQ ID NO: 36). A second expression plasmid was designed and constructed that encoded primarily a short domain which connects to the central repetitive region and only a portion of the tandem repeat residues (“MUC5AC-short” SEQ ID NO: 40 with the nucleic acid encoding it in SEQ ID NO: 41). The MUC5AC short peptide corresponds to amino acid residues 2636 to 2763 of the MUC5AC protein (SEQ ID NO: 36). These smaller fragments of the large MUC5AC molecule were predicted to comprise NEO-101 antibody binding regions that contain the NPC-1 epitope(s).

The DNA sequences that contained NEO-101 antibody binding regions, based on the amino acid sequence, were back-translated to nucleic acid sequence and the DNAs were synthesized by methods well-known in the art. These DNA fragments were cloned into a mammalian expression plasmid by standard techniques, and several independent clones were transfected into Chinese Hamster Ovary (CHO) cells that were shown previously not to express the NPC-1 epitope. Analysis of the CHO cells following the transfection demonstrated immunoreactivity with a NEO-100 antibody in several of the plasmid clones. Experiments were performed to test binding by immunofluorescence and immunoprotein blotting of extracts from transfected cells.

Immunofluorescence quantitation data showed that NEO-101 antibody bound to 11%-80% of CHO cells transfected with different plasmid clones of the MUC5AC short construct, and 76%-88% of CHO cells transfected with different plasmid clones of the MUC5AC long construct. Western blot analysis using NEO-101 to probe CHO cell extracts following transfection with the MUC5AC short and MUC5AC long plasmid clones was performed. The NEO-101 antibody binding region was expressed by both of these MUC5AC-related-peptides as confirmed by Western blot analysis. The molecular mass of the immunoreactive protein bands represents the predicted mass of the protein fragment, including glycosylation that occurs in the mammalian CHO cells. The data further confirm that the NPC-1 antigen (e.g., a NEO-100 antibody binding region) is contained in the MUC5AC-related fragments isolated and expressed in the transfected cells.

The results of these experiments show that at least one NPC-1 epitope is contained within both the 307 amino acid-fragment of the MUC5AC long peptide and within the 128 amino acid-fragment of the MUC5AC short peptide. These results also suggest that the NPC-1 epitope may be a conformational epitope rather than a liner epitope.

Example 4

Deletion Constructs for Detailed Epitope Mapping of the MUC5AC Long Antigen

The NEO-101 binding region was shown to be expressed by the MUC5AC, successive truncations starting at either the N-terminus or the C-terminus of the construct may be generated by standard molecular biology techniques to identify a region which is involved in NEO-101 antibody binding to MUC5AC. Six truncation constructs were made representing C-terminal truncations of the full-length MUC5AC protein (SEQ ID NO: 36).

TABLE 7

Truncation constructs of MUC5AC

| Construct | Modification | SEQ ID NO | Binds NPC-1? |
|---|---|---|---|
| 1-338 | C-terminal truncation | 50 | Yes |
| 1-289 | C-terminal truncation | 49 | Yes |
| 1-187 | C-terminal truncation | 48 | Yes |
| 1-151 | C-terminal truncation | 47 | Yes |
| 1-136 | C-terminal truncation | 46 | No |
| 1-85 | C-terminal truncation | 45 | No |

293T cells were cultured on FBS coated cover slips for 24 hours. Cells were transiently transfected with 2 μg of MUC5AC constructs of Table 8 with LIPOFECTAMINE®. Cells were grown for about 72 hours, fixed with about 4% PFA in PBS, washed with PBS, permeabilized with about 0.2% triton X-20 in PBS and washed with PBS. Cells were then blocked with about 1% BSA in PBS, and about 2 μg/ml NEO-101 antibody was added to sample wells and about 2

μg/ml of an Isotype control was added for 1 hour at room temp. Cells were washed with PBS and second anti human-FITC antibody (1:500) was added to all wells and to the second antibody control wells. Cells were washed and mounted on slides with DAPI hard mount. Cover slides were allowed to sit over night at about 4° C. Slides were visualized with a Nikon Eclipse Ti microscope with an Andor camera. At least 3 random fields were counted per transfection.

This strategy was used to identify an about 15 amino acid-region that contains a NPC-1 epitope: GCPVTSTPVTAPSTP (SEQ ID NO: 35). The MUC5AC constructs with 338, 289, 187, and 151 amino acid residues all had binding activity with the NEO-101 antibody. See TABLE 2B. The deletions 151 and 85 showed no binding. The second antibody and the IgG controls were also negative for binding to the 293T cell lines transfected with the MUC5AC 338 residue construct (SEQ ID NO: 50). These data suggest that the GCPVTSTPVTAPSTP (SEQ ID NO: 35) sequence is involved in the binding of the NPC-101 antibody to MUC5AC. This is a repetitive sequence that also has some changes in it which are also probable scaffold for the binding sites for the NEO-101 antibody. This repetitive sequence and variations can be found in the longer deletions of MUC5AC and MUC5AC itself.

Example 5

NPC-1 Epitope is a Specific Biomarker for Pancreatic and Colorectal Cancer

The NEO-101 antibody is specific for MUC5AC-related antigen expressed from human colon (LS174T) and pancreas (CFPAC-1) cancer cell lines. MUC5AC-related antigen expressed by these two cancer cell lines comprised the NPC-1 epitope, and competed effectively with native MUC5AC antigen previously coated on ELISA plates for binding to NEO-101 in the assay. As a control, non-NPC-1-bearing MUC5AC expressed by A549 lung adenocarcinoma cells did not compete with NEO-101 antibody binding to native MUC5AC coated to the ELISA plates.

LS174T and CFPAC-1 cells were grown on cover slips coated in 1-13S for 48 hours. Cells were then fixed with 4% PFA in PBS, washed with PBS, permeabilized with 0.2% Triton X-100, washed with PBS and blocked with 1% BSA in PBS. Cells were incubated with either 2 μg/ml NEO-101, MS-X, 2-11M1, H160, 351-450, 2-12M1, or 1-13M1. Cells were washed with PBS and then second antibody was added anti-human-FITC, anti-mouse-FITC or anti-rabbit-FITC (1:500), cells were washed and mounted on slides with DAPI hard mount. Cover slides were allowed to sit over night at 4° C. Slides were visualized with a Nikon Eclipse Ti microscope with an Andor camera.

All of the antibodies stained the LS174T cells. The staining patterns and localization looked about the same for all antibodies tested. There were differences in cell staining on the CFPAC-1 cells compared to the LS174T cells. NEO-101 stained about 50% of the cells. MS-X and 2-11M1 stained less than 5% of the cells. 351-450 and 2-12M1 did not have any staining with the CFPAC-1 cells. H160 and 1-13M1 stained 100% of the CFPAC-1 cells.

This data suggests that all the antibodies can detect the colorectal MUC5AC protein with the same efficiency but in pancreatic cancer cells there are variations in the staining patterns between different MUC5AC antibodies. This suggests that NEO-101 may detect both types of MUC5AC and that other commercial antibodies do not recognize the same epitope.

A homologous ELISA assay (adapted from an ImmunoBooster® ELISA kit, Bioworld Consulting Laboratories, LLC, Mt. Airy, Md.) was designed using NEO-101 antibody as both capture and detection reagent (e.g., a sandwich ELISA was developed using NEO-101 antibody as the capture reagent using a biotin-labeled NEO-101 used as the detection antibody.) This homologous antibody format was possible due to the discovery of multiple NPC-1 antigen binding sites expressed by the cancer-associated MUC5AC-related antigen. Serum samples were procured from various commercial and private sources. The assay developed here used serum from colorectal and pancreatic cancer patients, and serum from healthy blood donors.

Microtiter plates (96-well Nunc Maxisorp) were coated with purified unlabeled NEO-101 antibody at about 10 μg/mL in 0.5 M sodium carbonate pH 9.5 overnight at about 25° C. Plates were then blocked with 1% skim milk made in Tris-Buffered Saline (TBS) containing 5 mM EDTA and 1% sucrose for about 4 hours at about 2° C. Plates prepared in this manner may be stored dried and sealed for at least about 8 months. All dilutions were made in ImmunoBooster® buffers (Bioworld Consulting Laboratories, LLC) supplemented with 20 mM EDTA. Wash buffer was TBS containing 0.05% Tween®-20 non-ionic detergent. A detergent extract of cultured human LS174T colorectal tumor cells was used as a source of NPC-1 antigen to derive a standard curve. Extracts derived from human pancreatic CFPAC-1 tumor cells or human lung A549 tumor cells were generated similarly. Tumor cell lines were purchased from American Type Culture Collection (Manassas, Va.) and grown in RPMI medium containing 10% FBS (heat-inactivated) with 8 mM glutamine. To measure direct binding of NEO-101 to the MUC5AC-related antigen, CFPAC-1 cells were grown in serum-free medium for about 5 days and the conditioned medium was filtered and stored in large one large lot at about 4° C.

The sandwich ELISAs were performed by diluting the cell extract standard on each plate, next to patient or normal serum samples diluted 1:24 in the diluent. AU incubations were performed at about 25° C. and all volumes were about 100 μl per well. The plates were incubated for 15 min and washed three times with wash buffer. The biotin-labeled NEO-101 was then added to the wells at 1 g/mL, incubated for about 15 min, and plates were washed three times. Peroxidase-conjugated streptavidin (1:5,000 dilution) was added to the plates for about 15 min, and plates were washed three times with wash buffer and two times with TBS. The assay was developed by the addition of TMB substrate (BioFX Laboratories Inc.) to the plates, incubation for about 15 minutes, then the color reaction was stopped with the addition of 0.5 M sulfuric acid. The data was acquired by measuring absorbance at 450 nm. The data collected was processed using GraphPad Prism or Microsoft Excel software packages.

This ELISA was used to evaluate the serum of colorectal and pancreatic cancer patients (n=42), serum from healthy blood donors (n=75), and serum from potentially interfering disease states such as asthma, chronic obstructive pulmonary disease, irritable bowel syndrome and Crohn's disease (n=56). Analysis of these various serum samples demonstrates the use of the NPC-1 antigen biomarker assay to detect NPC-1 epitope (e.g., aberrant MUC5AC) shed into the blood of colorectal cancer patients. An NPC-1 ELISA test may detect aberrant MUC5AC from colon cancer patients. C1 and C2 are normal serum samples from healthy blood donors. AB pool is serum pooled from many healthy blood donors. All other samples numbered #1 through #17 are serum collected from colon cancer patients. The use of NEO-101 antibody as the coating antibody (capture antibody) and biotin-labeled NEO-101 as the detection antibody is highly specific, and may be explained by the presence of multiple binding regions (i.e., epitopes) on the same antigen molecule, such that steric hindrance is obviated.

Patients with colorectal or pancreas cancer were asked to participate in a study. Serum samples were received and stored at about −35° C. until the time of testing. Tumor biopsy slides were received at ambient room temperature and subsequently analyzed by IHC using biotin-labeled antibodies. Patient information was also provided, containing limited clinical data for the patient sample (disease stage, current medications). For each patient enrolled, 1, 2 or 3 serum samples were provided for each patient separated by approximately 1-month. A group of "normal healthy" serum samples was included for comparison. These were purchased from a large metropolitan blood bank and comprised a group of self-proclaimed normal individual males and females of mixed race aged 40- to 59-years-old. The actual health status of these donors is unknown, thus comparison of any sample to this normal donor group may be done with appropriate caution.

The NEO-101 serum ELISA was performed using a standard antigen prepared from a cultured cell line extract from tumor cells known to express the NPC-1 antigen. Triplicates of a 1/24 dilution of serum samples from groups of "healthy normal" donors and clinically diagnosed colon and pancreas cancer patients were tested in the assay and the raw data were interpolated from the standard curve. Expression of the NPC-1 antigen was determined relative to this standard antigen preparation (equivalents of LS174T cells/well).

Results showed that interfering disease states, which are expected typically to have elevated serum MUC5AC, did not express higher levels of NPC-1 epitope compared to controls. Further, comparison of the serum MUC5AC levels from colorectal and pancreatic cancer patients with serum from healthy controls demonstrated the assay's ability to differentiate the cancer patients from the normal donors with approximately 0.7 log units difference. Moreover, the NEO-101 ELISA accurately differentiated patients with active or metastatic disease from patients who had no evidence of disease. Notably, in a side-by-side comparison of the NEO-101 ELISA to a commercial ELISA for CA19-9, the NEO-101 ELISA proved superior.

Patients enrolled on the clinical diagnostic study agreed to provide their tumor biopsy or surgical specimen to be stained immunohistochemically with NEO-101. Tumor sections were prepared as slides, and two additional slides were prepared for negative control (human IgG1) and positive control (cytokeratin) staining to ensure quality controls for the IHC method. More specifically, tumor biopsy specimens from colorectal and pancreas cancer patients were deparaffinized at about 60° C. for 30 min prior to staining with NEO-101. Subsequently, all staining steps were carried out at about 25° C. Slides (4 μm) were blocked with Peroxo-Bloc® inhibitor (Zymed Laboratories) for about 2 min, rinsed with phosphate-buffered saline (PBS), and blocked with CAS (Zymed) for an additional about 10 minutes. Slides were stained with about 10 μg/mL of biotin-labeled NEO-101 for 1 hour, and washed three times with PBS containing 0.05% Tween®-20 non-ionic detergent. Previous titration of biotinylated-NEO-101 demonstrated about 10 μg/mL to be an optimal concentration for immunohistochemical detection of the NPC-1 antigen. A 1:400 dilution of peroxidase-conjugated streptavidin (Dako North America, Inc.) was then applied to the slides for about 30 minutes and slides were washed three times. A solution of DAB (Zymed) was applied for about 2-3 minutes then rinsed with PBS. A solution of hematoxylin was then applied for about 3 minutes and rinsed with tap water until clear. The slides were dehydrated with xylene and a coverslip was added using Permount® mounting medium. Additional consecutive slides were stained with human cytokeratin AE1/AE3 (Abcam plc) as a positive control, and human IgG1 isotype as a negative control (AXXORA, LLC).

All antibodies were biotinylated prior to use and tested independently at various concentrations using human tumor tissues known to react with the antibodies. Primary antibody (NEO-101) was used at about 10 μg/mL, detected with streptavidin-horseradish peroxidase conjugate, and mounted on slides. A positive staining scale ranging from +1 to +5 was applied to the staining results, measured by light microscopy. Tissues stained with NEO-101 were considered positive (+1 to +5) for an average of 79% of the patient tumor samples (30 of 38 of both colorectal and pancreatic cancer biopsies) including the 5 pancreatic tumor samples. Tissues that were negative or considered weak staining by the immunohistochemist were considered negative. These staining results are similar to results from several other studies completed with antibodies using tissue array slides, and both frozen and paraffin-embedded surgical specimens. Results of the IHC staining are shown in Table 8.

TABLE 8

IHC Staining Results

| Cancer Type | Number of Subjects | % Positive by IHC with NEO-101 |
|---|---|---|
| Colorectal | 33 | 76% (25/33) |
| Pancreatic | 5 | 100% (5/5) |

Notes:
(1) most tissue biopsy samples were collected when patients were staged with stage 2 to 4 cancer, (2) negative and positive control tissues slides were included and shown to stain negatively with secondary antibody only (negative) or anti-cytokeratin antibody (positive).

The IHC staining results using the NEO-101 antibody was then compared to the results for each serum ELISA for every subject where both sets of results (sera and biopsy) were available. For simplicity, the average of the serum ELISA from each blood draw was used for this comparison. The results of this analysis demonstrated that 84% (32/38) of the serum samples were positive using a cutoff of 335 units/mL and 79% (30/38) of the tissue samples were positive, providing a high concordance of the two assays using NEO-101.

A larger number of serum samples were procured to test the utility of the serum-based ELISA in detecting the NPC-1 antigen. A sampling of 41 colorectal or pancreas cancer patient sera was compared with sera collected from 28 normal healthy blood donors. In this population of cancer patients, blood was collected serially during an approximately 3-month period for several of the patients while they were undergoing various treatment regimens with a medical oncologist. For multiple reasons, blood was not collected from all patients at all three timepoints. Thus, there were 41 patients that donated blood at their first evaluation by the medical oncologist, followed by 33 patients that donated their blood at the second visit, and 25 patients who completed all three blood donations at the third visit. The majority of patients were diagnosed with Stage HI or IV disease.

Figure 2A:
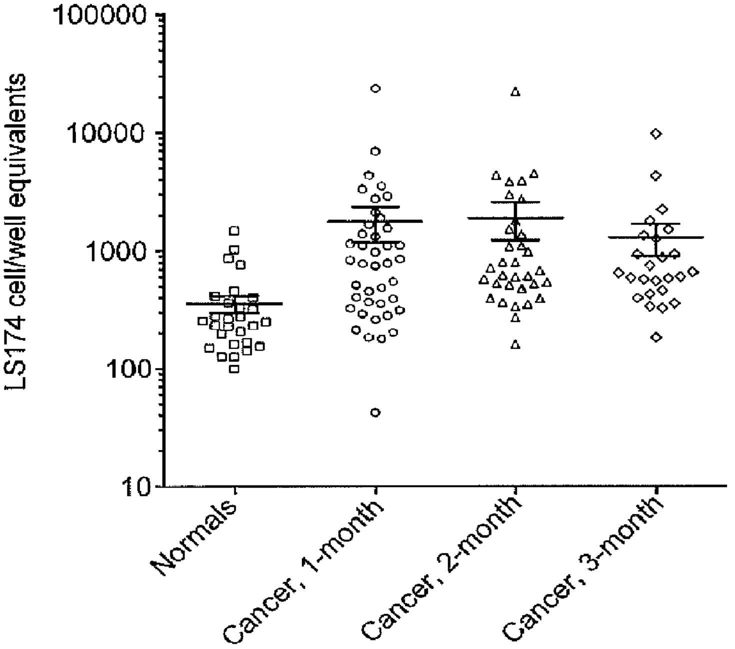
FIG. 2A-B depicts the detection of NPC-1 antigen in cancer patients using a NEO-101 antibody.

FIG. 2A shows the results of testing this larger panel of colorectal and pancreatic cancer patient serum specimens, compared to a group of normal healthy blood donors. Analysis of the results demonstrated approximately a 0.7 log difference between the cancer patients and the healthy donors at each of the three blood draws. The mean and standard error of the mean for each control group for the assays are: Normals (355±60), Col/Pan Ca, 1-month (1,757±580), Col/Pan Ca, 2-month (1,894±671), Col/Pan Ca, 3-month (1,293±390). Using the unpaired t-test (2-tailed) method to evaluate the difference between the Normal sera group and the cancer sera groups, the differences for each comparison were: Normal vs. 1-month [p=0.0511]; Normal vs. 2-month [p=0.0397]; Normal vs. 3-month 4)=0.01531 Furthermore, using a cutoff value of 355 cells/well derived from the Normal sera average, 73% of Col/Pan Ca, 1-month sera were above the cutoff (30 of 41 samples), and 88% were above the cutoff in each of the 2-month (29 of 33 samples) and 3-month (22 of 25 samples) in those groups. Overall, the samples represent an average of 82% positive above the cutoff established for the assay. These results show that the NPC-1 antigen ELISA can distinguish differences between serum from normal donors and colorectal or pancreas cancer patients, with a good level of confidence.

Figure 2B:
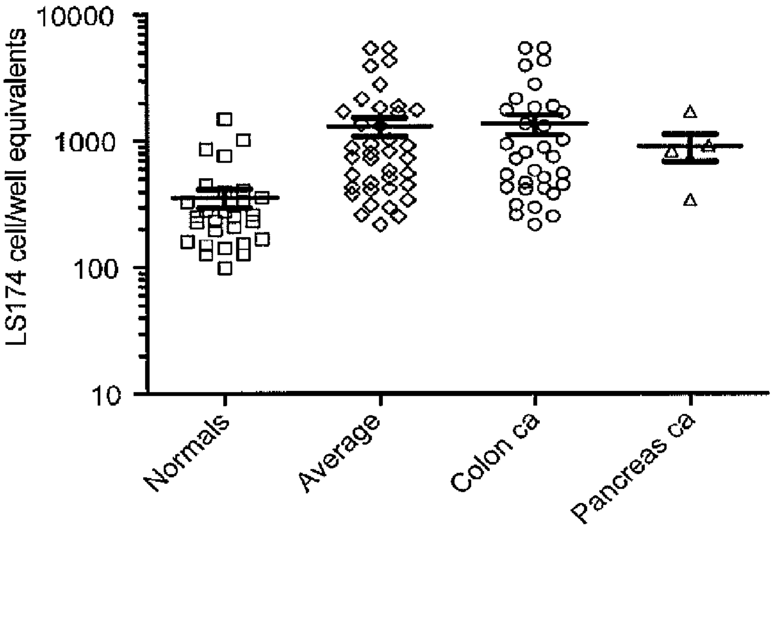

The cancer patient population tested in this study was further stratified by disease type. This analysis, in FIG. 2B, shows that there was no difference distinguished by the mean NEO-101 ELISA results among those patients diagnosed with colorectal cancer (n=36) from those patients diagnosed with pancreas cancer (n=5). Both groups separately demonstrated approximately 0.7 log units higher NPC-1 epitope expression levels compared to the group of healthy donors.

NPC-1 epitope may also be used in monitoring colon or pancreas cancer patients during the course of a treatment regimen, just as the CEA and CA19-9 assays are used currently. That is, as a surrogate marker for a treatment regimen for a cancer patient (is the patient responding or not). From patients that donated multiple serum samples, the amount of NPC-1 antigen biomarker detected in the assay was plotted versus the time of the blood draw. The results showed that some patients appeared to express similar amounts of the NPC-1 antigen during the 2- or 3-month period when blood was drawn (subjects 5, 14, 15, 19, 25, 28, 29), whereas some patients appeared to experience a 1.5× to 5× increase in NPC-1 antigen expression (subjects 1, 2, 7, 33, 39) or a 1.2× to 3× decrease in the NPC-1 antigen expression (subjects 18, 22, 23, 28, 34, 36, 40). The significance of these shifts over time are presently unclear, but may be related to the tumor burden of the patient at the time the blood was drawn, which may be directly related to the specific treatment regimen of individual patients. The results demonstrate trends for certain patients that may reflect cancer regression, progression, or stable disease. Once these data are coupled with the disease status in patients, the correlation is apparent. Additionally, the NEO-101 assay appears to be better than either of the CEA and CA19-9 assays (i.e., NPC-1 is more sensitive). Additionally, neither the CEA nor CA19-9 sera tests can be used to diagnose cancer (as does, for example, the prostate serum antigen test). Hence, the present invention provides for the predictive value of NPC-1 epitope as a new serum biomarker to diagnose and monitor treatment of colorectal and pancreatic cancer.

Example 6

NPC-1 Epitope is a Glycotope Comprising an Aberrant Tumor-Specific Glycosylation Pattern The MUC5AC epitope was mapped and further characterized in order to better elucidate the carbohydrate dependence of NEO-101 antibody binding. CFPAC-1 supernate (pancreatic cancer cell line CFPAC-1 supernate) containing NPC-1 epitope was exhaustively digested with thermolysin which resulted in no detectable activity in Western blot with NEO-101 antibody.

This was a two part experiment where the antigen (pancreatic cancer cell line CFPAC-1 supernate) was digested with the protease thermolysin (Sigma) at an enzyme:substrate ratio of 1:10. CFPAC supernate in 200 mM TRIS buffer, 500 mM NaCl, 25 mM $CaCl_2$ pH 7.6 overnight at either about 37° C. or 65° C. After digestion enzyme inactivated sample (in EDTA) were run in SDS-PAGE gels after which time a conventional western blot was performed with NEO-101 antibody and anti-human IgG peroxidase (Jackson Laboratories) detection. There was no longer detectable antigen activity after thermolysin digestion.

The digested CFPAC-1 supernate antigen still retained full inhibitory activity in a competition immunoassay where CFPAC-1 supernate antigen is coated onto a microplate and the binding of soluble NPC-1-C is followed as the readout. Both the CFPAC-1 supernate and its thermolysin digest were found to inhibit in a similar fashion but the filtrate from a 10,000 dalton cutoff spin filter did not. This suggested that the inhibitory fragment(s) are larger than 10,000 daltons but considerably smaller than the native antigen seen on the gel.

Thermolysin was then used to fragment MUC5AC. The thermolytic fragments from the three tandem repeat regions of MUC5AC were the selected in order to construct a multiple alignment of possible epitope containing fragments having a common consensus sequence. These experiments not only limited the size of the prospective epitope but also suggested a possible association with O-linked carbohydrate substitution given the presence of motifs. This data indicates that a NEO-100 antibody binds to a region of MUC5AC comprising the peptide sequence of (SEQ ID NO: 34 or 35) which serves as a scaffold for an aberrant, tumor-specific glycosylation pattern. This aberrant, tumor-specific glycosylation pattern (secondary structure) is apparently attached to residues in SEQ ID NO: 34 or 35 contained in the antigen bound by a NEO-100 antibody (e.g., NEO-101, NEO-102, NEO-103).

The carbohydrate dependence of NEO-101 binding was further confirmed by glycosidase enzyme digestions, chemical modifications, and mimicry. A panel of glycosidases (Northstar Bioproducts) was used to explore a possible change in the ability of CFPAC-1 supernate antigen to inhibit NEO-101 binding to the same antigen immobilized on microplates (competition assay). The commercial enzyme panel comprised a plurality of enzymes: (a) o-glycosidase, (b) β1→4 galactosidase, (c) PNGase F, α2→3,6, 8,9 specific neuraminidase, and (d) β N acetyl glucosaminidase. Of all enzymes tested neuraminidase (3, 6, 8 selective) stood out producing significant modifications to the antigen. This was observed in the competition ELISA using CFPAC coated plates and NEO-1.01. Surprisingly, of o-glycosidase, (b) β1→4 galactosidase, (c) PNGase F, α2→3,6,8,9 specific neuraminidase, and (d) β N acetyl glucosaminidase treatment, only the neuraminidase digestion eliminated activity of the antigen. Unexpectedly, it was observed that the antigen activity is sensitive to neuraminidase, mild sodium periodate oxidation treatment at 4° C. (a method that selectively destroys sensitive vicinal diol bonded hydroxyl groups found in sialic acids) also eliminated the binding of NEO-101 to the MUC5AC.

The results of the neuraminidase digestion result suggest that sialic acid is comprised in the carbohydrate residues which are attached to amino acids in the primary structure of the antigen that constitute the epitope. A neuraminidase from *Macrobdella decora* (Calbiochem) which is selective for α2→3 linkages was inactive. Only neuraminidase with broad spectrum (α2→3,6,8) from *Arthrobacter ureafaciens* showed activity. Since α2→8 linked sialic acid is relatively uncommon except in neuronal tissues, the results highly suggest that the epitope contains sialic acid α2→6 type linkages. The periodate treatment further narrows the binding to include C8 and C9 hydroxyl groups on sialic acid as possible contact points with NEO-101. A competition assay comparing CFPAC-1 supernatant treated with α2-3 neuraminidase, α2-3, 6, 8 neuraminidase, and sodium periodate to a CFPAC-1 control was also effected. Only CFPAC-1 supernatant treated with α2-3 neuraminidase and sodium periodate showed a lack of binding of the NEO-101 antibody. Thus, the antigen detected in the serum ELISA bound by the NEO-101 antibody is also sensitive to sodium periodate and α2-3 neuraminidase but not α2-3, 6, 8 neuraminidase.

Serum from a normal healthy individual (Normal Serum) or serum from a patient with a Colon Cancer was treated overnight with several concentrations of sodium periodate. The reaction was then stopped by addition of 50% glycerol. The treated samples were then assayed for NPC-1 epitope content by ELISA using NEO-101 antibody in a homologous format were NEO-101 was both the capture reagent and detector reagent in a biotinylated form.

A form of mimicry was unexpectedly discovered where bovine submaxillary mucin (BSM) (Sigma) bound very well to NEO-101 in ELISA, and western blot. This cross-reactive antigen provided a source of material to further explore the carbohydrate dependence of NEO-101 binding. The BSM reactivity with NEO-101 antibody was sensitive to both periodate and neuraminidase treatments. The competition assay comparing CFPAC-1 supernatant with BSM on the ability to inhibit NEO-101 antibody binding to CFPAC coated plates.

BSM or CFPAC-1 supernatant was treated with sodium periodate and neutralized essentially as described previously. The treated antigens were then coated onto a microplate which was subsequently probed with a titration of NEO-101 antibody. The readout after an anti-human IgG-peroxidase (Jackson) secondary antibody binding step was obtained with TMB substrate. This shows that BSM and CFPAC-1 supernate antigen both have a similar periodate sensitivity with respect to the NPC-1 epitope. This result is consistent with mild acid hydrolysis experiments which points to a common sialic acid partial glycotope.

The binding of NEO-101 to its antigen(s) is salt sensitive, further supporting the finding that the binding may have an ionic dependence, contributed by negatively charged sialic acid residues in the antigen. CFPAC-1 supernate coated plate was a capture and the readout was NEO-101 antibody binding in the presence of several concentrations of NaCl.

The NPC-1 monoclonal antibody was compared to the Sialyl Tn monoclonal antibody (Abeam) and antibodies that bind the CA19-9 antigen. With BSM coated plate as capture and variable amount of NEO-101 added, a constant amount of sialyl Tn antibody was added resulting in no competition of NEO-101 binding. When sialyl Tn was tested in preblocking a BSM plate, no such blocking of NEO-101 binding occurred. 50% of the 0-liked glycans on BSM have the following sequence which is defined by antibodies binding to Sialyl Tn: NeuAcα2→6GalNAcα1→Scr/Thr. Selective neuraminidase digestion showed that the epitope recognized by the NEO-101 antibody comprises a NeuAcα2→6 linkage. Sialyl Tn antibody blocking experiments demonstrated that NEO-101 and Sialyl Tn do not share an epitope as there is no competition for binding between these antibodies (e.g., Sialyl Tn binds a different epitope). These results also suggest that the epitope recognized by NEO-101 is sensitive to removal of α2→6,8 linked sialic acid but not α2→3 linked sialic acid, excluding CA19-9 as the antigen. Further, the epitope is sensitive to mild periodate oxidation thereby suggesting that sialic acid CS, C9 hydroxyl groups may be contact sites to NEO-101 or mucin. Therefore, the sialyl Tn monoclonal antibody does not bind the same epitope as a NEO-100 antibody. Further, a NEO-100 antibody does not bind to the CA19-9 antigen.

Accordingly, the NPC-1 epitope is sensitive to mild acid hydrolysis, periodate oxidation, and neuraminidase digestion, all treatments known to elicit a degradative effect on sialic acid, and suggesting that sialic acid is a key sugar forming part of the glycotope recognized by a NEO-100 antibody. Further, the linkage of sialic acid to the penultimate sugar of the epitope was suggested to be α2→6 rather than α2→3 by virtue of the epitope destructive effect only seen with neuraminidase from *Arthrobacter ureafaciens* (broad spectrum neuraminidase) and not neuramidase from *Macrobdella décora* selective only for α2→3 linkages. Additionally, the NEO-101 antibody binds effectively to bovine submaxillary mucin (BSM) and proteolytic digest thereof. This suggests that a homologous glycotope exists on BSM and there is diminished relevance of the peptide part of the molecule. The NPC-1 epitope is salt sensitive, thereby suggesting the importance of charged residues, possibly due to clustered negatively charged sialic acid residues having the appropriate ionic character.

Example 7

Pharmacology and Toxicology Data

Proposed Mechanism of Action of NEO-101

The NEO-101 antibody was tested for antibody-dependent cell cytotoxicity (ADCC) activity against several colorectal and pancreatic tumor cell targets in vitro. The ADCC assay measures the amount of cell cytotoxicity that an antibody facilitates in a defined time period by the release of radiolabelled cytoplasmic proteins into the culture medium. The data show that in a standard 4-hour 111-Indium release assay that NEO-101 facilitated the killing of the colorectal and pancreatic tumor cell lines. The specific lytic activity of NEO-101 is demonstrated with an isotype IgG control as well as cell line controls that do not express the MUC5AC antigen (DU145 and SK-mel). See Table 9. The specific lytic activity was titratable with the number of effector cells in the assay.

TABLE 9

ADCC Assay: NEO-101 Antibody Killing Against Tumor Cell Lines

| Tumor Cell Line Target | Effector:Target Cell Ratio | % Specific Killing (±SEM) Isotype control Ab | NEO-101 |
|---|---|---|---|
| Colo-205 (Colorectal) | 50:1 | 9.8 ± 1.9 | 66.7 ± 0.6 |
| | 25:1 | 0.8 ± 1.2 | 46.4 ± 1.6 |
| | 12.5:1 | −0.5 ± 0.1 | 32.8 ± 2.0 |
| SW620 (Colorectal) | 50:1 | 1.6 ± 0.2 | 63.7 ± 2.9 |
| | 25:1 | 3.5 ± 1.8 | 61.0 ± 1.8 |
| | 12.5:1 | 0.0 ± 0.3 | 51.5 ± 0.9 |
| SW1463 (Colorectal) | 50:1 | 0.1 ± 1.1 | 33.8 ± 1.0 |
| | 25:1 | −1.3 ± 0.2 | 25.5 ± 0.6 |
| | 12.5:1 | −1.2 ± 0.1 | 17.9 ± 1.7 |
| LS174T (Colorectal) | 50:1 | −1.2 ± 0.1 | 26.8 ± 2.9 |
| | 25:1 | −0.8 ± 0.1 | 18.5 ± 4.1 |
| | 12.5:1 | −1.1 ± 0.0 | 9.5 ± 0.5 |
| AsPC-1 (Pancreatic) | 50:1 | −0.8 ± 2.9 | 44.5 ± 6.8 |
| | 25:1 | −7.0 ± 2.2 | 36.2 ± 2.6 |
| | 12.5:1 | −1.2 ± 0.9 | 26.5 ± 6.7 |
| CFPAC-1 (Pancreatic) | 50:1 | −1.2 ± 2.3 | 26.9 ± 1.6 |
| | 25:1 | −2.4 ± 0.1 | 23.2 ± 2.2 |
| | 12.5:1 | −2.0 ± 0.4 | 11.1 ± 1.6 |
| PANC-1 (Pancreatic) | 50:1 | −2.2 ± 0.4 | 46.8 ± 2.1 |
| | 25:1 | −2.5 ± 0.4 | 33.2 ± 3.3 |
| | 12.5:1 | −3.9 ± 0.3 | 21.2 ± 0.6 |
| SK-MEL (Melanoma) | 50:1 | 2.7 ± 0.7 | 4.6 ± 1.1 |
| | 25:1 | 1.5 ± 0.3 | 3.3 ± 1.1 |
| | 12.5:1 | 1.6 ± 0.4 | 2.3 ± 0.6 |
| DU145 (Prostate) | 50:1 | −0.3 ± 0.2 | −0.5 ± 0.3 |
| | 25:1 | −0.7 ± 0.1 | 0.3 ± 0.8 |
| | 12.5:1 | −0.2 ± 0.2 | −0.3 ± 0.1 |

These in vitro results demonstrate that the NEO-101 antibody was capable of directing antibody-dependent cell cytotoxicity in the presence of normal human PBMCs.

Anti-Tumor Activity

The NEO-101 antibody was tested for anti-tumor activity using the human AsPC-1 pancreas tumor xenograft model in nude mice. In this activity model, mice were implanted with human AsPC-1 tumor cells and allowed to establish to approximately 20-50 $mm^3$, measurable with a caliper in approximately 4-6 days. The treatment regimen included intraperitoneal injection of 200 μg of research-grade NEO-101 or a negative control human IgG (Pierce), followed on the next day with an intraperitoneal injection of IL-2-activated normal human PBMCs (approximately $2\times10^7$ per mouse per injection). Two cycles of treatment were administered such that antibody injections occurred on days 5 and 8, and PBMC injections occurred on days 6 and 9 in this study. Throughout the study, the tumor growth was monitored twice weekly by measurement with a caliper. Tumor volume was calculated using the equation: Volume=(width× length)/2, in units of cubic millimeters. If a tumor reached approximately 800 $mm^3$, or became ulcerated or necrotic, the mouse was humanely sacrificed. The study was terminated on study day 35.

Figure 3:
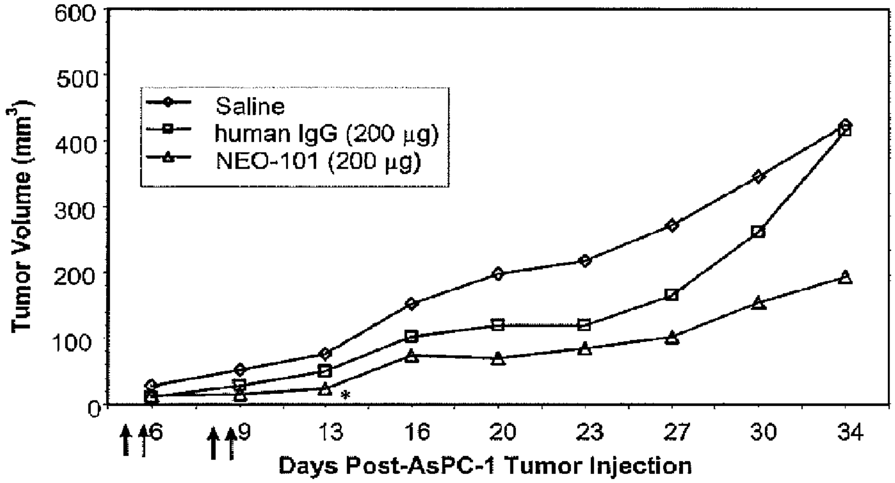
FIG. 3 depicts anti-tumor activity in human AsPC-1 pancreas tumor xenograft model in nude mice comparing administration of saline, human IgG (200 μg), and NEO-101 (200 μg) comprising two cycles of treatment. The heavy arrows indicate days of NEO-101 injection (ip), light arrows indicate days of PBMC injection (ip), the asterisk (*) indicates statistically significant differences between NEO-101 treated mice with human IgG treated mice.

FIG. 3 demonstrates the average tumor growth for each group plotted together. Tumor growth inhibition was observed during the antibody treatment phase of the study, and the difference between the NEO-101 treated mice and the control groups was statistically significant beginning on day 13 and continuing for the remainder of the study (P=0.0072 by one-way ANOVA), as indicated by the asterisk on the graph.

Figure 4:
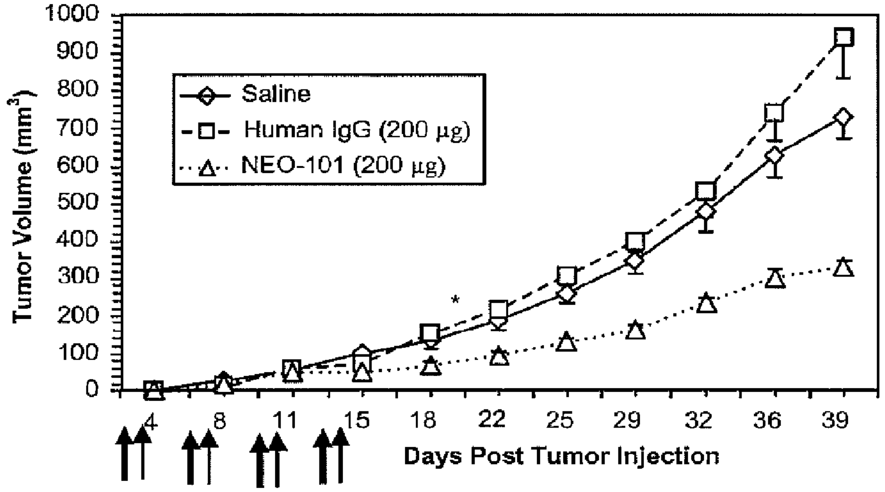
FIG. 4 depicts anti-tumor activity in human AsPC-1 pancreas tumor xenograft model in nude mice comparing administration of saline, human IgG (200 μg), and NEO-101 (200 μg) where four cycles of treatment were administered instead of two cycles. The heavy arrows indicate days of NEO-101 injection (ip), light arrows indicate days of PBMC injection (ip), the asterisk (*) indicates statistically significant differences between NEO-101 treated mice with human IgG treated mice.

This anti-tumor activity study was repeated in a separate study using the same AsPC-1 pancreas tumor model and the 200 μg dose of NEO-101 antibody. However, in the second study, four cycles of treatment were administered instead of two cycles. The antibody was administered on days 4, 7, 10, and 13 in this study while the PBMCs were injected on days 5, 8, 11, and 14. All other parameters were kept the same as the previous study. The data shown in FIG. 4 demonstrate very similar growth inhibition in response to treatment with NEO-101. Tumor inhibition was evident during the treatment phase of the study, and the difference between the NEO-101 treated mice and the human IgG control mice was statistically significant beginning on Day 18 and continuing for the remainder of the study (P=0.0044 by one-way ANOVA; n=8 per group). The fact that these two independent anti-AsPC-1 activity studies yielded such similar results supports the usefulness of the NEO-101 antibody for the treatment of pancreatic and colorectal cancer.

Figure 5:
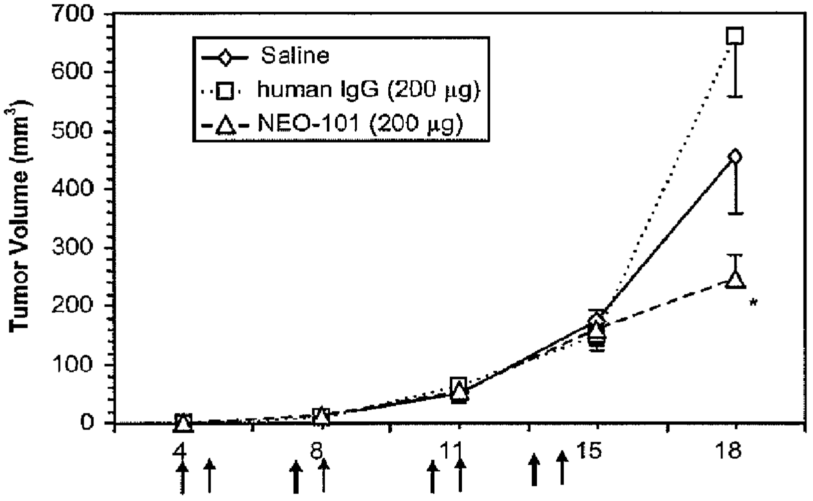
FIG. 5 depicts anti-tumor activity in human LS174T colorectal tumor xenograft model in nude mice comparing administration of saline, human IgG (200 μg), and NEO-101 (200 μg). The heavy arrows indicate days of NEO-101 injection (ip), light arrows indicate days of PBMC injection (ip), the asterisk (*) indicates statistically significant differences between NEO-101 treated mice with human IgG treated mice.

Since the LS174T colorectal tumor cell line served as a good target in vitro in the ADCC assay, this cell line was used in a xenograft tumor model. The LS174T cells were implanted subcutaneously in nude mice and the same treatment regimen was administered to these mice. The data shown in FIG. 5 demonstrate that this is a very aggressive tumor in vivo since the study had to be terminated in less than 3 weeks. Nonetheless, we observed a 2-3-fold reduction in tumor growth in NEO-101 treated mice compared to the 2 control groups of mice following the treatment cycles. The anti-tumor effect upon treatment with NEO-101 was significant on the last day of measuring tumors with P=0.0145 by one-way ANOVA. However, many of the tumors in the control groups became ulcerated and were greater than 1000 $mm^3$ and the study was terminated.

Cytokine Response

In a preliminary study designed to evaluate potential cytokine responses in vivo, normal BALB/c mice were injected intravenously with either 3.5 mg/kg or 14 mg/kg (5 mice per group) of research-grade NEO-101. Blood was collected on Study Day 3 (72 hours post-injection) and Study Day 10. Serum was prepared (including from the pre-bleed of each mouse) and tested for the presence of mouse IL-2, IFN-γ, IL-4, and IL-5 in a multiplex bead assay using the SearchLight Array service offered by Aushon BioSystems, Inc.

The data demonstrated that there was a small increase in the serum levels of IL-2 and IL-5, but no appreciable change in IFN-γ or IL-4 on day 3. There appeared to be no dose-dependency related to the increase of IL-2 or IFN-γ, and the minor elevation of these 2 cytokines showed evidence of beginning to resolve at the day 10 time point. Thus, in this study a small and apparently transient cytokine response was observed that might be expected upon injection of a bolus of foreign protein into a mouse.

Antibody Response

Mouse anti-NEO-101 antibody (MAHA) responses were also measured in this study (CB08-5110). The analysis employed an ELISA based assay to detect NEO-101-specific antibodies in mouse serum. The data demonstrated that normal BALB/c mice mounted an antibody response against the NEO-101 molecule. However, the antibody responses were highly variable on a mouse-to-mouse basis, and the overall responses were moderate, suggesting that the NEO-101 antibody was only mildly immunogenic in mice despite the fact that it is comprised in 67% of human IgG sequences. There were no differences between male and female mouse MAHA responses.

Toxicity

A preliminary non-GLP toxicity study using a research-grade preparation of NEO-101 was also conducted. Normal BALB/c mice were injected with a single IV dose of saline, or 3, 10, 30, or 100 mg/kg of NEO-101 (n=3 female mice per group). In-life parameters measured included body weights and clinical observations. Mice were humanely sacrificed 72 hours following the injection and specimens were collected for analysis. Post-mortem parameters included macroscopic examination, blood cell counts, serum chemistries, and histopathological evaluation of selected major organs and tissues. The results of the preliminary study demonstrated no significant changes in body weight, blood cell counts, and histopathology of 7 major organs and tissues (liver, spleen, kidney, lung, heart, intestine, pancreas). A mild, but statistically insignificant elevation of serum aspartate transaminase (AST) was observed in 2 out of 3 mice that received 100 mg/kg of NEO-101. No other toxicities were detected in these studies potentially associated with NEO-101, including during histopathological examination of the major organ systems in these mice.

Pharmocokinetics

To determine whether gender impacted the disposition of NEO-101 in vivo, each treatment group contained four males and four females. Clearance, $C_{max}$ and half-life following a single dose of 10 or 100 mg/kg were compared by non-parametric Mann-Whitney test. No significant gender-specific differences were observed in clearance or $C_{max}$. However, the serum half-life of NEO-101 was shorter in females than in males. This finding was only significant at the 100 mg/kg dose level (t½: 109.5±14.72 h versus 2854±139.5 h, P=0.029). However, it is likely that this is a spurious observation, arising from high inter-animal variability, as this difference in half-life was not replicated following multiple doses, regardless of dose level.

The data provides useful guidance for the dosing schedule of possible therapeutic regimes. Mice injected intravenously with 10 mg/kg of NEO-101 may be used for comparison to the doses used in therapy regiments for humans, for instance. Overall, the disposition of NEO-101 antibody in mice is characterized by low clearance, a limited volume of distribution and a long elimination half-life. The mean half-life at 10 mg/kg was 129 hours (5.4 days) after a single dose, increasing to 279 hours (11.6 days) after four doses, which should allow for adequate exposure when dosed every 2-3 weeks in a clinical trial.

Biodistribution

The biodistribution of the NEO-101 antibody was evaluated in tumor-bearing mice using radio-labeled antibody. The NEO-101 antibody was labeled on surface-exposed tyrosines with 125-Iodine and purified via gel filtration chromatography. Nude mice bearing established subcutaneous human pancreatic tumors (CFPAC-1) or colorectal tumors (LS174T) were injected intravenously with the radioiodinated NEO-101 on day 0. Mice were sacrificed on study day 1, 2, 4, and 6. On necropsy days, mice were exsanguinated and major organs (e.g., lungs, intestine, liver, pancreas, spleen, kidneys, blood) including the subcutaneous tumor were collected.

The data show that radiolabeled NEO-101 localized predominantly in the established tumor xenografts that are known to express the MUC5AC target antigen, and, not in other non-target tissues examined. In the pancreatic CPFAC-1 tumor model, NEO-101 uptake was statistically higher in tumors than in any other tissue type at all time-points, except when compared to those in blood in females only on day 6. Interestingly, mice harboring the colorectal LS174T tumor demonstrated NEO-101 uptake that increased in both sexes reaching the highest levels on day 6. The uptake was statistically higher in tumors than in any other tissue type examined at any timepoint during the study. These studies support the notion that NEO-101 can traffic to the tumor site following intravenous administration of the antibody, where it can bind to it target antigen, accumulate at the tumor site, and elicit an anti-tumor effect.

The biodistribution of NEO-101 in CFPAC-1 pancreatic tumor model was used to study the concentration of the NEO-101 antibody in tumors over the course of 6 days. Mice were injected with either $3\times10^6$ CFPAC-1 and allowed to grow to 50-100 $cm^3$. Afterward, $^{125}$I-labeled NEO-101 was injected at 400 μg/ml in 200 μl of PBS and the mice sacrificed. Organs were harvested and the amount of $^{125}$I labeled NEO-101 was counted and normalized to blood. The data demonstrated localization and accumulation of radio-labeled NEO-101 at the site of the tumor in vivo, whereas none of the major organ systems (e.g., kidneys, spleen, pancreas, stomach, lungs, liver, intestines) exhibited an enrichment of radiolabeled NEO-101.

Biodistribution of NEO-101 in LS174T colorectal tumor model was studied using NEO-101 antibody in tumors over the course of 6 days. Mice were injected with $3\times10^6$ LS174T cells and allowed to grow to 50-100 $cm^3$, Afterward, $^{125}$I-labeled NEO-101 was injected at 400 μg/ml in 200 μl of PBS and the mice sacrificed. Organs were harvested and the amount of $^{125}$I-labeled NEO-101 was counted and normalized to blood. The data demonstrate the time-dependent localization and accumulation of radiolabeled NEO-101 at the site of the tumor in vivo, whereas none of the major organ systems (e.g., kidneys, spleen, pancreas, stomach, lungs, liver, intestines) exhibited an enrichment of radiolabeled NEO-101.

In summary, the results, particularly the in vitro ADCC activity and the in vivo anti-tumor activity support the use of NEO-101 as a therapeutic for cancer patients who express the tumor target antigen, NPC-1. Tissue staining with NEO-101 revealed a strong positive correlation to colon and pancreas cancer tissues because little or no cross-reactivity with normal human pancreas or colon tissue, and no cross-reactivity to other normal tissues was seen. The pharmacokinetic data demonstrate that the NEO-101 serum half-life in mice is within a similar range compared to other therapeutic immunoglobulins, and supports administration of the antibody every two to three weeks. The bio-distribution study demonstrated the ability of NEO-101 antibody to traffic to, and accumulate in established tumors suggesting that a NEO-100 antibody may be used as a delivery vehicle to delivery agents (e.g., cytotoxic agents or labels) directly to tumors.

Example 8

Detection of NPC-1 Epitope in Fecal Samples

Stools are a rich source of cells derived from the gastrointestinal tract, and cancer antigens may be measured in fecal samples using standard techniques, e.g., immunochemistry such as ELISA. Kim, et al. (2003) *Annals Clin. & Lab. Sci.* 33: 32-38; Tøn, et al. (2000) *Clin. Chimica Acta.* 292: 41-54. A homologous format ELISA that uses NEO-101 antibody as both capture and detection reagent was developed. A preliminary control experiment with human pancreatic CFPAC-1 tumor cell supernate (containing the NPC-1 antigen) spiked into a healthy stool sample showed that stool did not interfere with the ELISA. Next, samples of stool collected during colonoscopy from colorectal cancer patients (n=4), stool from people with small polyps (n=4), stool from people with multiple polyps (n=2), stool from people with large polyps (n=3), and stool from healthy adults (n=13) were applied to the ELISA. A soluble extract of stool was prepared by detergent lysis and centrifugation. The level of NEO-101-specific NPC-1 epitope measured in this ELISA was compared among all groups. Table 10 shows data from two independent experiments in which some samples were spiked with CFPAC-1 cell line derived from pancreas duct carcinoma:

TABLE 10

Detection of NPC-1 epitope in human fecal extracts by ELISA

| Sample | Experiment 1 extract 1/10 | Experiment 1 extract 1/50 | Experiment 2 extract 1/10 | Experiment 2 extract 1/50 |
|---|---|---|---|---|
| 1 fecal sample from healthy donor | 285* | 187 | 204 | 159 |
| 2 fecal sample from pt with celiac disease | 291 | 204 | 224 | 181 |
| 3 fecal sample from pt with polyps | 855 | 281 | 723 | 231 |
| 4 fecal sample from pt with colon cancer (hyperplasia) | 3629 | 757 | 3217 | 624 |
| 5 fecal sample from pt with colon cancer | 5137 | 1043 | ND | ND |
| sample 1 spiked with 10 μl CFPAC-1 supernate | 1944 | 461 | 1354 | 346 |
| sample 2 spiked with 10 μl CFPAC-1 supernate | 2045 | 438 | ND | ND |
| sample 3 spiked with 10 μl CFPAC-1 supernate | 3219 | 582 | ND | ND |
| sample 4 spiked with 10 μl CFPAC-1 supernate | 5926 | 1373 | ND | ND |
| sample 5 spiked with 10 μl CFPAC-1 supernate | 7692 | 1694 | ND | ND |
| CFPAC-1 supernate | 2902 | ND | 2772 | ND |
| HTB 35 supernate | 143 | ND | 82 | ND |

*numbers represent NPC-1 epitope-positive cell equivalents/mL

ND = not done

HTB-35 = NPC-1 epitope negative control supernate

Results using CFPAC-1 supernate as a surrogate source of NPC-1 antigen showed that the contents of fecal material did not interfere with the ability of the ELISA to measure the NEO-101 antibody reactive NPC-1 epitope. When extracts of stool were applied to the ELISA, it was apparent that healthy people did not express NEO-101 antibody reactive NPC-1 epitope in their stool. The signal in the assay was similar to background levels (average about 723 units). In contrast, people with small polyps had higher levels (average about 3,819 units); people with multiple polyps expressed higher levels (average about 7,369 units); people with large polyps had even higher levels (average about 10,189 units); and colon cancer patients had the highest levels of NEO-101 reactive antigen (average about 175,983 units), more than about 240 times the level of NPC-1 epitope compared with healthy people. ELISA using NEO-101 antibody (to detect NPC-1 epitope) is a specific and useful assay for the diagnosis and monitoring of pancreas cancer using stool samples. Inhibitors of NEO-101 antibody ELISA are not present in fecal extracts. The assay is titratable and may be quantitative. See also FIG. 1.

This data establishes a correlate level of NEO-101 reactive antigen, measured by a novel stool-based ELISA, with colon cancer disease progression. The level of NEO-101-specific NPC-1 epitope detected increased concomitantly with the number and size of polyps observed during colonoscopy, and reached the highest levels in patients with colon cancer. Thus, this ELISA test provides for early non-invasive diagnostic screening for colorectal cancer using an anti-NEO-101 antibody.

Example 10

Neo-101 Antibody Shows Anti-Tumor Effects In Vitro and In Vivo

Introduction:

NEO-101 is a chimeric monoclonal antibody which may be used for the treatment of pancreatic and colorectal cancers. NEO-101 antibody appears to recognize a variant form of MUC5AC expressed specifically by human pancreatic and colorectal tumor tissues and cell lines.

Methods:

The NEO-101 antibody was selected from a panel of hybridomas generated from mice immunized with semi-purified membrane-associated proteins derived from biologically screened, pooled human allogeneic colon cancer tissues. In vitro assays and in vivo studies were performed to characterize the GMP-grade antibody.

Immunohistochemistry (IHC)

Slides were deparaffinized, rehydrated and antigen retrieval was performed. Slides were then stained with 10 μg/ml biotinylated NEO-101 antibody and then streptavidin-HRP was applied for color development. Slides were counter stained with H.E., hydrated and fixed. The results demonstrate NEO-101 binding specific for pancreatic or colorectal tumor tissue, but no binding to normal pancreas or colon tissue. See Table 11. The specificity of NEO-101 for pancreatic and colorectal tumor tissue was further shown by staining lung tumor tissue. While there was significant binding to these tissues with a commercial antibody that recognizes normal MUC5AC, there was no reactivity of NEO-101 with these lung tumor tissues.

TABLE 11—Specificity of NEO-101 Antibody

FACs data showing NEO-101 antibody binding to colon cancer and pancreatic cancer cell lines. Cells were washed and suspended in either 2 μg/ml NEO-101-FITC or isotype control antibody-FITC for 1 hour, washed and then subjected to FACS analysis. Experiments with all cell lines were repeated at least three times. The NEO-101 antibody reacts with colorectal and pancreatic tumor tissues, but does not cross-react with normal human tissues, except for sporadic, weak binding to certain GI tract tissues, which may indicate a pre-malignant state. NEO-101 antibody binds to cancer cells as observed by immunofluoresence (IF) staining results using a FITC labeled NEO-101 antibody (2 μg/ml) on pancreatic cancer cell line AsPC-1, colorectal cancer cell line LS174T, but does not bind to the lung cancer cell line A549. DAPI was used to stain the nucleus. The IF showed clear specific staining of the pancreatic and colorectal cells, but not the lung cancer cells. The staining pattern of these pancreatic and colorectal tumor cells was predominantly membrane-associated, consistent with the expression profile of MUC5AC. See Table 12.

TABLE 12

NEO-101 Antibody binding to Pancreatic and Colorectal Tumor Cell Lines

| Tumor Cell Lines | Isotype Control (Percent positive) | NEO-101 (Percent positive) |
|---|---|---|
| LS174 | 3.85 | 89.72 |
| Colo-205 | 2.33 | 94.67 |
| SW480 | 3.38 | 58.98 |
| CFPAC | 1.79 | 52.56 |

The NEO-101 antibody exhibits cell-specific binding and ADCC activity against human colorectal and pancreatic tumor cells, but not against control tumor cell lines. In vivo, the anti-tumor activity of NEO-101 antibody was tested using pre-established subcutaneous human tumor xenograft models. Surprisingly, the NEO-101 antibody showed significant, and reproducible, anti-tumor action, including some complete tumor regressions.

The results herein show that NEO-101 antibody may bind specifically to pancreatic and colon cancer tissue samples and also to cell lines. NEO-101 antibody may induce antibody dependent cell cytotoxicity in colon and pancreatic cells but not in melanoma and prostate cancer. In vivo studies suggest that NEO-101 antibody inhibits tumor growth in xenograft models of pancreatic and colon cancer. Bio-distribution studies showed that NEO-101 antibody accumulates in the tumor and not in any major organs. There was mild type I and II cytokine responses and expected? antibody responses in mice treated with NEO-101. Therefore, the NEO-101 antibody is specific for pancreatic and colon cancer, and induces ADCC activity in in vitro assays and inhibits tumor growth in vivo.

Particularly, the available data relating to the NEO-101 antibody indicates that it should be safe and efficacious, and that it may have clinical activity in patients whose tumor expresses the variant MUC5AC epitope. Indeed, this antibody should have broad clinical relevance as approximately 50-70% of human pancreatic and colon tumor tissues express an NPC-1 antigen (as shown by positive staining).

Example 11

Biopanning

The biopanning technique harnesses recombinant phage display peptide libraries, typically based on relatively short recombinant peptides fused to a phage coat protein. Phage display describes a selection technique in which a library of variants of a peptide or protein is expressed on the outside of a phage virion, while the genetic material encoding each variant resides on the inside. See, e.g., Sidhu, et al. (2003) *Chembiochem* 4(1): 14-25; Ferrer, et al. (1999) *J. Pept. Res.* 54(1): 32-42; BouHamden, et al. (1998) *J. Biol. Chem.* 273(14): 8009-8016; and Whaley, et al. (2000) *Nature* 405(6787): 665-667.

For example, the Ph.D.™-12 phage display peptide library is a recombinatorial library of random dodecapeptides fused to the minor coat protein (plll) of M13 phage. The displayed 12-mer is expressed at the N-terminus, followed by a short spacer peptide (GGGS), and then the wild-typs plll sequence. The library consists of approximately $2.7\times10^9$ sequences amplified once to yield approximately 100 copies of each sequence in 10 μl of phage. The 4B6 Id may be used in competitive immunoassays to release NEO-101-bound phage in biopanning (e.g., using the Ph.D.™-12 M13 library phage display system) to identify NEO-101 epitopes. 4B6 is an anti-idiotypic antibody described in International Patent Application No. PCT/US2011/41503.

More specifically, enrichment of clonal phage by phage tittering used several rounds of biopanning. The first round of biopanning captured a mixture of NEO-101-biotin and display phage to a streptavidin-coated plate, and bound phage was released by 100 μg/ml 4B6 in 0.1% Tween® 20 (polysorbate 20 non-ionic detergent), and yielded $1.6\times10^3$ pfu/10 μl. Another round of biopanning, NEO-101 antibody was coupled to Dynal® beads, and bound phage was released by 100 μg/ml 4B6 in 0.1% Tween® 20, yielding $1.1\times10^6$ pfu/10 μl. Another round of biopanning captured a mixture of NEO-101 antibody and phage to Protein G-agarose, and bound phage was released by 200 μg/ml of 4B6 in 0.5% Tween® 20, which resulted in $4.5\times10^5$ pfu/10 μl. Yet another round of biopanning captured a mixture of NEO-101 antibody and phage to Protein A-agarose, and bound phage was released by 200 μg/ml 4B6 in 0.5% Tween® 20, and yielded $1.3\times10^6$ pfu/10 Twelve phage clones from each of three biopanning rounds were selected for sequence analysis. The resulting peptides are shown in FIG. 6.

Figure 7:
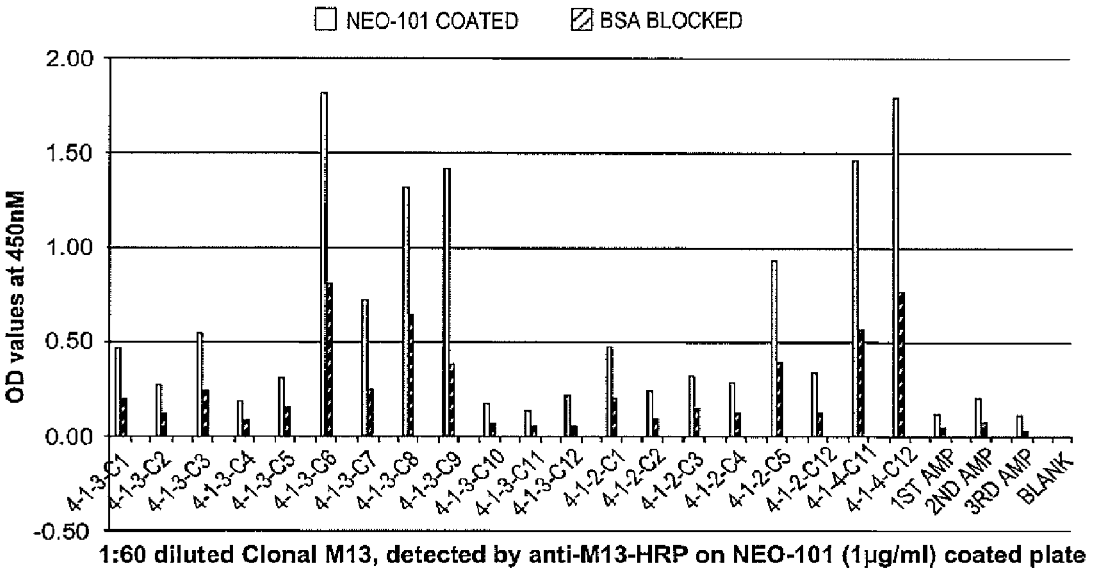
FIG. 7 is a bar graph depicting results of phage clones in NEO-101 ELISA.

The M13 clones identified from the several rounds of biopanning were ELISA-tested. Aliquots of 100 μl/well NEO-101 (1 μg/ml in CBS buffer) in 96 well plate were incubated at 4° C. overnight. Wells were then washed three times with TBST (0.05% Tween). Non-specific binding was inhibited by blocking with 200 μl of 5% BSA in 0.1 M $NaHCO_3$ at room temperature (RT) for 1 hr. Clonal M13 was diluted 1:60 in TBS and added at 100 and the wells incubated at RT for 1 hr. The wells were then washed three times with TBST. Aliquots of 100 μl anti-M13-HRP, diluted 1:5,000 in TBS, were added to each well, and incubated at RT for 1 hr. The wells were then washed three times, TMB was added, and the plates were read at 450 nm. Control wells did not contain NEO-101 antibody. The results of the clonal M13 binding ELISA are shown in FIG. 7, which indicated 6 clonal M13 phage bind to NPC-1C coated wells not BSA blocked control wells significantly.

The peptides identified in the biopanning experiments were used in competitive binding immunoassays using colon cancer antigens. Briefly, the antigen preparation (Colon Ag) was derived from pooled allogeneic colon cancer specimens from multiple patients, which was obtained post-operatively. Cell membranes were isolated from the tumor, and soluble membrane proteins were prepared by sonication and Sephadex G-200 chromatography. Semi-purified tumor-associated antigens were identified by in vitro and in vivo testing in colon cancers and controls for cell-mediated immunoreactivities. Tumor-associated antigens were detected in fetal intestine and cell membranes, and was localized on tumor cell membranes. Using discontinuous, gradient gel electrophoresis, both tumor-associated antigens and CEA were separated and cross-compared. The tumor-associated antigens (Colon Ag) was shown to be distinct from CEA (Hollinshead et al., 177 Science 887 (1972).

Figure 8A:
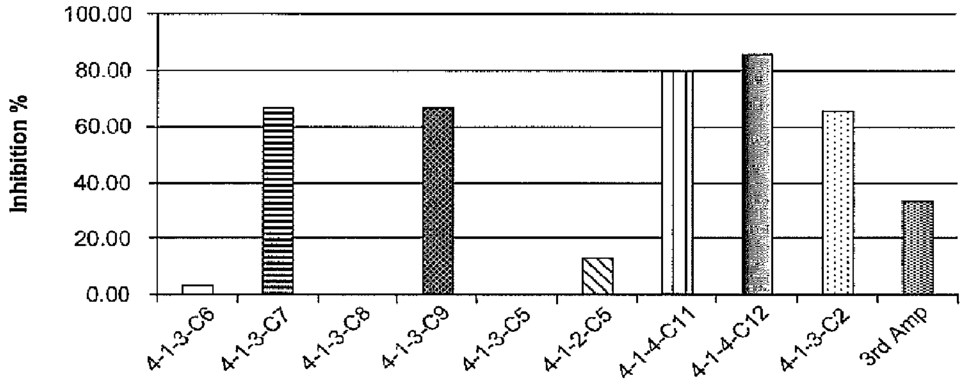
FIG. 8A-B depicts NEO-1.01 binding inhibition by phage M13 clones.
Figure 8B:
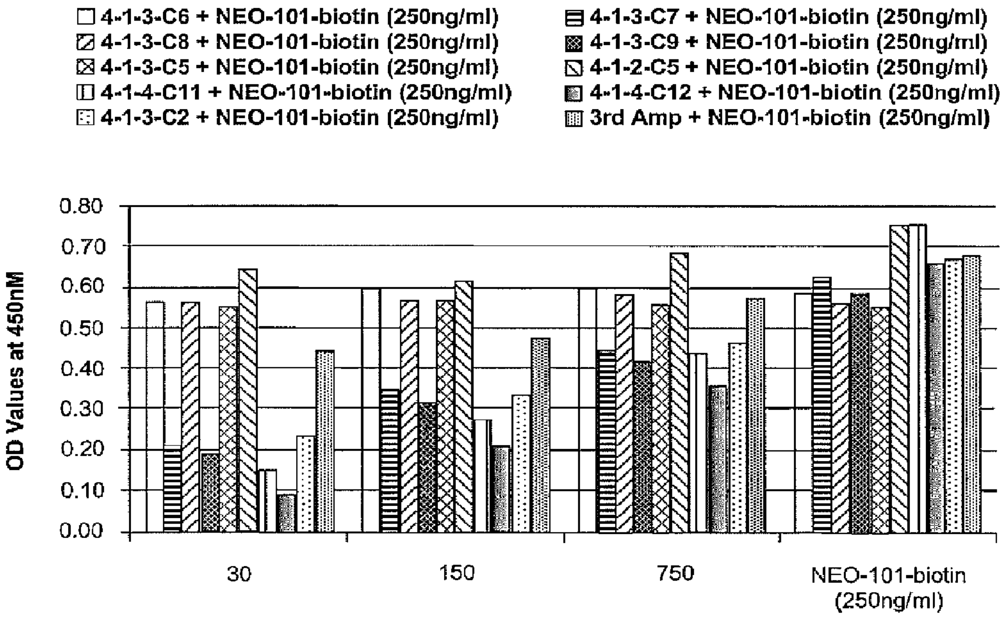

Aliquots of 100 μl/well Colon Ag (3 μg/ml in CBS buffer) in 96 well plate were incubated at 4° C. overnight. Wells were then washed three times with TBST (0.05% Tween). Non-specific binding was inhibited by blocking with 200 μl of 1% milk in TBS at RT for 1 hr. Aliquots of 100 μl/well premixed NEO-101-biotin and test peptide were added, and the wells incubated at RT for 1 hr. The wells were then washed three times with TBST. Aliquots of 100 μl streptavidin-HRP, diluted 1:2000, were added to each well, and incubated at RT for 1 hr. The wells were then washed three times, TMB was added, and the plates were read at 450 nm. Control wells contained NEO-101-biotin at a two-fold serial dilution. The results of the clonal M13 binding ELISA are shown in FIGS. 8A-B. FIG. 8A demonstrated 5/9 clonal M13 phages block NPC-1C binding to colon Ag significantly; the percentage of inhibition is more than 60%. The OD values from this competitive ELISA test was shown in FIG. 8B.

The M13 clones identified by the biopanning were also immunoassayed using magnetic beads. Aliquots of 5 μl M13 phage ($10^{11}$/10 μl) were mixed with 10 μl NEO-101-coupled Dynal® beads at RT for 20 min on a rotator. CFPAC1 cells (30 μl of $10^6$ cells/ml) were added and incubated at 4° C. for 30 min. Rosetted cells were counted (>8 beads/cell). Results are shown in Table 13. The experiments showed that clones 4-1-2-05, 4-1-3-C8, 4-1-3-C9, 4-1-4-C11 and 4-1-4-C12 blocked NEO-101-coupled beads from binding to the CFPAC1 cells.

TABLE 13

Binding of M13 clones to NEO-101 antibody-coupled beads.

| Dynal beads coupled with: | M13 Clone | Positive rosette cells (%) |
|---|---|---|
| H-IgG | TBS | 1 |
| NEO-101 | TBS | 41 |
| H16C3 | TBS | 60 |
| NEO-101 | 4-1-2-C5 | 0 |
| NEO-101 | 4-1-3-C8 | 0 |
| NEO-101 | 4-1-3-C9 | 0 |
| NEO-101 | 4-1-3-C11 | 38 |
| NEO-101 | 4-1-4-C11 | 0 |
| NEO-101 | 4-1-4-C12 | 0 |
| NEO-101 | 4-1-4-C11 + 4-1-2-C5 | 0 |
| H16C3 | 4-1-4-C11 | 36 |
| H16C3 | 4-1-4-C11 + 4-1-2-C5 | 59 |

Figure 9A:
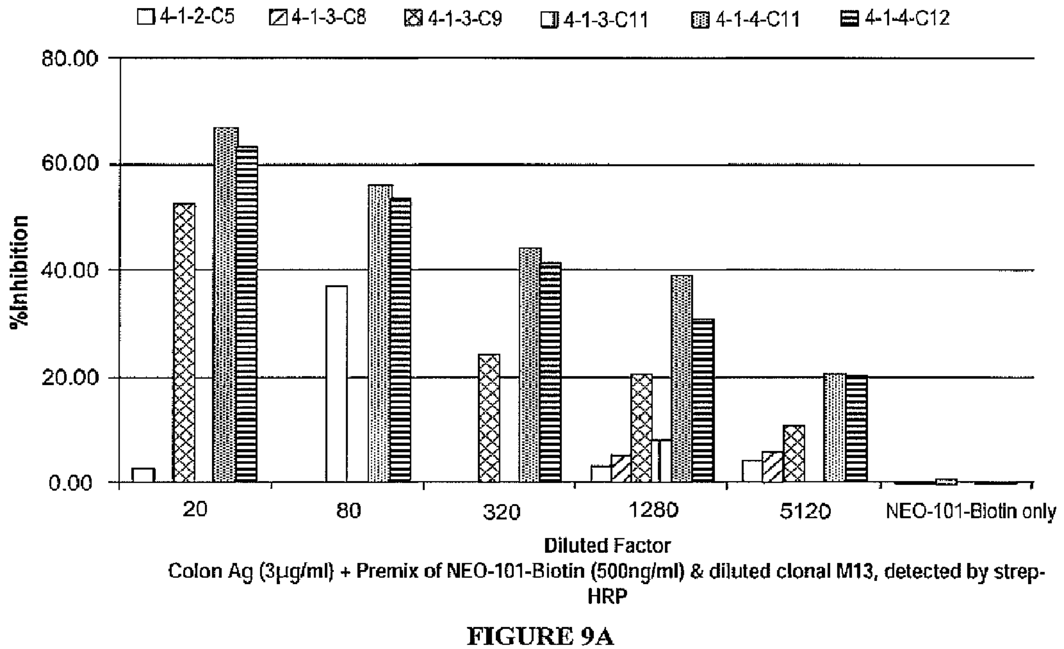
FIG. 9A depicts the percent NPC-1C binding inhibition by M13 clones in ELISA. The M13 clones were derived from the biopanning that yielded $10^{11}$ pfu/10 μl.
Figure 9B:
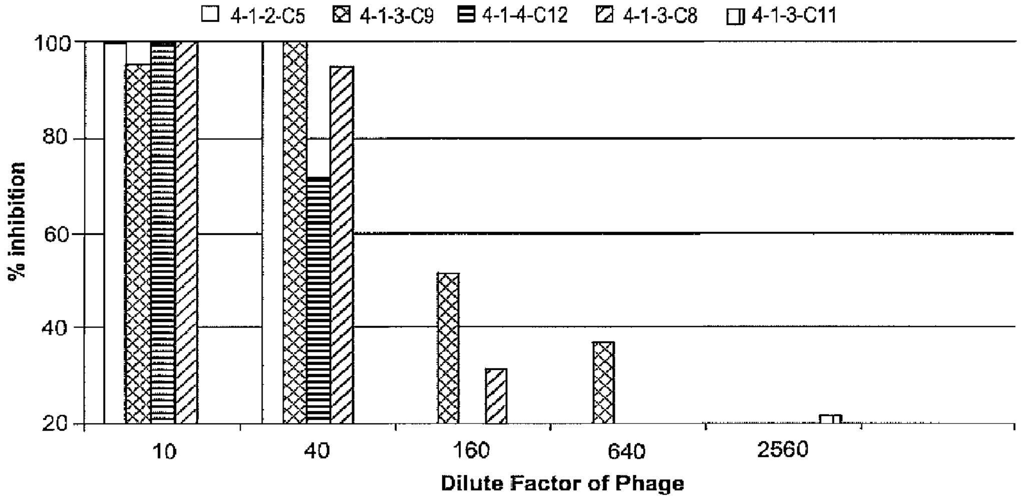
FIG. 9B shows NEO-101 binding inhibition by M13 clones on colon antigen (3 μg/ml)-coated plates.

In another experiment, wells were coaded with 100 μl/well Colon Ag (3 μg/ml in CBS buffer) and incubated at 4° C. overnight, and the wells washed three times with TBST (0.05% Tween). The wells were blocked with 200 μl of 1% milk at RT for 1 hr. A pre-mix of NEO-101-biotin and clonal M13 phages e was added at 100 μl/well and incubated at RT of 1 hr, followed by three washes with TBST. Streptavidin-HRP (100 μl of 1:2000 dilution) was added and the reaction incubated at RT for 1 hr, and the wells washed three time. TMB was added, and the wells were read at 450 nm. The results of clonal M13 phages blocking NPC-1C binding to colon Ag are shown in FIGS. 9A and 9B, which demonstrated the does dependent inhibition of clonal M13 phages on NPC-1C binding to colon Ag in separate experiments.

Several clones were identified by the biopanning and subsequent immunoassays. From this work, four clones (and one control) were selected to synthesizing peptides for further characterization as shown in Table 14. The M13 native sequences are the YSHS (SEQ ID NO: 25) at the N-terminal end of the peptide, and the GGGS (SEQ ID NO: 26) at the C-terminus of the peptide.

TABLE 14

NEO-101-binding peptides identified in biopanning and immunoassays

| Peptide ID | Amino Acid Sequence | SEQ ID NO |
|---|---|---|
| 4-13-C9 | YSHSFPEDYFRYTNQKGGGS | 19 |
| 4-1-4-C12 | YSHSSLPDDWFRYINYGGGS | 20 |

TABLE 14-continued

NEO-101-binding peptides identified in biopanning and immunoassays

| Peptide ID | Amino Acid Sequence | SEQ ID NO |
|---|---|---|
| 4-1-2-C5 | YSHSWHTLPEKSLDENGGGS | 21 |
| 4-1-3-C8 | YSHSWHTLPESGEVTSGGGS | 22 |
| 4-1-3-C11 (control peptide) | YSHSVHAIEDNWSPRGGGGS | 23 |

Figure 10:
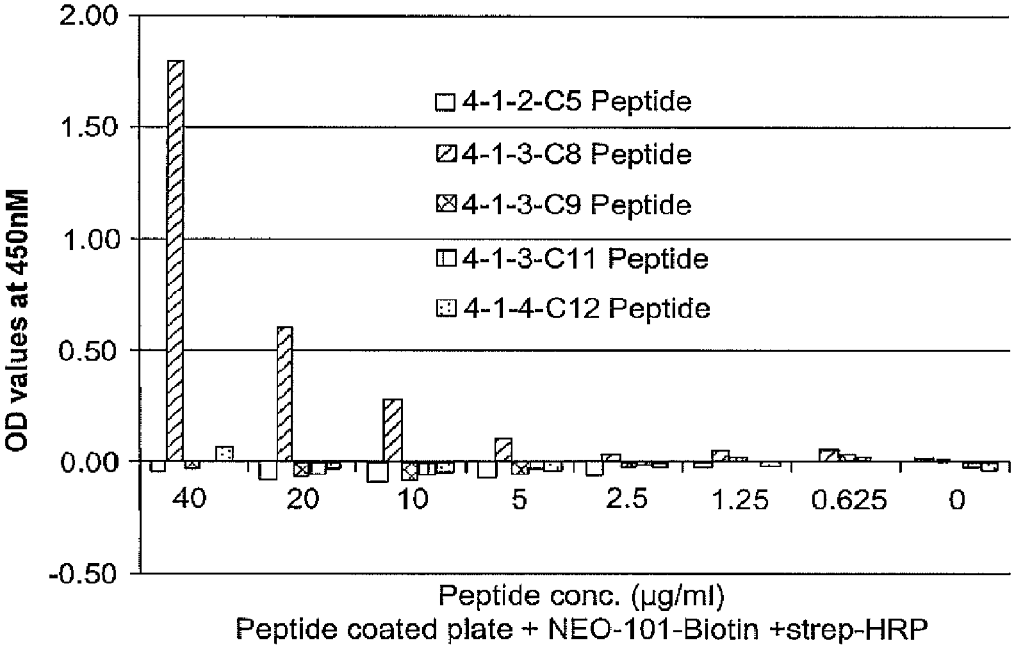
FIG. 10 depicts peptide binding of NEO-101 in an ELISA assay.

The peptide binding was analyzed in ELISA by adding 100 μl/well of peptide in CBS buffer to 96 well plate and incubating at 4° C. overnight, followed by three washes with TBST (0.05% Tween). The solution was blocked with 200 μl of 1% milk in TBS at RT for 20 min. Aliquots of 100 μl NEO-101-biotin (1 μg/ml) were added, and incubated at RT of 2 hours, followed by three washes with TBST. Streptavidin-HRP (100 μl of 1:2000 diluted in 1:10 diluted blocking buffer) was added, and the wells incubated at RT for 1 hr, followed by three washed. TMB was then added, and the wells were read at 450 nm. Controls used 4B6-coated wells. The results of peptide binding to NEO-101 are shown in FIG. 10, which indicates that the peptides failed to bind adequately to the ELISA plate.

Figure 11:
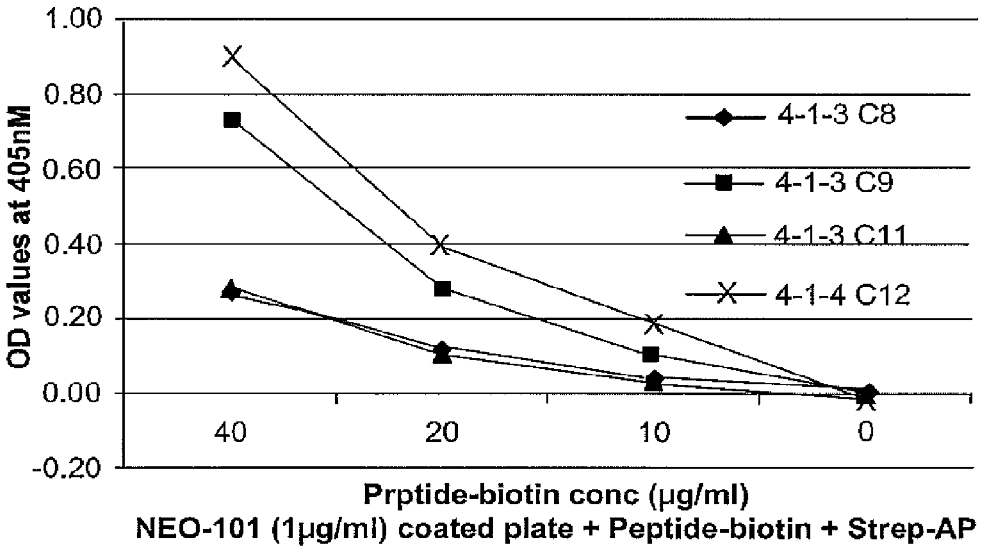
FIG. 11 depicts peptide-biotin binding to NEO-101.

To solve the poor binding of peptides to 96 well plate, peptides were biotinylated using EZ-link micro NHS Biotinylation kit (Pierce Cat#21955), and labeling efficiency checked by dot blot (50%). The biotinylated peptide binding was analyzed in ELISA by adding 100 μl/well of NEO-101 (1 μg/ml) in CBS buffer to 96 well plate and incubating at 4° C. overnight, followed by three washes with TBST (0.05% Tween). The solution was blocked with 200μ/of 1% milk in TBS at RT for 20 min. Aliquots of 100 μl peptide-biotin (1 μg/ml) in 0.1% milk-TBS were added, and incubated at RT of 2 hr, followed by three washes with TBST. Streptavidin-HRP (100 μl of 1:2000 diluted in 1:10 diluted blocking buffer) was added, and the wells incubated at RT for 1 hr, followed by three washed. TMB was then added, and the wells were read at 450 nm. Positive controls for NPC-1C binding used 4B6-biotin. The results are shown in FIG. 11, which indicates biotinlyated peptides bind to NPC-1C coated plate.

Figure 12:
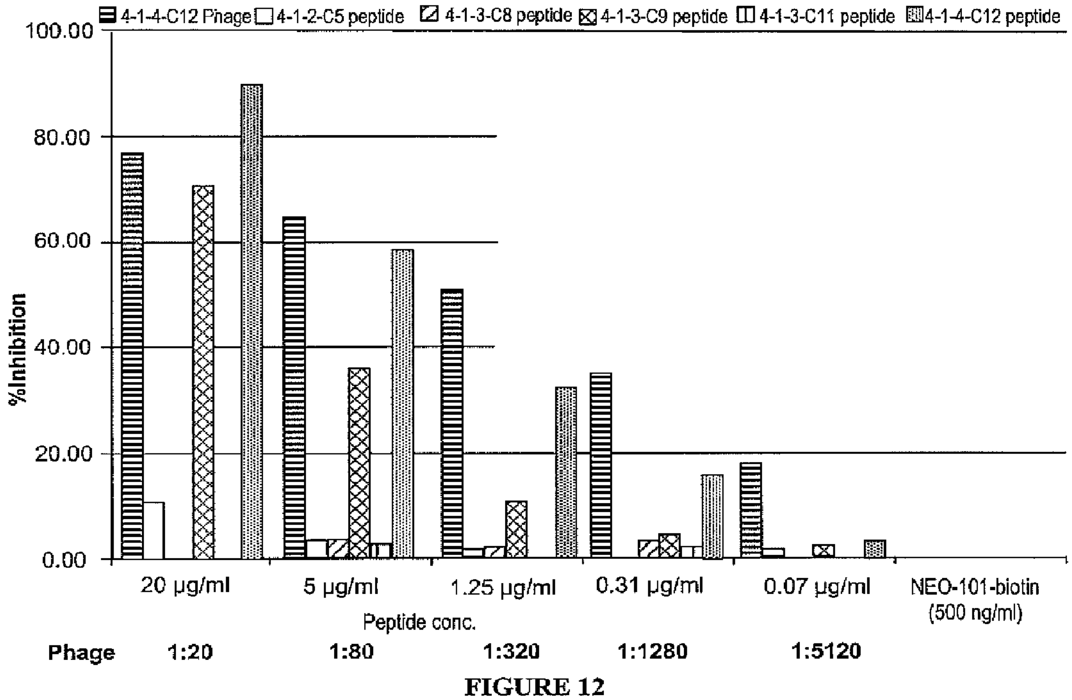
FIG. 12 is a bar graph depicting the percent inhibition of peptides to NEO-101 binding.

An ELISA analysis of the NEO-101 binding inhibition by peptide 4-1-3-C9 and 4-1-4-C12 against Colon Ag was conducted. Aliquots of 100 μl/well Colon Ag (3 μg/ml in CBS buffer) in 96 well plate were incubated at 4° C. overnight, and the wells washed three times with TBST (0.05% Tween). The wells were blocked with 200 μl of 1% milk at RT for 1 hour. A pre-mix of NEO-101-biotin and test peptide was added at 100 μl/well and incubated at RT of 1 hour, followed by three washes with TBST. Streptavidin-HRP (100 μl of 1:2000 dilution) was added and the reaction incubated at RT for 1 hour, and the wells washed three time. TMB was added, and the wells were read at 450 nm. The control was NEO-101-biotin. See FIG. 12. A summary of the data is shown in Table 15:

TABLE 15

Synthetic peptides immunoassay data.

| Peptide ID | Amino Acid | NEO-101 binding | Blocking of NEO-101 antibody binding to colon Ag | SEQ ID NO |
|---|---|---|---|---|
| 4-1-3-C9 | YSHSFPEDYFRYTNQKGGGS | Yes | Yes | 19 |
| 4-1-4-C12 | YSHSSLPDDWFRYINYGGGS | Yes | Yes | 20 |

TABLE 15-continued

| Synthetic peptides immunoassay data. | | | | |
|---|---|---|---|---|
| Peptide ID | Amino Acid | NEO-101 binding | Blocking of NEO-101 antibody binding to colon Ag | SEQ ID NO |
| 4-1-3-C8 | YSHSWHTLPESGEVTSGGGS | Yes | No | 22 |
| 4-1-3-C11 | YSHSVHAIEDNWSPRGGGGS | No | No (negative control) | 23 |
| An additional two peptides were synthesized for confirmation: | | | | |
| 4-1-4-C12-biotin | YSHSSLPDDWFRYINYGGGS-Biotin | | | 20 |
| 4-1-4C12-R2 (repeat 12mer) | SLPDDWFRYINYSLPDDWFRYINY | | | 24 |

The peptides thus identified were compared with the MUC5AC sequence, for example GeneID: 4586 (*Homo sapiens*), and the results are shown in FIG. 13. Among these three peptide, shared amino acids are underlined as follows:

TABLE 16

| Comparison of Three Peptidomimetics | | |
|---|---|---|
| Peptide ID | Amino Acid Sequence | SEQ ID NO |
| 4-1-3-C9 | YSHSFPEDYFRYTNQKGGGS | 19 |
| 4-1-4-C12 | YSHSSLPDDWFRYINYGGGS | 20 |
| 4-1-4C12-R2 | SLPDDWFRYINYSLPDDWFRYINY | 24 |

On this basis, it was concluded that the following peptidomimetics are antibody-binding peptides that bind NEO-101: $SX^1PX^2DX^3FRYX^4NX^5$ (SEQ ID NO: 1) wherein $X^1$ is for L; $X^2$ is E or D; $X^3$ is Y or W; $X^4$ is T or I and $X^5$ is Q or Y; $SX^1PX^2DX^3FRYX^4NX^5K$ (SEQ ID NO: 2) wherein $X^1$ is for L; $X^2$ is E or D; $X^3$ is Y or W; $X^4$ is T or I and $X^5$ is Q or Y and $SLEPEX^1DWX^2FRYX^3NY$ (SEQ ID NO: 3) wherein $X^1$ is E or D; $X^2$ is W or Y; and $X^3$ is T or I. Exemplary peptidomimetics include but are not limited to FPEDYFRYTNQK (SEQ ID NO: 4) and SLPDDWFRYINY (SEQ ID NO: 5) and additional peptidomimetics are described in SEQ ID NOs: 6-24.

Figure 14A:
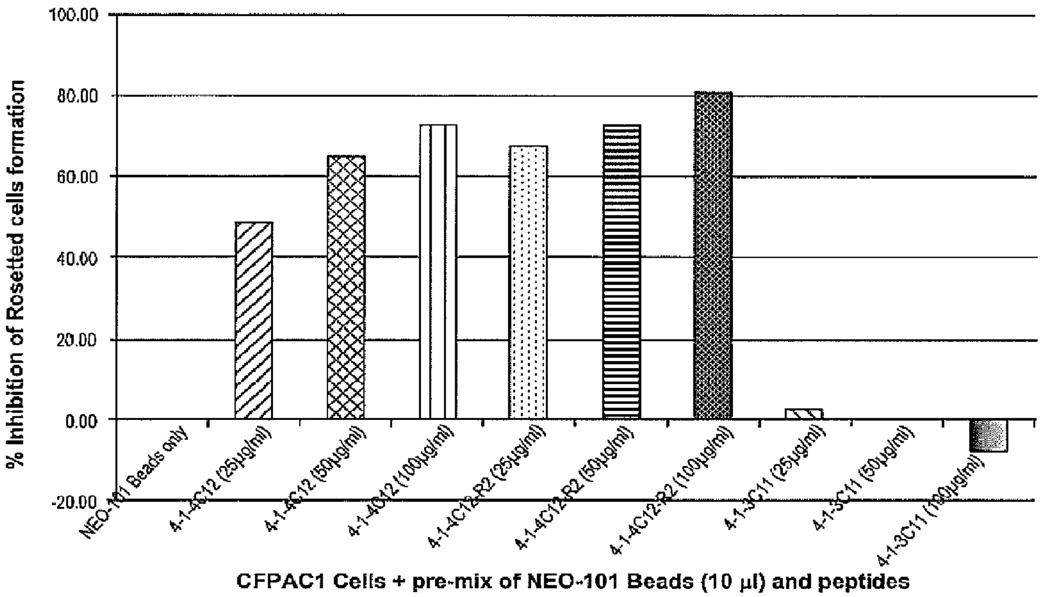
FIG. 14A depicts the binding of CFPAC1 cells by antibody coupled beads, as a percent inhibition of NEO-101 beads binding to CFPAC1 cells (rosetted cells) inhibited by the peptides 4-1-4-C12 and 4-1-4C12-R2.
Figure 14B:
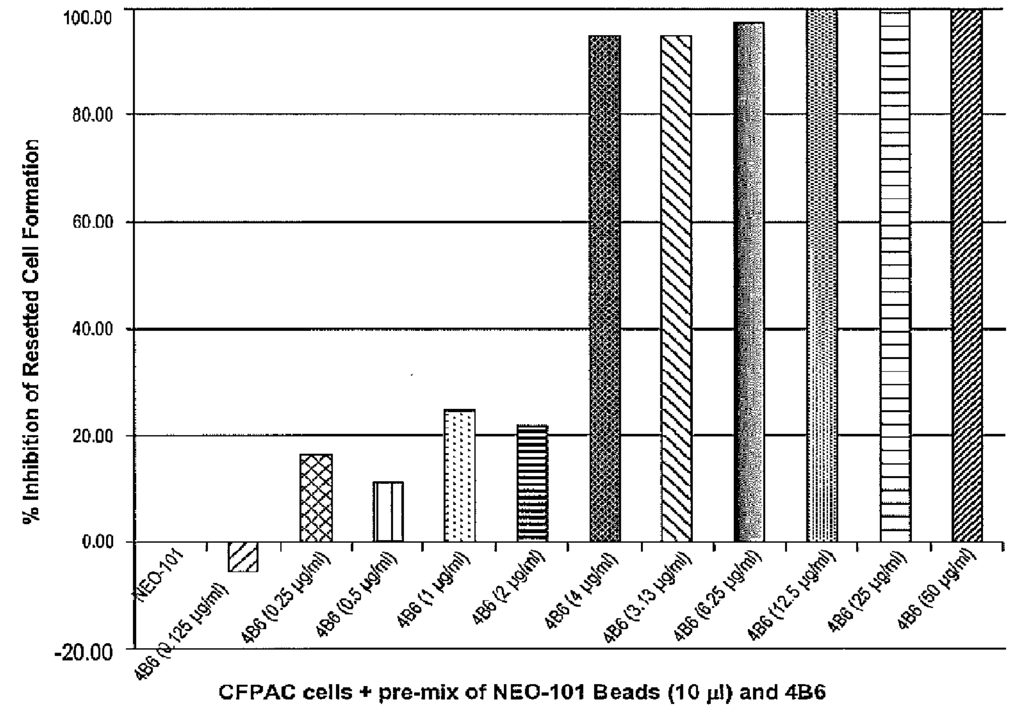
FIG. 14B is a bar graph showing the inhibition by 4B6 of NEO-101 beads binding to CFPAC1 cells (rosetted cells).
Figure 15A:
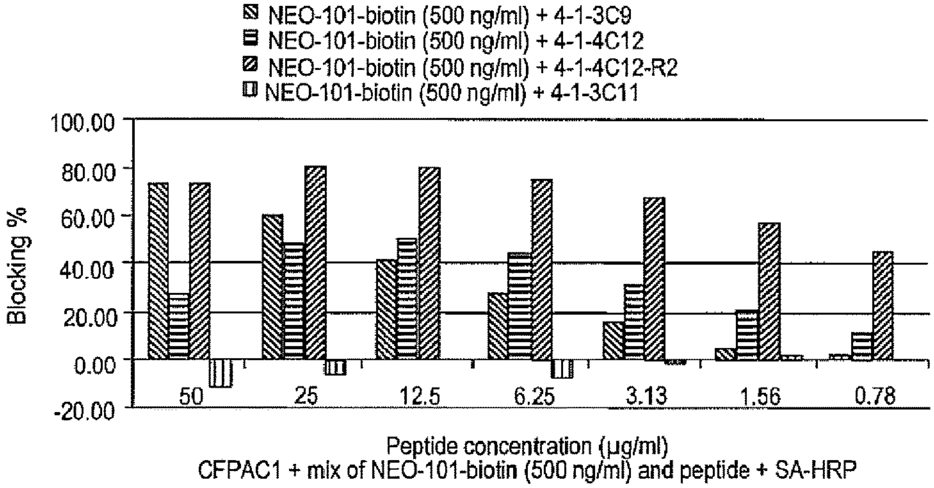
FIG. 15A is a bar graph showing the percent blocking of NEO-101 by peptides (identified by biopanning an M13 phage library) on CFPAC1 culture supernatant-coated plates.
Figure 15B:
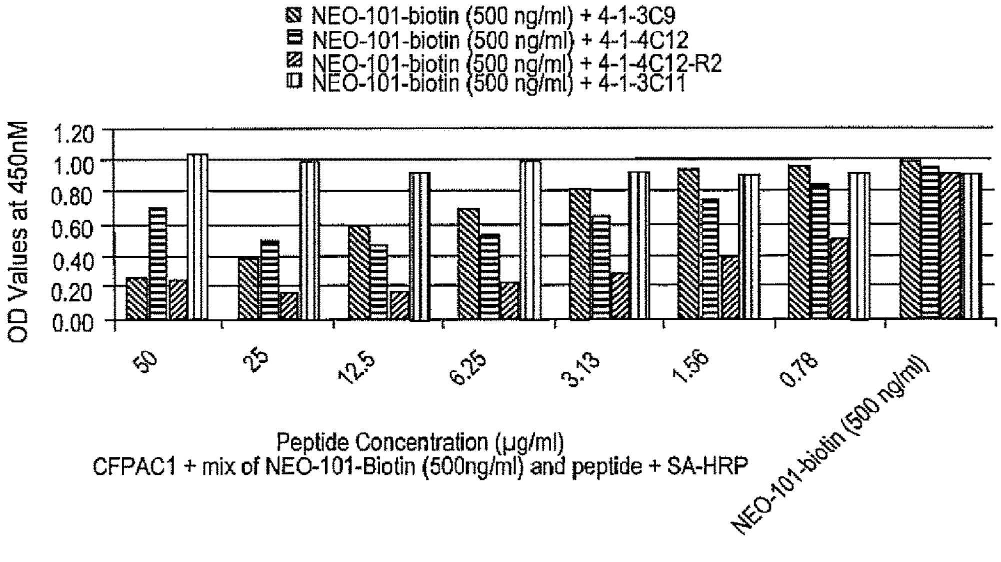
FIG. 15B is a bar graph of OD values showing blocking of NEO-101 by peptides (identified by biopanning an M13 phage library) on CFPAC1 culture supernatant-coated plates.

Next, the inhibition of NEO-101 beads binding to CFAC1 Cells (rosetted cells) by peptides 4-1-4C12 and 4-1-4C12-R2 was investigated, as shown in FIG. 14A. FIG. 14B was the results from positive control with 4B6 in competitive beads assay. As an alternative to observing rosetted cells, the supernatant from CFAC1 cultured cells was used to coat ELISA plates, and a series of competition assays were performed as shown in FIG. 15A-B. Both peptide 4-1-3C9 and 4-1-4C12-R2 showed significant competition against bound CFPAC1 antigen with NEO-101 binding, with peptide 4-1-4C12 exhibiting higher inhibition in low concentration comparing with 4-1-3C9. Therefore, the peptide 4-1-4-C12 is a peptidomimetic of the NPC-1 epitope and may be used to elicit a NPC-1 specific antibodies.

Example 12

4-1-4-C12 Peptidomimetic Conjugated to KLH is Immunogenic

Figure 16A:
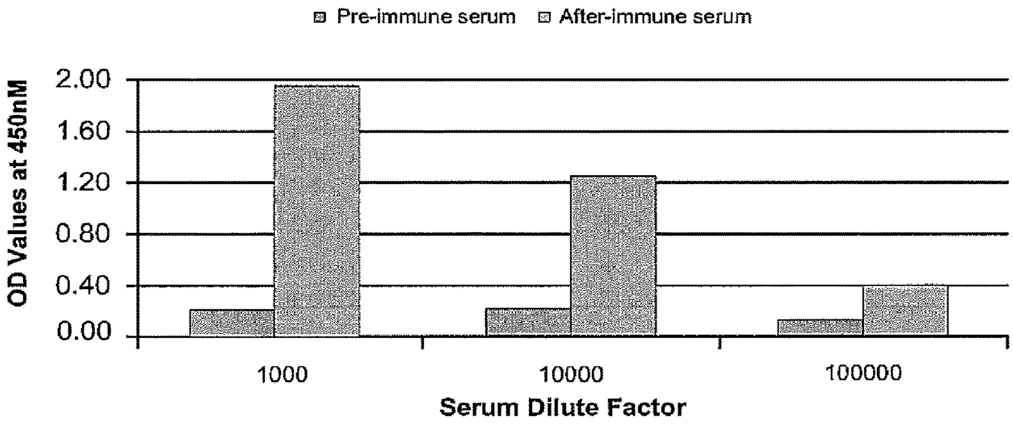
FIG. 16A-B depicts 4-1-4C12-KLH immunized serum binding to 4-1-4C12 (SEQ ID NO: 5) (A) and CFPAC1 human pancreatic cell line supernantant (B) in a dose dependent manner.
Figure 16B:
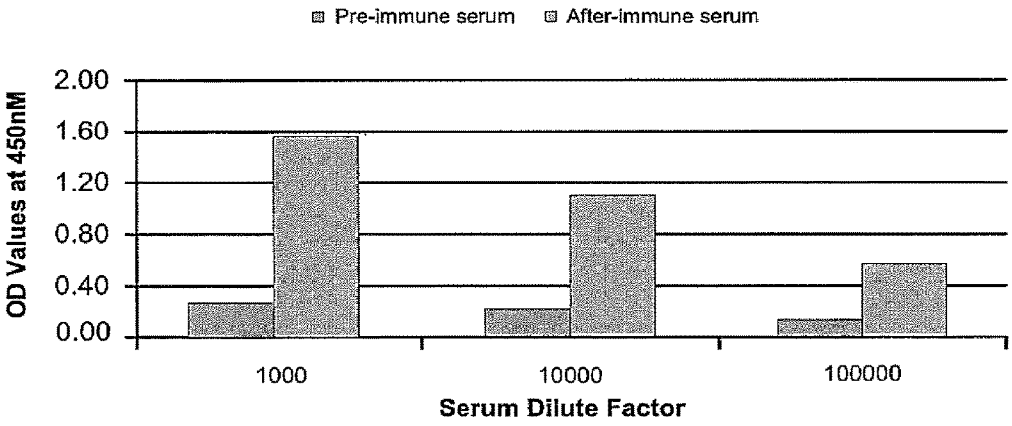

An exemplary NPC-1 antigen peptidomimetic, 4-1-4C12 (SEQ ID NO: 5) was conjugated to KLH (Keyhole Limpit Hemocyannin) ("4-1-4-C12-KLH"). The peptidomimetic-KLH conjugate, 4-1-4-C12-KLH, binds to NEO-101 antibody as shown in ELISA assays. Further, 4-1-4C12-KLH blocks NPC-1 binding to NPC-1C antigen specifically in competitive ELISA. After confirming the function of 4-1-4C12-KLH, 4-1-4C12-KLH was injected into rabbits. The immunized serum after third injection was tested by binding ELISA to check the function of 4-1-4C12-KLH induced antibody. The plate was coated with 4-1-4C12 peptide or CFPAC1 sup, diluted serum was added to the washed and blocked the plate. Bound rabbit IgG was detected by donkey anti-rabbit IgG-HRP. 4-1-4C12-KLH immunized serum binds to 4-1-4C12 (SEQ ID NO: 5) but also bind to CFPAC1 human pancreatic cell line supernantant in a dose dependent manner. FIG. 16A-B. This demonstrates that a NPC-1 epitope peptidomimetic may be injected into an animal and elicity an NPC-1 epitope specific immune response.

Figure 17:
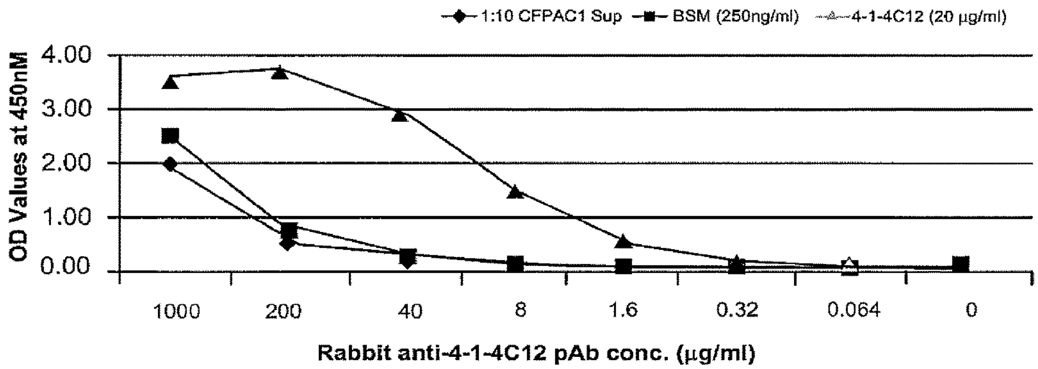
FIG. 17 depicts that anti 4-1-4C12 pAb binds to CFPAC1 human pancreatic cell line supernantant, BSM and 4-1-4C12 peptide in a dose dependent manner.
Figure 18:
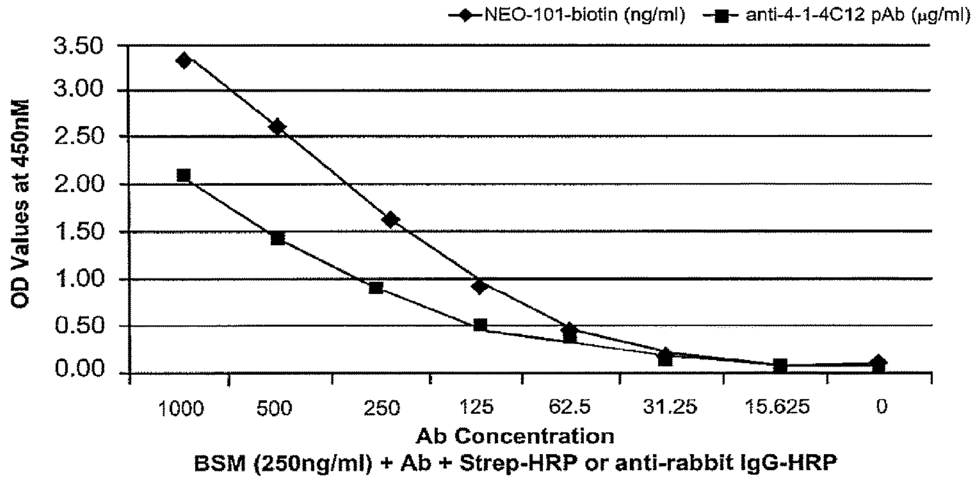
FIG. 18 depicts that anti 4-1-4C12 pAb has lower affinity to BSM when compared with NPC-1C antibody in binding ELISA.

Purified rabbit IgG (anti 4-1-4C12 pAb) was obtained from immunized rabbit for confirmation test. The plate was coated with NPC-1C antigen (CFPAC1 or BSM), 4-1-4C12 peptide as control. Anti-4-1-4C12 pAb was added to washed and blocked plate. Donkey anti-rabbit IgG-HRP was used to detect bound rabbit antibody. The results showed that anti 4-1-4C12 pAb binds to CFPAC1 human pancreatic cell line supernantant, BSM and 4-1-4C12 peptide in a dose dependent manner FIG. 17. Anti 4-1-4C12 pAb has lower affinity to BSM when comparing with NPC-1C antibody in binding ELISA. FIG. 18.

Therefore, the NPC-1 peptidomimetics described herein may be conjugated to carriers (e.g., KLH) and retain their antigenicity and elicit an immune response including antibodies which bind the NPC-1 eptiope. This immune response may then be active in clearing (e.g., lysis) NPC-1 expressing tumor cells, and thus, have a therapeutic effect in the animal (e.g., slowing tumor growth, shrinking tumors).

All publications, patents and patent applications are herein incorporated by reference in their entirety to the same extent as if each individual publication, patent or patent application was specifically and individually indicated to be incorporated by reference in its entirety.

Those skilled in the art will recognize, or be able to ascertain using no more than routine experimentation, many equivalents to the specific embodiments of the invention described herein. Such equivalents are intended to be encompassed by the following claims.

I claim:

1. An isolated nucleic acid comprising a coding sequence that encodes a polypeptide having at least 90% identity to the amino acid sequence of $SX^1PX^2DX^3FRYX^4NX^5$ (SEQ ID NO: 1), wherein $X^1$ is L; $X^2$ is E or D; $X^3$ is Y or W; $X^4$ is T or I and $X^5$ is Q or Y; $SX^1PX^2DX^3FRYX^4NX^5K$ (SEQ ID NO: 2), wherein $X^1$ is L; $X^2$ is E or D; $X^3$ is Y or W; $X^4$ is T or I and $X^5$ is Q or Y; SLPDDWFRYINY (SEQ ID NO: 5); YSHSSLPDDWFRYINYGGGS (SEQ ID NO:20); SLPDDWFRYINYSLPDDWFRYINY (SEQ ID NO:24); or FPEDYFRYTNQK (SEQ ID NO: 4).

2. The isolated nucleic acid of claim 1, wherein said polypeptide comprises the amino acid sequence of $SX^1PX^2DX^3FRYX^4NX^5$ (SEQ ID NO: 1), wherein $X^1$ is for L; $X^2$ is E or D; $X^3$ is Y or W; $X^4$ is T or I and $X^5$ is Q or Y; $SX^1PX^2DX^3FRYX^4NX^5K$ (SEQ ID NO: 2), wherein $X^1$ is for L; $X^2$ is E or D; $X^3$ is Y or W; $X^4$ is T or I and $X^5$ is Q or Y; SLPDDWFRYINY (SEQ ID NO: 5); YSHSSLPDDWFRYINYGGGS (SEQ ID NO:20); or SLPDDWFRYINYSLPDDWFRYINY (SEQ ID NO:24); or FPEDYFRYTNQK (SEQ ID NO: 4).

3. The isolated nucleic acid of claim 1, wherein said nucleic acid further comprises a promoter operably linked to said coding sequence.

4. An isolated nucleic acid encoding a fusion protein comprising the polypeptide of claim 1.

5. The isolated nucleic acid of claim 4, wherein said fusion protein comprises at least one of a polyhistidine tag, FLAG tag, maltose binding protein (MBP) tag, glutathione S-transferase (GST) protein, or green fluorescent protein (GFP).

6. A vector comprising the nucleic acid of claim 1.

7. The vector of claim 6, wherein said vector is a viral vector.

8. A method of making a peptidomimetic polypeptide, comprising culturing a host cell comprising the nucleic acid of claim 1 in a suitable medium such that said peptidomimetic polypeptide is produced, wherein said nucleic acid is operably linked to a promoter.

9. A method of making a peptidomimetic polypeptide, comprising introducing a recombinant expression vector comprising the nucleic acid of claim 1 into an in vitro transcription/translation system, wherein said nucleic acid is operably linked to a promoter.

* * * * *

SEQUENCE LISTING

```
<160> NUMBER OF SEQ ID NOS: 89

<210> SEQ ID NO 1
<211> LENGTH: 12
<212> TYPE: PRT
<213> ORGANISM: Artificial Sequence
<220> FEATURE:
<223> OTHER INFORMATION: NPC-1 Peptidomimetic
<220> FEATURE:
<221> NAME/KEY: VARIANT
<222> LOCATION: (2)..(2)
<223> OTHER INFORMATION: Xaa may be Leu
<220> FEATURE:
<221> NAME/KEY: VARIANT
<222> LOCATION: (4)..(4)
<223> OTHER INFORMATION: Xaa may be Glu or Asp
<220> FEATURE:
<221> NAME/KEY: VARIANT
<222> LOCATION: (6)..(6)
<223> OTHER INFORMATION: Xaa may be Tyr or Trp
<220> FEATURE:
<221> NAME/KEY: VARIANT
<222> LOCATION: (10)..(10)
<223> OTHER INFORMATION: Xaa may be Thr or Ile
<220> FEATURE:
<221> NAME/KEY: VARIANT
<222> LOCATION: (12)..(12)
<223> OTHER INFORMATION: Xaa may be Gln or Tyr

<400> SEQUENCE: 1

Ser Xaa Pro Xaa Asp Xaa Phe Arg Tyr Xaa Asn Xaa
1               5                   10


<210> SEQ ID NO 2
<211> LENGTH: 13
<212> TYPE: PRT
<213> ORGANISM: Artificial Sequence
<220> FEATURE:
<223> OTHER INFORMATION: NPC-1 epitope peptidomimetic
<220> FEATURE:
<221> NAME/KEY: VARIANT
<222> LOCATION: (2)..(2)
<223> OTHER INFORMATION: Xaa may be Leu
<220> FEATURE:
<221> NAME/KEY: VARIANT
<222> LOCATION: (4)..(4)
<223> OTHER INFORMATION: Xaa may be Glu or Asp
<220> FEATURE:
<221> NAME/KEY: VARIANT
<222> LOCATION: (6)..(6)
<223> OTHER INFORMATION: Xaa may be Tyr or Trp
<220> FEATURE:
<221> NAME/KEY: VARIANT
<222> LOCATION: (10)..(10)
<223> OTHER INFORMATION: Xaa may be Thr or Ile
<220> FEATURE:
<221> NAME/KEY: VARIANT
<222> LOCATION: (12)..(12)
<223> OTHER INFORMATION: Xaa may be Gln or Tyr

<400> SEQUENCE: 2

Ser Xaa Pro Xaa Asp Xaa Phe Arg Tyr Xaa Asn Xaa Lys
1               5                   10


<210> SEQ ID NO 3
<211> LENGTH: 15
<212> TYPE: PRT
<213> ORGANISM: Artificial Sequence
<220> FEATURE:
<223> OTHER INFORMATION: NPC-1 epitope peptidomimetic
<220> FEATURE:
<221> NAME/KEY: VARIANT
<222> LOCATION: (6)..(6)
<223> OTHER INFORMATION: Xaa may be Glu or Asp
```

<220> FEATURE:
<221> NAME/KEY: VARIANT
<222> LOCATION: (9)..(9)
<223> OTHER INFORMATION: Xaa may be Trp or Tyr
<220> FEATURE:
<221> NAME/KEY: VARIANT
<222> LOCATION: (13)..(13)
<223> OTHER INFORMATION: Xaa may be Thr or Ile

<400> SEQUENCE: 3

Ser Leu Glu Pro Glu Xaa Asp Trp Xaa Phe Arg Tyr Xaa Asn Tyr
1 5 10 15

<210> SEQ ID NO 4
<211> LENGTH: 12
<212> TYPE: PRT
<213> ORGANISM: Artificial Sequence
<220> FEATURE:
<223> OTHER INFORMATION: NPC-1 epitope peptidomimetic

<400> SEQUENCE: 4

Phe Pro Glu Asp Tyr Phe Arg Tyr Thr Asn Gln Lys
1 5 10

<210> SEQ ID NO 5
<211> LENGTH: 12
<212> TYPE: PRT
<213> ORGANISM: Artificial Sequence
<220> FEATURE:
<223> OTHER INFORMATION: NPC-1 epitope peptidomimetic

<400> SEQUENCE: 5

Ser Leu Pro Asp Asp Trp Phe Arg Tyr Ile Asn Tyr
1 5 10

<210> SEQ ID NO 6
<211> LENGTH: 12
<212> TYPE: PRT
<213> ORGANISM: Artificial Sequence
<220> FEATURE:
<223> OTHER INFORMATION: NPC-1 epitope peptidomimetic
<220> FEATURE:
<221> NAME/KEY: VARIANT
<222> LOCATION: (12)..(12)
<223> OTHER INFORMATION: Xaa may be any amino acid

<400> SEQUENCE: 6

Ser Phe Pro Val Asn Cys Cys Arg Tyr Lys Lys Xaa
1 5 10

<210> SEQ ID NO 7
<211> LENGTH: 11
<212> TYPE: PRT
<213> ORGANISM: Artificial Sequence
<220> FEATURE:
<223> OTHER INFORMATION: NPC-1 epitope peptidomimetic

<400> SEQUENCE: 7

Ser Phe Pro Val Asn Cys Cys Arg Tyr Lys Lys
1 5 10

<210> SEQ ID NO 8
<211> LENGTH: 29
<212> TYPE: PRT
<213> ORGANISM: Artificial Sequence
<220> FEATURE:
<223> OTHER INFORMATION: NPC-1 epitope peptidomimetic

<400> SEQUENCE: 8

Phe Leu Glu Val Tyr Ile Arg Lys Val Ile Arg Arg Val Glu Val Gln
1 5 10 15

Arg Asn Phe Asp Arg Cys Leu Ala Glu Ser His Thr Arg
20 25

<210> SEQ ID NO 9
<211> LENGTH: 20
<212> TYPE: PRT
<213> ORGANISM: Artificial Sequence
<220> FEATURE:
<223> OTHER INFORMATION: NPC-1 epitope peptidomimetic

<400> SEQUENCE: 9

Ala Glu Thr Val Glu Ser Cys Leu Ala Lys Ser His Thr Glu Asn Ser
1 5 10 15

Phe Thr Asn Val
20

<210> SEQ ID NO 10
<211> LENGTH: 16
<212> TYPE: PRT
<213> ORGANISM: Artificial Sequence
<220> FEATURE:
<223> OTHER INFORMATION: NPC-1 epitope peptidomimetic

<400> SEQUENCE: 10

Ala Glu Thr Val Glu Ser Cys Leu Ala Lys Ser His Thr Glu Asn Ser
1 5 10 15

<210> SEQ ID NO 11
<211> LENGTH: 12
<212> TYPE: PRT
<213> ORGANISM: Artificial Sequence
<220> FEATURE:
<223> OTHER INFORMATION: NPC-1 epitope peptidomimetic

<400> SEQUENCE: 11

Trp His Thr Leu Pro Glu Lys Ser Leu Asp Glu Asn
1 5 10

<210> SEQ ID NO 12
<211> LENGTH: 12
<212> TYPE: PRT
<213> ORGANISM: Artificial Sequence
<220> FEATURE:
<223> OTHER INFORMATION: NPC-1 epitope peptidomimetic

<400> SEQUENCE: 12

Trp His Thr Leu Pro Glu Ser Gly Glu Val Thr Ser
1 5 10

<210> SEQ ID NO 13
<211> LENGTH: 12
<212> TYPE: PRT
<213> ORGANISM: Artificial Sequence
<220> FEATURE:
<223> OTHER INFORMATION: NPC-1 epitope peptidomimetic

<400> SEQUENCE: 13

Glu Tyr Gly Leu Gln Gln Gly Thr Pro Asn Ser Lys
1 5 10

<210> SEQ ID NO 14
<211> LENGTH: 12
<212> TYPE: PRT

<213> ORGANISM: Artificial Sequence
<220> FEATURE:
<223> OTHER INFORMATION: NPC-1 epitope peptidomimetic

<400> SEQUENCE: 14

Phe Pro Ala Ile Met Ser Arg Thr Pro Ala Ala Thr
1 5 10

<210> SEQ ID NO 15
<211> LENGTH: 12
<212> TYPE: PRT
<213> ORGANISM: Artificial Sequence
<220> FEATURE:
<223> OTHER INFORMATION: NPC-1 epitope peptidomimetic

<400> SEQUENCE: 15

Val His Ala Ile Glu Asp Asn Trp Ser Pro Arg Gly
1 5 10

<210> SEQ ID NO 16
<211> LENGTH: 12
<212> TYPE: PRT
<213> ORGANISM: Artificial Sequence
<220> FEATURE:
<223> OTHER INFORMATION: NPC-1 epitope peptidomimetic

<400> SEQUENCE: 16

Glu Ala Ser Lys Ser Ser His Thr Leu Trp Thr Asp
1 5 10

<210> SEQ ID NO 17
<211> LENGTH: 12
<212> TYPE: PRT
<213> ORGANISM: Artificial Sequence
<220> FEATURE:
<223> OTHER INFORMATION: NPC-1 epitope peptidomimetic

<400> SEQUENCE: 17

Ser Gln Lys Pro Thr His Ile Gln Lys Ala Leu Ser
1 5 10

<210> SEQ ID NO 18
<211> LENGTH: 12
<212> TYPE: PRT
<213> ORGANISM: Artificial Sequence
<220> FEATURE:
<223> OTHER INFORMATION: NPC-1 epitope peptidomimetic

<400> SEQUENCE: 18

Phe Asn Asp Gly Gly Ala Leu Ser Ser Leu Arg Arg
1 5 10

<210> SEQ ID NO 19
<211> LENGTH: 20
<212> TYPE: PRT
<213> ORGANISM: Artificial Sequence
<220> FEATURE:
<223> OTHER INFORMATION: NPC-1 epitope peptidomimetic

<400> SEQUENCE: 19

Tyr Ser His Ser Phe Pro Glu Asp Tyr Phe Arg Tyr Thr Asn Gln Lys
1 5 10 15

Gly Gly Gly Ser
20

<210> SEQ ID NO 20

<211> LENGTH: 20
<212> TYPE: PRT
<213> ORGANISM: Artificial Sequence
<220> FEATURE:
<223> OTHER INFORMATION: NPC-1 epitope peptidomimetic

<400> SEQUENCE: 20

```
Tyr Ser His Ser Ser Leu Pro Asp Asp Trp Phe Arg Tyr Ile Asn Tyr
1               5                   10                  15

Gly Gly Gly Ser
            20
```

<210> SEQ ID NO 21
<211> LENGTH: 20
<212> TYPE: PRT
<213> ORGANISM: Artificial Sequence
<220> FEATURE:
<223> OTHER INFORMATION: NPC-1 epitope peptidomimetic

<400> SEQUENCE: 21

```
Tyr Ser His Ser Trp His Thr Leu Pro Glu Lys Ser Leu Asp Glu Asn
1               5                   10                  15

Gly Gly Gly Ser
            20
```

<210> SEQ ID NO 22
<211> LENGTH: 20
<212> TYPE: PRT
<213> ORGANISM: Artificial Sequence
<220> FEATURE:
<223> OTHER INFORMATION: NPC-1 epitope peptidomimetic

<400> SEQUENCE: 22

```
Tyr Ser His Ser Trp His Thr Leu Pro Glu Ser Gly Glu Val Thr Ser
1               5                   10                  15

Gly Gly Gly Ser
            20
```

<210> SEQ ID NO 23
<211> LENGTH: 20
<212> TYPE: PRT
<213> ORGANISM: Artificial Sequence
<220> FEATURE:
<223> OTHER INFORMATION: NPC-1 epitope peptidomimetic

<400> SEQUENCE: 23

```
Tyr Ser His Ser Val His Ala Ile Glu Asp Asn Trp Ser Pro Arg Gly
1               5                   10                  15

Gly Gly Gly Ser
            20
```

<210> SEQ ID NO 24
<211> LENGTH: 24
<212> TYPE: PRT
<213> ORGANISM: Artificial Sequence
<220> FEATURE:
<223> OTHER INFORMATION: NPC-1 epitope peptidomimetic

<400> SEQUENCE: 24

```
Ser Leu Pro Asp Asp Trp Phe Arg Tyr Ile Asn Tyr Ser Leu Pro Asp
1               5                   10                  15

Asp Trp Phe Arg Tyr Ile Asn Tyr
            20
```

<210> SEQ ID NO 25
<211> LENGTH: 4
<212> TYPE: PRT
<213> ORGANISM: Artificial Sequence
<220> FEATURE:
<223> OTHER INFORMATION: M13 N-terminal sequence

<400> SEQUENCE: 25

```
Tyr Ser His Ser
1
```

<210> SEQ ID NO 26
<211> LENGTH: 4
<212> TYPE: PRT
<213> ORGANISM: Artificial Sequence
<220> FEATURE:
<223> OTHER INFORMATION: M13 C-terminal sequence

<400> SEQUENCE: 26

```
Gly Gly Gly Ser
1
```

<210> SEQ ID NO 27
<211> LENGTH: 45
<212> TYPE: PRT
<213> ORGANISM: Artificial Sequence
<220> FEATURE:
<223> OTHER INFORMATION: MUC5AC thermolysin fragment

<400> SEQUENCE: 27

```
Leu Val Thr Thr Ser Thr Thr Ser Thr Pro Gln Thr Ser Thr Thr Ser
1               5                   10                  15

Ala Pro Thr Thr Ser Thr Thr Ser Ala Pro Thr Thr Ser Thr Thr Ser
            20                  25                  30

Ala Pro Thr Thr Ser Thr Thr Ser Thr Pro Gln Thr Ser
        35                  40                  45
```

<210> SEQ ID NO 28
<211> LENGTH: 46
<212> TYPE: PRT
<213> ORGANISM: Artificial Sequence
<220> FEATURE:
<223> OTHER INFORMATION: MUC5AC thermolysin fragment

<400> SEQUENCE: 28

```
Ser Ser Pro Thr Thr Ser Thr Thr Pro Thr Pro Gln Thr Ser Thr Thr
1               5                   10                  15

Ser Ser Pro Thr Thr Ser Thr Thr Ser Ala Pro Thr Thr Ser Thr Thr
            20                  25                  30

Ser Ala Pro Thr Thr Ser Thr Thr Ser Thr Pro Gln Thr Ser
        35                  40                  45
```

<210> SEQ ID NO 29
<211> LENGTH: 59
<212> TYPE: PRT
<213> ORGANISM: Artificial Sequence
<220> FEATURE:
<223> OTHER INFORMATION: MUC5AC thermolysin fragment

<400> SEQUENCE: 29

```
Ile Thr Ser Ala Pro Thr Thr Ser Thr Thr Ser Ala Pro Thr Thr Ser
1               5                   10                  15

Thr Thr Ser Ala Pro Thr Thr Ser Thr Thr Ser Ala Pro Thr Thr Ser
            20                  25                  30
```

```
Thr Thr Ser Ala Pro Thr Thr Ser Thr Thr Ser Thr Pro Thr Ser Ser
        35                  40                  45

Thr Thr Ser Thr Pro Gln Thr Ser Thr Thr Ser
    50                  55


<210> SEQ ID NO 30
<211> LENGTH: 54
<212> TYPE: PRT
<213> ORGANISM: Artificial Sequence
<220> FEATURE:
<223> OTHER INFORMATION: MUC5AC thermolysin fragment

<400> SEQUENCE: 30

Ala Ser Ile Pro Ser Thr Thr Ser Ala Pro Thr Thr Ser Thr Thr Ser
1               5                   10                  15

Ala Pro Thr Thr Ser Thr Thr Ser Ala Pro Thr Thr Ser Thr Thr Ser
            20                  25                  30

Thr Pro Gln Thr Thr Thr Ser Ser Ala Pro Thr Ser Ser Thr Thr Ser
        35                  40                  45

Ala Pro Thr Thr Ser Thr
    50


<210> SEQ ID NO 31
<211> LENGTH: 45
<212> TYPE: PRT
<213> ORGANISM: Artificial Sequence
<220> FEATURE:
<223> OTHER INFORMATION: MUC5AC thermolysin fragment

<400> SEQUENCE: 31

Met Thr Ser Gly Pro Gly Thr Thr Pro Ser Pro Val Pro Thr Thr Ser
1               5                   10                  15

Thr Thr Ser Ala Pro Thr Thr Ser Thr Thr Ser Gly Pro Gly Thr Thr
            20                  25                  30

Pro Ser Pro Val Pro Thr Thr Ser Thr Thr Ser Ala Pro
        35                  40                  45


<210> SEQ ID NO 32
<211> LENGTH: 54
<212> TYPE: PRT
<213> ORGANISM: Artificial Sequence
<220> FEATURE:
<223> OTHER INFORMATION: MUC5AC thermolysin fragment

<400> SEQUENCE: 32

Ile Thr Ser Met Pro Ser Gly Pro Gly Thr Thr Pro Ser Pro Val Pro
1               5                   10                  15

Thr Thr Ser Thr Thr Ser Ala Pro Thr Thr Ser Thr Thr Ser Gly Pro
            20                  25                  30

Gly Thr Thr Pro Ser Pro Val Pro Thr Thr Ser Thr Thr Ser Ala Pro
        35                  40                  45

Thr Thr Ser Thr Thr Ser
    50


<210> SEQ ID NO 33
<211> LENGTH: 59
<212> TYPE: PRT
<213> ORGANISM: Artificial Sequence
<220> FEATURE:
<223> OTHER INFORMATION: MUC5AC thermolysin fragment

<400> SEQUENCE: 33
```

```
Leu Ser Pro Val Pro Thr Thr Ser Thr Thr Ser Ala Pro Thr Thr Ser
1               5                   10                  15

Thr Thr Ser Gly Pro Gly Thr Thr Pro Ser Pro Val Pro Thr Thr Ser
            20                  25                  30

Thr Thr Ser Ala Pro Thr Thr Ser Thr Thr Ser Gly Pro Gly Thr Thr
        35                  40                  45

Pro Ser Pro Val Pro Thr Thr Ser Thr Thr Pro
    50                  55


<210> SEQ ID NO 34
<211> LENGTH: 16
<212> TYPE: PRT
<213> ORGANISM: Artificial Sequence
<220> FEATURE:
<223> OTHER INFORMATION: MUC5AC thermolysin consensus peptide

<400> SEQUENCE: 34

Thr Thr Ser Thr Thr Ser Ala Pro Thr Thr Ser Thr Thr Ser Ala Pro
1               5                   10                  15


<210> SEQ ID NO 35
<211> LENGTH: 15
<212> TYPE: PRT
<213> ORGANISM: Artificial Sequence
<220> FEATURE:
<223> OTHER INFORMATION: MUC5AC NPC-1 epitope identified by deletion
      studies

<400> SEQUENCE: 35

Gly Cys Pro Val Thr Ser Thr Pro Val Thr Ala Pro Ser Thr Pro
1               5                   10                  15


<210> SEQ ID NO 36
<211> LENGTH: 5030
<212> TYPE: PRT
<213> ORGANISM: Homo sapiens

<400> SEQUENCE: 36

Met Ser Val Gly Arg Arg Lys Leu Ala Leu Leu Trp Ala Leu Ala Leu
1               5                   10                  15

Ala Leu Ala Cys Thr Arg His Thr Gly His Ala Gln Asp Gly Ser Ser
            20                  25                  30

Glu Ser Ser Tyr Lys His His Pro Ala Leu Ser Pro Ile Ala Arg Gly
        35                  40                  45

Pro Ser Gly Val Pro Leu Arg Gly Ala Thr Val Phe Pro Ser Leu Arg
    50                  55                  60

Thr Ile Pro Val Val Arg Ala Ser Asn Pro Ala His Asn Gly Arg Val
65                  70                  75                  80

Cys Ser Thr Trp Gly Ser Phe His Tyr Lys Thr Phe Asp Gly Asp Val
                85                  90                  95

Phe Arg Phe Pro Gly Leu Cys Asn Tyr Val Phe Ser Glu His Cys Gly
            100                 105                 110

Ala Ala Tyr Glu Asp Phe Asn Ile Gln Leu Arg Arg Ser Gln Glu Ser
        115                 120                 125

Ala Ala Pro Thr Leu Ser Arg Val Leu Met Lys Val Asp Gly Val Val
    130                 135                 140

Ile Gln Leu Thr Lys Gly Ser Val Leu Val Asn Gly His Pro Val Leu
145                 150                 155                 160

Leu Pro Phe Ser Gln Ser Gly Val Leu Ile Gln Gln Ser Ser Ser Tyr
                165                 170                 175
```

-continued

```
Thr Lys Val Glu Ala Arg Leu Gly Leu Val Leu Met Trp Asn His Asp
            180                 185                 190

Asp Ser Leu Leu Leu Glu Leu Asp Thr Lys Tyr Ala Asn Lys Thr Cys
        195                 200                 205

Gly Leu Cys Gly Asp Phe Asn Gly Met Pro Val Val Ser Glu Leu Leu
    210                 215                 220

Ser His Asn Thr Lys Leu Thr Pro Met Glu Phe Gly Asn Leu Gln Lys
225                 230                 235                 240

Met Asp Asp Pro Thr Glu Gln Cys Gln Asp Pro Val Pro Glu Pro Pro
                245                 250                 255

Arg Asn Cys Ser Thr Gly Phe Gly Ile Cys Glu Glu Leu Leu His Gly
            260                 265                 270

Gln Leu Phe Ser Gly Cys Val Ala Leu Val Asp Val Gly Ser Tyr Leu
        275                 280                 285

Glu Ala Cys Arg Gln Asp Leu Cys Phe Cys Glu Asp Thr Asp Leu Leu
    290                 295                 300

Ser Cys Val Cys His Thr Leu Ala Glu Tyr Ser Arg Gln Cys Thr His
305                 310                 315                 320

Ala Gly Gly Leu Pro Gln Asp Trp Arg Gly Pro Asp Phe Cys Pro Gln
                325                 330                 335

Lys Cys Pro Asn Asn Met Gln Tyr His Glu Cys Arg Ser Pro Cys Ala
            340                 345                 350

Asp Thr Cys Ser Asn Gln Glu His Ser Arg Ala Cys Glu Asp His Cys
        355                 360                 365

Val Ala Gly Cys Phe Cys Pro Glu Gly Thr Val Leu Asp Asp Ile Gly
    370                 375                 380

Gln Thr Gly Cys Val Pro Val Ser Lys Cys Ala Cys Val Tyr Asn Gly
385                 390                 395                 400

Ala Ala Tyr Ala Pro Gly Ala Thr Tyr Ser Thr Asp Cys Thr Asn Cys
                405                 410                 415

Thr Cys Ser Gly Gly Arg Trp Ser Cys Gln Glu Val Pro Cys Pro Asp
            420                 425                 430

Thr Cys Ser Val Leu Gly Gly Ala His Phe Ser Thr Phe Asp Gly Lys
        435                 440                 445

Gln Tyr Thr Val His Gly Asp Cys Ser Tyr Val Leu Thr Lys Pro Cys
    450                 455                 460

Asp Ser Ser Ala Phe Thr Val Leu Ala Glu Leu Arg Arg Cys Gly Leu
465                 470                 475                 480

Thr Asp Ser Glu Thr Cys Leu Lys Ser Val Thr Leu Ser Leu Asp Gly
                485                 490                 495

Ala Gln Thr Val Val Val Ile Lys Ala Ser Gly Glu Val Phe Leu Asn
            500                 505                 510

Gln Ile Tyr Thr Gln Leu Pro Ile Ser Ala Ala Asn Val Thr Ile Phe
        515                 520                 525

Arg Pro Ser Thr Phe Phe Ile Ile Ala Gln Thr Ser Leu Gly Leu Gln
    530                 535                 540

Leu Asn Leu Gln Pro Val Pro Thr Met Gln Leu Phe Met Gln Leu Ala
545                 550                 555                 560

Pro Lys Leu Arg Gly Gln Thr Cys Gly Leu Cys Gly Asn Phe Asn Ser
                565                 570                 575

Ile Gln Ala Asp Asp Phe Arg Thr Leu Ser Gly Val Val Glu Ala Thr
            580                 585                 590
```

-continued

```
Ala Ala Ala Phe Phe Asn Thr Phe Lys Thr Gln Ala Ala Cys Pro Asn
        595                 600                 605

Ile Arg Asn Ser Phe Glu Asp Pro Cys Ser Leu Ser Val Glu Asn Glu
    610                 615                 620

Lys Tyr Ala Gln His Trp Cys Ser Gln Leu Thr Asp Ala Asp Gly Pro
625                 630                 635                 640

Phe Gly Arg Cys His Ala Ala Val Lys Pro Gly Thr Tyr Tyr Ser Asn
                645                 650                 655

Cys Val Phe Asp Thr Cys Asn Cys Glu Arg Ser Glu Asp Cys Leu Cys
            660                 665                 670

Ala Ala Leu Ser Ser Tyr Val His Ala Cys Ala Ala Lys Gly Val Gln
        675                 680                 685

Leu Gly Gly Trp Arg Asp Gly Val Cys Thr Lys Pro Met Thr Thr Cys
    690                 695                 700

Pro Lys Ser Met Thr Tyr His Tyr His Val Ser Thr Cys Gln Pro Thr
705                 710                 715                 720

Cys Arg Ser Leu Ser Glu Gly Asp Ile Thr Cys Ser Val Gly Phe Ile
                725                 730                 735

Pro Val Asp Gly Cys Ile Cys Pro Lys Gly Thr Phe Leu Asp Asp Thr
            740                 745                 750

Gly Lys Cys Val Gln Ala Ser Asn Cys Pro Cys Tyr His Arg Gly Ser
        755                 760                 765

Met Ile Pro Asn Gly Glu Ser Val His Asp Ser Gly Ala Ile Cys Thr
    770                 775                 780

Cys Thr His Gly Lys Leu Ser Cys Ile Gly Gly Gln Ala Pro Ala Pro
785                 790                 795                 800

Val Cys Ala Ala Pro Met Val Phe Phe Asp Cys Arg Asn Ala Thr Pro
                805                 810                 815

Gly Asp Thr Gly Ala Gly Cys Gln Lys Ser Cys His Thr Leu Asp Met
            820                 825                 830

Thr Cys Tyr Ser Pro Gln Cys Val Pro Gly Cys Val Cys Pro Asp Gly
        835                 840                 845

Leu Val Ala Asp Gly Glu Gly Gly Cys Ile Thr Ala Glu Asp Cys Pro
    850                 855                 860

Cys Val His Asn Glu Ala Ser Tyr Arg Ala Gly Gln Thr Ile Arg Val
865                 870                 875                 880

Gly Cys Asn Thr Cys Thr Cys Asp Ser Arg Met Trp Arg Cys Thr Asp
                885                 890                 895

Asp Pro Cys Leu Ala Thr Cys Ala Val Tyr Gly Asp Gly His Tyr Leu
            900                 905                 910

Thr Phe Asp Gly Gln Ser Tyr Ser Phe Asn Gly Asp Cys Glu Tyr Thr
        915                 920                 925

Leu Val Gln Asn His Cys Gly Gly Lys Asp Ser Thr Gln Asp Ser Phe
    930                 935                 940

Arg Val Val Thr Glu Asn Val Pro Cys Gly Thr Thr Gly Thr Thr Cys
945                 950                 955                 960

Ser Lys Ala Ile Lys Ile Phe Leu Gly Gly Phe Glu Leu Lys Leu Ser
                965                 970                 975

His Gly Lys Val Glu Val Ile Gly Thr Asp Glu Ser Gln Glu Val Pro
            980                 985                 990

Tyr Thr Ile Gln Gln Met Gly Ile  Tyr Leu Val Val Asp  Thr Asp Ile
        995                 1000                1005

Gly Leu  Val Leu Leu Trp Asp  Lys Lys Thr Ser Ile  Phe Ile Asn
```

```
    1010                1015                1020

Leu Ser  Pro Glu Phe Lys Gly  Arg Val Cys Gly Leu  Cys Gly Asn
    1025                1030                1035

Phe Asp  Asp Ile Ala Val Asn  Asp Phe Ala Thr Arg  Ser Arg Ser
    1040                1045                1050

Val Val  Gly Asp Val Leu Glu  Phe Gly Asn Ser Trp  Lys Leu Ser
    1055                1060                1065

Pro Ser  Cys Pro Asp Ala Leu  Ala Pro Lys Asp Pro  Cys Thr Ala
    1070                1075                1080

Asn Pro  Phe Arg Lys Ser Trp  Ala Gln Lys Gln Cys  Ser Ile Leu
    1085                1090                1095

His Gly  Pro Thr Phe Ala Ala  Cys His Ala His Val  Glu Pro Ala
    1100                1105                1110

Arg Tyr  Tyr Glu Ala Cys Val  Asn Asp Ala Cys Ala  Cys Asp Ser
    1115                1120                1125

Gly Gly  Asp Cys Glu Cys Phe  Cys Thr Ala Val Ala  Ala Tyr Ala
    1130                1135                1140

Gln Ala  Cys His Glu Val Gly  Leu Cys Val Cys Leu  Arg Thr Pro
    1145                1150                1155

Ser Ile  Cys Pro Leu Phe Cys  Asp Tyr Tyr Asn Pro  Glu Gly Gln
    1160                1165                1170

Cys Glu  Trp His Tyr Gln Pro  Cys Gly Val Pro Cys  Leu Arg Thr
    1175                1180                1185

Cys Arg  Asn Pro Arg Gly Asp  Cys Leu Arg Asp Val  Arg Gly Leu
    1190                1195                1200

Glu Gly  Cys Tyr Pro Lys Cys  Pro Pro Glu Ala Pro  Ile Phe Asp
    1205                1210                1215

Glu Asp  Lys Met Gln Cys Val  Ala Thr Cys Pro Thr  Pro Pro Leu
    1220                1225                1230

Pro Pro  Arg Cys His Val His  Gly Lys Ser Tyr Arg  Pro Gly Ala
    1235                1240                1245

Val Val  Pro Ser Asp Lys Asn  Cys Gln Ser Cys Leu  Cys Thr Glu
    1250                1255                1260

Arg Gly  Val Glu Cys Thr Tyr  Lys Ala Glu Ala Cys  Val Cys Thr
    1265                1270                1275

Tyr Asn  Gly Gln Arg Phe His  Pro Gly Asp Val Ile  Tyr His Thr
    1280                1285                1290

Thr Asp  Gly Thr Gly Gly Cys  Ile Ser Ala Arg Cys  Gly Ala Asn
    1295                1300                1305

Gly Thr  Ile Glu Arg Arg Val  Tyr Pro Cys Ser Pro  Thr Thr Pro
    1310                1315                1320

Val Pro  Pro Thr Thr Phe Ser  Phe Ser Thr Pro Pro  Leu Val Val
    1325                1330                1335

Ser Ser  Thr His Thr Pro Ser  Asn Gly Pro Ser Ser  Ala His Thr
    1340                1345                1350

Gly Pro  Pro Ser Ser Ala Trp  Pro Thr Thr Ala Gly  Thr Ser Pro
    1355                1360                1365

Arg Thr  Arg Leu Pro Thr Ala  Ser Ala Ser Leu Pro  Pro Val Cys
    1370                1375                1380

Gly Glu  Lys Cys Leu Trp Ser  Pro Trp Met Asp Val  Ser Arg Pro
    1385                1390                1395

Gly Arg  Gly Thr Asp Ser Gly  Asp Phe Asp Thr Leu  Glu Asn Leu
    1400                1405                1410
```

```
Arg Ala  His Gly Tyr Arg Val  Cys Glu Ser Pro Arg  Ser Val Glu
    1415                 1420                 1425

Cys Arg  Ala Glu Asp Ala Pro  Gly Val Pro Leu Arg  Ala Leu Gly
    1430                 1435                 1440

Gln Arg  Val Gln Cys Ser Pro  Asp Val Gly Leu Thr  Cys Arg Asn
    1445                 1450                 1455

Arg Glu  Gln Ala Ser Gly Leu  Cys Tyr Asn Tyr Gln  Ile Arg Val
    1460                 1465                 1470

Gln Cys  Cys Thr Pro Leu Pro  Cys Ser Thr Ser Ser  Ser Pro Ala
    1475                 1480                 1485

Gln Thr  Thr Pro Pro Thr Thr  Ser Lys Thr Thr Glu  Thr Arg Ala
    1490                 1495                 1500

Ser Gly  Ser Ser Ala Pro Ser  Ser Thr Pro Gly Thr  Val Ser Leu
    1505                 1510                 1515

Ser Thr  Ala Arg Thr Thr Pro  Ala Pro Gly Thr Ala  Thr Ser Val
    1520                 1525                 1530

Lys Lys  Thr Phe Ser Thr Pro  Ser Pro Pro Pro Val  Pro Ala Thr
    1535                 1540                 1545

Ser Thr  Ser Ser Met Ser Thr  Thr Ala Pro Gly Thr  Ser Val Val
    1550                 1555                 1560

Ser Ser  Lys Pro Thr Pro Thr  Glu Pro Ser Thr Ser  Ser Cys Leu
    1565                 1570                 1575

Gln Glu  Leu Cys Thr Trp Thr  Glu Trp Ile Asp Gly  Ser Tyr Pro
    1580                 1585                 1590

Ala Pro  Gly Ile Asn Gly Gly  Asp Phe Asp Thr Phe  Gln Asn Leu
    1595                 1600                 1605

Arg Asp  Glu Gly Tyr Thr Phe  Cys Glu Ser Pro Arg  Ser Val Gln
    1610                 1615                 1620

Cys Arg  Ala Glu Ser Phe Pro  Asn Thr Pro Leu Ala  Asp Leu Gly
    1625                 1630                 1635

Gln Asp  Val Ile Cys Ser His  Thr Glu Gly Leu Ile  Cys Leu Asn
    1640                 1645                 1650

Lys Asn  Gln Leu Pro Pro Ile  Cys Tyr Asn Tyr Glu  Ile Arg Ile
    1655                 1660                 1665

Gln Cys  Cys Glu Thr Val Asn  Val Cys Arg Asp Ile  Thr Arg Leu
    1670                 1675                 1680

Pro Lys  Thr Val Ala Thr Thr  Arg Pro Thr Pro His  Pro Thr Gly
    1685                 1690                 1695

Ala Gln  Thr Gln Thr Thr Phe  Thr Thr His Met Pro  Ser Ala Ser
    1700                 1705                 1710

Thr Glu  Gln Pro Thr Ala Thr  Ser Arg Gly Gly Pro  Thr Ala Thr
    1715                 1720                 1725

Ser Val  Thr Gln Gly Thr His  Thr Thr Leu Val Thr  Arg Asn Cys
    1730                 1735                 1740

His Pro  Arg Cys Thr Trp Thr  Lys Trp Phe Asp Val  Asp Phe Pro
    1745                 1750                 1755

Ser Pro  Gly Pro His Gly Gly  Asp Lys Glu Thr Tyr  Asn Asn Ile
    1760                 1765                 1770

Ile Arg  Ser Gly Glu Lys Ile  Cys Arg Arg Pro Glu  Glu Ile Thr
    1775                 1780                 1785

Arg Val  Gln Cys Arg Ala Lys  Ser His Pro Glu Val  Ser Ile Glu
    1790                 1795                 1800
```

```
His Leu Gly Gln Val Val Gln Cys Ser Arg Glu Glu Gly Leu Val
    1805                1810                1815

Cys Arg Asn Gln Asp Gln Gln Gly Pro Phe Lys Met Cys Leu Asn
    1820                1825                1830

Tyr Glu Val Arg Val Leu Cys Cys Glu Thr Pro Arg Gly Cys His
    1835                1840                1845

Met Thr Ser Thr Pro Gly Ser Thr Ser Ser Ser Pro Ala Gln Thr
    1850                1855                1860

Thr Pro Ser Thr Thr Ser Lys Thr Thr Glu Ile Gln Ala Ser Gly
    1865                1870                1875

Ser Ser Ala Pro Ser Ser Thr Pro Gly Thr Val Ser Leu Ser Thr
    1880                1885                1890

Ala Arg Thr Thr Pro Ala Pro Gly Thr Ala Thr Ser Val Lys Lys
    1895                1900                1905

Thr Phe Ser Thr Pro Ser Pro Pro Pro Val Pro Ala Thr Ser Thr
    1910                1915                1920

Ser Ser Met Ser Thr Thr Ala Pro Gly Thr Ser Val Val Ser Ser
    1925                1930                1935

Lys Pro Thr Pro Thr Glu Pro Ser Thr Ser Ser Cys Leu Gln Glu
    1940                1945                1950

Leu Cys Thr Trp Thr Glu Trp Ile Asp Gly Ser Tyr Pro Ala Pro
    1955                1960                1965

Gly Ile Asn Gly Gly Asp Phe Asp Thr Phe Gln Asn Leu Arg Asp
    1970                1975                1980

Glu Gly Tyr Thr Phe Cys Glu Ser Pro Arg Ser Val Gln Cys Arg
    1985                1990                1995

Ala Glu Ser Phe Pro Asn Thr Pro Leu Gly Arg Leu Gly Gln Asp
    2000                2005                2010

Val Ile Cys Ser His Thr Glu Gly Leu Ile Cys Leu Asn Lys Asn
    2015                2020                2025

Gln Leu Pro Pro Ile Cys Tyr Asn Tyr Glu Ile Arg Ile Gln Cys
    2030                2035                2040

Cys Glu Thr Val Asn Val Cys Arg Asp Ile Thr Arg Pro Pro Lys
    2045                2050                2055

Thr Val Ala Thr Thr Arg Pro Thr Pro His Pro Thr Gly Ala Gln
    2060                2065                2070

Thr Gln Thr Thr Phe Thr Thr His Met Pro Ser Ala Ser Thr Glu
    2075                2080                2085

Gln Pro Thr Ala Thr Ser Arg Gly Gly Pro Thr Ala Thr Ser Val
    2090                2095                2100

Thr Gln Gly Thr His Thr Thr Pro Val Thr Arg Asn Cys His Pro
    2105                2110                2115

Arg Cys Thr Trp Thr Thr Trp Phe Asp Val Asp Phe Pro Ser Pro
    2120                2125                2130

Gly Pro His Gly Gly Asp Lys Glu Thr Tyr Asn Asn Ile Ile Arg
    2135                2140                2145

Ser Gly Glu Lys Ile Cys Arg Arg Pro Glu Glu Ile Thr Arg Leu
    2150                2155                2160

Gln Cys Arg Ala Lys Ser His Pro Glu Val Ser Ile Glu His Leu
    2165                2170                2175

Gly Gln Val Val Gln Cys Ser Arg Glu Glu Gly Leu Val Cys Arg
    2180                2185                2190

Asn Gln Asp Gln Gln Gly Pro Phe Lys Met Cys Leu Asn Ile Glu
```

-continued

```
    2195                2200                2205

Val Arg  Val Leu Cys Cys Glu  Thr Pro Lys Gly Cys  Pro Val Thr
    2210                2215                2220

Ser Thr  Pro Val Thr Ala Pro  Ser Thr Pro Ser Gly  Arg Ala Ile
    2225                2230                2235

Ser Pro  Thr Gln Ser Thr Ser  Ser Trp Gln Lys Ser  Arg Thr Thr
    2240                2245                2250

Thr Leu  Val Thr Thr Ser Thr  Thr Ser Thr Pro Gln  Thr Ser Thr
    2255                2260                2265

Thr Tyr  Ala His Thr Thr Ser  Thr Thr Ser Ala Pro  Thr Ala Arg
    2270                2275                2280

Thr Thr  Ser Ala Pro Thr Thr  Ser Thr Thr Ser Val  Pro Thr Thr
    2285                2290                2295

Ser Thr  Ile Ser Gly Pro Lys  Thr Thr Pro Ser Pro  Val Pro Thr
    2300                2305                2310

Thr Ser  Thr Thr Ser Ala Ala  Thr Thr Ser Thr Ile  Ser Ala Pro
    2315                2320                2325

Thr Thr  Ser Thr Thr Ser Val  Pro Gly Thr Thr Pro  Ser Pro Val
    2330                2335                2340

Leu Thr  Thr Ser Thr Thr Ser  Ala Pro Thr Thr Arg  Thr Thr Ser
    2345                2350                2355

Ala Ser  Pro Ala Gly Thr Thr  Ser Gly Pro Gly Asn  Thr Pro Ser
    2360                2365                2370

Pro Val  Pro Thr Thr Ser Thr  Ile Ser Ala Pro Thr  Thr Ser Ile
    2375                2380                2385

Thr Ser  Ala Pro Thr Thr Ser  Thr Thr Ser Ala Pro  Thr Ser Ser
    2390                2395                2400

Thr Thr  Ser Gly Pro Gly Thr  Thr Pro Ser Pro Val  Pro Thr Thr
    2405                2410                2415

Ser Ile  Thr Ser Ala Pro Thr  Thr Ser Thr Thr Ser  Ala Pro Thr
    2420                2425                2430

Thr Ser  Thr Thr Ser Ala Pro  Thr Thr Ser Thr Thr  Ser Ala Pro
    2435                2440                2445

Thr Thr  Ser Thr Thr Ser Ala  Pro Thr Thr Ser Thr  Thr Ser Thr
    2450                2455                2460

Pro Thr  Ser Ser Thr Thr Ser  Thr Pro Gln Thr Ser  Thr Thr Ser
    2465                2470                2475

Ala Ser  Thr Thr Ser Ile Thr  Ser Gly Pro Gly Thr  Thr Pro Ser
    2480                2485                2490

Pro Val  Pro Thr Thr Ser Thr  Thr Ser Ala Pro Thr  Thr Ser Thr
    2495                2500                2505

Thr Ser  Ala Ala Thr Thr Ser  Thr Ile Ser Ala Pro  Thr Thr Ser
    2510                2515                2520

Thr Thr  Ser Ala Pro Thr Thr  Ser Thr Thr Ser Ala  Ser Thr Ala
    2525                2530                2535

Ser Lys  Thr Ser Gly Leu Gly  Thr Thr Pro Ser Pro  Ile Pro Thr
    2540                2545                2550

Thr Ser  Thr Thr Ser Pro Pro  Thr Thr Ser Thr Thr  Ser Ala Ser
    2555                2560                2565

Thr Ala  Ser Lys Thr Ser Gly  Pro Gly Thr Thr Pro  Ser Pro Val
    2570                2575                2580

Pro Thr  Thr Ser Thr Ile Phe  Ala Pro Arg Thr Ser  Thr Thr Ser
    2585                2590                2595
```

-continued

```
Ala Ser Thr Thr Ser Thr Thr Pro Gly Pro Gly Thr Thr Pro Ser
    2600                2605                2610

Pro Val Pro Thr Thr Ser Thr Ala Ser Val Ser Lys Thr Ser Thr
    2615                2620                2625

Ser His Val Ser Ile Ser Lys Thr Thr His Ser Gln Pro Val Thr
    2630                2635                2640

Arg Asp Cys His Leu Arg Cys Thr Trp Thr Lys Trp Phe Asp Val
    2645                2650                2655

Asp Phe Pro Ser Pro Gly Pro His Gly Gly Asp Lys Glu Thr Tyr
    2660                2665                2670

Asn Asn Ile Ile Arg Ser Gly Glu Lys Ile Cys Arg Arg Pro Glu
    2675                2680                2685

Glu Ile Thr Arg Leu Gln Cys Arg Ala Glu Ser His Pro Glu Val
    2690                2695                2700

Ser Ile Glu His Leu Gly Gln Val Val Gln Cys Ser Arg Glu Glu
    2705                2710                2715

Gly Leu Val Cys Arg Asn Gln Asp Gln Gln Gly Pro Phe Lys Met
    2720                2725                2730

Cys Leu Asn Tyr Glu Val Arg Val Leu Cys Cys Glu Thr Pro Lys
    2735                2740                2745

Gly Cys Pro Val Thr Ser Thr Pro Val Thr Ala Pro Ser Thr Pro
    2750                2755                2760

Ser Gly Arg Ala Thr Ser Pro Thr Gln Ser Thr Ser Ser Trp Gln
    2765                2770                2775

Lys Ser Arg Thr Thr Thr Leu Val Thr Thr Ser Thr Thr Ser Thr
    2780                2785                2790

Pro Gln Thr Ser Thr Thr Ser Ala Pro Thr Thr Ser Thr Thr Ser
    2795                2800                2805

Ala Pro Thr Thr Ser Thr Thr Ser Ala Pro Thr Thr Ser Thr Thr
    2810                2815                2820

Ser Thr Pro Gln Thr Ser Ile Ser Ser Ala Pro Thr Ser Ser Thr
    2825                2830                2835

Thr Ser Ala Pro Thr Ser Ser Thr Ile Ser Ala Arg Thr Thr Ser
    2840                2845                2850

Ile Ile Ser Ala Pro Thr Thr Ser Thr Thr Ser Ser Pro Thr Thr
    2855                2860                2865

Ser Thr Thr Ser Ala Thr Thr Thr Ser Thr Thr Ser Ala Pro Thr
    2870                2875                2880

Ser Ser Thr Thr Ser Thr Pro Gln Thr Ser Lys Thr Ser Ala Ala
    2885                2890                2895

Thr Ser Ser Thr Thr Ser Ser Ser Gly Thr Thr Pro Ser Pro Val
    2900                2905                2910

Thr Thr Thr Ser Thr Ala Ser Val Ser Lys Thr Ser Thr Ser His
    2915                2920                2925

Val Ser Val Ser Lys Thr Thr His Ser Gln Pro Val Thr Arg Asp
    2930                2935                2940

Cys His Pro Arg Cys Thr Trp Thr Lys Trp Phe Asp Val Asp Phe
    2945                2950                2955

Pro Ser Pro Gly Pro His Gly Gly Asp Lys Glu Thr Tyr Asn Asn
    2960                2965                2970

Ile Ile Arg Ser Gly Glu Lys Ile Cys Arg Arg Pro Gln Glu Ile
    2975                2980                2985
```

```
Thr Arg  Leu Gln Cys Arg Ala  Lys Ser His Pro Glu  Val Ser Ile
    2990                 2995                 3000

Glu His  Leu Gly Gln Val Val  Gln Cys Ser Arg Glu  Glu Gly Leu
    3005                 3010                 3015

Val Cys  Arg Asn Gln Asp Gln  Gln Gly Pro Phe Lys  Met Cys Leu
    3020                 3025                 3030

Asn Tyr  Glu Val Arg Val Leu  Cys Cys Glu Thr Pro  Lys Gly Cys
    3035                 3040                 3045

Pro Val  Thr Ser Thr Ser Val  Thr Ala Pro Ser Pro  Leu Val Gly
    3050                 3055                 3060

Glu Pro  Pro Ala Gln Thr Gln  Ser Thr Ser Ser Trp  Gln Lys Ser
    3065                 3070                 3075

Arg Thr  Thr Thr Leu Val Thr  Ser Ser Ile Thr Ser  Thr Thr Gln
    3080                 3085                 3090

Thr Ser  Thr Thr Ser Ala Pro  Thr Thr Ser Thr Thr  Pro Ala Ser
    3095                 3100                 3105

Ile Pro  Ser Thr Thr Ser Ala  Pro Thr Thr Ser Thr  Thr Ser Ala
    3110                 3115                 3120

Pro Thr  Thr Ser Thr Thr Ser  Ala Pro Thr Thr Ser  Thr Thr Ser
    3125                 3130                 3135

Thr Pro  Gln Thr Thr Thr Ser  Ser Ala Pro Thr Ser  Ser Thr Thr
    3140                 3145                 3150

Ser Ala  Pro Thr Thr Ser Thr  Ile Ser Ala Pro Thr  Thr Ser Thr
    3155                 3160                 3165

Ile Ser  Ala Pro Thr Thr Ser  Thr Thr Ser Ala Pro  Thr Ala Ser
    3170                 3175                 3180

Thr Thr  Ser Ala Pro Thr Ser  Thr Ser Ser Ala Pro  Thr Thr Asn
    3185                 3190                 3195

Thr Thr  Ser Ala Pro Thr Thr  Ser Thr Thr Ser Ala  Pro Ile Thr
    3200                 3205                 3210

Ser Thr  Ile Ser Ala Pro Thr  Thr Ser Thr Thr Ser  Thr Pro Gln
    3215                 3220                 3225

Thr Ser  Thr Ile Ser Ser Pro  Thr Thr Ser Thr Thr  Pro Thr Pro
    3230                 3235                 3240

Gln Thr  Ser Thr Thr Ser Ser  Pro Thr Thr Ser Thr  Thr Ser Ala
    3245                 3250                 3255

Pro Thr  Thr Ser Thr Thr Ser  Ala Pro Thr Thr Ser  Thr Thr Ser
    3260                 3265                 3270

Thr Pro  Gln Thr Ser Ile Ser  Ser Ala Pro Thr Ser  Ser Thr Thr
    3275                 3280                 3285

Ser Ala  Pro Thr Ala Ser Thr  Ile Ser Ala Pro Thr  Thr Ser Thr
    3290                 3295                 3300

Thr Ser  Phe His Thr Thr Ser  Thr Thr Ser Pro Pro  Thr Ser Ser
    3305                 3310                 3315

Thr Ser  Ser Thr Pro Gln Thr  Ser Lys Thr Ser Ala  Ala Thr Ser
    3320                 3325                 3330

Ser Thr  Thr Ser Gly Ser Gly  Thr Thr Pro Ser Pro  Val Pro Thr
    3335                 3340                 3345

Thr Ser  Thr Ala Ser Val Ser  Lys Thr Ser Thr Ser  His Val Ser
    3350                 3355                 3360

Val Ser  Lys Thr Thr His Ser  Gln Pro Val Thr Arg  Asp Cys His
    3365                 3370                 3375

Pro Arg  Cys Thr Trp Thr Lys  Trp Phe Asp Val Asp  Phe Pro Ser
```

```
    3380                3385                3390

Pro Gly Pro His Gly Gly Asp Lys Glu Thr Tyr Asn Asn Ile Ile
    3395                3400                3405

Arg Ser Gly Glu Lys Ile Cys Arg Arg Pro Glu Glu Ile Thr Arg
    3410                3415                3420

Leu Gln Cys Arg Ala Glu Ser His Pro Glu Val Ser Ile Glu His
    3425                3430                3435

Leu Gly Gln Val Val Gln Cys Ser Arg Glu Glu Gly Leu Val Cys
    3440                3445                3450

Arg Asn Gln Asp Gln Gln Gly Pro Phe Lys Met Cys Leu Asn Tyr
    3455                3460                3465

Glu Val Arg Val Leu Cys Cys Glu Thr Pro Lys Gly Cys Pro Val
    3470                3475                3480

Thr Ser Thr Pro Val Thr Ala Pro Ser Thr Pro Ser Gly Arg Ala
    3485                3490                3495

Thr Ser Pro Thr Gln Ser Thr Ser Ser Trp Gln Lys Ser Arg Thr
    3500                3505                3510

Thr Thr Leu Val Thr Thr Ser Thr Thr Ser Thr Pro Gln Thr Ser
    3515                3520                3525

Thr Thr Ser Ala Pro Thr Thr Ser Thr Ile Pro Ala Ser Thr Pro
    3530                3535                3540

Ser Thr Thr Ser Ala Pro Thr Thr Ser Thr Thr Ser Ala Pro Thr
    3545                3550                3555

Thr Ser Thr Thr Ser Ala Pro Thr His Arg Thr Thr Ser Gly Pro
    3560                3565                3570

Thr Thr Ser Thr Thr Leu Ala Pro Thr Thr Ser Thr Thr Ser Ala
    3575                3580                3585

Pro Thr Thr Ser Thr Asn Ser Ala Pro Thr Thr Ser Thr Ile Ser
    3590                3595                3600

Ala Ser Thr Thr Ser Thr Ile Ser Ala Pro Thr Thr Ser Thr Ile
    3605                3610                3615

Ser Ser Pro Thr Ser Ser Thr Thr Ser Thr Pro Gln Thr Ser Lys
    3620                3625                3630

Thr Ser Ala Ala Thr Ser Ser Thr Thr Ser Gly Ser Gly Thr Thr
    3635                3640                3645

Pro Ser Pro Val Pro Thr Thr Ser Thr Thr Ser Ala Ser Thr Thr
    3650                3655                3660

Ser Thr Thr Ser Ala Pro Thr Thr Ser Thr Thr Ser Gly Pro Gly
    3665                3670                3675

Thr Thr Pro Ser Pro Val Pro Ser Thr Ser Ile Thr Ser Ala Ala
    3680                3685                3690

Thr Thr Ser Thr Thr Ser Ala Pro Thr Thr Arg Thr Thr Ser Ala
    3695                3700                3705

Pro Thr Ser Ser Met Thr Ser Gly Pro Gly Thr Thr Pro Ser Pro
    3710                3715                3720

Val Pro Thr Thr Ser Thr Thr Ser Ala Pro Thr Thr Ser Thr Thr
    3725                3730                3735

Ser Gly Pro Gly Thr Thr Pro Ser Pro Val Pro Thr Thr Ser Thr
    3740                3745                3750

Thr Ser Ala Pro Ile Thr Ser Thr Thr Ser Gly Pro Gly Ser Thr
    3755                3760                3765

Pro Ser Pro Val Pro Thr Thr Ser Thr Thr Ser Ala Pro Thr Thr
    3770                3775                3780
```

```
Ser Thr Thr Ser Ala Ser Thr Ala Ser Thr Thr Ser Gly Pro Thr
    3785                3790                3795

Thr Ser Thr Thr Ser Ala Ser Thr Thr Ser Thr Ile Ser Pro Leu
    3800                3805                3810

Thr Thr Ser Thr Thr Ser Ala Pro Ile Thr Ser Met Pro Ser Gly
    3815                3820                3825

Pro Gly Thr Thr Pro Ser Pro Val Pro Thr Thr Ser Thr Thr Ser
    3830                3835                3840

Ala Pro Thr Thr Ser Thr Thr Ser Gly Pro Gly Thr Thr Pro Ser
    3845                3850                3855

Pro Val Pro Thr Thr Ser Thr Thr Ser Ala Pro Thr Thr Ser Thr
    3860                3865                3870

Thr Ser Ala Ser Thr Ala Ser Thr Thr Ser Gly Pro Gly Thr Thr
    3875                3880                3885

Pro Ser Pro Val Pro Thr Thr Ser Thr Thr Ser Ala Pro Thr Thr
    3890                3895                3900

Ser Thr Thr Ser Ala Ser Thr Ala Ser Thr Thr Ser Gly Pro Gly
    3905                3910                3915

Thr Ser Leu Ser Pro Val Pro Thr Thr Ser Thr Thr Ser Ala Pro
    3920                3925                3930

Thr Thr Ser Thr Thr Ser Gly Pro Gly Thr Thr Pro Ser Pro Val
    3935                3940                3945

Pro Thr Thr Ser Thr Thr Ser Ala Pro Thr Thr Ser Thr Thr Ser
    3950                3955                3960

Gly Pro Gly Thr Thr Pro Ser Pro Val Pro Thr Thr Ser Thr Thr
    3965                3970                3975

Pro Val Ser Lys Thr Ser Thr Ser His Leu Ser Val Ser Lys Thr
    3980                3985                3990

Thr His Ser Gln Pro Val Thr Ser Asp Cys His Pro Leu Cys Ala
    3995                4000                4005

Trp Thr Lys Trp Phe Asp Val Asp Phe Pro Ser Pro Gly Pro His
    4010                4015                4020

Gly Gly Asp Lys Glu Thr Tyr Asn Asn Ile Ile Arg Ser Gly Glu
    4025                4030                4035

Lys Ile Cys Arg Arg Pro Glu Glu Ile Thr Arg Leu Gln Cys Arg
    4040                4045                4050

Ala Glu Ser His Pro Glu Val Asn Ile Glu His Leu Gly Gln Val
    4055                4060                4065

Val Gln Cys Ser Arg Glu Glu Gly Leu Val Cys Arg Asn Gln Asp
    4070                4075                4080

Gln Gln Gly Pro Phe Lys Met Cys Leu Asn Tyr Glu Val Arg Val
    4085                4090                4095

Leu Cys Cys Glu Thr Pro Arg Gly Cys Pro Val Thr Ser Val Thr
    4100                4105                4110

Pro Tyr Gly Thr Ser Pro Thr Asn Ala Leu Tyr Pro Ser Leu Ser
    4115                4120                4125

Thr Ser Met Val Ser Ala Ser Val Ala Ser Thr Ser Val Ala Ser
    4130                4135                4140

Ser Ser Val Ala Ser Ser Ser Val Ala Tyr Ser Thr Gln Thr Cys
    4145                4150                4155

Phe Cys Asn Val Ala Asp Arg Leu Tyr Pro Ala Gly Ser Thr Ile
    4160                4165                4170
```

-continued

Tyr Arg His Arg Asp Leu Ala Gly His Cys Tyr Tyr Ala Leu Cys
4175 4180 4185

Ser Gln Asp Cys Gln Val Val Arg Gly Val Asp Ser Asp Cys Pro
4190 4195 4200

Ser Thr Thr Leu Pro Pro Ala Pro Ala Thr Ser Pro Ser Ile Ser
4205 4210 4215

Thr Ser Glu Pro Val Thr Glu Leu Gly Cys Pro Asn Ala Val Pro
4220 4225 4230

Pro Arg Lys Lys Gly Glu Thr Trp Ala Thr Pro Asn Cys Ser Glu
4235 4240 4245

Ala Thr Cys Glu Gly Asn Asn Val Ile Ser Leu Ser Pro Arg Thr
4250 4255 4260

Cys Pro Arg Val Glu Lys Pro Thr Cys Ala Asn Gly Tyr Pro Ala
4265 4270 4275

Val Lys Val Ala Asp Gln Asp Gly Cys Cys His His Tyr Gln Cys
4280 4285 4290

Gln Cys Val Cys Ser Gly Trp Gly Asp Pro His Tyr Ile Thr Phe
4295 4300 4305

Asp Gly Thr Tyr Tyr Thr Phe Leu Asp Asn Cys Thr Tyr Val Leu
4310 4315 4320

Val Gln Gln Ile Val Pro Val Tyr Gly His Phe Arg Val Leu Val
4325 4330 4335

Asp Asn Tyr Phe Cys Gly Ala Glu Asp Gly Leu Ser Cys Pro Arg
4340 4345 4350

Ser Ile Ile Leu Glu Tyr His Gln Asp Arg Val Val Leu Thr Arg
4355 4360 4365

Lys Pro Val His Gly Val Met Thr Asn Glu Ile Ile Phe Asn Asn
4370 4375 4380

Lys Val Val Ser Pro Gly Phe Arg Lys Asn Gly Ile Val Val Ser
4385 4390 4395

Arg Ile Gly Val Lys Met Tyr Ala Thr Ile Pro Glu Leu Gly Val
4400 4405 4410

Gln Val Met Phe Ser Gly Leu Ile Phe Ser Val Glu Val Pro Phe
4415 4420 4425

Ser Lys Phe Ala Asn Asn Thr Glu Gly Gln Cys Gly Thr Cys Thr
4430 4435 4440

Asn Asp Arg Lys Asp Glu Cys Arg Thr Pro Arg Gly Thr Val Val
4445 4450 4455

Ala Ser Cys Ser Glu Met Ser Gly Leu Trp Asn Val Ser Ile Pro
4460 4465 4470

Asp Gln Pro Ala Cys His Arg Pro His Pro Thr Pro Thr Thr Val
4475 4480 4485

Gly Pro Thr Thr Val Gly Ser Thr Thr Val Gly Pro Thr Thr Val
4490 4495 4500

Gly Ser Thr Thr Val Gly Pro Thr Thr Pro Pro Ala Pro Cys Leu
4505 4510 4515

Pro Ser Pro Ile Cys His Leu Ile Leu Ser Lys Val Phe Glu Pro
4520 4525 4530

Cys His Thr Val Ile Pro Pro Leu Leu Phe Tyr Glu Gly Cys Val
4535 4540 4545

Phe Asp Arg Cys His Met Thr Asp Leu Asp Val Val Cys Ser Ser
4550 4555 4560

Leu Glu Leu Tyr Ala Ala Leu Cys Ala Ser His Asp Ile Cys Ile

```
    4565                4570                4575

Asp Trp Arg Gly Arg Thr Gly His Met Cys Pro Phe Thr Cys Pro
    4580                4585                4590

Ala Asp Lys Val Tyr Gln Pro Cys Gly Pro Ser Asn Pro Ser Tyr
    4595                4600                4605

Cys Tyr Gly Asn Asp Ser Ala Ser Leu Gly Ala Leu Arg Glu Ala
    4610                4615                4620

Gly Pro Ile Thr Glu Gly Cys Phe Cys Pro Glu Gly Met Thr Leu
    4625                4630                4635

Phe Ser Thr Ser Ala Gln Val Cys Val Pro Thr Gly Cys Pro Arg
    4640                4645                4650

Cys Leu Gly Pro His Gly Glu Pro Val Lys Val Gly His Thr Val
    4655                4660                4665

Gly Met Asp Cys Gln Glu Cys Thr Cys Glu Ala Ala Thr Trp Thr
    4670                4675                4680

Leu Thr Cys Arg Pro Lys Leu Cys Pro Leu Pro Pro Ala Cys Pro
    4685                4690                4695

Leu Pro Gly Phe Val Pro Val Pro Ala Ala Pro Gln Ala Gly Gln
    4700                4705                4710

Cys Cys Pro Gln Tyr Ser Cys Ala Cys Asn Thr Ser Arg Cys Pro
    4715                4720                4725

Ala Pro Val Gly Cys Pro Glu Gly Ala Arg Ala Ile Pro Thr Tyr
    4730                4735                4740

Gln Glu Gly Ala Cys Cys Pro Val Gln Asn Cys Ser Trp Thr Val
    4745                4750                4755

Cys Ser Ile Asn Gly Thr Leu Tyr Gln Pro Gly Ala Val Val Ser
    4760                4765                4770

Ser Ser Leu Cys Glu Thr Cys Arg Cys Glu Leu Pro Gly Gly Pro
    4775                4780                4785

Pro Ser Asp Ala Phe Val Val Ser Cys Glu Thr Gln Ile Cys Asn
    4790                4795                4800

Thr His Cys Pro Val Gly Phe Glu Tyr Gln Glu Gln Ser Gly Gln
    4805                4810                4815

Cys Cys Gly Thr Cys Val Gln Val Ala Cys Val Thr Asn Thr Ser
    4820                4825                4830

Lys Ser Pro Ala His Leu Phe Tyr Pro Gly Glu Thr Trp Ser Asp
    4835                4840                4845

Ala Gly Asn His Cys Val Thr His Gln Cys Glu Lys His Gln Asp
    4850                4855                4860

Gly Leu Val Val Val Thr Thr Lys Lys Ala Cys Pro Pro Leu Ser
    4865                4870                4875

Cys Ser Leu Asp Glu Ala Arg Met Ser Lys Asp Gly Cys Cys Arg
    4880                4885                4890

Phe Cys Pro Leu Pro Pro Pro Pro Tyr Gln Asn Gln Ser Thr Cys
    4895                4900                4905

Ala Val Tyr His Arg Ser Leu Ile Ile Gln Gln Gln Gly Cys Ser
    4910                4915                4920

Ser Ser Glu Pro Val Arg Leu Ala Tyr Cys Arg Gly Asn Cys Gly
    4925                4930                4935

Asp Ser Ser Ser Met Tyr Ser Leu Glu Gly Asn Thr Val Glu His
    4940                4945                4950

Arg Cys Gln Cys Cys Gln Glu Leu Arg Thr Ser Leu Arg Asn Val
    4955                4960                4965
```

```
Thr Leu His Cys Thr Asp Gly Ser Ser Arg Ala Phe Ser Tyr Thr
    4970                4975                4980

Glu Val Glu Glu Cys Gly Cys Met Gly Arg Arg Cys Pro Ala Pro
    4985                4990                4995

Gly Asp Thr Gln His Ser Glu Glu Ala Glu Pro Glu Pro Ser Gln
    5000                5005                5010

Glu Ala Glu Ser Gly Ser Trp Glu Arg Gly Val Pro Val Ser Pro
    5015                5020                5025

Met His
    5030


<210> SEQ ID NO 37
<211> LENGTH: 921
<212> TYPE: PRT
<213> ORGANISM: Homo sapiens

<400> SEQUENCE: 37

Ala Cys Cys Ala Cys Cys Cys Ala Thr Thr Cys Thr Cys Ala Ala Cys
1               5                   10                  15

Cys Thr Gly Thr Thr Ala Cys Thr Cys Gly Thr Gly Ala Thr Thr Gly
            20                  25                  30

Thr Cys Ala Thr Cys Thr Gly Cys Gly Thr Thr Gly Cys Ala Cys Cys
        35                  40                  45

Thr Gly Gly Ala Cys Thr Ala Ala Ala Thr Gly Gly Thr Thr Cys Gly
    50                  55                  60

Ala Cys Gly Thr Thr Gly Ala Cys Thr Thr Cys Cys Cys Gly Thr Cys
65                  70                  75                  80

Cys Cys Cys Ala Gly Gly Thr Cys Cys Ala Cys Ala Cys Gly Gly Thr
                85                  90                  95

Gly Gly Thr Gly Ala Cys Ala Ala Gly Gly Ala Ala Ala Cys Cys Thr
            100                 105                 110

Ala Thr Ala Ala Cys Ala Ala Cys Ala Thr Cys Ala Thr Thr Cys Gly
        115                 120                 125

Thr Thr Cys Cys Gly Gly Thr Gly Ala Gly Ala Ala Ala Ala Thr Cys
    130                 135                 140

Thr Gly Cys Cys Gly Thr Cys Gly Thr Cys Cys Gly Gly Ala Gly Gly
145                 150                 155                 160

Ala Ala Ala Thr Cys Ala Cys Cys Cys Gly Thr Cys Thr Gly Cys Ala
                165                 170                 175

Gly Thr Gly Cys Cys Gly Thr Gly Cys Ala Gly Ala Gly Thr Cys Cys
            180                 185                 190

Cys Ala Cys Cys Cys Gly Gly Ala Gly Gly Thr Ala Thr Cys Thr Ala
        195                 200                 205

Thr Cys Gly Ala Ala Cys Ala Thr Cys Thr Gly Gly Gly Cys Cys Ala
    210                 215                 220

Gly Gly Thr Thr Gly Thr Gly Cys Ala Gly Thr Gly Cys Ala Gly Cys
225                 230                 235                 240

Cys Gly Thr Gly Ala Ala Gly Ala Ala Gly Gly Thr Cys Thr Gly Gly
                245                 250                 255

Thr Thr Thr Gly Cys Cys Gly Thr Ala Ala Cys Cys Ala Ala Gly Ala
            260                 265                 270

Thr Cys Ala Gly Cys Ala Gly Gly Gly Cys Cys Cys Gly Thr Thr Cys
        275                 280                 285

Ala Ala Ala Ala Thr Gly Thr Gly Cys Cys Thr Gly Ala Ala Cys Thr
```

```
    290                 295                 300

Ala Thr Gly Ala Ala Gly Thr Cys Cys Gly Thr Gly Thr Cys Cys Thr
305                 310                 315                 320

Gly Thr Gly Cys Thr Gly Cys Gly Ala Ala Ala Cys Cys Cys Cys Ala
                325                 330                 335

Ala Ala Ala Gly Gly Cys Thr Gly Thr Cys Cys Ala Gly Thr Thr Ala
            340                 345                 350

Cys Thr Thr Cys Thr Ala Cys Cys Cys Cys Gly Gly Thr Thr Ala Cys
        355                 360                 365

Cys Gly Cys Gly Cys Cys Gly Thr Cys Cys Ala Cys Thr Cys Cys Ala
    370                 375                 380

Ala Gly Cys Gly Gly Cys Cys Gly Cys Gly Cys Gly Ala Cys Cys Ala
385                 390                 395                 400

Gly Cys Cys Cys Gly Ala Cys Cys Cys Ala Gly Ala Gly Cys Ala Cys
                405                 410                 415

Cys Thr Cys Cys Thr Cys Thr Thr Gly Gly Cys Ala Gly Ala Ala Ala
            420                 425                 430

Thr Cys Cys Cys Gly Cys Ala Cys Cys Ala Cys Thr Ala Cys Cys Cys
        435                 440                 445

Thr Gly Gly Thr Thr Ala Cys Thr Ala Cys Cys Thr Cys Thr Ala Cys
    450                 455                 460

Thr Ala Cys Cys Thr Cys Cys Ala Cys Thr Cys Cys Ala Cys Ala Gly
465                 470                 475                 480

Ala Cys Thr Thr Cys Cys Ala Cys Cys Ala Cys Cys Thr Cys Cys Gly
                485                 490                 495

Cys Cys Cys Cys Gly Ala Cys Thr Ala Cys Cys Ala Gly Cys Ala Cys
            500                 505                 510

Thr Ala Cys Cys Ala Gly Cys Gly Cys Cys Cys Cys Gly Ala Cys Cys
        515                 520                 525

Ala Cys Thr Ala Gly Cys Ala Cys Thr Ala Cys Cys Thr Cys Cys Gly
    530                 535                 540

Cys Thr Cys Cys Gly Ala Cys Cys Ala Cys Cys Thr Cys Cys Ala Cys
545                 550                 555                 560

Cys Ala Cys Thr Thr Cys Thr Ala Cys Cys Cys Cys Gly Cys Ala Gly
                565                 570                 575

Ala Cys Cys Thr Cys Thr Ala Thr Cys Thr Cys Thr Thr Cys Thr Gly
            580                 585                 590

Cys Gly Cys Cys Gly Ala Cys Cys Ala Gly Cys Thr Cys Thr Ala Cys
        595                 600                 605

Cys Ala Cys Cys Ala Gly Cys Gly Cys Thr Cys Cys Gly Ala Cys Thr
    610                 615                 620

Ala Gly Cys Thr Cys Cys Ala Cys Gly Ala Thr Thr Thr Cys Thr Gly
625                 630                 635                 640

Cys Thr Cys Gly Thr Ala Cys Thr Ala Cys Thr Thr Cys Thr Ala Thr
                645                 650                 655

Cys Ala Thr Thr Thr Cys Cys Gly Cys Cys Cys Cys Thr Ala Cys Gly
            660                 665                 670

Ala Cys Cys Thr Cys Thr Ala Cys Cys Ala Cys Thr Thr Cys Thr Ala
        675                 680                 685

Gly Cys Cys Cys Thr Ala Cys Cys Ala Cys Cys Thr Cys Thr Ala Cys
    690                 695                 700

Cys Ala Cys Gly Thr Cys Cys Gly Cys Gly Ala Cys Cys Ala Cys Cys
705                 710                 715                 720
```

Ala Cys Cys Thr Cys Cys Ala Cys Thr Ala Cys Cys Thr Cys Thr Gly
725 730 735

Cys Ala Cys Cys Ala Ala Cys Thr Thr Cys Cys Thr Cys Thr Ala Cys
740 745 750

Thr Ala Cys Gly Ala Gly Cys Ala Cys Gly Cys Cys Gly Cys Ala Gly
755 760 765

Ala Cys Thr Thr Cys Thr Ala Ala Ala Ala Cys Cys Thr Cys Thr Gly
770 775 780

Cys Gly Gly Cys Ala Ala Cys Cys Thr Cys Thr Thr Cys Thr Ala Cys
785 790 795 800

Cys Ala Cys Cys Ala Gly Cys Ala Gly Cys Thr Cys Thr Gly Gly Cys
805 810 815

Ala Cys Cys Ala Cys Thr Cys Cys Gly Ala Gly Cys Cys Cys Gly Gly
820 825 830

Thr Gly Ala Cys Cys Ala Cys Cys Ala Cys Thr Ala Gly Cys Ala Cys
835 840 845

Cys Gly Cys Thr Thr Cys Thr Gly Thr Gly Thr Cys Cys Ala Ala Gly
850 855 860

Ala Cys Cys Ala Gly Cys Ala Cys Cys Thr Cys Thr Cys Ala Cys Gly
865 870 875 880

Thr Gly Thr Cys Thr Gly Thr Thr Thr Cys Thr Ala Ala Ala Ala Cys
885 890 895

Gly Ala Cys Cys Cys Ala Cys Thr Cys Cys Cys Ala Gly Cys Cys Gly
900 905 910

Gly Thr Thr Ala Cys Cys Cys Gly Cys
915 920

<210> SEQ ID NO 38
<211> LENGTH: 306
<212> TYPE: PRT
<213> ORGANISM: Artificial Sequence
<220> FEATURE:
<223> OTHER INFORMATION: N-terminal fragment of MUC5AC (long)

<400> SEQUENCE: 38

Thr Thr His Ser Gln Pro Val Thr Arg Asp Cys His Leu Arg Cys Thr
1 5 10 15

Trp Thr Lys Trp Phe Asp Val Asp Phe Pro Ser Pro Gly Pro His Gly
20 25 30

Gly Asp Lys Glu Thr Tyr Asn Asn Ile Ile Arg Ser Gly Glu Lys Ile
35 40 45

Cys Arg Arg Pro Glu Glu Ile Thr Arg Leu Gln Cys Arg Ala Glu Ser
50 55 60

His Pro Glu Val Ser Ile Glu His Leu Gly Gln Val Val Gln Cys Ser
65 70 75 80

Arg Glu Glu Gly Leu Val Cys Arg Asn Gln Asp Gln Gln Gly Pro Phe
85 90 95

Lys Met Cys Leu Asn Tyr Glu Val Arg Val Leu Cys Cys Glu Thr Pro
100 105 110

Lys Gly Cys Pro Val Thr Ser Thr Pro Val Thr Ala Pro Ser Thr Pro
115 120 125

Ser Gly Arg Ala Thr Ser Pro Thr Gln Ser Thr Ser Ser Trp Gln Lys
130 135 140

Ser Arg Thr Thr Thr Leu Val Thr Thr Ser Thr Thr Ser Thr Pro Gln
145 150 155 160

```
Thr Ser Thr Thr Ser Ala Pro Thr Thr Ser Thr Thr Ser Ala Pro Thr
                165                 170                 175

Thr Ser Thr Thr Ser Ala Pro Thr Thr Ser Thr Thr Ser Thr Pro Gln
            180                 185                 190

Thr Ser Ile Ser Ser Ala Pro Thr Ser Ser Thr Thr Ser Ala Pro Thr
        195                 200                 205

Ser Ser Thr Ile Ser Ala Arg Thr Thr Ser Ile Ile Ser Ala Pro Thr
    210                 215                 220

Thr Ser Thr Thr Ser Ser Pro Thr Thr Ser Thr Thr Ser Ala Thr Thr
225                 230                 235                 240

Thr Ser Thr Thr Ser Ala Pro Thr Ser Ser Thr Thr Ser Thr Pro Gln
                245                 250                 255

Thr Ser Lys Thr Ser Ala Ala Thr Ser Ser Thr Thr Ser Ser Ser Gly
            260                 265                 270

Thr Thr Pro Ser Pro Val Thr Thr Thr Ser Thr Ala Ser Val Ser Lys
        275                 280                 285

Thr Thr Ser His Val Ser Val Ser Lys Thr Thr His Ser Gln Pro Val
    290                 295                 300

Thr Arg
305


<210> SEQ ID NO 39
<211> LENGTH: 384
<212> TYPE: DNA
<213> ORGANISM: Artificial Sequence
<220> FEATURE:
<223> OTHER INFORMATION: N-terminal fragment of MUC5AC (long)

<400> SEQUENCE: 39

actactcatt ctcaacctgt aactcgtgat tgtcatctgc gctgtacttg gactaaatgg      60

tttgacgtgg acttcccgtc ccctggcccg cacggtggtg ataaagaaac ctacaataac     120

atcattcgct ctggtgagaa aatctgccgt cgtccggaag aaatcactcg tctgcaatgt     180

cgtgccgaat cccacccgga ggtgagcatc gaacacctgg gtcaggttgt tcagtgttct     240

cgtgaggaag gtctggtatg ccgtaaccaa gatcagcaag gcccattcaa aatgtgcctg     300

aactacgaag ttcgtgttct gtgttgcgag actccgaaag gttgcccggt tacgagcacg     360

cctgtcaccg caccgagcac gccg                                            384


<210> SEQ ID NO 40
<211> LENGTH: 128
<212> TYPE: PRT
<213> ORGANISM: Artificial Sequence
<220> FEATURE:
<223> OTHER INFORMATION: N-terminal fragment of MUC5AC (short)

<400> SEQUENCE: 40

Thr Thr His Ser Gln Pro Val Thr Arg Asp Cys His Leu Arg Cys Thr
1               5                   10                  15

Trp Thr Lys Trp Phe Asp Val Asp Phe Pro Ser Pro Gly Pro His Gly
            20                  25                  30

Gly Asp Lys Glu Thr Tyr Asn Asn Ile Ile Arg Ser Gly Glu Lys Ile
        35                  40                  45

Cys Arg Arg Pro Glu Glu Ile Thr Arg Leu Gln Cys Arg Ala Glu Ser
    50                  55                  60

His Pro Glu Val Ser Ile Glu His Leu Gly Gln Val Val Gln Cys Ser
65                  70                  75                  80
```

-continued

Arg Glu Glu Gly Leu Val Cys Arg Asn Gln Asp Gln Gln Gly Pro Phe
85 90 95

Lys Met Cys Leu Asn Tyr Glu Val Arg Val Leu Cys Cys Glu Thr Pro
100 105 110

Lys Gly Cys Pro Val Thr Ser Thr Pro Val Thr Ala Pro Ser Thr Pro
115 120 125

<210> SEQ ID NO 41
<211> LENGTH: 384
<212> TYPE: DNA
<213> ORGANISM: Artificial Sequence
<220> FEATURE:
<223> OTHER INFORMATION: N-terminal fragment of MUC5AC (short)

<400> SEQUENCE: 41
actactcatt ctcaacctgt aactcgtgat tgtcatctgc gctgtacttg gactaaatgg 60
tttgacgtgg acttcccgtc ccctggcccg cacggtggtg ataaagaaac ctacaataac 120
atcattcgct ctggtgagaa aatctgccgt cgtccggaag aaatcactcg tctgcaatgt 180
cgtgccgaat cccacccgga ggtgagcatc gaacacctgg gtcaggttgt tcagtgttct 240
cgtgaggaag gtctggtatg ccgtaaccaa gatcagcaag gcccattcaa aatgtgcctg 300
aactacgaag ttcgtgttct gtgttgcgag actccgaaag gttgcccggt tacgagcacg 360
cctgtcaccg caccgagcac gccg 384

<210> SEQ ID NO 42
<211> LENGTH: 8
<212> TYPE: PRT
<213> ORGANISM: Artificial Sequence
<220> FEATURE:
<223> OTHER INFORMATION: MUC5AC tandem repeat

<400> SEQUENCE: 42

Thr Thr Ser Thr Thr Ser Ala Pro
1 5

<210> SEQ ID NO 43
<211> LENGTH: 8
<212> TYPE: PRT
<213> ORGANISM: Artificial Sequence
<220> FEATURE:
<223> OTHER INFORMATION: MUC5AC tandem repeat

<400> SEQUENCE: 43

Gly Ser Thr Pro Ser Pro Val Pro
1 5

<210> SEQ ID NO 44
<211> LENGTH: 8
<212> TYPE: PRT
<213> ORGANISM: Artificial Sequence
<220> FEATURE:
<223> OTHER INFORMATION: MUC5AC tandem repeat

<400> SEQUENCE: 44

Thr Ala Ser Thr Thr Ser Gly Pro
1 5

<210> SEQ ID NO 45
<211> LENGTH: 85
<212> TYPE: PRT
<213> ORGANISM: Artificial Sequence
<220> FEATURE:

<223> OTHER INFORMATION: MUC5AC truncation construct (85)

<400> SEQUENCE: 45

```
Ala Thr Met Ser Val Gly Arg Arg Lys Leu Ala Leu Leu Trp Ala Leu
1               5                   10                  15

Ala Leu Ala Leu Ala Cys Thr Thr Thr His Ser Gln Pro Val Thr Arg
            20                  25                  30

Asp Cys His Leu Arg Cys Thr Trp Thr Lys Trp Phe Asp Val Asp Phe
        35                  40                  45

Pro Ser Pro Gly Pro His Gly Gly Asp Lys Glu Thr Tyr Asn Asn Ile
    50                  55                  60

Ile Arg Ser Gly Glu Lys Ile Cys Arg Arg Pro Glu Glu Ile Thr Arg
65                  70                  75                  80

Leu Gln Cys Arg Ala
                85
```

<210> SEQ ID NO 46
<211> LENGTH: 136
<212> TYPE: PRT
<213> ORGANISM: Artificial Sequence
<220> FEATURE:
<223> OTHER INFORMATION: MUC5AC truncation construct (136)

<400> SEQUENCE: 46

```
Ala Thr Met Ser Val Gly Arg Arg Lys Leu Ala Leu Leu Trp Ala Leu
1               5                   10                  15

Ala Leu Ala Leu Ala Cys Thr Thr Thr His Ser Gln Pro Val Thr Arg
            20                  25                  30

Asp Cys His Leu Arg Cys Thr Trp Thr Lys Trp Phe Asp Val Asp Phe
        35                  40                  45

Pro Ser Pro Gly Pro His Gly Gly Asp Lys Glu Thr Tyr Asn Asn Ile
    50                  55                  60

Ile Arg Ser Gly Glu Lys Ile Cys Arg Arg Pro Glu Glu Ile Thr Arg
65                  70                  75                  80

Leu Gln Cys Arg Ala Glu Ser His Pro Glu Val Ser Ile Glu His Leu
                85                  90                  95

Gly Gln Val Val Gln Cys Ser Arg Glu Glu Gly Leu Val Cys Arg Asn
            100                 105                 110

Gln Asp Gln Gln Gly Pro Phe Lys Met Cys Leu Asn Tyr Glu Val Arg
        115                 120                 125

Val Leu Cys Cys Glu Thr Pro Lys
    130                 135
```

<210> SEQ ID NO 47
<211> LENGTH: 151
<212> TYPE: PRT
<213> ORGANISM: Artificial Sequence
<220> FEATURE:
<223> OTHER INFORMATION: MUC5AC truncation construct (151)

<400> SEQUENCE: 47

```
Ala Thr Met Ser Val Gly Arg Arg Lys Leu Ala Leu Leu Trp Ala Leu
1               5                   10                  15

Ala Leu Ala Leu Ala Cys Thr Thr Thr His Ser Gln Pro Val Thr Arg
            20                  25                  30

Asp Cys His Leu Arg Cys Thr Trp Thr Lys Trp Phe Asp Val Asp Phe
        35                  40                  45

Pro Ser Pro Gly Pro His Gly Gly Asp Lys Glu Thr Tyr Asn Asn Ile
```

```
    50                  55                  60

Ile Arg Ser Gly Glu Lys Ile Cys Arg Arg Pro Glu Glu Ile Thr Arg
65                  70                  75                  80

Leu Gln Cys Arg Ala Glu Ser His Pro Glu Val Ser Ile Glu His Leu
                85                  90                  95

Gly Gln Val Val Gln Cys Ser Arg Glu Glu Gly Leu Val Cys Arg Asn
            100                 105                 110

Gln Asp Gln Gln Gly Pro Phe Lys Met Cys Leu Asn Tyr Glu Val Arg
        115                 120                 125

Val Leu Cys Cys Glu Thr Pro Lys Gly Cys Pro Val Thr Ser Thr Pro
    130                 135                 140

Val Thr Ala Pro Ser Thr Pro
145                 150


<210> SEQ ID NO 48
<211> LENGTH: 187
<212> TYPE: PRT
<213> ORGANISM: Artificial Sequence
<220> FEATURE:
<223> OTHER INFORMATION: MUC5AC truncation construct (187)

<400> SEQUENCE: 48

Ala Thr Met Ser Val Gly Arg Arg Lys Leu Ala Leu Leu Trp Ala Leu
1               5                   10                  15

Ala Leu Ala Leu Ala Cys Thr Thr Thr His Ser Gln Pro Val Thr Arg
            20                  25                  30

Asp Cys His Leu Arg Cys Thr Trp Thr Lys Trp Phe Asp Val Asp Phe
        35                  40                  45

Pro Ser Pro Gly Pro His Gly Gly Asp Lys Glu Thr Tyr Asn Asn Ile
    50                  55                  60

Ile Arg Ser Gly Glu Lys Ile Cys Arg Arg Pro Glu Glu Ile Thr Arg
65                  70                  75                  80

Leu Gln Cys Arg Ala Glu Ser His Pro Glu Val Ser Ile Glu His Leu
                85                  90                  95

Gly Gln Val Val Gln Cys Ser Arg Glu Glu Gly Leu Val Cys Arg Asn
            100                 105                 110

Gln Asp Gln Gln Gly Pro Phe Lys Met Cys Leu Asn Tyr Glu Val Arg
        115                 120                 125

Val Leu Cys Cys Glu Thr Pro Lys Gly Cys Pro Val Thr Ser Thr Pro
    130                 135                 140

Val Thr Ala Pro Ser Thr Pro Ser Gly Arg Ala Thr Ser Pro Thr Gln
145                 150                 155                 160

Ser Thr Ser Ser Trp Gln Lys Ser Arg Thr Thr Thr Leu Val Thr Thr
                165                 170                 175

Ser Thr Thr Ser Thr Pro Gln Thr Ser Thr Thr
            180                 185


<210> SEQ ID NO 49
<211> LENGTH: 289
<212> TYPE: PRT
<213> ORGANISM: Artificial Sequence
<220> FEATURE:
<223> OTHER INFORMATION: MUC5AC truncation construct (289)

<400> SEQUENCE: 49

Ala Thr Met Ser Val Gly Arg Arg Lys Leu Ala Leu Leu Trp Ala Leu
1               5                   10                  15
```

```
Ala Leu Ala Leu Ala Cys Thr Thr Thr His Ser Gln Pro Val Thr Arg
            20                  25                  30

Asp Cys His Leu Arg Cys Thr Trp Thr Lys Trp Phe Asp Val Asp Phe
        35                  40                  45

Pro Ser Pro Gly Pro His Gly Gly Asp Lys Glu Thr Tyr Asn Asn Ile
    50                  55                  60

Ile Arg Ser Gly Glu Lys Ile Cys Arg Arg Pro Glu Glu Ile Thr Arg
65                  70                  75                  80

Leu Gln Cys Arg Ala Glu Ser His Pro Glu Val Ser Ile Glu His Leu
                85                  90                  95

Gly Gln Val Val Gln Cys Ser Arg Glu Glu Gly Leu Val Cys Arg Asn
            100                 105                 110

Gln Asp Gln Gln Gly Pro Phe Lys Met Cys Leu Asn Tyr Glu Val Arg
        115                 120                 125

Val Leu Cys Cys Glu Thr Pro Lys Gly Cys Pro Val Thr Ser Thr Pro
    130                 135                 140

Val Thr Ala Pro Ser Thr Pro Ser Gly Arg Ala Thr Ser Pro Thr Gln
145                 150                 155                 160

Ser Thr Ser Ser Trp Gln Lys Ser Arg Thr Thr Thr Leu Val Thr Thr
                165                 170                 175

Ser Thr Thr Ser Thr Pro Gln Thr Ser Thr Thr Ser Ala Pro Thr Thr
            180                 185                 190

Ser Thr Thr Ser Ala Pro Thr Thr Ser Thr Thr Ser Ala Pro Thr Thr
        195                 200                 205

Ser Thr Thr Ser Thr Pro Gln Thr Ser Ile Ser Ser Ala Pro Thr Ser
    210                 215                 220

Ser Thr Thr Ser Ala Pro Thr Ser Ser Thr Ile Ser Ala Arg Thr Thr
225                 230                 235                 240

Ser Ile Ile Ser Ala Pro Thr Thr Ser Thr Thr Ser Ser Pro Thr Thr
                245                 250                 255

Ser Thr Thr Ser Ala Thr Thr Thr Ser Thr Thr Ser Ala Pro Thr Ser
            260                 265                 270

Ser Thr Thr Ser Thr Pro Gln Thr Ser Lys Thr Ser Ala Ala Thr Ser
        275                 280                 285

Ser


<210> SEQ ID NO 50
<211> LENGTH: 338
<212> TYPE: PRT
<213> ORGANISM: Artificial Sequence
<220> FEATURE:
<223> OTHER INFORMATION: MUC5AC truncation construct (338)

<400> SEQUENCE: 50

Ala Thr Met Ser Val Gly Arg Arg Lys Leu Ala Leu Leu Trp Ala Leu
1               5                   10                  15

Ala Leu Ala Leu Ala Cys Thr Thr Thr His Ser Gln Pro Val Thr Arg
            20                  25                  30

Asp Cys His Leu Arg Cys Thr Trp Thr Lys Trp Phe Asp Val Asp Phe
        35                  40                  45

Pro Ser Pro Gly Pro His Gly Gly Asp Lys Glu Thr Tyr Asn Asn Ile
    50                  55                  60

Ile Arg Ser Gly Glu Lys Ile Cys Arg Arg Pro Glu Glu Ile Thr Arg
65                  70                  75                  80

Leu Gln Cys Arg Ala Glu Ser His Pro Glu Val Ser Ile Glu His Leu
```

-continued

```
                85                  90                  95

Gly Gln Val Val Gln Cys Ser Arg Glu Glu Gly Leu Val Cys Arg Asn
            100                 105                 110

Gln Asp Gln Gln Gly Pro Phe Lys Met Cys Leu Asn Tyr Glu Val Arg
        115                 120                 125

Val Leu Cys Cys Glu Thr Pro Lys Gly Cys Pro Val Thr Ser Thr Pro
    130                 135                 140

Val Thr Ala Pro Ser Thr Pro Ser Gly Arg Ala Thr Ser Pro Thr Gln
145                 150                 155                 160

Ser Thr Ser Ser Trp Gln Lys Ser Arg Thr Thr Thr Leu Val Thr Thr
                165                 170                 175

Ser Thr Thr Ser Thr Pro Gln Thr Ser Thr Thr Ser Ala Pro Thr Thr
            180                 185                 190

Ser Thr Thr Ser Ala Pro Thr Thr Ser Thr Thr Ser Ala Pro Thr Thr
        195                 200                 205

Ser Thr Thr Ser Thr Pro Gln Thr Ser Ile Ser Ser Ala Pro Thr Ser
    210                 215                 220

Ser Thr Thr Ser Ala Pro Thr Ser Ser Thr Ile Ser Ala Arg Thr Thr
225                 230                 235                 240

Ser Ile Ile Ser Ala Pro Thr Thr Ser Thr Thr Ser Ser Pro Thr Thr
                245                 250                 255

Ser Thr Thr Ser Ala Thr Thr Thr Ser Thr Thr Ser Ala Pro Thr Ser
            260                 265                 270

Ser Thr Thr Ser Thr Pro Gln Thr Ser Lys Thr Ser Ala Ala Thr Ser
        275                 280                 285

Ser Thr Thr Ser Ser Ser Gly Thr Thr Pro Ser Pro Val Thr Thr Thr
    290                 295                 300

Ser Thr Ala Ser Val Ser Lys Thr Ser Thr Ser His Val Ser Val Ser
305                 310                 315                 320

Lys Thr Thr His Ser Gln Pro Val Thr Arg Cys Thr His His His His
                325                 330                 335

His His


<210> SEQ ID NO 51
<211> LENGTH: 21
<212> TYPE: DNA
<213> ORGANISM: Artificial Sequence
<220> FEATURE:
<223> OTHER INFORMATION: siRNA ID# s9074 (sense)

<400> SEQUENCE: 51

agaugugccu caacuacgat t                                               21


<210> SEQ ID NO 52
<211> LENGTH: 21
<212> TYPE: DNA
<213> ORGANISM: Artificial Sequence
<220> FEATURE:
<223> OTHER INFORMATION: siRNA ID# s9074 (antisense)

<400> SEQUENCE: 52

ucguaguuga ggcacaucut g                                               21


<210> SEQ ID NO 53
<211> LENGTH: 21
<212> TYPE: DNA
<213> ORGANISM: Artificial Sequence
<220> FEATURE:
```

-continued

<223> OTHER INFORMATION: siRNA ID# s9075 (sense)

<400> SEQUENCE: 53
gcucuggaac gugagcauat t 21

<210> SEQ ID NO 54
<211> LENGTH: 21
<212> TYPE: RNA
<213> ORGANISM: Artificial Sequence
<220> FEATURE:
<223> OTHER INFORMATION: siRNA ID# s9075 (antisense)

<400> SEQUENCE: 54
uaugcucacg uuccagagcc g 21

<210> SEQ ID NO 55
<211> LENGTH: 21
<212> TYPE: DNA
<213> ORGANISM: Artificial Sequence
<220> FEATURE:
<223> OTHER INFORMATION: siRNA ID# s9076

<400> SEQUENCE: 55
gcgugcucgu cgacaacuat t 21

<210> SEQ ID NO 56
<211> LENGTH: 21
<212> TYPE: RNA
<213> ORGANISM: Artificial Sequence
<220> FEATURE:
<223> OTHER INFORMATION: siRNA ID# s9076 (antisense)

<400> SEQUENCE: 56
uaguugucga cgagcacgcg g 21

<210> SEQ ID NO 57
<211> LENGTH: 965
<212> TYPE: DNA
<213> ORGANISM: Artificial Sequence
<220> FEATURE:
<223> OTHER INFORMATION: NPC-1 antibody light chain

<400> SEQUENCE: 57
atgagaatac cattaattag ctagggacca aaattcaaag acaaaatgga ttttcaggtg 60
cagattttca gcttcctgct aatcagtgcc tcagtcatac tgtccagagg acaagttgtt 120
ctcacccagt ctccagtaat catgtctgca tctccagggg agaaggtcac catgacctgc 180
agtgccagct caagtataag ttacatgtac tggtaccagc agaagccagg cacctccccc 240
aaaagatgga tttatgacac atccaaactg gcttctggag tccctgctcg cttcagtggc 300
agtgggtctg ggacctctta ttctctcaca atcagcaaca tggaggctgg agatgctgcc 360
acttattact gccatcagcg ggattcttac ccatggacgt tcggtggagg caccaacctg 420
gaaatcaaac gggctgatgc tgcaccaact gtatccatct tcccaccatc cagtgagcag 480
ttaacatctg gaggtgcctc agtcgtgtgc ttcttgaaca acttctaccc caaagacatc 540
aatgtcaagt ggaagattga tggcagtgaa cgacaaaatg gcgtcctgaa cagttggact 600
gatcaggaca gcaaagacag cacctacagc atgagcagca ccctcacgtt gaccaaggac 660
gagtatgaac gacataacag ctatacctgt gaggccactc acaagacatc aacttcaccc 720
attgtcaaga gcttcaacag gaatgagtgt tagagacaaa ggtcctgaga cgccaccacc 780
agctccccag ctccatccta tcttcccttc taaggtcttg gaggcttccc cacaagcgac 840

```
ctaccactgt tgcggtgctc caaacctcct ccccacctcc ttctcctcct cctccctttc    900

cttggctttt atcatgctaa tatttgcaga aaatattcaa taaagtgagt ctttgcactt    960

gaaaa                                                                965


<210> SEQ ID NO 58
<211> LENGTH: 235
<212> TYPE: PRT
<213> ORGANISM: Artificial Sequence
<220> FEATURE:
<223> OTHER INFORMATION: NPC-1 antibody light chain
<220> FEATURE:
<221> NAME/KEY: MISC_FEATURE
<222> LOCATION: (46)..(55)
<223> OTHER INFORMATION: CDR1
<220> FEATURE:
<221> NAME/KEY: MISC_FEATURE
<222> LOCATION: (71)..(77)
<223> OTHER INFORMATION: CDR2
<220> FEATURE:
<221> NAME/KEY: MISC_FEATURE
<222> LOCATION: (110)..(118)
<223> OTHER INFORMATION: CDR3

<400> SEQUENCE: 58

Met Asp Phe Gln Val Gln Ile Phe Ser Phe Leu Leu Ile Ser Ala Ser
1               5                   10                  15

Val Ile Leu Ser Arg Gly Gln Val Val Leu Thr Gln Ser Pro Val Ile
            20                  25                  30

Met Ser Ala Ser Pro Gly Glu Lys Val Thr Met Thr Cys Ser Ala Ser
        35                  40                  45

Ser Ser Ile Ser Tyr Met Tyr Trp Tyr Gln Gln Lys Pro Gly Thr Ser
    50                  55                  60

Pro Lys Arg Trp Ile Tyr Asp Thr Ser Lys Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Asn Met Glu Ala Gly Asp Ala Ala Thr Tyr Tyr Cys His Gln Arg
            100                 105                 110

Asp Ser Tyr Pro Trp Thr Phe Gly Gly Gly Thr Asn Leu Glu Ile Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser
    210                 215                 220

Pro Ile Val Lys Ser Phe Asn Arg Asn Glu Cys
225                 230                 235


<210> SEQ ID NO 59
<211> LENGTH: 10
<212> TYPE: PRT
<213> ORGANISM: Artificial Sequence
```

<220> FEATURE:
<223> OTHER INFORMATION: NPC-1 light chain CDR1

<400> SEQUENCE: 59

Ser Ala Ser Ser Ser Ile Ser Tyr Met Tyr
1 5 10

<210> SEQ ID NO 60
<211> LENGTH: 7
<212> TYPE: PRT
<213> ORGANISM: Artificial Sequence
<220> FEATURE:
<223> OTHER INFORMATION: NPC-1 light chain CDR2

<400> SEQUENCE: 60

Asp Thr Ser Lys Leu Ala Ser
1 5

<210> SEQ ID NO 61
<211> LENGTH: 9
<212> TYPE: PRT
<213> ORGANISM: Artificial Sequence
<220> FEATURE:
<223> OTHER INFORMATION: NPC-1 antibody light chain CDR3

<400> SEQUENCE: 61

His Gln Arg Asp Ser Tyr Pro Trp Thr
1 5

<210> SEQ ID NO 62
<211> LENGTH: 1520
<212> TYPE: DNA
<213> ORGANISM: Artificial Sequence
<220> FEATURE:
<223> OTHER INFORMATION: NPC-1 antibody heavy chain

<400> SEQUENCE: 62
ttttccatcc tcttctcata gagcctccat cagaccatgg ctgtcctggc actgctcctc 60
tgcctggtga cattcccaag ctgtgtcctg tcccaggtgc agctgaagga gtcaggacct 120
gacctggtgg cgccctcaca gagcctgtcc atcacatgca ctgtctcagg attctcatta 180
agcaaatttg gtgtaaactg ggttcgccag cctccaggaa agggtctgga gtggctggga 240
gtaatatggg gtgacgggag cacaagttat aattcaggtc tcatatcaag actgagcatc 300
agcaaggaga actccaagag ccaggttttc ttaaaactga acagtctgca agctgatgac 360
acagccacat actactgtgt caaaccgggg ggtgactact ggggtcacgg aacctcagtc 420
accgtctcct cagccaaaac gacaccccca tctgtctatc cactggcccc tggatctgct 480
gcccaaacta actccatggt gaccctggga tgcctggtca agggctattt ccctgagcca 540
gtgacagtga cctggaactc tggatccctg tccagcggtg tgcacacctt cccagctgtc 600
ctgcagtctg acctctacac tctgagcagc tcagtgactg tcccctccag cacctggccc 660
agcgagaccg tcacctgcaa cgttgcccac ccggccagca gcaccaaggt ggacaagaaa 720
attgtgccca gggattgtgg ttgtaagcct tgcatatgta cagtcccaga agtatcatct 780
gtcttcatct tccccccaaa gcccaaggat gtgctcacca ttactctgac tcctaaggtc 840
acgtgtgttg tggtagacat cagcaaggat gatcccgagg tccagttcag ctggtttgta 900
gatgtggagg tgcacacagc tcagacgcaa ccccgggagg agcagttcaa cagcactttc 960
cgctcagtca gtgaacttcc catcatgcac caggactggc tcaatggcaa ggagttcaaa 1020
tgcagggtca acagtgcagc tttccctgcc cccatcgaga aaaccatctc caaaaccaaa 1080
ggcagaccga aggctccaca ggtgtacacc attccacctc ccaaggagca gatggccaag 1140
gataaagtca gtctgacctg catgataaca gacttcttcc ctgaagacat tactgtggag 1200
tggcagtgga atgggcagcc agcggagaac tacaagaaca ctcagcccat catggacaca 1260
gatggctctt acttcgtcta cagcaagctc aatgtgcaga agagcaactg ggaggcagga 1320
aatactttca cctgctctgt gttacatgag ggcctgcaca accaccatac tgagaagagc 1380
ctctcccact ctcctggtaa atgatcccag tgtccttgga gccctctggt cctacaggac 1440
tctgacacct acctccaccc ctccctgtat aaataaagca cccagcactg ccttgggacc 1500
ctgcaaaaaa aaaaaaaaaa 1520

<210> SEQ ID NO 63
<211> LENGTH: 456
<212> TYPE: PRT
<213> ORGANISM: Artificial Sequence
<220> FEATURE:
<223> OTHER INFORMATION: NPC-1 antibody heavy chain
<220> FEATURE:
<221> NAME/KEY: MISC_FEATURE
<222> LOCATION: (49)..(54)
<223> OTHER INFORMATION: CDR1
<220> FEATURE:
<221> NAME/KEY: MISC_FEATURE
<222> LOCATION: (69)..(84)
<223> OTHER INFORMATION: CDR2
<220> FEATURE:
<221> NAME/KEY: MISC_FEATURE
<222> LOCATION: (114)..(121)
<223> OTHER INFORMATION: CDR3

<400> SEQUENCE: 63

Met Ala Val Leu Ala Leu Leu Leu Cys Leu Val Thr Phe Pro Ser Cys
1 5 10 15

Val Leu Ser Gln Val Gln Leu Lys Glu Ser Gly Pro Asp Leu Val Ala
20 25 30

Pro Ser Gln Ser Leu Ser Ile Thr Cys Thr Val Ser Gly Phe Ser Leu
35 40 45

Ser Lys Phe Gly Val Asn Trp Val Arg Gln Pro Pro Gly Lys Gly Leu
50 55 60

Glu Trp Leu Gly Val Ile Trp Gly Asp Gly Ser Thr Ser Tyr Asn Ser
65 70 75 80

Gly Leu Ile Ser Arg Leu Ser Ile Ser Lys Glu Asn Ser Lys Ser Gln
85 90 95

Val Phe Leu Lys Leu Asn Ser Leu Gln Ala Asp Asp Thr Ala Thr Tyr
100 105 110

Tyr Cys Val Lys Pro Gly Gly Asp Tyr Trp Gly His Gly Thr Ser Val
115 120 125

Thr Val Ser Ser Ala Lys Thr Thr Pro Pro Ser Val Tyr Pro Leu Ala
130 135 140

Pro Gly Ser Ala Ala Gln Thr Asn Ser Met Val Thr Leu Gly Cys Leu
145 150 155 160

Val Lys Gly Tyr Phe Pro Glu Pro Val Thr Val Thr Trp Asn Ser Gly
165 170 175

Ser Leu Ser Ser Gly Val His Thr Phe Pro Ala Val Leu Gln Ser Asp
180 185 190

Leu Tyr Thr Leu Ser Ser Ser Val Thr Val Pro Ser Ser Thr Trp Pro
195 200 205

Ser Glu Thr Val Thr Cys Asn Val Ala His Pro Ala Ser Ser Thr Lys

```
    210                 215                 220

Val Asp Lys Lys Ile Val Pro Arg Asp Cys Gly Cys Lys Pro Cys Ile
225                 230                 235                 240

Cys Thr Val Pro Glu Val Ser Ser Val Phe Ile Phe Pro Pro Lys Pro
                245                 250                 255

Lys Asp Val Leu Thr Ile Thr Leu Thr Pro Lys Val Thr Cys Val Val
            260                 265                 270

Val Asp Ile Ser Lys Asp Asp Pro Glu Val Gln Phe Ser Trp Phe Val
        275                 280                 285

Asp Asp Val Glu Val His Thr Ala Gln Thr Gln Pro Arg Glu Glu Gln
    290                 295                 300

Phe Asn Ser Thr Phe Arg Ser Val Ser Glu Leu Pro Ile Met His Gln
305                 310                 315                 320

Asp Trp Leu Asn Gly Lys Glu Phe Lys Cys Arg Val Asn Ser Ala Ala
                325                 330                 335

Phe Pro Ala Pro Ile Glu Lys Thr Ile Ser Lys Thr Lys Gly Arg Pro
            340                 345                 350

Lys Ala Pro Gln Val Tyr Thr Ile Pro Pro Pro Lys Glu Gln Met Ala
        355                 360                 365

Lys Asp Lys Val Ser Leu Thr Cys Met Ile Thr Asp Phe Phe Pro Glu
    370                 375                 380

Asp Ile Thr Val Glu Trp Gln Trp Asn Gly Gln Pro Ala Glu Asn Tyr
385                 390                 395                 400

Lys Asn Thr Gln Pro Ile Met Asp Thr Asp Gly Ser Tyr Phe Val Tyr
                405                 410                 415

Ser Lys Leu Asn Val Gln Lys Ser Asn Trp Glu Ala Gly Asn Thr Phe
            420                 425                 430

Thr Cys Ser Val Leu His Glu Gly Leu His Asn His His Thr Glu Lys
        435                 440                 445

Ser Leu Ser His Ser Pro Gly Lys
    450                 455


<210> SEQ ID NO 64
<211> LENGTH: 6
<212> TYPE: PRT
<213> ORGANISM: Artificial Sequence
<220> FEATURE:
<223> OTHER INFORMATION: NPC-1 antibody heavy chain CDR1

<400> SEQUENCE: 64

Ser Lys Phe Gly Val Asn
1               5


<210> SEQ ID NO 65
<211> LENGTH: 16
<212> TYPE: PRT
<213> ORGANISM: Artificial Sequence
<220> FEATURE:
<223> OTHER INFORMATION: NPC-1 heavy chain CDR2

<400> SEQUENCE: 65

Val Ile Trp Gly Asp Gly Ser Thr Ser Tyr Asn Ser Gly Leu Ile Ser
1               5                   10                  15


<210> SEQ ID NO 66
<211> LENGTH: 8
<212> TYPE: PRT
<213> ORGANISM: Artificial Sequence
<220> FEATURE:
```

<223> OTHER INFORMATION: NPC-1 antibody heavy chain CDR3

<400> SEQUENCE: 66

Cys Val Lys Pro Gly Gly Asp Tyr
1 5

<210> SEQ ID NO 67
<211> LENGTH: 737
<212> TYPE: DNA
<213> ORGANISM: Artificial Sequence
<220> FEATURE:
<223> OTHER INFORMATION: NPC-1 Chi-antibody light chain

<400> SEQUENCE: 67
gcatagatct gccaccatgg actttcaggt ccagatattt agctttctat tgattagcgc 60
ctctgtcatt ctgagtaggg ggcaggtggt gctcacccag tctccagtga tcatgtcagc 120
ctcaccagga gaaaaagtga ctatgacctg ctcagcatcc tccagcatca gttacatgta 180
ctggtaccag cagaagccag gcacctcgcc caagcgttgg atctacgata cttccaagct 240
ggcaagtggg gtacccgcac gcttcagtgg aagtggctcc ggaacctcgt acagtttgac 300
catttcaaat atggaagctg gggacgcagc tacatattat tgccaccaga gagactccta 360
cccgtggacc ttcggaggcg gtactaattt agagatcaag aggaccgtag ccgctccttc 420
cgtgttcatc tttccccctt ccgacgaaca actgaaaagc ggtacagcct ccgtggtttg 480
tctgctgaac aacttctacc cccgggaggc taaagttcag tggaaggttg acaatgctct 540
gcagtcaggc aactctcaag agagcgtcac ggagcaagat agcaaagatt ctacatattc 600
tctctcttct acacttacac ttagcaaggc cgattatgag aagcacaagg tgtatgcctg 660
cgaggtgact catcagggtc tttcttctcc tgtcactaaa agcttcaacc gaggcgaatg 720
ttgatgaaga tcttacg 737

<210> SEQ ID NO 68
<211> LENGTH: 235
<212> TYPE: PRT
<213> ORGANISM: Artificial Sequence
<220> FEATURE:
<223> OTHER INFORMATION: NPC-1 chi-antibody light chain with signal peptide
<220> FEATURE:
<221> NAME/KEY: SIGNAL
<222> LOCATION: (1)..(22)
<220> FEATURE:
<221> NAME/KEY: MISC_FEATURE
<222> LOCATION: (46)..(55)
<223> OTHER INFORMATION: CDR1
<220> FEATURE:
<221> NAME/KEY: MISC_FEATURE
<222> LOCATION: (71)..(77)
<223> OTHER INFORMATION: CDR2
<220> FEATURE:
<221> NAME/KEY: MISC_FEATURE
<222> LOCATION: (110)..(118)
<223> OTHER INFORMATION: CDR3

<400> SEQUENCE: 68

Met Asp Phe Gln Val Gln Ile Phe Ser Phe Leu Leu Ile Ser Ala Ser
1 5 10 15

Val Ile Leu Ser Arg Gly Gln Val Val Leu Thr Gln Ser Pro Val Ile
20 25 30

Met Ser Ala Ser Pro Gly Glu Lys Val Thr Met Thr Cys Ser Ala Ser
35 40 45

Ser Ser Ile Ser Tyr Met Tyr Trp Tyr Gln Gln Lys Pro Gly Thr Ser

```
    50                  55                  60

Pro Lys Arg Trp Ile Tyr Asp Thr Ser Lys Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Asn Met Glu Ala Gly Asp Ala Ala Thr Tyr Tyr Cys His Gln Arg
            100                 105                 110

Asp Ser Tyr Pro Trp Thr Phe Gly Gly Gly Thr Asn Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235


<210> SEQ ID NO 69
<211> LENGTH: 10
<212> TYPE: PRT
<213> ORGANISM: Artificial Sequence
<220> FEATURE:
<223> OTHER INFORMATION: NPC-1 chi-antibody light chain CDR1

<400> SEQUENCE: 69

Ser Ala Ser Ser Ser Ile Ser Tyr Met Tyr
1               5                   10


<210> SEQ ID NO 70
<211> LENGTH: 7
<212> TYPE: PRT
<213> ORGANISM: Artificial Sequence
<220> FEATURE:
<223> OTHER INFORMATION: NPC-1 chi-antibody light chain CDR2

<400> SEQUENCE: 70

Asp Thr Ser Lys Leu Ala Ser
1               5


<210> SEQ ID NO 71
<211> LENGTH: 9
<212> TYPE: PRT
<213> ORGANISM: Artificial Sequence
<220> FEATURE:
<223> OTHER INFORMATION: NPC-1 chi-antibody light chain CDR3

<400> SEQUENCE: 71

His Gln Arg Asp Ser Tyr Pro Trp Thr
1               5


<210> SEQ ID NO 72
<211> LENGTH: 1418
<212> TYPE: DNA
<213> ORGANISM: Artificial Sequence
```

<220> FEATURE:
<223> OTHER INFORMATION: NPC-1 chi-antibody heavy chain

<400> SEQUENCE: 72

```
gagcggtacc gccaccatgg cagtgctggc ccttcttcta tgtctggtga ccttcccatc     60

ctgcgtcctg agccaggtac aactgaagga gtcgggccca gacctagtgg ctccgtcaca    120

atcactctcc attacgtgca ctgtctccgg cttctctttg tctaaattcg gcgtgaattg    180

ggtgcgacag ccccccggga aggggcttga gtggttagga gttatctggg gtgacggctc    240

aaccagctac aactcaggac taatctcacg cttgtcaatt tcaaaggaga attcaaagtc    300

tcaggtgttc cttaagctca actcgctgca agccgacgat accgcaacct attactgcgt    360

caaacctggc ggggactact ggggccatgg cacctccgtc acagtgagtt ccgcatccac    420

aaagggtccc agtgtttttc ctttggcgcc ctctagcaaa tcgacatctg gcggcacagc    480

cgcacttggg tgcttggtta aagactactt ccccgaaccg gtgacagtat cttggaactc    540

tggcgctctt accagcggag ttcatacctt ccctgccgta ttacagtcta gcgggcccta    600

ctccctctcc tctgtcgtga cagtcccaag ctcttctctg ggaactcaaa cctacatctg    660

caatgtgaac cataaaccta gcaacacgaa agtggacaaa aaggtcgaac ccaagagttg    720

cgacaagaca cacacctgcc ctccttgtcc tgctccagag ctcctcggcg gacctagcgt    780

ttttcttgttc cctccgaaac caaaggacac cttgatgatt tctcggaccc ccgaggtgac    840

atgtgtagta gttgatgtct cccacgagga ccctgaggtc aagtttaatt ggtatgtgga    900

cggtgtggag gtccacaacg ccaaaacaaa accacgggag gaacagtaca attccacata    960

tagggtggtg agcgtcctta ccgtcctgca tcaggattgg ttaaatggta aggagtataa   1020

gtgtaaggtg tctaacaagg ctctgcctgc tcccatcgaa aaaactataa gtaaggccaa   1080

aggacagccc agggaacctc aggtgtatac tcttccaccc agtagagatg agctgactaa   1140

aaaccaggtg tccctgactt gtctggtgaa gggattttac ccatccgata tcgccgtgga   1200

atgggagtcc aacggacagc cagaaaacaa ttataaaact atgccaccag tgctggatag   1260

tgatggtagt tttttctgt acagtaagct gactgttgat aagagtagat ggcagcaggg   1320

taatgttttt agttgtagcg ttatgcacga agctctgcac aatcactata ctcagaagag   1380

cctgagcctg agccccggta agtgatgagg taccgagc                           1418
```

<210> SEQ ID NO 73
<211> LENGTH: 462
<212> TYPE: PRT
<213> ORGANISM: Artificial Sequence
<220> FEATURE:
<223> OTHER INFORMATION: NPC-1 chi-antibody heavy chain
<220> FEATURE:
<221> NAME/KEY: SIGNAL
<222> LOCATION: (1)..(19)

<400> SEQUENCE: 73

```
Met Ala Val Leu Ala Leu Leu Leu Cys Leu Val Thr Phe Pro Ser Cys
1               5                   10                  15

Val Leu Ser Gln Val Gln Leu Lys Glu Ser Gly Pro Asp Leu Val Ala
            20                  25                  30

Pro Ser Gln Ser Leu Ser Ile Thr Cys Thr Val Ser Gly Phe Ser Leu
        35                  40                  45

Ser Lys Phe Gly Val Asn Trp Val Arg Gln Pro Pro Gly Lys Gly Leu
    50                  55                  60

Glu Trp Leu Gly Val Ile Trp Gly Asp Gly Ser Thr Ser Tyr Asn Ser
```

-continued

```
65                  70                  75                  80

Gly Leu Ile Ser Arg Leu Ser Ile Ser Lys Glu Asn Ser Lys Ser Gln
                85                  90                  95

Val Phe Leu Lys Leu Asn Ser Leu Gln Ala Asp Asp Thr Ala Thr Tyr
            100                 105                 110

Tyr Cys Val Lys Pro Gly Gly Asp Tyr Trp Gly His Gly Thr Ser Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Pro Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Met Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460
```

<210> SEQ ID NO 74
<211> LENGTH: 10
<212> TYPE: PRT
<213> ORGANISM: Artificial Sequence
<220> FEATURE:
<223> OTHER INFORMATION: NPC-1 chi-antibody heavy chain CDR1

<400> SEQUENCE: 74

Gly Phe Ser Leu Ser Lys Phe Gly Val Asn
1 5 10

<210> SEQ ID NO 75
<211> LENGTH: 16
<212> TYPE: PRT
<213> ORGANISM: Artificial Sequence
<220> FEATURE:
<223> OTHER INFORMATION: NPC-1 chi-antibody heavy chain CDR2

<400> SEQUENCE: 75

Val Ile Trp Gly Asp Gly Ser Thr Ser Tyr Asn Ser Gly Leu Ile Ser
1 5 10 15

<210> SEQ ID NO 76
<211> LENGTH: 5
<212> TYPE: PRT
<213> ORGANISM: Artificial Sequence
<220> FEATURE:
<223> OTHER INFORMATION: NPC-1 chi-antibody heavy chain CDR3

<400> SEQUENCE: 76

Pro Gly Gly Asp Tyr
1 5

<210> SEQ ID NO 77
<211> LENGTH: 735
<212> TYPE: DNA
<213> ORGANISM: Artificial Sequence
<220> FEATURE:
<223> OTHER INFORMATION: Humanized NEO 103 light chain

<400> SEQUENCE: 77
aagcttgcca ccatgaagta cctgctgccc accgctgctg ctggcttgct gctgctggca 60
gctcagcctg ccatggccga gatcgtgctg acccagtctc ctggcaccct gtctctgagc 120
cctggcgaga gagctaccct gtcctgctcc gcctcctcca gcatctccta catgtactgg 180
tatcagcaga agcccggcca ggcccctcgg ctgctgatct acgatacctc caagctggcc 240
tccggcatcc ccgacagatt ctccggctct ggctctggca ccgacttcac cctgaccatc 300
tcccggctgg aacccgagga cttcgccgtg tactactgcc accagcggga ctcctacccc 360
tggacctttg gccagggcac caagctggaa atcaagcgga ccgtggccgc tccctccgtg 420
ttcatcttcc caccttccga cgagcagctg aagtccggca ccgcttctgt cgtgtgcctg 480
ctgaacaact tctacccccg cgaggccaag gtgcagtgga aggtggacaa cgccctgcag 540
tccggcaact cccaggaatc cgtgaccgag caggactcca aggacagcac ctactccctg 600
tcctctaccc tgaccctgtc caaggccgac tacgagaagc acaaggtgta cgcctgcgaa 660
gtgacccacc agggcctgtc tagccccgtg accaagtctt tcaaccgggg cgagtgctga 720
tgaggatcct gatga 735

<210> SEQ ID NO 78
<211> LENGTH: 239
<212> TYPE: PRT
<213> ORGANISM: Artificial Sequence
<220> FEATURE:
<223> OTHER INFORMATION: Humanized NEO 103 light chain

<400> SEQUENCE: 78

```
Lys Leu Ala Thr Met Lys Tyr Leu Leu Pro Thr Ala Ala Ala Gly Leu
1               5                   10                  15

Leu Leu Leu Ala Ala Gln Pro Ala Met Ala Glu Ile Val Leu Thr Gln
            20                  25                  30

Ser Pro Gly Thr Leu Ser Leu Ser Pro Gly Glu Arg Ala Thr Leu Ser
        35                  40                  45

Cys Ser Ala Ser Ser Ser Ile Ser Tyr Met Tyr Trp Tyr Gln Gln Lys
    50                  55                  60

Pro Gly Gln Ala Pro Arg Leu Leu Ile Tyr Asp Thr Ser Lys Leu Ala
65                  70                  75                  80

Ser Gly Ile Pro Asp Arg Phe Ser Gly Ser Gly Ser Gly Thr Asp Phe
                85                  90                  95

Thr Leu Thr Ile Ser Arg Leu Glu Pro Glu Asp Phe Ala Val Tyr Tyr
            100                 105                 110

Cys His Gln Arg Asp Ser Tyr Pro Trp Thr Phe Gly Gln Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

<210> SEQ ID NO 79
<211> LENGTH: 1437
<212> TYPE: DNA
<213> ORGANISM: Artificial Sequence
<220> FEATURE:
<223> OTHER INFORMATION: Humanized NEO 103 heavy chain

<400> SEQUENCE: 79

```
aagcttgcca ccatggacct gctgtgcaag aacatgaagc acctgtggtt ctttctgctg     60

ctggtggccg ctcccagatg ggtgctgtct caggtgcagc tggtggaatc tggccctggc    120

ctggtgcagc cttccagatc cctgtctctg acctgctcct ccagcggctt cagcctgtcc    180

aagttcggcg tgaactgggt gcgacagcct cctggcaagg gcctggaatg ggtgggagtg    240

atctggggcg acggctccac ctcctacaac tccggcctga tctccagagt gaccatctcc    300

cgggacacct ccaagaacca gctgttcctg aagatggact ccctgaccgc cgaggacacc    360

gccgtgtact actgtgctag acctggcggc gactactggg gccagggcac aacagtgacc    420

gtgtcctccg cttccaccaa gggcccctct gtgtttcctc tggcccccctc cagcaagtcc    480

acctctggtg gaactgccgc tctgggctgc ctcgtgaagg actacttccc cgagcccgtg    540

acagtgtcct ggaactctgg cgctctgacc tccggcgtgc acacctttcc agctgtgctg    600

cagtccagcg gcctgtactc cctgtcctcc gtcgtgaccg tgccttccag ctctctgggc    660

acccagacct acatctgcaa cgtgaaccac aagccctcca ataccaaggt ggacaagaag    720
```

```
gtggaaccca agtcctgcga caagacccac acctgtcccc cttgtcctgc ccctgaactg    780

ctgggcggac cttccgtgtt cctgttcccc ccaaagccca aggacaccct gatgatctcc    840

cggacccccg aagtgacctg cgtggtggtg gatgtgtccc acgaggaccc tgaagtgaag    900

ttcaattggt acgtggacgg cgtggaagtg cacaacgcca agaccaagcc tagagaggaa    960

cagtacaact ccacctaccg ggtggtgtcc gtgctgaccg tgctgcatca ggactggctg   1020

aacggcaaag agtacaagtg caaggtgtcc aacaaggccc tgcctgcccc catcgaaaag   1080

accatcagca aggctaaggg ccagccccgc gagccccagg tgtacacact gcctccatcc   1140

cgggaagaga tgaccaagaa tcaggtgtcc ctgacctgtc tcgtgaaagg cttctacccc   1200

tccgatatcg ccgtggaatg ggagtccaac ggccagcccg agaacaacta caagaccacc   1260

ccccctgtgc tggactccga cggctcattc ttcctgtaca gcaagctgac agtggacaag   1320

tcccggtggc agcagggcaa cgtgttctcc tgctccgtga tgcacgaggc cctgcacaac   1380

cactacaccc agaagtccct gtccctgagc cccggcaagt gatgatgagg atcctga      1437
```

```
<210> SEQ ID NO 80
<211> LENGTH: 473
<212> TYPE: PRT
<213> ORGANISM: Artificial Sequence
<220> FEATURE:
<223> OTHER INFORMATION: Humanized NEO 103 heavy chain

<400> SEQUENCE: 80

Lys Leu Ala Thr Met Asp Leu Leu Cys Lys Asn Met Lys His Leu Trp
1               5                   10                  15

Phe Phe Leu Leu Leu Val Ala Ala Pro Arg Trp Val Leu Ser Gln Val
            20                  25                  30

Gln Leu Val Glu Ser Gly Pro Gly Leu Val Gln Pro Ser Arg Ser Leu
        35                  40                  45

Ser Leu Thr Cys Ser Ser Ser Gly Phe Ser Leu Ser Lys Phe Gly Val
    50                  55                  60

Asn Trp Val Arg Gln Pro Pro Gly Lys Gly Leu Glu Trp Val Gly Val
65                  70                  75                  80

Ile Trp Gly Asp Gly Ser Thr Ser Tyr Asn Ser Gly Leu Ile Ser Arg
                85                  90                  95

Val Thr Ile Ser Arg Asp Thr Ser Lys Asn Gln Leu Phe Leu Lys Met
            100                 105                 110

Asp Ser Leu Thr Ala Glu Asp Thr Ala Val Tyr Tyr Cys Ala Arg Pro
        115                 120                 125

Gly Gly Asp Tyr Trp Gly Gln Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240
```

Val Glu Pro Lys Ser Cys Asp Lys Thr His Thr Cys Pro Pro Cys Pro
245 250 255

Ala Pro Glu Leu Leu Gly Gly Pro Ser Val Phe Leu Phe Pro Pro Lys
260 265 270

Pro Lys Asp Thr Leu Met Ile Ser Arg Thr Pro Glu Val Thr Cys Val
275 280 285

Val Val Asp Val Ser His Glu Asp Pro Glu Val Lys Phe Asn Trp Tyr
290 295 300

Val Asp Gly Val Glu Val His Asn Ala Lys Thr Lys Pro Arg Glu Glu
305 310 315 320

Gln Tyr Asn Ser Thr Tyr Arg Val Val Ser Val Leu Thr Val Leu His
325 330 335

Gln Asp Trp Leu Asn Gly Lys Glu Tyr Lys Cys Lys Val Ser Asn Lys
340 345 350

Ala Leu Pro Ala Pro Ile Glu Lys Thr Ile Ser Lys Ala Lys Gly Gln
355 360 365

Pro Arg Glu Pro Gln Val Tyr Thr Leu Pro Pro Ser Arg Glu Glu Met
370 375 380

Thr Lys Asn Gln Val Ser Leu Thr Cys Leu Val Lys Gly Phe Tyr Pro
385 390 395 400

Ser Asp Ile Ala Val Glu Trp Glu Ser Asn Gly Gln Pro Glu Asn Asn
405 410 415

Tyr Lys Thr Thr Pro Pro Val Leu Asp Ser Asp Gly Ser Phe Phe Leu
420 425 430

Tyr Ser Lys Leu Thr Val Asp Lys Ser Arg Trp Gln Gln Gly Asn Val
435 440 445

Phe Ser Cys Ser Val Met His Glu Ala Leu His Asn His Tyr Thr Gln
450 455 460

Lys Ser Leu Ser Leu Ser Pro Gly Lys
465 470

<210> SEQ ID NO 81
<211> LENGTH: 554
<212> TYPE: DNA
<213> ORGANISM: Artificial Sequence
<220> FEATURE:
<223> OTHER INFORMATION: 4B6 antibody light chain

<400> SEQUENCE: 81
aacctgtggg gacattgtga tgtcacagtc tccatcctcc ctggctgtgt cagcaggaga 60
aaaggtcact ttgaactgca aatccagtca gagtctgctc aacagtagaa cccgaaagaa 120
ctacttggct tggtaccagc aaaaaccagg gcagtctcct aaattactga tctactgggc 180
atccactagg gaatctgggg tccctgatcg cttcacaggc agtggatctg ggacagattt 240
cactctcacc atcaacagtg tgcaggctga agacctggca gtttattact gcaagcaatc 300
ttataatctc ttcacgttcg gctcggggac aaagtmgaag taaaacgggc tgatgctgca 360
ccaactgtat ccatcttccc accatccagt gagcagttaa catctggagg tgcctcagtc 420
gtgtgcttct tgaacaactt ctaccccaaa gacaccaatg tcaagtggaa gattgatggc 480
agtgaacgac aaaatggcgt cctgaacagt tggactgatc aggacagcaa agacagcacc 540
tacagcatga gcag 554

<210> SEQ ID NO 82
<211> LENGTH: 184

<212> TYPE: PRT
<213> ORGANISM: Artificial Sequence
<220> FEATURE:
<223> OTHER INFORMATION: 4B6 antibody light chain
<220> FEATURE:
<221> NAME/KEY: MISC_FEATURE
<222> LOCATION: (30)..(41)
<223> OTHER INFORMATION: 4B6 antibody light chain CDR1
<220> FEATURE:
<221> NAME/KEY: MISC_FEATURE
<222> LOCATION: (59)..(61)
<223> OTHER INFORMATION: 4B6 antibody light chain CDR2
<220> FEATURE:
<221> NAME/KEY: MISC_FEATURE
<222> LOCATION: (98)..(105)
<223> OTHER INFORMATION: 4B6 antibody light chain CDR3

<400> SEQUENCE: 82

```
Thr Cys Gly Asp Ile Val Met Ser Gln Ser Pro Ser Ser Leu Ala Val
1               5                   10                  15

Ser Ala Gly Glu Lys Val Thr Leu Asn Cys Lys Ser Ser Gln Ser Leu
            20                  25                  30

Leu Asn Ser Arg Thr Arg Lys Asn Tyr Leu Ala Trp Tyr Gln Gln Lys
        35                  40                  45

Pro Gly Gln Ser Pro Lys Leu Leu Ile Tyr Trp Ala Ser Thr Arg Glu
    50                  55                  60

Ser Gly Val Pro Asp Arg Phe Thr Gly Ser Gly Ser Gly Thr Asp Phe
65                  70                  75                  80

Thr Leu Thr Ile Asn Ser Val Gln Ala Glu Asp Leu Ala Val Tyr Tyr
                85                  90                  95

Cys Lys Gln Ser Tyr Asn Leu Phe Thr Phe Gly Ser Gly Thr Lys Leu
            100                 105                 110

Glu Val Lys Arg Ala Asp Ala Ala Pro Thr Val Ser Ile Phe Pro Pro
        115                 120                 125

Ser Ser Glu Gln Leu Thr Ser Gly Gly Ala Ser Val Val Cys Phe Leu
    130                 135                 140

Asn Asn Phe Tyr Pro Lys Asp Thr Asn Val Lys Trp Lys Ile Asp Gly
145                 150                 155                 160

Ser Glu Arg Gln Asn Gly Val Leu Asn Ser Trp Thr Asp Gln Asp Ser
                165                 170                 175

Lys Asp Ser Thr Tyr Ser Met Ser
            180
```

<210> SEQ ID NO 83
<211> LENGTH: 12
<212> TYPE: PRT
<213> ORGANISM: Artificial Sequence
<220> FEATURE:
<223> OTHER INFORMATION: 4B6 antibody light chain CDR1

<400> SEQUENCE: 83

```
Gln Ser Leu Leu Asn Ser Arg Thr Arg Lys Asn Tyr
1               5                   10
```

<210> SEQ ID NO 84
<211> LENGTH: 8
<212> TYPE: PRT
<213> ORGANISM: Artificial Sequence
<220> FEATURE:
<223> OTHER INFORMATION: 4B6 light chain CDR3

<400> SEQUENCE: 84

```
Lys Gln Ser Tyr Asn Leu Phe Thr
```

1 5

<210> SEQ ID NO 85
<211> LENGTH: 351
<212> TYPE: DNA
<213> ORGANISM: Artificial Sequence
<220> FEATURE:
<223> OTHER INFORMATION: 4B6 heavy chain

<400> SEQUENCE: 85
tgaggtgcag ctggaggagt ctggagctga actggcgagg cccggggctt cagtgaagct 60
gtcttgtaag gcttctggct actccttcac tgactattat ataaattggg tgaagcagag 120
gactggacag ggccttgagt ggattggaga aatttatcct ttaggtggta ctagtttcta 180
caatgagagg ttcaaggaca aggccacact gactgcagac aaatcctcca gcacagtcta 240
catggaactc agcagcctga catctgagga ctcggcagtc tatttctgtg caagagggga 300
taattattac gacgtctact ttgactactg gggccaaggg accacggtca c 351

<210> SEQ ID NO 86
<211> LENGTH: 111
<212> TYPE: PRT
<213> ORGANISM: Artificial Sequence
<220> FEATURE:
<223> OTHER INFORMATION: 4B6 antibody heavy chain
<220> FEATURE:
<221> NAME/KEY: MISC_FEATURE
<222> LOCATION: (26)..(33)
<223> OTHER INFORMATION: CDR1
<220> FEATURE:
<221> NAME/KEY: MISC_FEATURE
<222> LOCATION: (51)..(58)
<223> OTHER INFORMATION: CDR2
<220> FEATURE:
<221> NAME/KEY: MISC_FEATURE
<222> LOCATION: (97)..(109)
<223> OTHER INFORMATION: CDR3

<400> SEQUENCE: 86

Glu Val Gln Leu Glu Glu Ser Gly Ala Glu Leu Ala Arg Pro Gly Ala
1 5 10 15

Ser Val Lys Leu Ser Cys Lys Ala Ser Gly Tyr Ser Phe Thr Asp Tyr
20 25 30

Tyr Ile Asn Trp Val Lys Gln Arg Thr Gly Gln Gly Leu Glu Trp Ile
35 40 45

Gly Glu Ile Tyr Pro Leu Gly Gly Thr Ser Phe Tyr Asn Glu Arg Phe
50 55 60

Lys Asp Lys Ala Thr Leu Thr Ala Asp Lys Ser Ser Ser Thr Val Tyr
65 70 75 80

Met Glu Leu Ser Ser Leu Thr Ser Glu Asp Ser Ala Val Tyr Phe Cys
85 90 95

Ala Arg Gly Asp Asn Tyr Tyr Asp Val Tyr Phe Asp Tyr Trp Gly
100 105 110

<210> SEQ ID NO 87
<211> LENGTH: 8
<212> TYPE: PRT
<213> ORGANISM: Artificial Sequence
<220> FEATURE:
<223> OTHER INFORMATION: 4B6 heavy chain CDR1

<400> SEQUENCE: 87

Gly Tyr Ser Phe Thr Asp Tyr Tyr
1 5

-continued

```
<210> SEQ ID NO 88
<211> LENGTH: 8
<212> TYPE: PRT
<213> ORGANISM: Artificial Sequence
<220> FEATURE:
<223> OTHER INFORMATION: 4B6 heavy chain CDR2

<400> SEQUENCE: 88

Ile Tyr Pro Leu Gly Gly Thr Ser
1               5


<210> SEQ ID NO 89
<211> LENGTH: 13
<212> TYPE: PRT
<213> ORGANISM: Artificial Sequence
<220> FEATURE:
<223> OTHER INFORMATION: 4B6 heavy chain CDR3

<400> SEQUENCE: 89

Ala Arg Gly Asp Asn Tyr Tyr Asp Val Tyr Phe Asp Tyr
1               5                   10
```